US007700727B2

(12) United States Patent
Berthet et al.

(10) Patent No.: US 7,700,727 B2
(45) Date of Patent: Apr. 20, 2010

(54) COMPOSITIONS AND KITS FOR DETECTING PATHOGEN INFECTION

(75) Inventors: François Xavier Berthet, Barcelona (ES); Francesc Vayreda Casadevall, Barcelona (ES); Maria Cruz Sanz Maria, Mollet Del Vall (ES); Teresa Llop Garcia, Granollers (ES); Angels Mor Olle, Barcelona (ES)

(73) Assignee: Biokit, S.A., Barcelona (ES)

(*) Notice: Subject to any disclaimer, the term of this patent is extended or adjusted under 35 U.S.C. 154(b) by 0 days.

(21) Appl. No.: 11/116,144

(22) Filed: Apr. 27, 2005

(65) Prior Publication Data

US 2005/0277181 A1 Dec. 15, 2005

Related U.S. Application Data

(63) Continuation of application No. PCT/ES2004/000581, filed on Dec. 23, 2004.

(30) Foreign Application Priority Data

Dec. 23, 2003 (EP) ................................ 03380307

(51) Int. Cl.
*C07K 14/00* (2006.01)
*C12N 9/00* (2006.01)

(52) U.S. Cl. ...................................... 530/350; 435/183

(58) Field of Classification Search ...................... None
See application file for complete search history.

(56) References Cited

U.S. PATENT DOCUMENTS 4,076,797 A 2/1978 Davis ........................... 424/1
4,288,426 A 9/1981 Stevens ......................... 424/1
4,294,817 A 10/1981 Burgett et al.
4,514,498 A 4/1985 Kettman et al.
4,618,588 A 10/1986 Sato et al. ................... 436/511
4,683,195 A 7/1987 Mullis et al.
4,740,467 A 4/1988 Kettman et al. ................ 435/7
4,777,133 A 10/1988 Picciolo et al.
4,894,328 A 1/1990 Alderete et al. ................ 435/7
4,959,304 A 9/1990 Simonson
4,997,932 A * 3/1991 Reardon et al. ............ 536/25.4
5,008,199 A 4/1991 Wang et al.
5,055,405 A 10/1991 Wang et al.
5,155,022 A 10/1992 Naqui et al. ............... 435/7.32
5,350,842 A 9/1994 Norgard
5,372,928 A 12/1994 Miyamura et al.
5,474,900 A 12/1995 Ishikawa et al. ........... 435/71.1
5,514,553 A 5/1996 Simonson
5,578,456 A 11/1996 Fujimura et al. ........... 435/7.36
5,635,182 A * 6/1997 McCoy et al. ............ 424/192.1
5,643,733 A 7/1997 Robinson et al.
5,643,751 A 7/1997 Robinson et al.
5,681,934 A 10/1997 Norgard ..................... 540/403
5,719,060 A 2/1998 Hutchens et al.
5,894,063 A 4/1999 Hutchens et al.
5,965,702 A 10/1999 Robinson et al.
5,969,108 A 10/1999 McCafferty et al.
6,120,990 A * 9/2000 Brust et al. .................... 435/5
6,225,047 B1 5/2001 Hutchens et al.
6,248,331 B1 * 6/2001 Ise et al. .................. 424/192.1
6,300,064 B1 10/2001 Knappik et al.
6,313,094 B1 11/2001 Mimoto et al.
6,329,502 B1 12/2001 Mimoto et al.
6,479,248 B1 11/2002 Krell et al. ................. 435/7.22
6,515,106 B1 2/2003 Düring ....................... 530/350

FOREIGN PATENT DOCUMENTS

EP 0 274 826 A1 7/1988
EP 0 670 494 A2 6/1995
EP 0 984 065 A1 8/2000
WO WO 02/34777 A1 5/2002

OTHER PUBLICATIONS

NCBI Sequence of proteinase K ABA60899.*

Appendix A—sequence alignment of SEQ ID No. 31 vs. Akins et al. 17 kDa sequence (AAA27472/P29722). No Date.*

Chung et al. Cloning the human lysozyme cDNA: Inverted Alu Repeat in the mRNA and in situ hybridization for macrophages and Paneth cells. Proceedings from the National Academies of Science USA. 1988. vol. 85, pp. 6227-6231.*

Appendix B—sequence alignment of SEQ ID No. 295 vs. Chung et al. (AAA59535). No date.*

Verner et al. Protein Translocation Across Membranes. Science. 1988. vol. 241, No. 4871, pp. 1307-1313.*

Lewin, B. "Genes V", Oxford University Press Inc., New York, 1994, Chapter 11, p. 282.*

Lundblad et al. Human Serum Lysozyme (Muramidase). Scandinavian Jouranl of Clinical & Laboratory Investigation, 1966, vol. 18, pp. 201-208.*

(Continued)

*Primary Examiner*—Suzanne M. Noakes
(74) *Attorney, Agent, or Firm*—Burns & Levinson LLP

(57) ABSTRACT

The present invention generally features therapeutic and diagnostic compositions and methods for increasing or decreasing the binding of a lysozyme polypeptide to a *Treponema pallidum* P17 polypeptide (Tp17) or a Tp17-like polypeptide. More particularly, the invention relates to compositions and methods for detecting, treating, or preventing a pathogen infection or a chronic disorder; and to binding assays using a Tp17-like polypeptide and a lysozyme polypeptide.

29 Claims, 59 Drawing Sheets

OTHER PUBLICATIONS

Appendix A—sesquence alignment of instant SEQ ID No. 31 and Akins et al. sequence as noted in Office action, 35 U.S.C. 102(b) rejection . No date.*

MedlinePlus- Merriam-Webster Medical Dictionary definition of blood serum. No date.*

Gruden et al., "Autoimmuune Responses to Amyloid Structures of $A\beta_{(25-35)}$ Peptide and Human Lysozyme in the Serum of Patients with Progressive Alzheimer's Disease," *Dement. Geriatr. Cogn. Disord.*, 18:165-171, DOI: 10.1159/000079197, 2004.

Mandal et al., "SLLPI, A Unique, Intra-acrosomal, Non-bacteriolytic, c Lysozyme-Like Protein of Human Spermatoza," Biology of Reproduction 68, 1525-1537, 2003.

Akins et al., (1993), "Lipid Modification of the 17-Kilodalton Membrane Immunogen of *Treponema pallidum* Determines Macrophage Activation as well as Amphiphilicity," *Infect. Immun.*, 61:1202-1210.

Andreotti et al., (2003), "Immunoassay of infectious agents," *Biotechniques*, 35:850-859.

Blanco et at., (1997), "Surface Antigens of the Syphilis Spirochete and Their Potential as Virulence Determinants," *Emerging Infectious Diseases*, 3(1):11-20.

Boyden et al., (1951), "The Adsorption of Proteins on Erythrocytes Treated with Tannic Acid and Subsequent Hemagglutination by Antiprotein Sera," *J. Exp. Med.*, 93:107-120.

Bruisten et al., (2003), "Genital Ulcers in Women," *Curr. Womens Health Report*, 3:288-98.

Cisani et al., (1989), "Cell fusion induced by herpes simplex is inhibited by hen egg-white lysozyme," *Microbios*, 59:73-83.

Davies et al., (1999), "Profiling of Amyloid β Peptide Variants Using SELDI ProteinChip® Arrays," *Biotechniques*, 27:1258-61.

Eylan et al., (1977), "Lysozyme tear level in patients with herpes simplex virus eye infection," *Investigative Opthalmology & Visual Science*, 16(9):850-853.

Fernie-King et al., (2002), "Streptococcal Inhibitor of Complement Inhibits Two Additional Components of the Mucosal Innate Immune System: Secretory Leukocyte Proteinase Inhibitor and Lysozyme," *Infection and Immunity*, 70(9):4908-4916.

Gayle et al., (2001), "Global Impact of Human Immunodeficiency Virus and AIDS," *Clin. Micro. Reviews*, 14:327-335.

Herbert et al., (1979), "Passive Haemagglutination With Special Reference to the Tanned Cell Technique," *Handbook of Experimental Immunology*, 20.1-22.20.

Hirata et al., (1968), "Passive Hemagglutination Procedures for Protein and Polysaccharide Antigens Using Erythrocytes Stabilized by Aldehydes," *J. Immunol.*, 100:641-46.

Hsu et al., (1989), "Sequence Analysis of the 47-Kilodalton Major Integral Membrane Immunogen of *Treponema pallidum," Infect Immun.*, 57:196-203.

Jerome et al., (2001), "HSV and Glycoprotein J Inhibit Caspase Activation and Apoptosis Induced by Granzyme B or Fas[1]," *J. Immunol.*, 167:3928-3935.

Kaiser et al., (1999), "Enhancement of Cyanogen Bromide Cleavage Yields for Methionyl-Serine and Methionyl-Threonine Peptide Bonds," *Anal. Biochem.*, 266:1-8.

Kiernan et al., (2002), "High-Throughput Protein Characterization Using Mass Spectrometric Immunoassay," *Anal. Biochem.*, 301:49-56.

Lampis et al., (2001), "Enhancement of anti-herpetic activity of glycyrrhizic acid by physiological proteins," *Antiviral Chemistry & Chemotherapy*, 12(2):125-131.

Lee-Huang et al., (1999), "Lysozyme and RNases as anti-HIV components in β-core preparations of human chorionic gonadotropin," *Proc. Natl. Acad. Sci. USA*, 96:2678-2681.

Löwhagen et al., (2002), "Proportion of Herpes Simplex Virus (HSV) Type 1 and Type 2 Among Genital and Extragenital HSV Isolates," *Acta Derm. Venereol.*, 82:118-20.

Lukomski et al., (2000), "Nonpolar Inactivation of the Hypervariable Streptococcal Inhibitor of Complement Gene (*sic*) in Serotype M1 *Strepococcus pyogenes* Significantly Decreases Mouse Mucosal Colonization," *Infection and Immunity*, 68(2):535-542.

Mackay et al., (2000), "Advances in Immunology," *N.E. J. Medicine*, 343(5):338-344.

Malcolm et al., (1989), "Site-directed mutagenesis of the catalytic residues Asp-52 and Glu-35 of chicken egg white lysozyme," *Proc. Natl. Acad. Sci. USA*, 86:133-7.

Merrifield, (1963), "Solid Phase Peptide Synthesis. I. The Synthesis of a Tetrapeptide," *J. Am. Chem. Soc.*, 85:2149-2154.

Monchois et al., (2001), "*Escherichia coli ykfE* ORFan Gene Encodes a Potent Inhibitor of C-type Lysozyme," *J. Biol. Chem.*, 276:18437-18441.

Müller et al., (2005), "A Dictyostelium Mutant with Reduced Lysozome Levels Compensates by Increased Phagocytic Activity," *J. Biol. Chem.*, 280:10435-10443.

Muyldermans et al., (2001), "Single domain camel antibodies: current status," *J. Biotechnol.*, 74:277-302.

Oevermann et al., (2003), "The antiviral activity of naturally occuring proteins and their peptide fragments after chemical modification," *Antivir. Res.*, 59:23-33.

Pramanik et al., (2002), "Microwave-enhanced enzyme reaction for protein mapping by mass spectrometry: A new approach to protein digestion in minutes," *Protein Sci.*, 11:2676-87.

Risler et al., (1998), "Amino Acid Substitutions in Structurally Related Proteins A Pattern Recognition Approach," *J. Mol. Biol.*, 204:1019-1029.

Shimizu et al., (2002), "Detection and identification of protein variants and adducts in blood and tissues: an application of soft ionization mass spectrometry to clinical diagnosis," *J. Chromatogr. B.*, 25:15-30.

Shugar et al., (1952), "The Measurement of Lysozyme Activity and the Ultra-Violet Inactivation of Lysozyme," Biochem. Biophys. ACTA, 8:302-309.

Weigel et al., (1992), "Analysis of the N-Terminal Region of the 47-Kilodalton Integral Membrane Lipoprotein of *Treponema pallidum," Infect. Immun.*, 60:1568-1576.

Zielinski et al., (1997), "Studies on the lysozyme independence of immune immobilisation of *Treponema pallidum* and the frequency of lysozyme autoantibodies in syphilitic sera," *J. Med. Microbiol.*, 46:669-674.

PCT International Search Report for International Application No. PCT/ES 2004/000581 (Date of Completion of Search Report: Jun. 16, 2005).

Dialog Search Dated Aug. 25, 2003.

Bowie et al., (1990), "Deciphering the Message in Protein Sequences: Tolerance to Amino Acid Substitutions," *Science*, 247:1306-1310.

Guise et al., (1998), "Recovery and Reuse of the Molecular Chaperone GroEL for in Vitro Protein Refolding," *Biotechnology Progress*, 14:343-346, attaching GenBank accession No. AAS75782.

Herring et al., (2004), "Frequent Hepatitis C Virus Superinfection in Injection Drug Users," *Journal of Infectious Disease*, 190:1396-1403, attaching GenBank accession No. AAU06693.

Hotta et al., (1994), "Analysis of the core and E1 envelope region sequences of a novel variant of hepatitis C virus obtained in Indonesia," *Archives of Virology*, 136:53-62, attaching GenBank accession No. BAA00969.

Kien et al., (2003), "Analysis of the subcellular localization of hepatitis C virus E2 glycoprotein in live cells using EGFP fusion proteins," *Journal of General Virology*, 84:561-566.

Lagging et al., (2002), "Nosocomial Transmission of HCV in a Cardiology Ward During the Window Phase of Infection: An Epidemiological and Molecular Investigation," *Scand. J. of Infect. Dis.*, 34:580-582, attaching GenBank accession No. AAM18609.

Okamato et al., (1993), "Characterization of the genomic sequence of type V (or 3a) hepatitis C virus isolates and PCR primers for specific detection," *Journal of General Virology*, 74:2385-2390.

Todar, in "Todar's Online Textbook of Bacteriology," Chapter on "constitutive (Innate) Host Defences," pp. 1-13, 2000, www.textbookofbacteriology.net.

Wells, (1990), "Additivity of Mutational Effects in Proteins," *Biochemistry*, 29(37):8509-8517.

Appendix A—sequence alignment of SEQ ID No. 31 vs. Fujimura et al. SEQ ID No. 2, no date.

Appendix B—sequence alignment of SEQ ID No. 31 with E2 protein from P27958 (CM Rice), no date.

NCBI sequences for HCV polyprotein, 1-3011 amino acids NP_671491; and just the E2 protein NP_751921.
Appendices A (alignments of SEQ ID No. 317), C (alignments of SEQ ID No. 319), and D (alignments of SEQ ID No. 321).
U.S. Appl. No. 11/220,372 filed Sep. 6, 2005 entitled "Compositions and methods for detecting pathogen infection."
U.S. Appl. No. 11/398,377 filed Apr. 5, 2006 entitled "Method for Reducing Lysozyme Enzymatic Activity."
U.S. Appl. No. 11/398,889 filed Apr. 6, 2006 entitled "Diagnosis and treatment of Alzheimer disease."
U.S. Appl. No. 11/398,884 filed Apr. 6, 2006 entitled "Method for detecting pathogen."
U.S. Appl. No. 11/398,937 filed Apr. 6, 2006 entitled "Compositions and methods for treatment of chronic and infectious diseases."

* cited by examiner

| FIG. 1A-1 |
|---|
| FIG. 1A-2 |
| FIG. 1A-3 |

FIG. 1

| /TrEMBL Accession number | DESCRIPTION | HOST | PEPTIDE SEQUENCE | LOCATION (aa) | SEQ ID NO: |
|---|---|---|---|---|---|
| P45502 | IVY lysozyme inhibitor | *E.coli* | C k . . P H . . . . . . . . . D C | 85 to 90 | 24 |
| Q9HXB1 | IVY-like lysozyme inhibitor | *P. aeruginosa* | C k . . P H . . . . . . . . . D C | 83 to 88 | 24 |
| P58483 | IVY-like lysozyme inhibitor | *Y. pestis* | C k . . P H . . . . . . . . . D C | 85 to 90 | 24 |
| Q83M91 | IVY-like lysozyme inhibitor | *S. flexneri* | C k . . P H . . . . . . . . . D C | 85 to 90 | 24 |
| Q9E147 | Neuraminidase | *Influenza A virus* | C g . . P H . . . . . . . . . E C | 124 to 129 | 44 |

FIG. 1A-1

| | | | | | | | | | | | | | | | | | | | | | |
|---|---|---|---|---|---|---|---|---|---|---|---|---|---|---|---|---|---|---|---|---|---|
| O97273 | Uncharacterized protein | *P. falciparum* | C | . | . | . | P | H | n | . | . | . | . | . | . | . | . | D | C | 96 to 101 | 45 |
| EAA39977 | Uncharacterized protein | *G. lamblia* | C | . | . | . | P | H | g | . | . | . | . | . | . | . | . | E | C | 66 to 71 | 46 |
| Q87LP5 | TrmA-like protein | *V. parahaemolyticus* | C | | . | . | P | H | y | h | . | . | . | . | . | . | . | E | C | 82 to 88 | 47 |
| Q9I4C2 | Uncharacterized protein | *P. aeruginosa* | C | . | . | . | P | H | l | r | . | . | . | . | . | . | . | D | C | 173 to 179 | 48 |
| Q9CMU6 | Dnt protein | *P. multocida* | C | . | . | . | P | H | y | n | . | . | . | . | . | . | . | D | C | 184 to 190 | 49 |
| Q8YIK0 | Methyltransferase | *B. melitensis* | C | . | . | . | P | H | g | l | . | . | . | . | . | . | . | D | C | 215 to 221 | 50 |
| Q8FZB6 | Uncharacterized protein | *B. Suis* | C | . | . | . | P | H | g | l | . | . | . | . | . | . | . | D | C | 215 to 221 | 50 |
| Q50682 | Uncharacterized protein | *M.tuberculosis* | C | . | . | . | P | H | a | s | v | . | . | . | . | . | . | D | C | 5 to 12 | 51 |
| Q8I957 | Erythrocyte varPAM1 | *P. falciparum* | C | . | . | . | P | H | c | k | v | . | . | . | . | . | . | D | C | 280 to 287 | 52 |
| Q8I3E6 | PfEMP1 antigen | *P. falciparum* | C | . | . | . | P | H | c | e | v | . | . | . | . | . | . | D | C | 474 to 481 | 53 |
| Q9PNE3 | Putative phosphatase | *C. jejuni* | C | . | . | . | P | H | l | e | g | c | . | . | . | . | . | E | C | 104 to 112 | 54 |
| Q83R05 | HisB | *S. flexneri* | C | . | . | . | P | H | l | p | a | d | | . | . | . | . | E | C | 91 to 101 | 55 |
| Q9I7C0 | Uncharacterized protein | *P. aeruginosa* | C | . | . | . | P | H | g | p | d | d | g | . | . | . | . | D | C | 91 to 101 | 56 |
| Q88RS0 | Hydrolase | *P. putida* | C | . | . | . | P | H | g | p | d | e | g | . | . | . | . | D | C | 89 to 99 | 57 |
| Q7VFZ1 | Uncharacterized protein | *H. hepaticus* | C | . | . | . | P | H | l | p | s | e | n | c | . | . | . | D | C | 90 to 100 | 58 |
| P16823 | Protein UL71 | *HCMV* | C | l | . | . | P | H | t | r | p | a | a | e | v | . | . | E | C | 93 to 105 | 59 |
| Q7X5N2 | Uncharacterized protein | *P. aeruginosa* | C | . | . | . | P | H | r | l | s | a | i | q | t | . | . | E | C | 205 to 216 | 60 |
| Q91TM5 | Protein U44 | *Tupaia herpesvirus* | C | r | . | . | P | H | m | r | p | a | a | e | v | . | . | E | C | 105 to 117 | 61 |
| Q8QS28 | Tegument protein UL71 | *Chimp. CMV* | C | l | . | . | P | H | t | r | p | a | a | e | v | . | . | E | C | 93 to 105 | 62 |
| P36778 | Regulatory protein E2 | *HPV 3* | C | . | . | . | P | H | p | i | g | h | r | s | d | p | . | D | C | 289 to 301 | 63 |
| P27915 | Polyprotein | *Dengue 3 virus* | C | . | . | . | P | H | i | t | e | v | e | p | e | d | i | D | C | 167 to 180 | 64 |
| P29722 | Tp17 antigen | *T. pallidum* | C | . | . | . | P | H | a | g | k | a | k | a | e | k | v | E | C | 29 to 42 | 65 |
| Q8B5V5 | VP1 protein | *FMDV virus* | x | a | . | . | P | H | r | c | l | a | t | l | y | n | g | D | C | 27 to 41 | 66 |
| Q8Q6W1 | Integrase | *HIV-1* | C | s | . | . | P | e | v | g | q | m | | . | . | . | . | D | C | 56 to 65 | 67 |

FIG. 1A-2

| | | | | | | | | | | | | | | | | | | | | | |
|---|---|---|---|---|---|---|---|---|---|---|---|---|---|---|---|---|---|---|---|---|---|
| P05067 | Amyloid beta A4 protein | Human | C | k | t | h | P | H | f | v | i | p | y | r | - | - | - | - | C | 105 to 117 | 68 |
| P51693 | Amyloid-like protein | Human | C | a | h | - | P | H | h | q | v | v | p | f | r | - | - | - | C | 128 to 140 | 69 |
| Q9UKF5 | ADAM 29 protease | Human | C | t | - | - | P | H | r | s | - | - | - | - | - | - | - | - | C | 307 to 313 | 70 |
| P01730 | T-cell CD4 glycoprotein | Human | C | q | c | - | P | H | r | f | q | k | t | - | - | - | - | - | C | 445 to 455 | 71 |
| P3676 | Adenovirus type 12 | Human virus | C | r | q | - | P | H | c | g | a | r | d | i | - | - | - | - | C | 17 to 28 | 72 |
| P19556 | virus Env | Bovine virus | C | k | - | - | P | H | g | r | y | - | - | - | - | - | - | - | C | 615 to 622 | 73 |
| P03437 | Hemagglutinin Influenza A | Human virus | C | n | n | - | P | H | r | i | l | d | g | i | . | - | - | D | C | 68 to 80 | 74 |
| Q9H293 | Interleukin-17E | Human | C | l | c | - | P | H | - | . | - | - | - | - | - | - | - | - | C | 110 to 115 | 75 |
| Q07568 | IpgF | Shigella | C | f | i | - | P | H | l | g | r | a | d | - | - | - | - | - | C | 10 to 20 | 76 |
| P59868 | Imperatoxin IpTxA | Scorpion | C | l | | | P | H | l | k | r | c | k | a | d | n | - | D | C | 3 to 17 | 77 |
| P78395 | Melanoma antigen (OIP4) | human | C | - | - | - | P | H | - | - | - | - | - | - | - | - | - | - | C | 487 to 490 | 78 |
| P04637 | Cellular tumor antigen p53 | Human | C | - | - | - | P | H | h | e | r | - | - | - | - | - | - | - | C | 176 to 182 | 79 |
| Q65900 | Coat protein VP4 | Coxsackievirus | C | - | - | - | P | H | q | w | i | n | l | r | t | n | n | - | C | 247 to 259 | 80 |
| P27960 | Capsid protein C | Hepatitis C virus | C | - | - | - | P | H | r | l | s | v | - | - | - | - | - | - | C | 452 to 459 | 82 |
| P13889 | Nonstructural polyprotein | Rubella virus | C | g | - | - | P | H | y | a | n | n | - | - | - | - | - | - | C | 1446 to 1454 | 83 |
| P08768 | Structural polyprotein | EEE virus | C | t | s | k | P | H | p | d | y | q | - | - | - | - | - | - | C | 866 to 876 | 84 |
| P15358 | Antistatin clotting inhibitor | Leech | C | - | - | - | P | H | g | f | q | r | s | r | y | g | - | - | C | 54 to 65 | 85 |
| P17690 | Beta-2-glycoprotein I ( ApoH ) | Bovine | C | l | - | - | P | H | h | a | m | f | g | n | d | t | v | t | C | 174 to 188 | 86 |
| P03148 | Core antigen | Hepatitis B virus | C | s | - | - | P | H | h | t | a | l | r | q | a | i | l | - | C | 48 to 61 | 87 |
| P31627 | Env polyprotein | CAE virus | C | s | l | - | P | H | k | n | e | s | n | k | w | t | - | - | C | 528 to 541 | 88 |
| P11268 | Env polyprotein | Visna lentivirus | C | p | g | - | P | H | r | p | r | w | a | r | s | - | - | - | C | 152 to 164 | 89 |
| | | | | | | | | | | | | | | | | | | | | | |
| | | Consensus | C | X | X | X | P | H | X | X | X | X | X | X | X | X | X | X | C | | |
| | | | | | | | | | | | | | | | | | | | | | |

FIG. 1A-3

| ORGANISM | ACCESSION NUMBER | SEQUENCE | LOCATION | SEQ ID NO: |
|---|---|---|---|---|
| *Haemophilus ducreyi* | Q7VL21 | CPHYPEGQGEYQQKC-DC | 91 - 107 | 179 |
| *Haemophilus influenzae* | P46452 | CPHHSEGKGEYKE---DC | 89 - 103 | 180 |
| *Salmonella typhi* | Q8Z989 | CPHHPQGSIEEFRQVCDC | 92 - 109 | 181 |
| *Vibrio cholerae* | Q9KTJ4 | CPHHAEHGIGQYKEECDC | 89 - 105 | 182 |
| *Vibrio vulnificus* | Q7MN24 | CPHHAEHGVGDYKQ--DC | 129 - 144 | 183 |
| *Porphyromonas gingivalis* | Q7MU89 | CGHHGNTNQKSS----DC | 7 - 20 | 184 |
| *Helicobacter pylori* | O25531 | CRHAPEE---------NC | 92 - 100 | 185 |
| *Neisseria meningitidis* A | Q9JXI5 | CPHTDAD---------NC | 89 - 97 | 186 |
| *Neisseria meningitidis* B | Q9JWE9 | CPHTDAD---------NC | 89 - 97 | 187 |
| *Coxiella burnetti* | Q83AA9 | CPHAPQA---------NC | 93 - 101 | 188 |
| *Bordetella pertussis* | Q7W0Q4 | CPHGPDDG---------C | 89 - 97 | 189 |
| *Treponema denticola* | Q73JB5 | CPHCGRFFASVR-----C | 28 - 40 | 190 |
| *Bacteroides thetaiotaomicron* | Q89Z72 | CPHSGKRRMLLNLL---C | 77 - 91 | 191 |
| *Legionella pneumophila* | CAH12563 | CPHYQM-----------C | 77 - 88 | 192 |
| *Staphylococcus aureus* | NP_646083 | CPHADGRRVI-------C | 63 - 74 | 193 |
| *Neisseria gonorrhoeae* | ORF1557 | CPHPRPRRRQGR-----C | 86 - 99 | 194 |

FIG. 1B

| |
|---|
| FIG. 2A |
| FIG. 2B |
| FIG. 2C |

FIG. 2

| ORGANISM | CLASS | HOST | PEPTIDE SEQUENCE | | | | | | PROTEIN NAME | AMINO ACID LOCATION | Swiss-Prot TrEMBL ACCESSION NUMBER | SEQ ID NO: |
|---|---|---|---|---|---|---|---|---|---|---|---|---|
| **Bacterial pathogens** | | | | | | | | | | | | |
| *Escherichia coli* | Bacteria | Human | C | K | P | H | D | C | Ivy | 85-90 | P45502 | 24 |
| *Yersinia pestis* | Bacteria | Human | C | K | P | H | D | C | YS57 | 85-90 | P58483 | 24 |
| *Yersinia pestis* | Bacteria | Human | V | C | P | H | A | G | Racemase | 322-327 | Q8ZFW0 | 3 |
| *Yersinia pestis* | Bacteria | Human | V | C | P | H | A | G | Hypot | 347-352 | Q8CKY6 | 5 |

FIG. 2A

| | | | | | | | | | | | | |
|---|---|---|---|---|---|---|---|---|---|---|---|---|
| *Shigella flexneri* | Bacteria | Human | V | A | P | H | D | C | Cgs | 154-159 | Q83PD3 | 6 |
| *Shigella flexneri* | Bacteria | Human | C | K | P | H | D | C | ykfE | 85-90 | Q83M91 | 24 |
| *Vibrio cholerae* | Bacteria | Human | V | A | P | H | D | C | Cgs | 96-101 | Q9KNP8 | 6 |
| *Vibrio vulnificus* | Bacteria | Human | V | A | P | H | D | C | Cbl | 96-101 | Q8DCN6 | 6 |
| *Vibrio parahemolyticus* | Bacteria | Human | V | A | P | H | D | C | Cgs | 96-101 | Q87L50 | 6 |
| *Pseudomonas aeruginosa* | Bacteria | Human | C | K | P | H | D | C | Ivy-like | 83-88 | Q9HXB1 | 24 |
| *Chlamydia pneumoniae* | Bacteria | Human | K | K | P | H | A | K | Lnt | 183-188 | Q9Z7Q1 | 7 |
| *Treponema pallidum* | Bacteria | Human | V | C | P | H | A | G | P17 | 28-33 | P29722 | 5 |
| *Treponema pallidum* | Bacteria | Human | K | A | P | H | E | K | P17 | 114-119 | P29722 | 10 |
| *Staphylococcus aureus* | Bacteria | Human | K | A | P | H | D | K | SBI | 168-173 | O52187 | 7 |
| *Staphylococcus epidermidis* | Bacteria | Human | K | K | P | H | A | C | Hypot | 14-19 | Q8CQP2 | 11 |
| *Streptococcus pneumoniae* | Bacteria | Human | K | K | P | H | A | C | ???? | 11-16 | O06673 | 11 |
| *Streptococcus agalactiae* | Bacteria | Human | K | K | P | H | A | C | Hypot | 11-16 | Q8E7Z1 | 11 |
| *Streptococcus mutans* | Bacteria | Human | K | K | P | H | A | C | Hypot | 11-16 | Q8DWN7 | 11 |
| *Streptococcus pyogenes* | Bacteria | Human | K | K | P | H | A | C | SpyM-003 | 11-16 | Q9A208 | 11 |
| *Enterococcus faecalis* | Bacteria | Human | K | K | P | H | A | C | Hypot | 11-16 | Q82YY4 | 11 |
| *Bordetella bronchiseptica* | Bacteria | Human | V | A | P | H | A | G | Autotransporter | 266-271 | CAE31320 | 12 |
| *Bordetella bronchiseptica* | Bacteria | Human | V | A | P | H | A | G | Mb prot | 113-118 | CAE34070 | 12 |
| *Bordetella parapertussis* | Bacteria | Human | V | A | P | H | A | G | Autotransporter | 266-271 | CAE40144 | 12 |
| *Bordetella parapertussis* | Bacteria | Human | V | A | P | H | A | G | Mb prot | 113-118 | CAE38460 | 12 |
| *Helicobacter hepaticus* | Bacteria | Animal | V | K | P | H | A | K | DskA | 96-101 | AAP77833 | 13 |
| *Salmonella typhimurium* | Bacteria | Animal | V | A | P | H | D | C | Cgs | 95-100 | Q8ZKN5 | 6 |
| *Ralstonia solanacearum* | Bacteria | Plant | V | A | P | H | A | G | RSp0380 | 267-272 | Q8XST7 | 12 |

FIG. 2B

| | | | | | | | | | | | | |
|---|---|---|---|---|---|---|---|---|---|---|---|---|
| *Xanthomonas campestris* | Bacteria | Plant | V | C | P | H | A | G | XCC3153 | 49-54 | **Q8P629** | 5 |
| *Pseudomonas syringae* | Bacteria | Plant | V | K | P | H | A | C | Monooxygenase | 123-128 | **Q88B22** | 14 |
| *Pseudomonas syringae* | Bacteria | Plant | V | A | P | H | E | G | Ggt | 368-373 | **Q889G3** | 15 |
| *Pseudomonas syringae* | Bacteria | Plant | V | K | P | H | D | G | Pepsynth | 1429-1434 | **Q881Q4** | 8 |
| *Agrobacterium tumefaciens* | Bacteria | Plant | V | A | P | H | D | C | Racemase | 325-330 | **Q8UIM3** | 6 |
| **Viral pathogens** | | | | | | | | | | | | |
| Influenza A virus | Virus | Human | V | K | P | H | E | K | PA | 323-328 | **P21427** | 16 |
| Influenza A virus | Virus | Human | A | C | P | H | A | G | Hemagglutinin | 45-49 | **AAL29696** | 19 |
| Herpes Simplex Virus type 2 | Virus | Human | C | C | P | H | A | G | gJ | 83-88 | **P13293** | 4 |
| TACARIBE virus | Virus | Animal | V | C | P | H | E | K | RNA Pol | 320-325 | **P20430** | 17 |
| Bluetongue virus | Virus | Animal | V | C | P | H | A | G | VP2 | 302-307 | **Q9WHT6** | 5 |
| Chimpanzee Cytomegalovirus | Virus | Animal | C | K | P | H | A | G | TRS1 | 24-29 | **Q8QRS5** | 18 |
| LdMNPV | Virus | Insects | V | K | P | H | E | K | ORF60 | 112-117 | **Q9YMR4** | 16 |
| **Parasites** | | | | | | | | | | | | |
| *Plasmodium falciparum* | Protozoan | Human | K | C | P | H | D | C | Hypot | 749-754 | **Q8IKS0** | 20 |
| *Plasmodium ovale* | Protozoan | Human | V | K | P | H | D | K | Plasmepsin | 86-91 | **Q61163** | 21 |
| *Anopheles gambiae* | Blood-sucking insects | Human | K | K | P | H | A | G | AgCP3043 | 186-191 | **EAA08475** | 22 |
| *Anopheles gambiae* | Blood-sucking insects | Human | K | K | P | H | A | G | AgCP11774 | 288-293 | **EEA09890** | 22 |
| *Emeiria tenella* | Protozoan | animal | C | A | P | H | E | K | eimepsin | 138-143 | **Q9GN67** | 23 |

Consensus (C/V/K/A)(C/A/K)P H(A/D/E)(C/G/K)

```
                     1        10        20        30        40        50        60        70
                     |--------+---------+---------+---------+---------+---------+---------|
       DUCK_P00705   KvysRCELAaaMKrlGlDnYrGySLgNWVCaAnyESgfNTqATNrNt-dGSTDYGIlQINSrwWCDNGK
       DUCK_P00706   KvyeRCELAaaMKrlGlDnYrGySLgNWVCaAnyESsfNTqATNrNt-dGSTDYGIlEINSrwWCDNGK
    CHICKEN_P00698   KvfgRCELAaaMKrhGlDnYrGySLgNWVCaAkfESnfNTqATNrNt-dGSTDYGIlQINSrwWCNDGr
      QUAIL_P00700   KvfgRCELAaaMKrhGlDnYrGySLgNWVCaAkfESnfNsqATNrNt-dGSTDYGVlQINSrwWCNDGK
      QUAIL_P00699   KvfgRCELAaaMKrhGlDnYrGySLgNWVCaAkfESnfNsqATNrNt-dGSTDYGVlQINSrwWCNDGr
 GUINEAFOWL_P00704   KvfgRCELAaaMKrhGlDnYrGySLgNWVCaAkfESnfNsqATNrNt-dGSTDYGVlQINSrwWCNDGr
      QUAIL_P00701   KvygRCELAaaMKrhGlDkYqGySLgNWVCaAkfESnfNTqATNrNt-dGSTDYGIlQINSrwWCNDGr
   PHEASANT_P22910   KvygRCELAaaMKrlGlDnYrGySLgNWVCaAkfESnfNThATNrNt-dGSTDYGIlQINSrwWCNDGr
   PHEASANT_P24364   KvygRCELAaaMKrlGlDnYrGySLgNWVCaAkyESnfNThATNrNt-dGSTDYGIlQINSrwWCNDGK
    PEAFOWL_P19849   KvygRCELAaaMKrlGlDnYrGySLgNWVCaAkfESnfNThATNrNt-dGSTDYGIlQINSrwWCNDGr
   PHEASANT_P24533   KvygRCELAaaMKrlGlDnYrGySLgNWVCaAkfESnfNThATNrNt-dGSTDYGIlQINSrwWCNDGr
     TURKEY_P00703   KvygRCELAaaMKrlGlDnYrGySLgNWVCaAkfESnfNThATNrNt-dGSTDYGIlQINSrwWCNDGr
   PHEASANT_P81711   KvygRCELAaaMKrlGlDnFrGySLgNWVCaAkfESnfNThATNrNt-dGSTDYGIlQINSrwWCNDGr
   PHEASANT_P00702   KvygRCELAaaMKrmGlDnYrGySLgNWVCaAkfESnfNTgATNrNt-dGSTDYGIlQINSrwWCNDGr
CHACHALACA-_P00707   KiykRCELAaaMKryGlDnYrGySLgNWVCaAryESnyNTqATNrNs-nGSTDYGIlQINSrwWCNDGr
```

| | |
|---|---|
| GOAT_P37713 | KvfeRCELArtLKklGlDdYkGvSLaNWlCLtkwESgyNTkATNyNpgseSTDYGIFQINSkFWCNDGK |
| SHEEP_Q9TUN1 | KvfeRCELArtLKklGlDdYkGvSLaNWlCLskwESgyNTkATNyNpgseSTDYGIFQINSkwWCNDGK |
| GOAT_P37714 | KvfeRCELArtLKelGlDGYkGvSLaNWlCLtkwESsyNTkATNyNpgseSTDYGIFQINSkFWCNDGK |
| BOVINE_P04421 | KvfeRCELArtLKklGlDGYkGvSLaNWlCLtkwESsyNTkATNyNpsseSTDYGIFQINSkwWCNDGK |
| BOVINE_Q06283 | KvfeRCELArtLKklGlDGYkGvSLaNWlCLtkwESsyNTkATNyNpsseSTDYGIFQINSkwWCNDGK |
| BOVINE_Q06284 | KvfeRCELArtLKklGlDGYkGvSLaNWlCLtkwESsyNTkATNyNpsseSTDYGIFQINSkwWCNDGK |
| BOVINE_Q06285 | KvfeRCELArtLKklGlDGYkGvSLaNWlCLtkwESsyNTkATNyNpgseSTDYGIFQINSkwWCNDGK |
| SHEEP_P17607 | KvfeRCELArtLKelGlDGYkGvSLaNWlCLtkwESsyNTkATNyNpgseSTDYGIFQINSkwWCNDGK |
| SHEEP_Q9TUN2 | KvfeRCELArtLKelGlDGYkGvSLaNWlCLtkwESsyNTkATNyNpgseSTDYGIFQINSkwWCNDGK |
| DEER_P12066 | KvfeRCELArtLKelGlDGYkGvSLaNWlCLtkwESsyNTkATNyNpgseSTDYGIFQINSkwWCDDGK |
| BOVINE_Q27996 | KtfkRCELAktLKnlGlaGYkGvSLaNWmCLAkgESnyNTqAkNyNpgskSTDYGIFQINSkwWCNDGK |
| PIG_P12067 | KvydRCEfAriLKksGmDGYrGvSLaNWVCLAkwESdfNTkAiNrNvgs--TDYGIFQINSrYWCNDGK |
| PIG_P12068 | KvydRCEfAriLKksGmDGYrGvSLaNWVCLAkwESdfNTkAiNhNvgs--TDYGIFQINSrYWCNDGK |
| PIG_P12069 | KvydRCEfAriLKksGmDGYrGvSLaNWVCLAkwESnfNTkATNyNpgsqSTDYGIFQINSrYWCNDGK |
| RAT_P00697 | KiyeRCQfArtLKrnGmsGYyGvSLaDWVCLAqhESnyNTqArNyNpgdqSTDYGIFQINSrYWCNDGK |
| MOUSE_P08905 | KvyeRCEfArtLKrnGmaGYyGvSLaDWVCLAqhESnyNTrATNyNrgdqSTDYGIFQINSrYWCNDGK |
| MOUSE_P17897 | KvynRCELAriLKrnGmDGYrGvkLaDWVCLAqhESnyNTrATNyNrgdrSTDYGIFQINSrYWCNDGK |
| RAT_Q05820 | KvfkhCELAriLrssalaGYrGvSLeNWmCMAqhESnfDTeAiNyNstdqSTDYGIFQINSrYWCNDGK |
| DOG_P81709 | KifeRCELArtLKnlGlaGYkGvSLaNWVCLAkwESnyNTrATNyNpgskSTDYGIFQINSrYWCNDGK |
| RABBIT_P16973 | KiyeRCELArtLKklGlDGYkGvSLaNWmCLAkwESsyNTrATNyNpgdkSTDYGIFQINSrYWCNDGK |
| MONKEY_P79687 | KifeRCELArtLKrlGlDGYrGiSLaNWVCLAkwESdyNTqATNyNpgdqSTDYGIFQINShYWCNNGK |
| MONKEY_P79806 | KifeRCELArtLKrlGlDGYrGiSLaNWVCLAkwESdyNTqATNyNpgdqSTDYGIFQINShYWCNNGK |
| GRIVET_P30200 | KifeRCELArtLKrlGlDGYrGiSLaNWVCLAkwESgyNTqATNyNpgdqSTDYGIFQINShYWCNNGK |
| RHESUS_P30201 | KifeRCELArtLKrlGlDGYrGiSLaNWVCLAkwESnyNTqATNyNpgdqSTDYGIFQINShYWCNNGK |
| BABOON_P00696 | KifeRCELArtLKrlGlDGYrGiSLaNWVCLAkwESdyNTqATNyNpgdqSTDYGIFQINShYWCNNGK |
| MARMOSET_P79158 | KvfeRCELArtLKrfGlDGYrGiSLaNWmCLAkwESdyNTrATNyNpgdqSTDYGIFQINShYWCNNGr |
| TAMARIN_P79268 | KvfeRCELArtLKrlGlDGYrGiSLaNWmCLAkwESdyNTrATNyNpgdqSTDYGIFQINShYWCNNGr |
| SAIMIRI_P79294 | KvfeRCELArtLKrlGmDGYrGiSLaNWmCLAkwESdyNTrATNyNpgdqSTDYGIFQINShYWCNNGr |
| GORILLA_P79179 | KvfeRCELArtLKrlGmDGYrGiSLaNWmCLAkwESgyNTrATNyNagdrSTDYGIFQINSrYWCNDGK |
| HUMAN_P00695 | KvfeRCELArtLKrlGmDGYrGiSLaNWmCLAkwESgyNTrATNyNagdrSTDYGIFQINSrYWCNDGK |
| ORANGUTAN_P79239 | KvfeRCELArtLKrlGmDGYrGiSLaNWmCLAkwESgyNTrATNyNpgdrSTDYGIFQINSrYWCNDGK |

FIG. 3A-2

```
GIBBON_P79180       KvfeRCELArtLKrlGmDGYrGiSLaNWmCLAkwESgyNTrATNyNpgdrSTDYGIFQINSrYWCNDGK
COLOBUS_P79698      KifeRCELArtLKklGlDGYkGvSLaNWVCLAkwESgyNTdATNyNpgdeSTDYGIFQINSrYWCNNGK
MONKEY_P79811       KifeRCELArtLKklGlDGYkGvSLaNWVCLAkwESgyNTeATNyNpgdeSTDYGIFQINSrYWCNNGK
LANGUR_P07232       KifeRCELArtLKklGlDGYkGvSLaNWVCLAkwESgyNTeATNyNpgdeSTDYGIFQINSrYWCNNGK
LANGUR_P87493       KifeRCELArtLKklGlDGYkGvSLaNWVCLAkwESgyNTeATNyNpgdeSTDYGIFQINSrYWCNNGK
LANGUR_P79847       KifeRCELArtLKklGlDGYkGvSLaNWVCLAkwESgyNTeATNyNpgdeSTDYGIFQINSrYWCNNGK
SHEEP_P80190        KvfeRCELArtLKrfGmDGFrGiSLaNWmCLArwESsyNTqATNyNsgdrSTDYGIFQINShwWCNDGK
BOVINE_Q29447       KvfeRCELArsLKrfGmDnFrGiSLaNWmCLArwESnyNTqATNyNagdqSTDYGIFQINShwWCNDGK
CAMEL_P37712        KvweRCaLArkLKelGmDGYrGvSLaNWmCLtkwESdyNTdATNyNpsseSTDYGIFQINSrYWCNNGK
POSSUM_P51782       KrmeRCEfArriKqlhlDGYhqiSLaNWVCLAqwESgfDTkATNyNpgdqSTDYGIlQINShYWCDDGK
TROUT_Q9DDK3        KvydRCELAraLKasGmDGYaGnSLpNWVCLskwESsyNTqATNrNt-dGSTDYGIFQINSrYWCDDGr
FLOUNDER_Q9DD65     rvyeRCEwArlLrnqGmDGYrGiSLaNWVCLtewEShyNTrATNhNt-dGSTDYGIFQINSrwWCNDsq
FISH_Q9PU28         KvfeRCEwArlLKrnGmsnYrGiSLaDWVCLsqwESsyNTrATNrNt-dGSTDYGIFQINSrwWCDNGq
DOG_P81708          KifskCELArkLKsmGmDGFhGySLaNWVCMAeyESnfNTqAfNgrnsnGSsDYGIFQlNSkwWCksns
HORSE_P11376        KvfskCELAhkLKaqemDGFgGySLaNWVCMAeyESnfNTrAfNgknanGSsDYGlFQlNnkwWCkDnK
DONKEY_P11375       KvfskCELAhkLKaqemDGFgGySLaNWVCMAeyESnfNTrAfNgknanGSyDYGlFQlNSkwWCkDnK
ECHIDNA_P37156      KilkkqELcknLvaqGmNGYqhitLpNWVCtAfhESsyNTrATNhNt-dGSTDYGIlQINSrYWChDGK
HUMAN_Q9H1R9        KiytRCkLAkifsraGlDnYwGfSLgNWICMAyyESgyNTtAqtvld-dGSiDYGIFQINSfaWCrrGK
MOUSE_Q9CPX3        KiytRCkLAkifakaGlDnYgGfaLgNWlCMAyyEShyNTtAeNvle-dGSTDYGIFQINSftWCrNar
PIGEON_P00708       KdipRCELvkiLrrhGfEGFvGktvaNWVCLvkhESgyrTtAfN-NngpnSrDYGIFQINSkYWCNDGK
HOATZIN_Q91159             vkiLrehGfEGFeGttiaDWICLvqhESdyNTeAyN-Nngp-SrDYGIFQINSkYWCNDGK
MOUSE_Q9DA11             RCsLAkiLyeedlDGFeGySLpDWlCLAfvESnfNiskvNeNv-dGSfDYGIFQINSrYWCNDyq
ANOPHELES_Q17005    ktf-gkCELAkaLannGiak---aSLpDWVCLvqnESafsTsATNk-nknGSTDYGIFQINnkYWCDsGy
BOMBYX_P48816       ktf-tRCgLvheLrkhGfEe---nlMrNWVCLvehESsrDTskTN-tnrnGSkDYGlFQINdrYWCskGa
CECROPIA_P05105     krf-tRCgLvqeLrrlGfDe---tlMsNWVCLvenESgrfTdkigkvnknGSrDYGlFQINdkYWCskGt
SILKMOTH_Q9GNL4     krf-tRCgLvqeLrrqGfDe---slMsNWVCLvenESgrfTdkigkvnknGSrDYGlFQINdkYWCstGs
TRICHOPLUSIA_P50718 kyfatnCELvheLrrqGfpe---dkMrDWVCLiqnESgrNTskmgtinknGSrDYGlFQINdkYWCskts
HORNWORM_Q26363     khfs-RCELvheLrrqGfpe---nlMrDWVCLvenESsryTdkvgrvnknGSrDYGlFQINdkYWCsNGs
WEBWORM_P50717      kyystRCDLvreLrkqGfpe---nqMgDWVCLvenESgrkTdkvgpvnknGSkDYGlFQINdkYWCsNtr
Consensus           .k...rCela..$k..g.dgy.g.s$.#WvCla..ES..nT.atn.n...gStDYGifQINs.yWCndgk
```

FIG. 3A-3

| |
|---|
| FIG. 3B |
| FIG. 3B-2 |
| FIG. 3B-3 |

```
                    71      80        90       100       110       120      130 132
                    |--------+---------+---------+---------+---------+---------+-| SEQ ID NO:
      DUCK_P00705   TPrskNaCgIpCSvLLrsDITeAvrCAKrIVsDgdGmnAWVAWrnrCrGtDvSkwirGCrl -90
      DUCK_P00706   TPrakNaCgIpCSvLLrsDITeAvkCAKrIVsDgdGmnAWVAWrnrCkGtDvSrwirGCrl -91
   CHICKEN_P00698   TPgsrNlCnIpCSaLLssDITasvnCAKKIVsDgnGmnAWVAWrnrCkGtDvqawirGCrl -92
     QUAIL_P00700   TPgsrNlCnIpCSaLLssDITatvnCAKKIVsDgnGmnAWVAWrnrCkGtDvqawirGCrl -93
     QUAIL_P00699   TPgsrNlCnIpCSaLLssDITatvnCAKKIVsDgnGmnAWVAWrnrCkGtDvhawirGCrl -94
GUINEAFOWL_P00704   TPgsrNlCnIpCSaLqssDITatanCAKKIVsDgnGmnAWVAWrkHCkGtDvrvwikGCrl -95
     QUAIL_P00701   TPgsrNlCnIpCSaLLssDITasvnCAKKIVsDvhGmnAWVAWrnrCkGtDvnawirGCrl -96
  PHEASANT_P22910   TPgsrNlChIpCSaLLssDITasvnCAKKIVsDgnGmnAWVAWrnrCkGtDvnawtrGCrl -97
  PHEASANT_P24364   TPgsrNlChIpCSaLLssDITasvnCAKKIVsDgnGmnAWVAWrnrCkGtDvSvwtrGCrl -98
   PEAFOWL_P19849   TPgsrNlCnIpCSaLLssDITasvnCAKKIVsDrnGmnAWVAWrnrCkGtDvhawirGCrl -99
  PHEASANT_P24533   TPgsrNlChIsCSaLLssDITasvnCAKKIVsDrnGmnAWVAWrnrCkGtDvnawirGCrl -100
    TURKEY_P00703   TPgskNlCnIpCSaLLssDITasvnCAKKIasggnGmnAWVAWrnrCkGtDvhawirGCrl -101
  PHEASANT_P81711   TPgsrNlCnIpCSaLLssDtiasvnCAKKIVsDgnGmnAWVAWrkrCkGtDvnawtrGCrl -102
  PHEASANT_P00702   TPgskNlChIpCSaLLssDITasvnCAKKIVsDgnGmnAWVAWrkHCkGtDvnvwirGCrl -103
CHACHALACA-_P00707  TPgtkNlChIsCSaLMgaDIapsvrCAKrIVsDgdGmnAWVAWrkHCkGtDvStwikdCkl -104
```

| | | |
|---|---|---|
| GOAT_P37713 | TPdavDgChVsCSeLMeNDIekAvaCAKhIVsE-qGitAWVAWKsHCrdhDvSsYveGCtl | -105 |
| SHEEP_Q9TUN1 | TPnavDgChVsCSaLMeNDIekAvaCAKhIVsE-qGitAWVAWKsHCrvhDvSsYveGCkl | -106 |
| GOAT_P37714 | TPnavDgChVsCSeLMeNNIakAvaCAKqIVsE-qGitAWVAWKsHCrdhDvSsYveGCtl | -107 |
| BOVINE_P04421 | TPnavDgChVsCreLMeNDIakAvaCAKhIVsE-qGitAWVAWKsHCrdhDvSsYveGCtl | -108 |
| BOVINE_Q06283 | TPnavDgChVsCSeLMeNDIakAvaCAKhIVsE-qGitAWVAWKsHCrdhDvSsYveGCtl | -109 |
| BOVINE_Q06284 | TPnavDgChVsCSeLMeNDIakAvaCAKhIVsE-qGitAWVAWKsHCrdhDvSsYvqGCtl | -110 |
| BOVINE_Q06285 | TPnavDgChVsCSeLMeNDIakAvaCAKqIVsE-qGitAWVAWKsHCrdhDvSsYveGCtl | -111 |
| SHEEP_P17607 | TPnavDgChVsCSeLMeNNIakAvaCAKhIVsE-qGitAWVAWKsHCrdhDvSsYveGCsl | -112 |
| SHEEP_Q9TUN2 | TPnavDgChVsCSeLMeNNIakAvaCAKhIVsE-qGitAWVAWKsHCrdhDvSsYveGCsl | -113 |
| DEER_P12066 | TPnavDgChVaCSeLMeNNIdkAvtCAKqIVrE-qGitAWVAWKsHCrGhDvSsYveGCtl | -114 |
| BOVINE_Q27996 | TPkavNgCgVsCSaLLkDDITqAvaCAKKIVsQ-qGitAWVAWKnkCrnrDLtsYvkGCgv | -115 |
| PIG_P12067 | TPkavNaChIsCkvLLdDDlsqdieCAKrVVrDpqGikAWVAWrtHCqnkDvSqYirGCkl | -116 |
| PIG_P12068 | TPkavNaChIsCkvLLdDDlsqdieCAKrVVrDplGvkAWVAWraHCqnkDvSqYirGCkl | -117 |
| PIG_P12069 | TPkavNaChIsCkvLLdDDlsqdieCAKrVVrDpqGikAWVAWKaHCqnkDvSqYirGCkl | -118 |
| RAT_P00697 | TPrakNaCgIpCSaLLqDDITqAiqCAKrVVrDpqGirAWVAWqrHCknrDLSgYirnCgv | -119 |
| MOUSE_P08905 | TPravNaCgInCSaLLqDDITaAiqCAKrVVrDpqGirAWVAWraHCqnrDLSqYirnCgv | -120 |
| MOUSE_P17897 | TPrskNaCgInCSaLLqDDITaAiqCAKrVVrDpqGirAWVAWrtqCqnrDLSqYirnCgv | -121 |
| RAT_Q05820 | TPravNaCgIpCSaLLqDDITqAiqCAKrVVrDpqGirAWVAWqrHCqnrDLSgYirnCgv | -122 |
| DOG_P81709 | TPravNaChIsCSaLLqDDITqAvaCAKrVVsDpnGirAWVAWraHCenrDvSqYvrnCgv | -123 |
| RABBIT_P16973 | TPravNaChIpCSdLLkDDITqAvaCAKrVVsDpqGirAWVAWrnHCqnqDLtpYirGCgv | -124 |
| MONKEY_P79687 | TPgavNaCrIsCnaLLqDNIadAvtCAKrVVrDpqGirAWVAWrnHCqnrDvSqYvqGCgv | -125 |
| MONKEY_P79806 | TPgavNaChIsCnaLLqDNIadAvtCAKrVVrDpqGirAWVAWrnHChnrDvSqYvqGCgv | -126 |
| GRIVET_P30200 | TPgavNaChIsCnaLLqDNIadAvtCAKrVVrDpqGirAWVAWrnHCqnrDvSqYvqGCgv | -127 |
| RHESUS_P30201 | TPgavNaChIsCnaLLqDNIadAvtCAKrVVsDpqGirAWVAWrnHCqnrDvSqYvqGCgv | -128 |
| BABOON_P00696 | TPgavNaChIsCnaLLqDNIadAvtCAKrVVsDpqGirAWVAWrnHCqnrDvSqYvqGCgv | -129 |
| MARMOSET_P79158 | TPgavNaChIsCnaLLqDDITeAvaCAKrVVrDpqGirAWVAWKaHCqnrDvSqYvqGCgv | -130 |
| TAMARIN_P79268 | TPgavNaChIsCnaLLqDDITeAvaCAKrVVrDpqGirAWVAWKaHCqnrDvSqYiqGCgv | -131 |
| SAIMIRI_P79294 | TPgavNaChIsCnaLLqDDITqAvaCAKrVVrDpqGirAWVAWKaHCqnrDvSqYvqGCgv | -132 |
| GORILLA_P79179 | TPgavNaChlsCSaLLqDNIadAvaCAKrVVrDpqGirAWVAWrnrCqnrDvrqYvqGCgv | -133 |
| HUMAN_P00695 | TPgavNaChlsCSaLLqDNIadAvaCAKrVVrDpqGirAWVAWrnrCqnrDvrqYvqGCgv | -134 |
| ORANGUTAN_P79239 | TPgavNaChlsCSaLLqDNIadAvaCAKrVVrDpqGirAWVAWrnrCqnrDvrqYvqGCgv | -135 |

FIG. 3B-2

| | | |
|---|---|---|
| GIBBON_P79180 | TPgavNaChlsCnaLLqDNIadAvaCAKrVVrDpqGirAWVAWrnrCqnrDLrqYiqGCgv | -136 |
| COLOBUS_P79698 | TPgavNaChIsCnaLLqNNIadAvaCAKrVVsDpqGirAWVAWKkHCqnrDvSqYveGCgv | -137 |
| MONKEY_P79811 | TPgavDaChIsCSaLLqNNIadAvaCAKrVVsDpqGirAWVAWrnHCqnrDvSqYvkGCgv | -138 |
| LANGUR_P07232 | TPgavDaChIsCSaLLqNNIadAvaCAKrVVsDpqGirAWVAWrnHCqnkDvSqYvkGCgv | -139 |
| LANGUR_P87493 | TPgavDaChIsCSaLLqNNIadAvaCAKrVVsDpqGirAWVAWrnHCqnkDvSqYvkGCgv | -140 |
| LANGUR_P79847 | TPgavDaChIsCSaLLqNNIadAvaCAKrVVsDpqGvrAWVAWrnHCqnkDvSqYvkGCgv | -141 |
| SHEEP_P80190 | TPgavNaChIpCSaLLqDDITqAvaCAKrVVsDpqGirAWVAWrsHCqnqDLtsYiqGCgv | -142 |
| BOVINE_Q29447 | TPgavNaChlpCgaLLqDDITqAvaCtKrdVsDpqGirAWVAWrsHCqnqDLtsYiqGCgv | -143 |
| CAMEL_P37712 | TPhavNgCgInCnvLLeDDITkAvqCAKrVVrDpqGvrAWVAWKnHCeGhDveqYveGCdl | -144 |
| POSSUM_P51782 | TPhaaNeCkVrCSeLqeDDlvkAvnCAKKIV-DqqGirAWVAWrnkCeGkDLSkYleGChl | -145 |
| TROUT_Q9DDK3 | TPgakNvCgIhCSqLLtDDlTvAirCAKrVVlDpnGigAWVAWrlHCqnqDLrsYvaGCgv | -146 |
| FLOUNDER_Q9DD65 | TP-tsNaCnIrCSeLLtDDVivAikCAKrVVrDpnGigAWVAWrqHCqGqDLSsYlaGCgl | -147 |
| FISH_Q9PU28 | TP-tsNaCgIsCSaLLtDDVgaAiiCAKhVVrDpnGigAWVAWKrHCqGqDLSsYvaGCgv | -148 |
| DOG_P81708 | h-ssaNaCnImCSkfLdDNIdddiaCAKrVVkDpnGmsAWVAWvkHCkGkDLSkYlasCnl | -149 |
| HORSE_P11376 | r-sssNaCnImCSkLLdENIdddisCAKrVVrDpkGmsAWkAWvkHCkdkDLSeYlasCnl | -150 |
| DONKEY_P11375 | r-sssNaCnImCSkLLdDNIdddisCAKrVVrDpkGmsAWkAWvkHCkdkDLSeYlasCnl | -151 |
| ECHIDNA_P37156 | TPgskNaCnIsCSkLLdDDITddlkCAKKIagEakGltpWVAWKskCrGhDLSkFkc | -152 |
| HUMAN_Q9H1R9 | l-kenNhChVaCSaLitDDlTdAiiCArKIVkEtqGmnyWqgWKkHCeGrDLSewkkGCevs | -153 |
| MOUSE_Q9CPX3 | k-hqkNhChVaCSaLitDDlTdAilCAKKIVkEtqGmnyWqgWKknCenkDMSewkrGCevs | -154 |
| PIGEON_P00708 | TrgskNaCnInCSkLrdDNIaddiqCAKKIarEarGltpWVAWKkyCqGkDLSsYvrGC | -155 |
| HOATZIN_Q91159 | TsgavDgChIsCSeLMtNDleddikCAKKIarDahGltpWygWKnHCeGrDLSsYvkGC | -156 |
| MOUSE_Q9DA11 | s-hseNfChVdCqeLLspNlistihCAKKIVsgpgGmknWVeWKlHClGrpLSywmtGChlg | -157 |
| ANOPHELES_Q17005 | g-s--NdCkIaCknLLnDDITddikCAKlIhkr-hGfnAWygWKnHCnGkkLpn-vssCf | -158 |
| BOMBYX_P48816 | sPg--kdCnVkCSdLLtDDITkAakCAKKIykr-hrfdAWygWKnHCqG-sLpd-issC | -159 |
| CECROPIA_P05105 | TPg--kdCnVtCnqLLtDDIsvAatCAKKIykr-hkfdAWygWKnHCqh-gLpd-isdC | -160 |
| SILKMOTH_Q9GNL4 | TPg--kdChVtCnqLLtDDIsvAatCAKKIykr-hkfdAWygWKnHCqh-gLpd-isdC | -161 |
| TRICHOPLUSIA_P50718 | TPg--kdCnVtCaeMLlDDITkAskCAKKIykr-hkfqAWygWrnHCqG-tLpd-iskC | -162 |
| HORNWORM_Q26363 | TPg--kdCnVkCSdLLiDDITkAstCAKKIykr-hkfqAWygWrnHCqG-sLpd-issC | -163 |
| WEBWORM_P50717 | TPg--kdCnVtCadLLlDDITkAstCAKKIfkr-hnfrAWygWrnHCdGktLpd-tsnC | -164 |
| Consensus | tp...n.C.!.Cs.Ll.d#it.a..CAKk!v.d..g..aWvaWk.hC.g.dls.y..gC... | |

FIG. 3B-3

| |
|---|
| FIG. 6A |
| FIG. 6B |
| FIG. 6C |

FIG. 6

```
    Met Ser Pro Ile Leu Gly Tyr Trp Lys Ile Lys Gly Leu Val Gln Pro Thr Arg Leu Leu
  1 ATG TCC CCT ATA CTA GGT TAT TGG AAA ATT AAG GGC CTT GTG CAA CCC ACT CGA CTT CTT
    TAC AGG GGA TAT GAT CCA ATA ACC TTT TAA TTC CCG GAA CAC GTT GGG TGA GCT GAA GAA
    Leu Glu Tyr Leu Glu Glu Lys Tyr Glu Glu His Leu Tyr Glu Arg Asp Glu Gly Asp Lys
 61 TTG GAA TAT CTT GAA GAA AAA TAT GAA GAG CAT TTG TAT GAG CGC GAT GAA GGT GAT AAA
    AAC CTT ATA GAA CTT CTT TTT ATA CTT CTC GTA AAC ATA CTC GCG CTA CTT CCA CTA TTT
    Trp Arg Asn Lys Lys Phe Glu Leu Gly Leu Glu Phe Pro Asn Leu Pro Tyr Tyr Ile Asp
121 TGG CGA AAC AAA AAG TTT GAA TTG GGT TTG GAG TTT CCC AAT CTT CCT TAT TAT ATT GAT
    ACC GCT TTG TTT TTC AAA CTT AAC CCA AAC CTC AAA GGG TTA GAA GGA ATA ATA TAA CTA
    Gly Asp Val Lys Leu Thr Gln Ser Met Ala Ile Ile Arg Tyr Ile Ala Asp Lys His Asn
181 GGT GAT GTT AAA TTA ACA CAG TCT ATG GCC ATC ATA CGT TAT ATA GCT GAC AAG CAC AAC
    CCA CTA CAA TTT AAT TGT GTC AGA TAC CGG TAG TAT GCA ATA TAT CGA CTG TTC GTG TTG
    Met Leu Gly Gly Cys Pro Lys Glu Arg Ala Glu Ile Ser Met Leu Glu Gly Ala Val Leu
```

FIG. 6A

GST

241 ATG TTG GGT GGT TGT CCA AAA GAG CGT GCA GAG ATT TCA ATG CTT GAA GGA GCG GTT TTG
TAC AAC CCA CCA ACA GGT TTT CTC GCA CGT CTC TAA AGT TAC GAA CTT CCT CGC CAA AAC
Asp Ile Arg Tyr Gly Val Ser Arg Ile Ala Tyr Ser Lys Asp Phe Glu Thr Leu Lys Val
301 GAT ATT AGA TAC GGT GTT TCG AGA ATT GCA TAT AGT AAA GAC TTT GAA ACT CTC AAA GTT
CTA TAA TCT ATG CCA CAA AGC TCT TAA CGT ATA TCA TTT CTG AAA CTT TGA GAG TTT CAA
Asp Phe Leu Ser Lys Leu Pro Glu Met Leu Lys Met Phe Glu Asp Arg Leu Cys His Lys
361 GAT TTT CTT AGC AAG CTA CCT GAA ATG CTG AAA ATG TTC GAA GAT CGT TTA TGT CAT AAA
CTA AAA GAA TCG TTC GAT GGA CTT TAC GAC TTT TAC AAG CTT CTA GCA AAT ACA GTA TTT
Thr Tyr Leu Asn Gly Asp His Val Thr His Pro Asp Phe Met Leu Tyr Asp Ala Leu Asp
421 ACA TAT TTA AAT GGT GAT CAT GTA ACC CAT CCT GAC TTC ATG TTG TAT GAC GCT CTT GAT
TGT ATA AAT TTA CCA CTA GTA CAT TGG GTA GGA CTG AAG TAC AAC ATA CTG CGA GAA CTA
Val Val Leu Tyr Met Asp Pro Met Cys Leu Asp Ala Phe Pro Lys Leu Val Cys Phe Lys
481 GTT GTT TTA TAC ATG GAC CCA ATG TGC CTG GAT GCG TTC CCA AAA TTA GTT TGT TTT AAA
CAA CAA AAT ATG TAC CTG GGT TAC ACG GAC CTA CGC AAG GGT TTT AAT CAA ACA AAA TTT
Lys Arg Ile Glu Ala Ile Pro Gln Ile Asp Lys Tyr Leu Lys Ser Ser Lys Tyr Ile Ala
541 AAA CGT ATT GAA GCT ATC CCA CAA ATT GAT AAG TAC TTG AAA TCC AGC AAG TAT ATA GCA
TTT GCA TAA CTT CGA TAG GGT GTT TAA CTA TTC ATG AAC TTT AGG TCG TTC ATA TAT CGT
Trp Pro Leu Gln Gly Trp Gln Ala Thr Phe Gly Gly Gly Asp His Pro Pro Lys Ser Asp
601 TGG CCT TTG CAG GGC TGG CAA GCC ACG TTT GGT GGT GGC GAC CAT CCT CCA AAA TCG GAT
ACC GGA AAC GTC CCG ACC GTT CGG TGC AAA CCA CCA CCG CTG GTA GGA GGT TTT AGC CTA
Leu Val Pro Arg Gly Ser Cys Val Ser Cys Thr Thr Val Cys Pro His Ala Gly Lys Ala
661 CTG GTT CCG CGT GGA TCC TGT GTC TCG TGC ACA ACC GTG TGT CCG CAC GCC GGG AAG GCC

```
     GAC CAA GGC GCA CCT AGG ACA CAG AGC ACG TGT TGG CAC ACA GGC GTG CGG CCC TTC CGG
     Lys Ala Glu Lys Val Glu Cys Ala Leu Lys Gly Gly Ile Phe Arg Gly Thr Leu Pro Ala
 721 AAA GCG GAA AAG GTA GAG TGC GCG TTG AAG GGA GGT ATC TTT CGG GGT ACG CTA CCT GCG
     TTT CGC CTT TTC CAT CTC ACG CGC AAC TTC CCT CCA TAG AAA GCC CCA TGC GAT GGA CGC
     Ala Asp Cys Pro Gly Ile Asp Thr Thr Val Thr Phe Asn Ala Asp Gly Thr Ala Gln Lys
 781 GCC GAT TGC CCG GGA ATC GAT ACG ACT GTG ACG TTC AAC GCG GAT GGC ACT GCG CAA AAG
     CGG CTA ACG GGC CCT TAG CTA TGC TGA CAC TGC AAG TTG CGC CTA CCG TGA CGC GTT TTC
     Val Glu Leu Ala Leu Glu Lys Lys Ser Ala Pro Ser Pro Leu Thr Tyr Arg Gly Thr Trp
 841 GTA GAG CTT GCC CTT GAG AAG AAG TCG GCA CCT TCT CCT CTT ACC TAT CGC GGT ACG TGG
     CAT CTC GAA CGG GAA CTC TTC TTC AGC CGT GGA AGA GGA GAA TGG ATA GCG CCA TGC ACC
     Met Val Arg Glu Asp Gly Ile Val Glu Leu Ser Leu Val Ser Ser Glu Gln Ser Lys Ala
 901 ATG GTA CGT GAA GAC GGA ATT GTC GAA CTC TCG CTT GTG TCC TCG GAG CAA TCG AAG GCA
     TAC CAT GCA CTT CTG CCT TAA CAG CTT GAG AGC GAA CAC AGG AGC CTC GTT AGC TTC CGT
     Pro His Glu Lys Glu Leu Tyr Glu Leu Ile Asp Ser Asn Ser Val Arg Tyr Met Gly Ala
 961 CCG CAC GAG AAA GAG CTG TAC GAG CTG ATA GAC AGT AAC TCC GTT CGC TAC ATG GGC GCT
     GGC GTG CTC TTT CTC GAC ATG CTC GAC TAT CTG TCA TTG AGG CAA GCG ATG TAC CCG CGA
     Pro Gly Ala Gly Lys Pro Ser Lys Glu Met Ala Pro Phe Tyr Val Leu Lys Lys Thr Lys
1021 CCC GGC GCA GGA AAG CCT TCA AAG GAG ATG GCG CCG TTT TAC GTG CTC AAA AAA ACA AAG
     GGG CCG CGT CCT TTC GGA AGT TTC CTC TAC CGC GGC AAA ATG CAC GAG TTT TTT TGT TTC
     Lys ***    (SEQ ID NO: 29)
1081 AAA TAG C  (SEQ ID NO: 30)
     TTT ATC G  (SEQ ID NO: 165)
```

FIG. 6C

<u>M</u>VSCTTVCPHAGKAKAEKVECALKGGIFRG
TLPAADCPGIDTTVTFNADGTAQKVELALEK
KSAPSPLTYRGTWMVREDGIVELSLVSSEQS
KAPHEKELYELIDSNSVRYMGAPGAGKPSKE
MAPFYVLKKTKK<u>LEHHHHHH</u> (SEQ ID NO: 166)

```
             1        10        20        30        40        50        60
             |--------+---------+---------+---------+---------+---------|
IVY_ECOLI    MGRISSGGMMFKAITTVAALVIATSAMAQDDLTISSLAKGETTKAAFNQMVQGHKLPAWV
TP17_TREPA   M---KGSVRALCAFLGVGALGSALCVSCTTVCPHAGKAKAEKVECALKGGIFRGTLPAAD
Consensus    M...kgggralcAilgVaALgiAlcamaqddcphaglAKaEkteaAlnqg!qrgkLPAad

             61       70        80        90        100       110       120
             |--------+---------+---------+---------+---------+---------|
IVY_ECOLI    MKGGTYTPAQTVTLGDETYQVMSACKPHDCG-SQRIAVMWSEKSNQMTGLFSTIDEKTSQ
TP17_TREPA   CPGIDTTVTFNADGTAQKVELALEKKSAPSPLTYRGTWMVREDGIVELSLVSSEQSKAPH
Consensus    ckGgdtTpaqnadgga#ky#lalacKpadcg.sqRgawMwrEdgnqelgLfSse#eKapq

             121     130       140       150       159
             |--------+---------+---------+--------|
IVY_ECOLI    EK-LTWLNVNDALSIDGKTVLFAALTGSLENHPDGFNFK (SEQ ID NO: 167)
TP17_TREPA   EKELYELIDSNSVRYMGAPGAGKPSKEMAPFYVLKKTKK (SEQ ID NO: 168)
Consensus    EK.LteLndn#alridGapgagaalkemaenhpdgknkK (SEQ ID NO: 169)
```

FIG. 11A

| Serum ID | Reagent (R) | R+ChickenLyz | R+HumanLyz |
|---|---|---|---|
| HPM10 | 80 | 80 | 160 |
| HG38 | 80 | 80 | 320 or more |
| HG48 | 80 | Negative | 320 |
| HG82 | 80 | 80 | 640 |

| Serum ID | Reagent R | R+LyzN | R+LyzR |
|---|---|---|---|
| Syph71 | 80 | 320 | 320 |
| 09-4 | 160 | 640 | 320 |
| 09-3 | <80 | 320 | 160 |
| HSP91 | 80 | 640 | 320 |
| HSP17 | 160 | 640 | 640 |
| HSP3 | 160 | 640 | 320 |
| 4932 | 320 | 640 | 640 |
| 5895 | 160 | 640 | 640 |
| HG62 | 640 | 640 | 640 |
| HG82 | <80 | 640 | 640 |

FIG. 17A

Control sera

| | Conventional ELISA plate | ELISA plate + Human Lysozyme |
|---|---|---|
| Negative control | 79 | 121 |
| | | |
| Positive control | 2009 | 2177 |

Syphilis Negative sera

| Serum code | conventional ELISA plate | ELISA plate + human lysozyme |
|---|---|---|
| BB 01 | 70 | 81 |
| BB 02 | 51 | 60 |
| BB 03 | 80 | 133 |
| BB 04 | 86 | 66 |

Syphilis Positive sera

| Serum code | conventional ELISA plate | ELISA plate + human lysozyme |
|---|---|---|
| BQ 110 | 1113 | 1319 |
| BQ 62 | 1381 | 1684 |
| SC 57 1/10 | 737 | 1000 |
| SC 77 | 1453 | 1801 |

FIG. 21A

Second generation syphilis ELISA

| | Sample dil. buffer | Sample dil. buffer + HuLys | Sample dil. buffer + HuLys |
|---|---|---|---|
| | Conjugate dil. buffer | Conjugate dil. buffer | Conjugate dil. buffer + HuLys |
| | | | |
| Serum code | Absorbance at 450 nm | Absorbance at 450 nm | Absorbance at 450 nm |
| | | | |
| Negative control | 11 | 11 | 15 |
| | | | |
| Positive control | 1377 | 1271 | 1705 |
| | | | |
| Syph. negative sera | | | |
| BB01 | 5 | 1 | 7 |
| BB02 | 3 | 0 | 7 |
| BB03 | 5 | 2 | 57 |
| BB04 | 7 | 4 | 7 |
| Syph. positive sera | | | |
| BQ 110 | 544 | 450 | 1171 |
| BQ 62 | 1408 | 1407 | 2643 |
| SC57 1/10 | 685 | 646 | 1415 |
| SC77 | 1955 | 1838 | 2070 |

FIG. 21B

Third generation syphilis ELISA

|  |  |  |  |  |  | SEQ ID NO: |
|---|---|---|---|---|---|---|
| Ec_Ivy | P45502 | VM--SACKPH | ------ | ------ | DGGSQRIA--VM--WS | 195 |
| Pa_Ivy | Q9HXB1 | VLANS-CKPH | ------ | ------ | DCGNNRLL--VA--FR | 196 |
| Yp_Ivy | P58483 | VG---SLCKPH | ------ | ------ | DCSNN--FMWVA--FS | 197 |
| Tp17 | P29722 | VSCTTVCEPHAGKAKA | EKVECAL | ------ | -KGG--I---FR | 198 |
| APP770 | AAB59502 | VTIQNWCK---- | RGR--K | QC- | KTHPHFVIPYR | 199 |
| APP751 | NP_958816 | VTIQNWCK---- | RGR--K | QC- | KTHPHFVIPYR | 200 |
| APP695 | NP_958817 | VTIQNWCK---- | RGR--K | QC- | KTHPHFVIPYR | 201 |

CX(1,5)[KRH][AG][KRH]X(0,2)[KR]X(0,1)[EDQN]C

PROSITE Consensus sequence

| Swis-Prot /TrEMBL Accesion number | DESCRIPTION | HOST | PEPTIDE SEQUENCE | | | | | | | | | | | | | | | LOCATION | SEQ ID NO: |
|---|---|---|---|---|---|---|---|---|---|---|---|---|---|---|---|---|---|---|---|
| P11215 | ITAM_HUMAN | Human | C | p | l | p | . | . | R | G | R | a | . | R | w | Q | C | 478 to 489 | 202 |
| O93279 | Amyloid beta A4 protein | Fugu rubripes | C | k | . | . | . | . | K | G | R | . | . | K | . | Q | C | 99 to 106 | 203 |
| P05067 | Amyloid beta A4 protein | Homo Sapiens | C | k | . | . | . | . | R | G | R | . | . | K | . | Q | C | 98 to 105 | 204 |
| P53601 | Amyloid beta A4 protein | Macaca fascicularis | C | k | . | . | . | . | R | G | R | . | . | K | . | Q | C | 98 to 105 | 205 |
| P12023 | Amyloid beta A4 protein | Mus musculus | C | k | . | . | . | . | R | G | R | . | . | K | . | Q | C | 98 to 105 | 206 |
| P08592 | Amyloid beta A4 protein | Rattus norvegicus | C | k | . | . | . | . | R | G | R | . | . | K | . | Q | C | 98 to 105 | 207 |
| O73683 | Amyloid beta A4 protein | Tetraodon fluviatilis | C | k | . | . | . | . | K | G | R | . | . | K | . | Q | C | 99 to 106 | 208 |
| P03543 | Coat protein | Cauliflower mosaic virus | C | p | . | . | . | . | K | G | K | . | . | K | . | D | C | 403 to 410 | 209 |
| Q8NG35 | Beta-defensin 105 precursor | Homo Sapiens | C | k | l | g | . | . | R | G | K | c | r | K | . | E | C | 46 to 57 | 210 |
| Q8Y0V3 | Probable GTPase engC | Ralstonia solanacearum | C | f | p | . | . | . | R | G | K | . | . | R | s | E | C | 44 to 53 | 211 |
| P03341 | Gag polyprotein | Baboon endogenous virus | C | a | y | c | k | e | R | G | H | w | i | K | . | D | C | 503 to 516 | 212 |
| P33458 | Gag polyprotein | Caprine arthritis encephalitis virus | C | h | n | c | g | k | R | G | H | m | q | K | . | E | C | 400 to 413 | 213 |
| P10262 | Gag polyprotein | Feline leukemia virus | C | a | y | c | k | e | K | G | H | w | v | R | . | D | C | 549 to 562 | 214 |
| P21416 | Gag polyprotein | Gibbon ape leukemia virus | C | a | y | c | k | e | K | G | H | w | a | R | . | E | C | 491 to 504 | 215 |
| P07567 | Gag polyprotein | Simian Mason-Pfizer virus | C | f | k | c | g | k | K | G | H | f | a | K | . | N | C | 549 to 562 | 216 |

FIG. 34A-1

| | | | | | | | | | | | | | | | | | | | |
|---|---|---|---|---|---|---|---|---|---|---|---|---|---|---|---|---|---|---|---|
| P16900 | Gag polyprotein | Ovine lentivirus | C | h | h | c | g | k | R | G | H | m | q | K | . | D | C | 405 to 418 | 217 |
| P03352 | Gag polyprotein | Visna lentivirus | C | h | h | c | g | k | R | G | H | m | q | K | . | D | C | 406 to 419 | 218 |
| Q9KLP4 | Glucose-1-pfosphate adenylytranferasa 2 | Vibrio cholerae | C | s | g | . | . | . | K | G | R | v | a | R | . | D | C | 243 to 253 | 219 |
| Q87HX3 | Glucose-1-pfosphate adenylytranferasa 3 | Vibrio parahaemolyticus | C | g | s | . | . | . | K | G | R | v | d | K | . | D | C | 243 to 253 | 220 |
| Q8D7E0 | Glucose-1-pfosphate adenylytranferasa 4 | Vibrio vulnificus | C | g | s | . | . | . | K | G | R | v | d | K | . | D | C | 243 to 253 | 221 |
| Q9H9B1 | Histone-lysine N-methyltranferase | Homo Sapiens | C | e | d | h | . | . | R | G | R | m | v | K | h | Q | C | 544 to 556 | 222 |
| Q9NUK0 | Muslebind-like X-linked protein | Homo Sapiens | C | f | d | s | l | . | K | G | R | c | t | R | e | N | C | 54 to 67 | 223 |
| P27285 | Structural polyprotein (P130) | Sindbis virus | C | a | c | . | . | . | K | A | R | . | . | R | . | E | C | 716 to 724 | 224 |
| Q13591 | Semaphorin 5A precursor | Homo sapiens | C | y | s | . | . | . | K | G | K | s | . | K | e | E | C | 104 to 114 | 225 |
| Q9H2E6 | Semaphorin 6A precursor | Homo Sapiens | C | r | m | . | . | . | K | G | K | h | . | K | d | E | C | 107 to 117 | 226 |
| O35464 | Semaphorin 6A precursor | Mus musculus | C | r | m | . | . | . | K | G | K | h | . | K | d | E | C | 107 to 117 | 227 |
| P29722 | Lipoprotein precursor | Treponema pallidum | C | p | h | a | g | . | K | A | K | a | e | K | v | E | C | 29 to 42 | 228 |
| Q9UKW4 | Vav-3 protein | Homo Sapiens | C | f | k | c | g | a | R | A | H | . | . | K | . | E | C | 544 to 555 | 229 |
| Q8IUB2 | WAP four-disulfure core domain protein | Homo Sapiens | C | r | d | i | p | . | K | G | R | k | . | R | . | D | C | 65 to 76 | 230 |
| P43446 | Wnt-10a protein precursor | Brachydanio rerio | C | q | h | q | f | . | R | G | H | . | . | R | w | N | C | 133 to 144 | 231 |
| P56704 | Wnt-3a protein precursor | Homo Sapiens | C | q | h | q | f | . | R | G | R | . | . | R | w | N | C | 77 to 88 | 232 |
| P27467 | Wnt-3a protein precursor | Mus musculus | C | q | h | q | f | . | R | G | R | . | . | R | w | N | C | 77 to 88 | 233 |

FIG. 34A-2

| | | | | | | | | | | | | | | | | | | | |
|---|---|---|---|---|---|---|---|---|---|---|---|---|---|---|---|---|---|---|---|
| P56703 | Wnt-3 proto-oncogene protein precursor | Homo Sapiens | C | q | h | q | f | . | R | G | R | . | . | R | w | N | C | 80 to 91 | 234 |
| O38533 | Gag protein | HIV-1 | C | w | k | c | g | k | K | G | H | q | m | K | . | D | C | 11 to 24 | 235 |
| O57394 | EL amyloid protein 699 | Narke japonica | C | k | . | . | . | . | K | G | R | . | . | K | . | Q | C | 110 to 117 | 236 |
| O83919 | Pheromone shutdown protein | Treponema pallidum | C | v | r | r | t | i | R | A | R | . | . | R | p | Q | C | 34 to 46 | 237 |
| O95205 | Zinc finger protein | Homo Sapiens | C | f | d | s | l | . | K | G | R | c | s | R | e | N | C | 53 to 66 | 238 |
| Q6PKH4 | PS1D protein (fragment) | Homo Sapiens | C | k | k | c | g | c | K | G | H | f | a | k | . | D | C | 133 to 146 | 239 |
| Q6QK90 | Gag protein (fragment) | HIV-1 | C | w | k | c | g | k | X | G | H | q | m | K | . | D | C | 37 to 50 | 240 |
| Q6RH28 | Beta amyloid protein isoform APP751 | Canis familiaris | C | k | . | . | . | . | K | G | R | . | . | K | . | Q | C | 98 to 105 | 241 |
| Q6SP03 | Gag protein (fragment) | Small ruminant lentivirus | C | h | h | c | g | k | R | G | H | m | q | K | . | D | C | 198 to 211 | 242 |
| Q6T3V4 | Gag protein | Porcine endogenous retrovirus | C | a | y | c | k | e | K | G | H | w | a | R | . | D | C | 493 to 506 | 243 |
| Q6TE65 | Gag protein | HIV-1 | C | w | k | c | x | k | X | G | H | q | m | K | . | D | C | 416 to 429 | 244 |
| Q6TIU6 | Gag protein (fragment) | HIV-1 | C | g | r | e | . | . | R | G | H | l | a | R | . | N | C | 102 to 113 | 245 |

FIG. 34A-3

| |
|---|
| FIG. 34B-1 |
| FIG. 34B-2 |
| FIG. 34B-3 |

FIG. 34B

| Accession number | Description | Host | SEQUENCE | | | | | | | | | | | | | | | Location | SEQ ID NO: |
|---|---|---|---|---|---|---|---|---|---|---|---|---|---|---|---|---|---|---|---|
| Q708Y9 | Amyloid beta-like protein B precursor | Xenopus laevis | C | k | . | . | . | . | R | G | K | . | . | K | . | Q | C | 105 to 112 | 246 |
| Q708YZ0 | Amyloid beta-like protein A precursor | Xenopus laevis | C | k | . | . | . | . | K | G | K | . | . | K | . | Q | C | 105 to 112 | 247 |
| Q72ML6 | Exonuclease | Leptospira interrogans | C | d | w | y | e | . | K | G | K | . | . | K | m | E | C | 375 to 386 | 248 |
| Q76069 | P24/p25/p7 (Fragment) | HIV-1 | C | w | k | y | g | k | X | G | H | q | m | k | . | D | C | 56 to 69 | 249 |
| Q7MEE9 | ADP-glucose pyrophosphorylase | Vibrio vulnificus | C | g | s | . | . | . | K | G | R | v | d | k | . | D | C | 243 to 253 | 250 |
| Q7PCN0 | AgCP2651 | Anopheles gambiae str.PEST | C | h | n | c | l | r | K | G | H | l | a | R | . | N | C | 205 to 218 | 251 |
| Q7PCN8 | AgCP10176 | Anopheles gambiae str.PEST | C | h | n | c | g | k | K | G | H | m | k | K | . | D | C | 221 to 234 | 252 |
| Q7PD62 | AgCP11877 | Anopheles gambiae str.PEST | C | h | n | c | l | r | K | G | H | l | a | r | . | N | C | 245 to 258 | 253 |
| Q7RI00 | Putative zinc finger in N-recognin | Plasmodium yoelii yoelii | C | e | y | e | . | . | K | A | K | e | . | K | . | N | C | 2024 to 2034 | 254 |
| Q7RI20 | Homo sapiens KIAA1035 protein-related | Plasmodium yoelii yoelii | C | d | f | . | . | . | H | G | H | s | s | K | y | N | C | 945 to 956 | 255 |
| Q7RJH0 | Development protein DG1124 | Plasmodium yoelii yoelii | C | h | m | c | g | k | K | G | H | s | i | K | . | N | C | 314 to 327 | 256 |
| Q7RM64 | Protein phosphatase 2C | Plasmodium yoelii yoelii | C | k | . | . | . | . | K | G | R | . | . | K | l | D | C | 379 to 387 | 257 |
| Q7RMK0 | Hypothetical protein | Plasmodium yoelii yoelii | C | s | y | i | d | . | H | G | K | s | g | K | n | N | C | 1553 to 1566 | 258 |
| Q7RQW4 | Capn7-related | Plasmodium yoelii yoelii | C | v | k | e | n | . | K | A | K | . | . | K | . | N | C | 620 to 630 | 259 |
| Q7VF47 | Hypothetical protein | Helicobacter hepaticus | C | q | . | . | . | . | K | G | K | l | . | K | . | Q | C | 290 to 298 | 260 |
| Q7YUJ3 | Hypothetical protein | Trypanosoma brucei | C | t | t | h | n | f | R | G | R | . | . | K | . | E | C | 233 to 244 | 261 |
| Q7ZJH5 | Gag protein | HIV-1 | C | f | n | c | g | k | R | X | H | i | a | R | . | N | C | 397 to 410 | 262 |

FIG. 34B-1

| | | | | | | | | | | | | | | | | | | | |
|---|---|---|---|---|---|---|---|---|---|---|---|---|---|---|---|---|---|---|---|
| Q80S43 | Structural polyprotein | Kyzylagach virus | C | t | c | . | . | . | K | A | R | . | . | R | . | E | C | 716 to 724 | 263 |
| Q80S45 | Structural polyprotein | Babanki virus | C | a | c | . | . | . | K | A | R | . | . | R | . | E | C | 716 to 724 | 264 |
| Q80S47 | Structural polyprotein | Highlands J virus | C | i | s | . | . | . | K | A | R | . | . | R | . | D | C | 707 to 715 | 265 |
| Q80S49 | Structural polyprotein | Fort Morgan virus | C | l | c | . | . | . | R | A | R | . | . | R | . | D | C | 709 to 717 | 266 |
| Q80S51 | Structural polyprotein | Buggy Creek virus | C | l | c | . | . | . | R | A | R | . | . | R | . | D | C | 709 to 717 | 267 |
| Q86UV8 | Muscleblind-like protein EXP41s | Human | C | f | d | s | l | . | K | G | R | c | s | R | e | N | C | 53 to 66 | 268 |
| Q86UV9 | Muscleblind-like protein EXP40s | Human | C | f | d | s | l | . | K | G | R | c | s | R | e | N | C | 53 to 66 | 269 |
| Q86VU5 | Catechol-O-methyltransferase | Human | C | p | p | w | . | . | R | G | R | . | . | R | e | Q | C | 35 to 45 | 270 |
| Q86W82 | LOC285498 protein | Human | C | d | a | c | l | g | K | G | K | . | . | K | n | E | C | 62 to 74 | 271 |
| Q86WY7 | Williams Beuren syndrome | Human | C | r | y | m | n | p | R | A | R | . | . | K | . | N | C | 65 to 76 | 272 |
| Q86X08 | Eu-HMTase1 protein | Human | C | e | d | h | . | . | R | G | R | m | v | K | h | Q | C | 575 to 587 | 273 |
| Q87100 | Envelope protein | SIV | C | r | d | s | d | y | R | G | H | . | . | K | . | N | C | 17 to 28 | 274 |
| Q87PT6 | Hypothetical protein VP1415 | Vibrio parahaemolyticus | C | n | k | k | i | g | K | G | K | . | . | K | . | E | C | 503 to 514 | 275 |
| Q8AD21 | Gag protein | HIV-1 | C | f | n | c | g | k | K | G | H | l | a | R | . | N | C | 127 to 140 | 276 |
| Q8AD40 | Gag protein | HIV-1 | C | f | n | y | g | k | K | G | H | l | a | R | . | N | C | 346 to 359 | 277 |
| Q8EZ82 | Hypothetical protein | Leptospira interrogans | C | d | w | y | e | . | K | G | K | . | . | K | m | E | C | 252 to 263 | 278 |
| Q8YBE0 | Protease | Brucella melitensis | C | a | h | a | r | s | K | G | H | i | . | K | d | N | C | 179 to 192 | 279 |
| Q908M0 | Gag polyprotein | HIV-1 | C | w | k | c | g | r | K | G | H | q | m | K | . | D | C | 408 to 421 | 280 |

FIG. 34B-2

| | | | | | | | | | | | | | | | | | | | |
|---|---|---|---|---|---|---|---|---|---|---|---|---|---|---|---|---|---|---|---|
| Q90MF6 | Gag protein | HIV-1 | C | f | n | c | g | r | K | G | H | i | a | R | . | N | C | 387 to 400 | 281 |
| Q90QF8 | Gag protein | HIV-1 | C | w | k | c | g | k | X | G | H | q | m | K | . | D | C | 4 to 17 | 282 |
| Q90RE5 | Envelope glycoprotein | HIV-1 | C | i | p | p | d | q | K | G | K | m | . | K | . | N | C | 162 to 174 | 283 |
| Q90UI6 | Env | SIV | C | r | d | f | d | y | R | G | H | . | . | K | . | D | C | 3 to 14 | 284 |
| Q95X00 | Poly-zinc finger protein 2 | Trypanosoma cruzi | C | y | v | c | g | e | K | G | H | l | a | R | . | D | C | 171 to 184 | 285 |
| Q96RE3 | 36 kDa muscleblind protein | Human | C | f | d | s | l | . | K | G | R | c | s | R | e | N | C | 53 to 66 | 286 |
| Q97583 | P24/NCp7 | HIV-1 | C | f | n | c | g | k | X | G | H | l | a | R | . | N | C | 41 to 54 | 287 |
| Q9J120 | Gag protein | HIV-1 | C | f | n | x | g | k | X | G | H | i | a | R | . | N | C | 40 to 53 | 288 |
| Q9J126 | Gag protein | HIV-1 | C | f | n | c | g | k | X | G | H | i | a | R | . | N | C | 38 to 51 | 289 |
| Q9J128 | Gag protein | HIV-1 | C | f | n | c | g | x | X | G | H | i | a | K | . | N | C | 38 to 51 | 290 |
| Q9J185 | Gag protein | HIV-1 | C | f | n | c | g | k | X | G | H | i | a | K | . | N | C | 37 to 50 | 291 |
| Q9J193 | Gag protein | HIV-1 | C | f | n | c | g | k | X | G | H | i | a | R | . | N | C | 14 to 27 | 292 |
| Q9J197 | Gag protein | HIV-1 | C | f | n | c | g | k | X | G | H | i | a | R | . | N | C | 37 to 50 | 293 |
| Q9U5J7 | Hypothetical protein | Trypanosoma brucei | C | t | t | h | n | f | R | G | R | . | . | K | . | E | C | 134 to 145 | 294 |

FIG. 34B-3

| GST-Tp17 | Lysozyme inhibition (%) huLYS | chkLYS |
|---|---|---|
| Wild-type | 100 | 100 |
| CPA mutant | 49 ± 4 | 42 ± 2 |
| KPA mutant | 51 ± 4 | 58 ± 6 |

```
        1         10        20        30        40        50        60
        |---------+---------+---------+---------+---------+---------|
huLYS   MKALIVLGLVLLSVTVQGKVFERCELARTLKRLGMDGYRGISLANWMCLAKWESGYNTRA
chkLYS  MRSLLILVLCFLPLAALGKVFGRCELAAAMKRHGLDNYRGYSLGNWVCAAKFESNFNTQA
        61        70        80        90        100       110       120
        |---------+---------+---------+---------+---------+---------|
huLYS   TNYNAGDRSTDYGIFQINSRYWCNDGKTPGAVNACHLSCSALLQDNIADAVACAKRVVRD
chkLYS  TNRNT-DGSTDYGILQINSRWWCNDGRTPGSRNLCNIPCSALLSSDITASVNCAKKIVSD
        121       130       140     148
        |---------+---------+-------|
huLYS   PQGIRAWVAWRNRCQNRDVRQYVQGCGV (SEQ ID NO: 295)
chkLYS  GNGMNAWVAWRNRCKGTDVQAWIRGCRL (SEQ ID NO: 296)
```

Idendity: 63%

```
        1         10        20        30        40        50        60
        |---------+---------+---------+---------+---------+---------|
SLLP1   MVSALRGAPLIRVHSSPVSSPSVSGPRRLVSCLSSQSSALSQSGGGSTSAAGIEARSRAL
huLYS
        61        70        80        90        100       110       120
        |---------+---------+---------+---------+---------+---------|
SLLP1   RRRWCPAGIMLLALVCLLSCLLPSSEAKLYGRCELARVLHDFGLDGYRGYSLADWVCLAY
huLYS            MKALIVLGLVLLSVTVQGKVFERCELARTLKRLGMDGYRGISLANWMCLAK
        121       130       140       150       160       170       180
        |---------+---------+---------+---------+---------+---------|
SLLP1   FTSGFNAAALDYEA-DGSTNNGIFQINSRRWCSN-LTPNVPNVCRMYCSDLLNPNLKDTV
huLYS   WESGYNTRATNYNAGDRSTDYGIFQINSRYWCNDGKTPGAVNACHLSCSALLQDNIADAV
        181       190       200       210      217
        |---------+---------+---------+------|
SLLP1   ICAMKITQEPQGLGYWEAWRHHCQGKDLTEWVDGCDF (SEQ ID NO: 297)
huLYS   ACAKRVVRDPQGIRAWVAWRNRCQNRDVRQYVQGCGV (SEQ ID NO: 295)
```

Idendity:58%

FIG. 37

SEQUENCE LISTING

```
<160> NUMBER OF SEQ ID NOS: 301

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Variable amino acid; see specification as filed
      for detailed description of substitutions and preferred
      embodiments
<220> FEATURE:
<221> NAME/KEY: MOD_RES
<222> LOCATION: (4)..(4)
<223> OTHER INFORMATION: Variable amino acid; see specification as filed
      for detailed description of substitutions and preferred
      embodiments

<400> SEQUENCE: 1

Xaa Pro His Xaa
1


<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: any amino acid or is absent; region may
      encompass 0-3 residues
<220> FEATURE:
<221> NAME/KEY: MOD_RES
<222> LOCATION: (7)..(16)
<223> OTHER INFORMATION: any amino acid or is absent; region may
      encompass 0-10 residues

<400> SEQUENCE: 2

Cys Xaa Xaa Xaa Pro His Xaa Xaa Xaa Xaa Xaa Xaa Xaa Xaa Xaa Xaa
1               5                   10                  15

Cys


<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys, Lys, Val, Ala, or absent
<220> FEATURE:
<221> NAME/KEY: MOD_RES
<222> LOCATION: (2)..(2)
<223> OTHER INFORMATION: Ala, Cys, or Lys
<220> FEATURE:
<221> NAME/KEY: MOD_RES
<222> LOCATION: (5)..(5)
<223> OTHER INFORMATION: Ala, Asp, or Glu
<220> FEATURE:
<221> NAME/KEY: MOD_RES
<222> LOCATION: (6)..(6)
```

-continued

<223> OTHER INFORMATION: Cys, Gly, or Lys

<400> SEQUENCE: 3

Xaa Xaa Pro His Xaa Xaa
1 5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 4

Cys Cys Pro His Ala Gly
1 5

<210> SEQ ID NO 5
<211> LENGTH: 6
<212> TYPE: PRT
<213> ORGANISM: Unknown
<220> FEATURE:
<223> OTHER INFORMATION: Description of unknown species: Yersinia pestis or Bluetongue virus

<400> SEQUENCE: 5

Val Cys Pro His Ala Gly
1 5

<210> SEQ ID NO 6
<211> LENGTH: 6
<212> TYPE: PRT
<213> ORGANISM: Unknown
<220> FEATURE:
<223> OTHER INFORMATION: Description of unknown species: Shigella flexneri, Vibrio cholerae, Vibrio parahemolyticus, Salmonella typhimurium, or Agrobacterium tumefaciens

<400> SEQUENCE: 6

Val Ala Pro His Asp Cys
1 5

<210> SEQ ID NO 7
<211> LENGTH: 6
<212> TYPE: PRT
<213> ORGANISM: Staphylococcus aureus

<400> SEQUENCE: 7

Lys Ala Pro His Asp Lys
1 5

<210> SEQ ID NO 8
<211> LENGTH: 6
<212> TYPE: PRT
<213> ORGANISM: Pseudomonas syringae

<400> SEQUENCE: 8

Val Lys Pro His Asp Gly
1 5

<210> SEQ ID NO 9
<211> LENGTH: 6
<212> TYPE: PRT
<213> ORGANISM: Chlamydia pneumoniae

<400> SEQUENCE: 9

-continued

Lys Lys Pro His Ala Lys
1 5

<210> SEQ ID NO 10
<211> LENGTH: 6
<212> TYPE: PRT
<213> ORGANISM: Treponema pallidum

<400> SEQUENCE: 10

Lys Ala Pro His Glu Lys
1 5

<210> SEQ ID NO 11
<211> LENGTH: 6
<212> TYPE: PRT
<213> ORGANISM: Staphylococcus sp.

<400> SEQUENCE: 11

Lys Lys Pro His Ala Cys
1 5

<210> SEQ ID NO 12
<211> LENGTH: 6
<212> TYPE: PRT
<213> ORGANISM: Bordetella sp.

<400> SEQUENCE: 12

Val Ala Pro His Ala Gly
1 5

<210> SEQ ID NO 13
<211> LENGTH: 6
<212> TYPE: PRT
<213> ORGANISM: Helicobacter hepaticus

<400> SEQUENCE: 13

Val Lys Pro His Ala Lys
1 5

<210> SEQ ID NO 14
<211> LENGTH: 6
<212> TYPE: PRT
<213> ORGANISM: Pseudomonas syringae

<400> SEQUENCE: 14

Val Lys Pro His Ala Cys
1 5

<210> SEQ ID NO 15
<211> LENGTH: 6
<212> TYPE: PRT
<213> ORGANISM: Pseudomonas syringae

<400> SEQUENCE: 15

Val Ala Pro His Glu Gly
1 5

<210> SEQ ID NO 16
<211> LENGTH: 6
<212> TYPE: PRT
<213> ORGANISM: Unknown
<220> FEATURE:
<223> OTHER INFORMATION: Description of unknown species: Influenza A
virus or LdMNPV -continued

<400> SEQUENCE: 16

Val Lys Pro His Glu Lys
1 5

<210> SEQ ID NO 17
<211> LENGTH: 6
<212> TYPE: PRT
<213> ORGANISM: Tacaribe virus

<400> SEQUENCE: 17

Val Cys Pro His Glu Lys
1 5

<210> SEQ ID NO 18
<211> LENGTH: 6
<212> TYPE: PRT
<213> ORGANISM: Chimpanzee cytomegalovirus

<400> SEQUENCE: 18

Cys Lys Pro His Ala Gly
1 5

<210> SEQ ID NO 19
<211> LENGTH: 6
<212> TYPE: PRT
<213> ORGANISM: Influenza A virus

<400> SEQUENCE: 19

Ala Cys Pro His Ala Gly
1 5

<210> SEQ ID NO 20
<211> LENGTH: 6
<212> TYPE: PRT
<213> ORGANISM: Plasmodium falciparum

<400> SEQUENCE: 20

Lys Cys Pro His Asp Cys
1 5

<210> SEQ ID NO 21
<211> LENGTH: 6
<212> TYPE: PRT
<213> ORGANISM: Plasmodium ovale

<400> SEQUENCE: 21

Val Lys Pro His Asp Lys
1 5

<210> SEQ ID NO 22
<211> LENGTH: 6
<212> TYPE: PRT
<213> ORGANISM: Anopheles gambiae

<400> SEQUENCE: 22

Lys Lys Pro His Ala Gly
1 5

<210> SEQ ID NO 23
<211> LENGTH: 6
<212> TYPE: PRT
<213> ORGANISM: Eimeria tenella

<400> SEQUENCE: 23

-continued

Cys Ala Pro His Glu Lys
1 5

<210> SEQ ID NO 24
<211> LENGTH: 6
<212> TYPE: PRT
<213> ORGANISM: Unknown
<220> FEATURE:
<223> OTHER INFORMATION: Description of unknown species: Pseudomonas aeruginosa, Yersinia pestis, Escherichia coli, or Shigella flexneri

<400> SEQUENCE: 24

Cys Lys Pro His Asp Cys
1 5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(1)
<223> OTHER INFORMATION: Cys or Val

<400> SEQUENCE: 25

Xaa Cys Pro His Ala Gly
1 5

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

Thr Ala Pro His Arg Gly Leu Ala Thr Leu Tyr Asn Gly Asp Cys
1 5 10 15

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 27

Cys Ser Pro Glu Val Gly Gln Met Asp Cys
1 5 10

<210> SEQ ID NO 28
<211> LENGTH: 128
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(6)
<223> OTHER INFORMATION: any amino acid or is absent; region may encompass 0-7 residues
<220> FEATURE:
<221> NAME/KEY: MOD_RES
<222> LOCATION: (8)..(28)
<223> OTHER INFORMATION: any amino acid or is absent; region may
encompass 0-21 residues
<220> FEATURE:
<221> NAME/KEY: MOD_RES
<222> LOCATION: (30)..(30)
<223> OTHER INFORMATION: any amino acid or is absent
<220> FEATURE:
<221> NAME/KEY: MOD_RES
<222> LOCATION: (32)..(35)
<223> OTHER INFORMATION: any amino acid or is absent; region may
encompass 0-4 residues
<220> FEATURE:
<221> NAME/KEY: MOD_RES
<222> LOCATION: (38)..(40)
<223> OTHER INFORMATION: any amino acid or is absent; region may
encompass 0-3 residues
<220> FEATURE:
<221> NAME/KEY: MOD_RES
<222> LOCATION: (42)..(51)
<223> OTHER INFORMATION: any amino acid or is absent; region may
encompass 0-10 residues
<220> FEATURE:
<221> NAME/KEY: MOD_RES
<222> LOCATION: (53)..(53)
<223> OTHER INFORMATION: any amino acid or is absent
<220> FEATURE:
<221> NAME/KEY: MOD_RES
<222> LOCATION: (57)..(58)
<223> OTHER INFORMATION: any amino acid or is absent; region may
encompass 0-2 residues
<220> FEATURE:
<221> NAME/KEY: MOD_RES
<222> LOCATION: (62)..(64)
<223> OTHER INFORMATION: any amino acid or is absent; region may
encompass 0-3 residues
<220> FEATURE:
<221> NAME/KEY: MOD_RES
<222> LOCATION: (67)..(77)
<223> OTHER INFORMATION: any amino acid or is absent; region may
encompass 0-11 residues
<220> FEATURE:
<221> NAME/KEY: MOD_RES
<222> LOCATION: (79)..(81)
<223> OTHER INFORMATION: any amino acid or is absent; region may
encompass 0-3 residues
<220> FEATURE:
<221> NAME/KEY: MOD_RES
<222> LOCATION: (83)..(84)
<223> OTHER INFORMATION: any amino acid or is absent; region may
encompass 0-2 residues
<220> FEATURE:
<221> NAME/KEY: MOD_RES
<222> LOCATION: (86)..(93)
<223> OTHER INFORMATION: any amino acid or is absent; region may
encompass 0-8 residues
<220> FEATURE:
<221> NAME/KEY: MOD_RES
<222> LOCATION: (97)..(107)
<223> OTHER INFORMATION: any amino acid or is absent; region may
encompass 0-11 residues
<220> FEATURE:
<221> NAME/KEY: MOD_RES
<222> LOCATION: (109)..(110)
<223> OTHER INFORMATION: any amino acid or is absent; region may
encompass 0-2 residues
<220> FEATURE:
<221> NAME/KEY: MOD_RES
<222> LOCATION: (112)..(114)
<223> OTHER INFORMATION: any amino acid or is absent; region may
encompass 0-3 residues
<220> FEATURE:
<221> NAME/KEY: MOD_RES
<222> LOCATION: (116)..(124)
<223> OTHER INFORMATION: any amino acid or is absent; region may
encompass 0-9 residues
<220> FEATURE:
<221> NAME/KEY: MOD_RES
<222> LOCATION: (126)..(128)

-continued

<223> OTHER INFORMATION: any amino acid or is absent; region may
encompass 0-3 residues

<400> SEQUENCE: 28

```
Xaa Xaa Xaa Xaa Xaa Xaa Cys Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Trp Xaa Cys Xaa
            20                  25                  30

Xaa Xaa Xaa Glu Ser Xaa Xaa Xaa Thr Xaa Xaa Xaa Xaa Xaa Xaa Xaa
        35                  40                  45

Xaa Xaa Xaa Ser Xaa Asp Tyr Gly Xaa Xaa Gln Ile Asn Xaa Xaa Xaa
    50                  55                  60

Trp Cys Xaa Xaa Xaa Xaa Xaa Xaa Xaa Xaa Xaa Xaa Xaa Cys Xaa Xaa
65                  70                  75                  80

Xaa Cys Xaa Xaa Leu Xaa Xaa Xaa Xaa Xaa Xaa Xaa Xaa Cys Ala Lys
                85                  90                  95

Xaa Xaa Xaa Xaa Xaa Xaa Xaa Xaa Xaa Xaa Xaa Trp Xaa Xaa Trp Xaa
            100                 105                 110

Xaa Xaa Cys Xaa Xaa Xaa Xaa Xaa Xaa Xaa Xaa Xaa Cys Xaa Xaa Xaa
        115                 120                 125
```

<210> SEQ ID NO 29
<211> LENGTH: 361
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 29

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asp Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205
```

-continued

```
Thr Phe Gly Gly Gly Asp His Pro Pro Lys Ser Asp Leu Val Pro Arg
    210                 215                 220

Gly Ser Cys Val Ser Cys Thr Thr Val Cys Pro His Ala Gly Lys Ala
225                 230                 235                 240

Lys Ala Glu Lys Val Glu Cys Ala Leu Lys Gly Gly Ile Phe Arg Gly
                245                 250                 255

Thr Leu Pro Ala Ala Asp Cys Pro Gly Ile Asp Thr Thr Val Thr Phe
            260                 265                 270

Asn Ala Asp Gly Thr Ala Gln Lys Val Glu Leu Ala Leu Glu Lys Lys
        275                 280                 285

Ser Ala Pro Ser Pro Leu Thr Tyr Arg Gly Thr Trp Met Val Arg Glu
    290                 295                 300

Asp Gly Ile Val Glu Leu Ser Leu Val Ser Ser Glu Gln Ser Lys Ala
305                 310                 315                 320

Pro His Glu Lys Glu Leu Tyr Glu Leu Ile Asp Ser Asn Ser Val Arg
                325                 330                 335

Tyr Met Gly Ala Pro Gly Ala Gly Lys Pro Ser Lys Glu Met Ala Pro
            340                 345                 350

Phe Tyr Val Leu Lys Lys Thr Lys Lys
        355                 360


<210> SEQ ID NO 30
<211> LENGTH: 1087
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30

atgtccccta tactaggtta ttggaaaatt aagggccttg tgcaacccac tcgacttctt      60

ttggaatatc ttgaagaaaa atatgaagag catttgtatg agcgcgatga aggtgataaa     120

tggcgaaaca aaaagtttga attgggtttg gagtttccca atcttcctta ttatattgat     180

ggtgatgtta aattaacaca gtctatggcc atcatacgtt atatagctga caagcacaac     240

atgttgggtg gttgtccaaa agagcgtgca gagatttcaa tgcttgaagg agcggttttg     300

gattaatcta tgccacaaag ctcttaacgt atatcatttc tgaaactttg agagtttcaa     360

gattttctta gcaagctacc tgaaatgctg aaaatgttcg aagatcgttt atgtcataaa     420

acatatttaa atggtgatca tgtaacccat cctgacttca tgttgtatga cgctcttgat     480

gttgttttat acatggaccc aatgtgcctg gatgcgttcc caaaattagt ttgttttaaa     540

aaacgtattg aagctatccc acaaattgat aagtacttga aatccagcaa gtatatagca     600

tggcctttgc agggctggca agccacgttt ggtggtggcg accatcctcc aaaatcggat     660

ctggttccgc gtggatcctg tgtctcgtgc acaaccgtgt gtccgcacgc cgggaaggcc     720

aaagcggaaa aggtagagtg cgcgttgaag ggaggtatct ttcggggtac gctacctgcg     780

gccgattgcc cgggaatcga tacgactgtg acgttcaacg cggatggcac tgcgcaaaag     840

gtagagcttg cccttgagaa gaagtcggca ccttctcctc ctacctatcg cggtacgtgg     900

atggtacgtg aagacggaat tgtcgaactc tcgcttgtgt cctcggagca atcgaaggca     960

ccgcacgaga aagagctgta cgagctgata gacagtaact ccgttcgcta catgggcgct    1020

cccggcgcag gaaagccttc aaaggagatg gcgccgtttt acgtgctcaa aaaaacaaag    1080

aaatagc                                                              1087
```

<210> SEQ ID NO 31
<211> LENGTH: 156
<212> TYPE: PRT
<213> ORGANISM: Treponema pallidum

<400> SEQUENCE: 31

```
Met Lys Gly Ser Val Arg Ala Leu Cys Ala Phe Leu Gly Val Gly Ala
1               5                   10                  15

Leu Gly Ser Ala Leu Cys Val Ser Cys Thr Thr Val Cys Pro His Ala
            20                  25                  30

Gly Lys Ala Lys Ala Glu Lys Val Glu Cys Ala Leu Lys Gly Gly Ile
        35                  40                  45

Phe Arg Gly Thr Leu Pro Ala Ala Asp Cys Pro Gly Ile Asp Thr Thr
    50                  55                  60

Val Thr Phe Asn Ala Asp Gly Thr Ala Gln Lys Val Glu Leu Ala Leu
65                  70                  75                  80

Glu Lys Lys Ser Ala Pro Ser Pro Leu Thr Tyr Arg Gly Thr Trp Met
                85                  90                  95

Val Arg Glu Asp Gly Ile Val Glu Leu Ser Leu Val Ser Ser Glu Gln
            100                 105                 110

Ser Lys Ala Pro His Glu Lys Glu Leu Tyr Glu Leu Ile Asp Ser Asn
        115                 120                 125

Ser Val Arg Tyr Met Gly Ala Pro Gly Ala Gly Lys Pro Ser Lys Glu
    130                 135                 140

Met Ala Pro Phe Tyr Val Leu Lys Lys Thr Lys Lys
145                 150                 155
```

<210> SEQ ID NO 32
<211> LENGTH: 130
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (1)..(1)
<223> OTHER INFORMATION: any amino acid or is absent
<220> FEATURE:
<221> NAME/KEY: MOD_RES
<222> LOCATION: (3)..(5)
<223> OTHER INFORMATION: any amino acid or is absent; region may
encompass 0-2 residues
<220> FEATURE:
<221> NAME/KEY: MOD_RES
<222> LOCATION: (11)..(12)
<223> OTHER INFORMATION: any amino acid or is absent; region may
encompass 0-2 residues
<220> FEATURE:
<221> NAME/KEY: MOD_RES
<222> LOCATION: (13)..(13)
<223> OTHER INFORMATION: Leu, or Met
<220> FEATURE:
<221> NAME/KEY: MOD_RES
<222> LOCATION: (15)..(16)
<223> OTHER INFORMATION: any amino acid or is absent; region may
encompass 0-2 residues
<220> FEATURE:
<221> NAME/KEY: MOD_RES
<222> LOCATION: (18)..(18)
<223> OTHER INFORMATION: any amino acid or is absent
<220> FEATURE:
<221> NAME/KEY: MOD_RES
<222> LOCATION: (22)..(22)
<223> OTHER INFORMATION: any amino acid or is absent
<220> FEATURE:
<221> NAME/KEY: MOD_RES -continued
<222> LOCATION: (24)..(24)
<223> OTHER INFORMATION: any amino acid or is absent
<220> FEATURE:
<221> NAME/KEY: MOD_RES
<222> LOCATION: (26)..(26)
<223> OTHER INFORMATION: Leu or Met
<220> FEATURE:
<221> NAME/KEY: MOD_RES
<222> LOCATION: (27)..(27)
<223> OTHER INFORMATION: any amino acid or is absent
<220> FEATURE:
<221> NAME/KEY: MOD_RES
<222> LOCATION: (28)..(28)
<223> OTHER INFORMATION: Asn or Asp
<220> FEATURE:
<221> NAME/KEY: MOD_RES
<222> LOCATION: (34)..(35)
<223> OTHER INFORMATION: any amino acid or is absent; region may
encompass 0-2 residues
<220> FEATURE:
<221> NAME/KEY: MOD_RES
<222> LOCATION: (38)..(39)
<223> OTHER INFORMATION: any amino acid or is absent; region may
encompass 0-2 residues
<220> FEATURE:
<221> NAME/KEY: MOD_RES
<222> LOCATION: (42)..(42)
<223> OTHER INFORMATION: any amino acid or is absent
<220> FEATURE:
<221> NAME/KEY: MOD_RES
<222> LOCATION: (46)..(46)
<223> OTHER INFORMATION: any amino acid or is absent
<220> FEATURE:
<221> NAME/KEY: MOD_RES
<222> LOCATION: (48)..(50)
<223> OTHER INFORMATION: any amino acid or is absent; region may
encompass 0-3 residues
<220> FEATURE:
<221> NAME/KEY: MOD_RES
<222> LOCATION: (63)..(63)
<223> OTHER INFORMATION: any amino acid or is absent
<220> FEATURE:
<221> NAME/KEY: MOD_RES
<222> LOCATION: (73)..(75)
<223> OTHER INFORMATION: any amino acid or is absent; region may
encompass 0-3 residues
<220> FEATURE:
<221> NAME/KEY: MOD_RES
<222> LOCATION: (77)..(77)
<223> OTHER INFORMATION: any amino acid or is absent
<220> FEATURE:
<221> NAME/KEY: MOD_RES
<222> LOCATION: (79)..(79)
<223> OTHER INFORMATION: any amino acid or is absent
<220> FEATURE:
<221> NAME/KEY: MOD_RES
<222> LOCATION: (80)..(80)
<223> OTHER INFORMATION: Ile or Val
<220> FEATURE:
<221> NAME/KEY: MOD_RES
<222> LOCATION: (81)..(81)
<223> OTHER INFORMATION: any amino acid or is absent
<220> FEATURE:
<221> NAME/KEY: MOD_RES
<222> LOCATION: (84)..(84)
<223> OTHER INFORMATION: any amino acid or is absent
<220> FEATURE:
<221> NAME/KEY: MOD_RES
<222> LOCATION: (87)..(87)
<223> OTHER INFORMATION: any amino acid or is absent
<220> FEATURE:
<221> NAME/KEY: MOD_RES
<222> LOCATION: (89)..(89)
<223> OTHER INFORMATION: Asp or Asn
<220> FEATURE:
<221> NAME/KEY: MOD_RES
<222> LOCATION: (92)..(92)
<223> OTHER INFORMATION: any amino acid or is absent
<220> FEATURE:

-continued

<221> NAME/KEY: MOD_RES
<222> LOCATION: (98)..(98)
<223> OTHER INFORMATION: Ile or Val
<220> FEATURE:
<221> NAME/KEY: MOD_RES
<222> LOCATION: (100)..(100)
<223> OTHER INFORMATION: any amino acid or is absent
<220> FEATURE:
<221> NAME/KEY: MOD_RES
<222> LOCATION: (102)..(103)
<223> OTHER INFORMATION: any amino acid or is absent; region may encompass 0-2 residues
<220> FEATURE:
<221> NAME/KEY: MOD_RES
<222> LOCATION: (105)..(106)
<223> OTHER INFORMATION: any amino acid or is absent; region may encompass 0-2 residues
<220> FEATURE:
<221> NAME/KEY: MOD_RES
<222> LOCATION: (113)..(113)
<223> OTHER INFORMATION: any amino acid or is absent
<220> FEATURE:
<221> NAME/KEY: MOD_RES
<222> LOCATION: (116)..(116)
<223> OTHER INFORMATION: any amino acid or is absent
<220> FEATURE:
<221> NAME/KEY: MOD_RES
<222> LOCATION: (118)..(118)
<223> OTHER INFORMATION: any amino acid or is absent
<220> FEATURE:
<221> NAME/KEY: MOD_RES
<222> LOCATION: (122)..(122)
<223> OTHER INFORMATION: any amino acid or is absent
<220> FEATURE:
<221> NAME/KEY: MOD_RES
<222> LOCATION: (124)..(125)
<223> OTHER INFORMATION: any amino acid or is absent; region may encompass 0-2 residues
<220> FEATURE:
<221> NAME/KEY: MOD_RES
<222> LOCATION: (128)..(130)
<223> OTHER INFORMATION: any amino acid or is absent; region may encompass 0-3 residues

<400> SEQUENCE: 32

```
Xaa Lys Xaa Xaa Xaa Arg Cys Glu Leu Ala Xaa Xaa Xaa Lys Xaa Xaa
1               5                   10                  15

Gly Xaa Asp Gly Tyr Xaa Gly Xaa Ser Xaa Xaa Xaa Trp Val Cys Leu
            20                  25                  30

Ala Xaa Xaa Glu Ser Xaa Xaa Asn Thr Xaa Ala Thr Asn Xaa Asn Xaa
        35                  40                  45

Xaa Xaa Gly Ser Thr Asp Tyr Gly Ile Phe Gln Ile Asn Ser Xaa Tyr
    50                  55                  60

Trp Cys Asn Asp Gly Lys Thr Pro Xaa Xaa Xaa Asn Xaa Cys Xaa Xaa
65                  70                  75                  80

Xaa Cys Ser Xaa Leu Leu Xaa Asp Xaa Ile Thr Xaa Ala Cys Ala Lys
                85                  90                  95

Lys Xaa Val Xaa Asp Xaa Xaa Gly Xaa Xaa Ala Trp Val Ala Trp Lys
            100                 105                 110

Xaa His Cys Xaa Gly Xaa Asp Leu Ser Xaa Tyr Xaa Xaa Gly Cys Xaa
        115                 120                 125

Xaa Xaa
```

<210> SEQ ID NO 33
<211> LENGTH: 54
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 33
agatatacat atggtctcgt gcacaaccgt gtgtccgcac gccgggaagg ccaa 54

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 34
atgtagcgaa cggagtta 18

<210> SEQ ID NO 35
<211> LENGTH: 6
<212> TYPE: PRT
<213> ORGANISM: Treponema pallidum

<400> SEQUENCE: 35

Val Ser Cys Thr Thr Val
1 5

<210> SEQ ID NO 36
<211> LENGTH: 10
<212> TYPE: PRT
<213> ORGANISM: Gallus gallus

<400> SEQUENCE: 36

Lys Val Phe Gly Arg Cys Glu Leu Ala Ala
1 5 10

<210> SEQ ID NO 37
<211> LENGTH: 17
<212> TYPE: PRT
<213> ORGANISM: Gallus gallus

<400> SEQUENCE: 37

Gln Gly His Lys Leu Pro Ala Trp Val Met Lys Gly Gly Thr Tyr Thr
1 5 10 15

Pro

<210> SEQ ID NO 38
<211> LENGTH: 7
<212> TYPE: PRT
<213> ORGANISM: Gallus gallus

<400> SEQUENCE: 38

Cys Lys Pro His Asp Cys Gly
1 5

<210> SEQ ID NO 39
<211> LENGTH: 11
<212> TYPE: PRT
<213> ORGANISM: Gallus gallus

<400> SEQUENCE: 39

Gly Ser Leu Glu Asn His Pro Asp Gly Phe Asn
1 5 10

<210> SEQ ID NO 40
<211> LENGTH: 4

-continued

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 40

Lys Pro His Asp
1

<210> SEQ ID NO 41
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 41

Cys Pro His Ala Gly Lys Ala Lys Ala Glu Lys Val Glu Cys
1 5 10

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 42

Lys Ala Pro His Glu Lys Glu
1 5

<210> SEQ ID NO 43
<211> LENGTH: 15
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (2)..(2)
<223> OTHER INFORMATION: any amino acid, or is not present
<220> FEATURE:
<221> NAME/KEY: MOD_RES
<222> LOCATION: (5)..(13)
<223> OTHER INFORMATION: any amino acid or is not present; region may
encompass 0-9 residues
<220> FEATURE:
<221> NAME/KEY: MOD_RES
<222> LOCATION: (14)..(14)
<223> OTHER INFORMATION: Glu or Asp

<400> SEQUENCE: 43

Cys Xaa Pro His Xaa Xaa Xaa Xaa Xaa Xaa Xaa Xaa Xaa Xaa Cys
1 5 10 15

<210> SEQ ID NO 44
<211> LENGTH: 6
<212> TYPE: PRT
<213> ORGANISM: Influenza A virus

<400> SEQUENCE: 44

Cys Gly Pro His Glu Cys
1 5

<210> SEQ ID NO 45

-continued

<211> LENGTH: 6
<212> TYPE: PRT
<213> ORGANISM: Plasmodium falciparum

<400> SEQUENCE: 45

Cys Pro His Asn Asp Cys
1 5

<210> SEQ ID NO 46
<211> LENGTH: 6
<212> TYPE: PRT
<213> ORGANISM: Giardia lamblia

<400> SEQUENCE: 46

Cys Pro His Gly Glu Cys
1 5

<210> SEQ ID NO 47
<211> LENGTH: 7
<212> TYPE: PRT
<213> ORGANISM: Vibrio parahaemolyticus

<400> SEQUENCE: 47

Cys Pro His Tyr His Glu Cys
1 5

<210> SEQ ID NO 48
<211> LENGTH: 7
<212> TYPE: PRT
<213> ORGANISM: Pseudomonas aeruginosa

<400> SEQUENCE: 48

Cys Pro His Leu Arg Asp Cys
1 5

<210> SEQ ID NO 49
<211> LENGTH: 7
<212> TYPE: PRT
<213> ORGANISM: Pasteurella multocida

<400> SEQUENCE: 49

Cys Pro His Tyr Asn Asp Cys
1 5

<210> SEQ ID NO 50
<211> LENGTH: 7
<212> TYPE: PRT
<213> ORGANISM: Brucella sp.

<400> SEQUENCE: 50

Cys Pro His Gly Leu Asp Cys
1 5

<210> SEQ ID NO 51
<211> LENGTH: 8
<212> TYPE: PRT
<213> ORGANISM: Mycobacterium tuberculosis

<400> SEQUENCE: 51

Cys Pro His Ala Ser Val Asp Cys
1 5

<210> SEQ ID NO 52
<211> LENGTH: 8
<212> TYPE: PRT

-continued

<213> ORGANISM: Plasmodium falciparum

<400> SEQUENCE: 52

Cys Pro His Cys Lys Val Asp Cys
1 5

<210> SEQ ID NO 53
<211> LENGTH: 8
<212> TYPE: PRT
<213> ORGANISM: Plasmodium falciparum

<400> SEQUENCE: 53

Cys Pro His Cys Glu Val Asp Cys
1 5

<210> SEQ ID NO 54
<211> LENGTH: 8
<212> TYPE: PRT
<213> ORGANISM: Campylobacter jejuni

<400> SEQUENCE: 54

Cys Pro His Glu Gly Cys Glu Cys
1 5

<210> SEQ ID NO 55
<211> LENGTH: 9
<212> TYPE: PRT
<213> ORGANISM: Shigella flexneri

<400> SEQUENCE: 55

Cys Pro His Leu Pro Ala Asp Glu Cys
1 5

<210> SEQ ID NO 56
<211> LENGTH: 10
<212> TYPE: PRT
<213> ORGANISM: Pseudomonas aeruginosa

<400> SEQUENCE: 56

Cys Pro His Gly Pro Asp Asp Gly Asp Cys
1 5 10

<210> SEQ ID NO 57
<211> LENGTH: 10
<212> TYPE: PRT
<213> ORGANISM: Pseudomonas putida

<400> SEQUENCE: 57

Cys Pro His Gly Pro Asp Glu Gly Asp Cys
1 5 10

<210> SEQ ID NO 58
<211> LENGTH: 10
<212> TYPE: PRT
<213> ORGANISM: Helicobacter hepaticus

<400> SEQUENCE: 58

Cys Pro His Leu Pro Ser Glu Asn Asp Cys
1 5 10

<210> SEQ ID NO 59
<211> LENGTH: 12
<212> TYPE: PRT
<213> ORGANISM: Human herpesvirus 5
<220> FEATURE:

<223> OTHER INFORMATION: strain AD169

<400> SEQUENCE: 59

Cys Leu Pro His Thr Arg Pro Ala Ala Val Glu Cys
1 5 10

<210> SEQ ID NO 60
<211> LENGTH: 11
<212> TYPE: PRT
<213> ORGANISM: Pseudomonas aeruginosa

<400> SEQUENCE: 60

Cys Pro His Arg Leu Ser Ala Ile Thr Glu Cys
1 5 10

<210> SEQ ID NO 61
<211> LENGTH: 12
<212> TYPE: PRT
<213> ORGANISM: Tupaia herpesvirus

<400> SEQUENCE: 61

Cys Leu Pro His Thr Arg Pro Ala Ala Val Glu Cys
1 5 10

<210> SEQ ID NO 62
<211> LENGTH: 12
<212> TYPE: PRT
<213> ORGANISM: Pongine herpesvirus 4

<400> SEQUENCE: 62

Cys Leu Pro His Thr Arg Pro Ala Ala Val Glu Cys
1 5 10

<210> SEQ ID NO 63
<211> LENGTH: 12
<212> TYPE: PRT
<213> ORGANISM: Human papillomavirus 3

<400> SEQUENCE: 63

Cys Pro His Pro Ile Gly His Arg Asp Pro Asp Cys
1 5 10

<210> SEQ ID NO 64
<211> LENGTH: 13
<212> TYPE: PRT
<213> ORGANISM: Dengue virus 3

<400> SEQUENCE: 64

Cys Pro His Ile Thr Glu Val Glu Glu Asp Ile Asp Cys
1 5 10

<210> SEQ ID NO 65
<211> LENGTH: 14
<212> TYPE: PRT
<213> ORGANISM: Treponema pallidum

<400> SEQUENCE: 65

Cys Pro His Ala Gly Lys Ala Lys Ala Glu Lys Val Glu Cys
1 5 10

<210> SEQ ID NO 66
<211> LENGTH: 15
<212> TYPE: PRT
<213> ORGANISM: Foot-and-mouth disease virus -continued

<400> SEQUENCE: 66

Thr Ala Pro His Arg Gly Leu Ala Thr Leu Tyr Asn Gly Asp Cys
1 5 10 15

<210> SEQ ID NO 67
<211> LENGTH: 10
<212> TYPE: PRT
<213> ORGANISM: Human immunodeficiency virus 1

<400> SEQUENCE: 67

Cys Ser Pro Glu Val Gly Gln Met Asp Cys
1 5 10

<210> SEQ ID NO 68
<211> LENGTH: 13
<212> TYPE: PRT
<213> ORGANISM: Homo sapiens

<400> SEQUENCE: 68

Cys Lys Thr His Pro His Phe Gly Ile Pro Tyr Arg Cys
1 5 10

<210> SEQ ID NO 69
<211> LENGTH: 13
<212> TYPE: PRT
<213> ORGANISM: Homo sapiens

<400> SEQUENCE: 69

Cys Ala His Pro His His Gly Val Val Pro Phe Arg Cys
1 5 10

<210> SEQ ID NO 70
<211> LENGTH: 7
<212> TYPE: PRT
<213> ORGANISM: Homo sapiens

<400> SEQUENCE: 70

Cys Thr Pro His Arg Gly Cys
1 5

<210> SEQ ID NO 71
<211> LENGTH: 11
<212> TYPE: PRT
<213> ORGANISM: Homo sapiens

<400> SEQUENCE: 71

Cys Gln Cys Pro His Arg Gly Gln Lys Thr Cys
1 5 10

<210> SEQ ID NO 72
<211> LENGTH: 12
<212> TYPE: PRT
<213> ORGANISM: Human adenovirus 12

<400> SEQUENCE: 72

Cys Arg Gln Pro His Cys Gly Ala Arg Asp Ile Cys
1 5 10

<210> SEQ ID NO 73
<211> LENGTH: 8
<212> TYPE: PRT
<213> ORGANISM: Bos taurus immunodeficiency virus

<400> SEQUENCE: 73

-continued

```
Cys Lys Pro His Gly Gly Tyr Cys
1               5


<210> SEQ ID NO 74
<211> LENGTH: 13
<212> TYPE: PRT
<213> ORGANISM: Influenza A virus

<400> SEQUENCE: 74

Cys Asn Asn Pro His Arg Gly Leu Asp Gly Ile Asp Cys
1               5                   10


<210> SEQ ID NO 75
<211> LENGTH: 7
<212> TYPE: PRT
<213> ORGANISM: Homo sapiens

<400> SEQUENCE: 75

Cys Leu Cys Pro His Gly Cys
1               5


<210> SEQ ID NO 76
<211> LENGTH: 11
<212> TYPE: PRT
<213> ORGANISM: Shigella sp.

<400> SEQUENCE: 76

Cys Phe Ile Pro His Leu Gly Arg Ala Asp Cys
1               5                   10


<210> SEQ ID NO 77
<211> LENGTH: 14
<212> TYPE: PRT
<213> ORGANISM: Pandinus imperator

<400> SEQUENCE: 77

Cys Leu Pro His Leu Gly Arg Cys Lys Ala Asp Asn Asp Cys
1               5                   10


<210> SEQ ID NO 78
<211> LENGTH: 5
<212> TYPE: PRT
<213> ORGANISM: Homo sapiens

<400> SEQUENCE: 78

Cys Pro His Gly Cys
1               5


<210> SEQ ID NO 79
<211> LENGTH: 7
<212> TYPE: PRT
<213> ORGANISM: Homo sapiens

<400> SEQUENCE: 79

Cys Pro His His Gly Arg Cys
1               5


<210> SEQ ID NO 80
<211> LENGTH: 13
<212> TYPE: PRT
<213> ORGANISM: Coxsackie virus

<400> SEQUENCE: 80

Cys Pro His Gln Gly Ile Asn Leu Arg Thr Asn Asn Cys
1               5                   10
```

-continued

<210> SEQ ID NO 81
<211> LENGTH: 14
<212> TYPE: PRT
<213> ORGANISM: Dengue virus 3

<400> SEQUENCE: 81

Cys Pro His Ile Gly Glu Val Glu Pro Glu Asp Ile Asp Cys
1 5 10

<210> SEQ ID NO 82
<211> LENGTH: 13
<212> TYPE: PRT
<213> ORGANISM: Hepatitis C virus

<400> SEQUENCE: 82

Cys Pro His Gln Gly Ile Asn Leu Arg Thr Asn Asn Cys
1 5 10

<210> SEQ ID NO 83
<211> LENGTH: 9
<212> TYPE: PRT
<213> ORGANISM: Rubella virus

<400> SEQUENCE: 83

Cys Gly Pro His Tyr Gly Asn Asn Cys
1 5

<210> SEQ ID NO 84
<211> LENGTH: 11
<212> TYPE: PRT
<213> ORGANISM: Eastern equine encephalitis virus

<400> SEQUENCE: 84

Cys Thr Ser Lys Pro His Pro Gly Tyr Gln Cys
1 5 10

<210> SEQ ID NO 85
<211> LENGTH: 12
<212> TYPE: PRT
<213> ORGANISM: Haementeria officinalis

<400> SEQUENCE: 85

Cys Pro His Gly Gly Gln Arg Ser Arg Tyr Gly Cys
1 5 10

<210> SEQ ID NO 86
<211> LENGTH: 15
<212> TYPE: PRT
<213> ORGANISM: Bos taurus

<400> SEQUENCE: 86

Cys Leu Pro His Tyr Gly Met Phe Gly Asn Asp Thr Ile Thr Cys
1 5 10 15

<210> SEQ ID NO 87
<211> LENGTH: 14
<212> TYPE: PRT
<213> ORGANISM: Hepatitis B virus

<400> SEQUENCE: 87

Cys Ser Pro His His Gly Ala Leu Arg Gln Ala Ile Leu Cys
1 5 10

-continued

<210> SEQ ID NO 88
<211> LENGTH: 14
<212> TYPE: PRT
<213> ORGANISM: Caprine arthritis encephalitis virus

<400> SEQUENCE: 88

Cys Ser Leu Pro His Lys Gly Glu Ser Asn Lys Trp Thr Cys
1 5 10

<210> SEQ ID NO 89
<211> LENGTH: 14
<212> TYPE: PRT
<213> ORGANISM: Radiation murine leukemia virus

<400> SEQUENCE: 89

Cys Ser Leu Pro His Arg Gly Glu Ser Asn Lys Trp Thr Cys
1 5 10

<210> SEQ ID NO 90
<211> LENGTH: 129
<212> TYPE: PRT
<213> ORGANISM: Anas platyrhynchos

<400> SEQUENCE: 90

Lys Val Tyr Ser Arg Cys Glu Leu Ala Ala Ala Met Lys Arg Leu Gly
1 5 10 15

Leu Asp Asn Tyr Arg Gly Tyr Ser Leu Gly Asn Trp Val Cys Ala Ala
20 25 30

Asn Tyr Glu Ser Gly Phe Asn Thr Gln Ala Thr Asn Arg Asn Thr Asp
35 40 45

Gly Ser Thr Asp Tyr Gly Ile Leu Gln Ile Asn Ser Arg Trp Trp Cys
50 55 60

Asp Asn Gly Lys Thr Pro Arg Ser Lys Asn Ala Cys Gly Ile Pro Cys
65 70 75 80

Ser Val Leu Leu Arg Ser Asp Ile Thr Glu Ala Val Arg Cys Ala Lys
85 90 95

Arg Ile Val Ser Asp Gly Asp Gly Met Asn Ala Trp Val Ala Trp Arg
100 105 110

Asn Arg Cys Arg Gly Thr Asp Val Ser Lys Trp Ile Arg Gly Cys Arg
115 120 125

Leu

<210> SEQ ID NO 91
<211> LENGTH: 127
<212> TYPE: PRT
<213> ORGANISM: Anas platyrhynchos

<400> SEQUENCE: 91

Lys Val Tyr Glu Arg Cys Glu Leu Ala Ala Ala Met Lys Arg Leu Gly
1 5 10 15

Leu Asp Asn Tyr Arg Gly Tyr Ser Leu Gly Asn Trp Val Cys Ala Ala
20 25 30

Asn Tyr Glu Ser Ser Phe Asn Thr Gln Ala Thr Asn Arg Asn Thr Asp
35 40 45

Gly Ser Thr Asp Tyr Gly Ile Ile Asn Ser Arg Trp Trp Cys Asp Asn
50 55 60

Gly Lys Thr Pro Arg Ala Lys Asn Ala Cys Gly Ile Pro Cys Ser Val
65 70 75 80

Leu Leu Arg Ser Asp Ile Thr Glu Ala Val Lys Cys Ala Lys Arg Ile

-continued

```
                85                  90                  95

Val Ser Asp Gly Asp Gly Met Asn Ala Trp Val Ala Trp Arg Asn Arg
            100                 105                 110

Cys Lys Gly Thr Asp Val Ser Arg Trp Ile Arg Gly Cys Arg Leu
        115                 120                 125


<210> SEQ ID NO 92
<211> LENGTH: 129
<212> TYPE: PRT
<213> ORGANISM: Gallus gallus

<400> SEQUENCE: 92

Lys Val Phe Gly Arg Cys Glu Leu Ala Ala Ala Met Lys Arg His Gly
  1               5                  10                  15

Leu Asp Asn Tyr Arg Gly Tyr Ser Leu Gly Asn Trp Val Cys Ala Ala
             20                  25                  30

Lys Phe Glu Ser Asn Phe Asn Thr Gln Ala Thr Asn Arg Asn Thr Asp
         35                  40                  45

Gly Ser Thr Asp Tyr Gly Ile Leu Gln Ile Asn Ser Arg Trp Trp Cys
     50                  55                  60

Asn Asp Gly Arg Thr Pro Gly Ser Arg Asn Leu Cys Asn Ile Pro Cys
 65                  70                  75                  80

Ser Ala Leu Leu Ser Ser Asp Ile Thr Ala Ser Val Asn Cys Ala Lys
                 85                  90                  95

Lys Ile Val Ser Asp Gly Asn Gly Met Asn Ala Trp Val Ala Trp Arg
            100                 105                 110

Asn Arg Cys Lys Gly Thr Asp Val Gln Ala Trp Ile Arg Gly Cys Arg
        115                 120                 125

Leu


<210> SEQ ID NO 93
<211> LENGTH: 129
<212> TYPE: PRT
<213> ORGANISM: Coturnix japonica

<400> SEQUENCE: 93

Lys Val Phe Gly Arg Cys Glu Leu Ala Ala Ala Met Lys Arg His Gly
  1               5                  10                  15

Leu Asp Asn Tyr Arg Gly Tyr Ser Leu Gly Asn Trp Val Cys Ala Ala
             20                  25                  30

Lys Phe Glu Ser Asn Phe Asn Ser Gln Ala Thr Asn Arg Asn Thr Asp
         35                  40                  45

Gly Ser Thr Asp Tyr Gly Val Leu Gln Ile Asn Ser Arg Trp Trp Cys
     50                  55                  60

Asn Asp Gly Lys Thr Pro Gly Ser Arg Asn Leu Cys Asn Ile Pro Cys
 65                  70                  75                  80

Ser Ala Leu Leu Ser Ser Asp Ile Thr Ala Thr Val Asn Cys Ala Lys
                 85                  90                  95

Lys Ile Val Ser Asp Gly Asn Gly Met Asn Ala Trp Val Ala Trp Arg
            100                 105                 110

Asn Arg Cys Lys Gly Thr Asp Val Gln Ala Trp Ile Arg Gly Cys Arg
        115                 120                 125

Leu


<210> SEQ ID NO 94
<211> LENGTH: 129
```

-continued

<212> TYPE: PRT
<213> ORGANISM: Coturnix japonica

<400> SEQUENCE: 94

Lys Val Phe Gly Arg Cys Glu Leu Ala Ala Ala Met Lys Arg His Gly
1 5 10 15

Leu Asp Asn Tyr Arg Gly Tyr Ser Leu Gly Asn Trp Val Cys Ala Ala
20 25 30

Lys Phe Glu Ser Asn Phe Asn Ser Gln Ala Thr Asn Arg Asn Thr Asp
35 40 45

Gly Ser Thr Asp Tyr Gly Val Leu Gln Ile Asn Ser Arg Trp Trp Cys
50 55 60

Asn Asp Gly Arg Thr Pro Gly Ser Arg Asn Leu Cys Asn Ile Pro Cys
65 70 75 80

Ser Ala Leu Leu Ser Ser Asp Ile Thr Ala Thr Val Asn Cys Ala Lys
85 90 95

Lys Ile Val Ser Asp Gly Asn Gly Met Asn Ala Trp Val Ala Trp Arg
100 105 110

Asn Arg Cys Lys Gly Thr Asp Val His Ala Trp Ile Arg Gly Cys Glu
115 120 125

Leu

<210> SEQ ID NO 95
<211> LENGTH: 129
<212> TYPE: PRT
<213> ORGANISM: Numida meleagris

<400> SEQUENCE: 95

Lys Val Phe Gly Arg Cys Glu Leu Ala Ala Ala Met Lys Arg His Gly
1 5 10 15

Leu Asp Asn Tyr Arg Gly Tyr Ser Leu Gly Asn Trp Val Cys Ala Ala
20 25 30

Lys Phe Glu Ser Asn Phe Asn Ser Gln Ala Thr Asn Arg Asn Thr Asp
35 40 45

Gly Ser Thr Asp Tyr Gly Val Leu Gln Ile Asn Ser Arg Trp Trp Cys
50 55 60

Asn Asp Gly Arg Thr Pro Gly Ser Arg Asn Leu Cys Asn Ile Pro Cys
65 70 75 80

Ser Ala Leu Gln Ser Ser Asp Ile Thr Ala Thr Ala Asn Cys Ala Lys
85 90 95

Lys Ile Val Ser Asp Gly Asn Gly Met Asn Ala Trp Val Ala Trp Arg
100 105 110

Lys His Cys Lys Gly Thr Asp Val Arg Val Trp Ile Lys Gly Cys Arg
115 120 125

Leu

<210> SEQ ID NO 96
<211> LENGTH: 129
<212> TYPE: PRT
<213> ORGANISM: Coturnix japonica

<400> SEQUENCE: 96

Lys Val Tyr Gly Arg Cys Glu Leu Ala Ala Ala Met Lys Arg His Gly
1 5 10 15

Leu Asp Lys Tyr Gln Gly Tyr Ser Leu Gly Asn Trp Val Cys Ala Ala
20 25 30

-continued

```
Lys Phe Glu Ser Asn Phe Asn Thr Gln Ala Thr Asn Arg Asn Thr Asp
         35                  40                  45

Gly Ser Thr Asp Tyr Gly Ile Leu Gln Ile Asn Ser Arg Trp Trp Cys
     50                  55                  60

Asn Asp Gly Arg Thr Pro Gly Ser Arg Asn Leu Cys Asn Ile Pro Cys
 65                  70                  75                  80

Ser Ala Leu Leu Ser Ser Asp Ile Thr Ala Ser Val Asn Cys Ala Lys
                 85                  90                  95

Lys Ile Val Ser Asp Val His Gly Met Asn Ala Trp Val Ala Trp Arg
            100                 105                 110

Asn Arg Cys Lys Gly Thr Asp Val Asn Ala Trp Ile Arg Gly Cys Arg
        115                 120                 125

Leu


<210> SEQ ID NO 97
<211> LENGTH: 129
<212> TYPE: PRT
<213> ORGANISM: Phasianus colchicus

<400> SEQUENCE: 97

Lys Val Tyr Gly Arg Cys Glu Leu Ala Ala Ala Met Lys Arg Leu Gly
  1               5                  10                  15

Leu Asp Asn Tyr Arg Gly Tyr Ser Leu Gly Asn Trp Val Cys Ala Ala
             20                  25                  30

Lys Phe Glu Ser Asn Phe Asn Thr His Ala Thr Asn Arg Asn Thr Asp
         35                  40                  45

Gly Ser Thr Asp Tyr Gly Ile Leu Gln Ile Asn Ser Arg Trp Trp Cys
     50                  55                  60

Asn Asp Gly Arg Thr Pro Gly Ser Arg Asn Leu Cys His Ile Pro Cys
 65                  70                  75                  80

Ser Ala Leu Leu Ser Ser Asp Ile Thr Ala Ser Val Asn Cys Ala Lys
                 85                  90                  95

Lys Ile Val Ser Asp Gly Asn Gly Met Asn Ala Trp Val Ala Trp Arg
            100                 105                 110

Asn Arg Cys Lys Gly Thr Asp Val Asn Ala Trp Thr Arg Gly Cys Arg
        115                 120                 125

Leu


<210> SEQ ID NO 98
<211> LENGTH: 129
<212> TYPE: PRT
<213> ORGANISM: Phasianus colchicus

<400> SEQUENCE: 98

Lys Val Tyr Gly Arg Cys Glu Leu Ala Ala Ala Met Lys Arg Leu Gly
  1               5                  10                  15

Leu Asp Asn Tyr Arg Gly Tyr Ser Leu Gly Asn Trp Val Cys Ala Ala
             20                  25                  30

Lys Tyr Glu Ser Asn Phe Asn Thr His Ala Thr Asn Arg Asn Thr Asp
         35                  40                  45

Gly Ser Thr Asp Tyr Gly Ile Leu Gln Ile Asn Ser Arg Trp Trp Cys
     50                  55                  60

Asn Asp Gly Lys Thr Pro Gly Ser Arg Asn Leu Cys His Ile Pro Cys
 65                  70                  75                  80

Ser Ala Leu Leu Ser Ser Asp Ile Thr Ala Ser Val Asn Cys Ala Lys
                 85                  90                  95
```

-continued

```
Lys Ile Val Ser Asp Gly Asn Gly Met Asn Ala Trp Val Ala Trp Arg
            100                 105                 110

Asn Arg Cys Lys Gly Thr Asp Val Ser Val Trp Thr Arg Gly Cys Arg
        115                 120                 125

Leu


<210> SEQ ID NO 99
<211> LENGTH: 129
<212> TYPE: PRT
<213> ORGANISM: Pavo cristatus

<400> SEQUENCE: 99

Lys Val Tyr Gly Arg Cys Glu Leu Ala Ala Ala Met Lys Arg Leu Gly
  1               5                  10                  15

Leu Asp Asn Tyr Arg Gly Tyr Ser Leu Gly Asn Trp Val Cys Ala Ala
             20                  25                  30

Lys Phe Glu Ser Asn Phe Asn Thr His Ala Thr Asn Arg Asn Thr Asp
         35                  40                  45

Gly Ser Thr Asp Tyr Gly Ile Leu Gln Ile Asn Ser Arg Trp Trp Cys
     50                  55                  60

Asn Asp Gly Arg Thr Pro Gly Ser Arg Asn Leu Cys Asn Ile Pro Cys
 65                  70                  75                  80

Ser Ala Leu Leu Ser Ser Asp Ile Thr Ala Ser Val Asn Cys Ala Lys
                 85                  90                  95

Lys Ile Val Ser Asp Arg Asn Gly Met Asn Ala Trp Val Ala Trp Arg
            100                 105                 110

Asn Arg Cys Lys Gly Thr Asp Val His Ala Trp Ile Arg Gly Cys Arg
        115                 120                 125

Leu


<210> SEQ ID NO 100
<211> LENGTH: 129
<212> TYPE: PRT
<213> ORGANISM: Phasianus colchicus

<400> SEQUENCE: 100

Lys Val Tyr Gly Arg Cys Glu Leu Ala Ala Ala Met Lys Arg Leu Gly
  1               5                  10                  15

Leu Asp Asn Tyr Arg Gly Tyr Ser Leu Gly Asn Trp Val Cys Ala Ala
             20                  25                  30

Lys Phe Glu Ser Asn Phe Asn Thr His Ala Thr Asn Arg Asn Thr Asp
         35                  40                  45

Gly Ser Thr Asp Tyr Gly Ile Leu Gln Ile Asn Ser Arg Trp Trp Cys
     50                  55                  60

Asn Asp Gly Arg Thr Pro Gly Ser Arg Asn Leu Cys His Ile Ser Cys
 65                  70                  75                  80

Ser Ala Leu Leu Ser Ser Asp Ile Thr Ala Ser Val Asn Cys Ala Lys
                 85                  90                  95

Lys Ile Val Ser Asp Arg Asn Gly Met Asn Ala Trp Val Ala Trp Arg
            100                 105                 110

Asn Arg Cys Lys Gly Thr Asp Val Asn Ala Trp Ile Arg Gly Cys Arg
        115                 120                 125

Leu


<210> SEQ ID NO 101
```

-continued

```
<211> LENGTH: 129
<212> TYPE: PRT
<213> ORGANISM: Pavo cristatus

<400> SEQUENCE: 101

Lys Val Tyr Gly Arg Cys Glu Leu Ala Ala Ala Met Lys Arg Leu Gly
  1               5                  10                  15

Leu Asp Asn Tyr Arg Gly Tyr Ser Leu Gly Asn Trp Tyr Cys Ala Ala
             20                  25                  30

Lys Phe Glu Ser Asn Phe Asn Thr His Ala Thr Asn Arg Asn Thr Asp
         35                  40                  45

Gly Ser Thr Asp Tyr Gly Ile Leu Gln Ile Asn Ser Arg Trp Trp Cys
     50                  55                  60

Asn Asp Gly Arg Thr Pro Gly Ser Lys Asn Leu Cys Asn Ile Pro Cys
 65                  70                  75                  80

Ser Ala Leu Leu Ser Ser Asp Ile Thr Ala Ser Val Asn Cys Ala Lys
                 85                  90                  95

Lys Ile Ala Ser Gly Gly Asn Gly Met Asn Ala Trp Val Ala Trp Arg
            100                 105                 110

Asn Arg Cys Lys Gly Thr Asp Val His Ala Trp Ile Arg Gly Cys Arg
        115                 120                 125

Leu


<210> SEQ ID NO 102
<211> LENGTH: 129
<212> TYPE: PRT
<213> ORGANISM: Phasianus colchicus

<400> SEQUENCE: 102

Lys Val Tyr Gly Arg Cys Glu Leu Ala Ala Ala Met Lys Arg Leu Gly
  1               5                  10                  15

Leu Asp Asn Phe Arg Gly Tyr Ser Leu Gly Asn Trp Val Cys Ala Ala
             20                  25                  30

Lys Phe Glu Ser Asn Phe Asn Thr His Ala Thr Asn Arg Asn Thr Asp
         35                  40                  45

Gly Ser Thr Asp Tyr Gly Ile Leu Gln Ile Asn Ser Arg Trp Trp Cys
     50                  55                  60

Asn Asp Gly Arg Thr Pro Gly Ser Arg Asn Leu Cys Asn Ile Pro Cys
 65                  70                  75                  80

Ser Ala Leu Leu Ser Ser Asp Thr Ile Ala Ser Val Asn Cys Ala Lys
                 85                  90                  95

Lys Ile Val Ser Asp Gly Asn Gly Met Asn Ala Trp Val Ala Trp Arg
            100                 105                 110

Lys Arg Cys Lys Gly Thr Asp Val Asn Ala Trp Thr Arg Gly Cys Arg
        115                 120                 125

Leu


<210> SEQ ID NO 103
<211> LENGTH: 129
<212> TYPE: PRT
<213> ORGANISM: Phasianus colchicus

<400> SEQUENCE: 103

Lys Val Tyr Gly Arg Cys Glu Leu Ala Ala Ala Met Lys Arg Met Gly
  1               5                  10                  15

Leu Asp Asn Tyr Arg Gly Tyr Ser Leu Gly Asn Trp Val Cys Ala Ala
             20                  25                  30
```

-continued

```
Lys Phe Glu Ser Asn Phe Asn Thr Gly Ala Thr Asn Arg Asn Thr Asp
        35                  40                  45

Gly Ser Thr Asp Tyr Gly Ile Leu Gln Ile Asn Ser Arg Trp Trp Cys
    50                  55                  60

Asn Asp Gly Arg Thr Pro Gly Ser Lys Asn Leu Cys His Ile Pro Cys
 65                 70                  75                  80

Ser Ala Leu Leu Ser Ser Asp Ile Thr Ala Ser Val Asn Cys Ala Lys
                85                  90                  95

Lys Ile Val Ser Asp Gly Asn Gly Met Asn Ala Trp Val Ala Trp Arg
            100                 105                 110

Lys His Cys Lys Gly Thr Asp Val Asn Val Trp Ile Arg Gly Cys Arg
        115                 120                 125

Leu


<210> SEQ ID NO 104
<211> LENGTH: 129
<212> TYPE: PRT
<213> ORGANISM: Ortalis vetula

<400> SEQUENCE: 104

Lys Ile Tyr Lys Arg Cys Glu Leu Ala Ala Ala Met Lys Arg Tyr Gly
  1               5                  10                  15

Leu Asp Asn Tyr Arg Gly Tyr Ser Leu Gly Asn Trp Val Cys Ala Ala
            20                  25                  30

Arg Tyr Glu Ser Asn Tyr Asn Thr Gln Ala Thr Asn Arg Asn Ser Asn
        35                  40                  45

Gly Ser Thr Asp Tyr Gly Ile Leu Gln Ile Asn Ser Arg Trp Trp Cys
    50                  55                  60

Asn Asp Gly Arg Thr Pro Gly Thr Lys Asn Leu Cys His Ile Ser Cys
 65                 70                  75                  80

Ser Ala Leu Met Gly Ala Asp Ile Ala Pro Ser Val Arg Cys Ala Lys
                85                  90                  95

Arg Ile Val Ser Asp Gly Asp Gly Met Asn Ala Trp Val Ala Trp Arg
            100                 105                 110

Lys His Cys Lys Gly Thr Asp Val Ser Thr Trp Ile Lys Asp Cys Lys
        115                 120                 125

Leu


<210> SEQ ID NO 105
<211> LENGTH: 129
<212> TYPE: PRT
<213> ORGANISM: Capra aegagrus

<400> SEQUENCE: 105

Lys Val Phe Glu Arg Cys Glu Leu Ala Arg Thr Leu Lys Lys Leu Gly
  1               5                  10                  15

Leu Asp Asp Tyr Lys Gly Val Ser Leu Ala Asn Trp Leu Cys Leu Thr
            20                  25                  30

Lys Trp Glu Ser Gly Tyr Asn Thr Lys Ala Thr Asn Tyr Asn Pro Gly
        35                  40                  45

Ser Glu Ser Thr Asp Tyr Gly Ile Phe Gln Ile Asn Ser Lys Phe Trp
    50                  55                  60

Cys Asn Asp Gly Lys Thr Pro Asp Ala Val Asp Gly Cys His Val Ser
 65                 70                  75                  80

Cys Ser Glu Leu Met Glu Asn Asp Ile Glu Lys Ala Val Ala Cys Ala
```

-continued

```
                85                  90                  95

Lys His Ile Val Ser Glu Gln Gly Ile Thr Ala Trp Val Ala Trp Lys
            100                 105                 110

Ser His Cys Arg Asp His Asp Val Ser Ser Tyr Val Glu Gly Cys Thr
        115                 120                 125

Leu


<210> SEQ ID NO 106
<211> LENGTH: 129
<212> TYPE: PRT
<213> ORGANISM: Ovis aries

<400> SEQUENCE: 106

Lys Val Phe Glu Arg Cys Glu Leu Ala Arg Thr Leu Lys Lys Leu Gly
  1               5                  10                  15

Leu Asp Asp Tyr Lys Gly Val Ser Leu Ala Asn Trp Leu Cys Leu Ser
            20                  25                  30

Lys Trp Glu Ser Gly Tyr Asn Thr Lys Ala Thr Asn Tyr Asn Pro Gly
         35                  40                  45

Ser Glu Ser Thr Asp Tyr Gly Ile Phe Gln Ile Asn Ser Lys Trp Trp
     50                  55                  60

Cys Asn Asp Gly Lys Thr Pro Asn Ala Val Asp Gly Cys His Val Ser
 65                  70                  75                  80

Cys Ser Ala Leu Met Glu Asn Asp Ile Glu Lys Ala Val Ala Cys Ala
                85                  90                  95

Lys His Ile Val Ser Glu Gln Gly Ile Thr Ala Trp Val Ala Trp Lys
            100                 105                 110

Ser His Cys Arg Val His Asp Val Ser Ser Tyr Val Glu Gly Cys Lys
        115                 120                 125

Leu


<210> SEQ ID NO 107
<211> LENGTH: 129
<212> TYPE: PRT
<213> ORGANISM: Capra aegagrus

<400> SEQUENCE: 107

Lys Val Phe Glu Arg Cys Glu Leu Ala Arg Thr Leu Lys Glu Leu Gly
  1               5                  10                  15

Leu Asp Gly Tyr Lys Gly Val Ser Leu Ala Asn Trp Leu Cys Leu Thr
            20                  25                  30

Lys Trp Glu Ser Ser Tyr Asn Thr Lys Ala Thr Asn Tyr Asn Pro Gly
         35                  40                  45

Ser Glu Ser Thr Asp Tyr Gly Ile Phe Gln Ile Asn Ser Lys Phe Trp
     50                  55                  60

Cys Asn Asp Gly Lys Thr Pro Asn Ala Val Asp Gly Cys His Val Ser
 65                  70                  75                  80

Cys Ser Glu Leu Met Glu Asn Asn Ile Ala Lys Ala Val Ala Cys Ala
                85                  90                  95

Lys Gln Ile Val Ser Glu Gln Gly Ile Thr Ala Trp Val Ala Trp Lys
            100                 105                 110

Ser His Cys Arg Asp His Asp Val Ser Ser Tyr Val Glu Gly Cys Thr
        115                 120                 125

Leu
```

```
<210> SEQ ID NO 108
<211> LENGTH: 129
<212> TYPE: PRT
<213> ORGANISM: Bos taurus

<400> SEQUENCE: 108

Lys Val Phe Glu Arg Cys Glu Leu Ala Arg Thr Leu Lys Lys Leu Gly
  1               5                  10                  15

Leu Asp Gly Tyr Lys Gly Val Ser Leu Ala Asn Trp Leu Cys Leu Thr
             20                  25                  30

Lys Trp Glu Ser Ser Tyr Asn Thr Lys Ala Thr Asn Tyr Asn Pro Ser
         35                  40                  45

Ser Glu Ser Thr Asp Tyr Gly Ile Phe Gln Ile Asn Ser Lys Trp Trp
     50                  55                  60

Cys Asn Asp Gly Lys Thr Pro Asn Ala Val Asp Gly Cys His Val Ser
 65                  70                  75                  80

Cys Arg Glu Leu Met Glu Asn Asp Ile Ala Lys Ala Val Ala Cys Ala
                 85                  90                  95

Lys His Ile Val Ser Glu Gln Gly Ile Thr Ala Trp Val Ala Trp Lys
            100                 105                 110

Ser His Cys Arg Asp His Asp Val Ser Ser Tyr Val Glu Gly Cys Thr
        115                 120                 125

Leu


<210> SEQ ID NO 109
<211> LENGTH: 129
<212> TYPE: PRT
<213> ORGANISM: Bos taurus

<400> SEQUENCE: 109

Lys Val Phe Glu Arg Cys Glu Leu Ala Arg Thr Leu Lys Lys Leu Gly
  1               5                  10                  15

Leu Asp Gly Tyr Lys Gly Val Ser Leu Ala Asn Trp Leu Cys Leu Thr
             20                  25                  30

Lys Trp Glu Ser Ser Tyr Asn Thr Lys Ala Thr Asn Tyr Asn Pro Ser
         35                  40                  45

Ser Glu Ser Thr Asp Tyr Gly Ile Phe Gln Ile Asn Ser Lys Trp Trp
     50                  55                  60

Cys Asn Asp Gly Lys Thr Pro Asn Ala Val Asp Gly Cys His Val Ser
 65                  70                  75                  80

Cys Ser Glu Leu Met Glu Asn Asp Ile Ala Lys Ala Val Ala Cys Ala
                 85                  90                  95

Lys His Ile Val Ser Glu Gln Gly Ile Thr Ala Trp Val Ala Trp Lys
            100                 105                 110

Ser His Cys Arg Asp His Asp Val Ser Ser Tyr Val Glu Gly Cys Thr
        115                 120                 125

Leu


<210> SEQ ID NO 110
<211> LENGTH: 129
<212> TYPE: PRT
<213> ORGANISM: Bos taurus

<400> SEQUENCE: 110

Lys Val Phe Glu Arg Cys Glu Leu Ala Arg Thr Leu Lys Lys Leu Gly
  1               5                  10                  15

Leu Asp Gly Tyr Lys Gly Val Ser Leu Ala Asn Trp Leu Cys Leu Thr
```

-continued

```
            20                  25                  30

Lys Trp Glu Ser Ser Tyr Asn Thr Lys Ala Thr Asn Tyr Asn Pro Ser
        35                  40                  45

Ser Glu Ser Thr Asp Tyr Gly Ile Phe Gln Ile Asn Ser Lys Trp Trp
    50                  55                  60

Cys Asn Asp Gly Lys Thr Pro Asn Ala Val Asp Gly Cys His Val Ser
65                  70                  75                  80

Cys Ser Glu Leu Met Glu Asn Asp Ile Ala Lys Ala Val Ala Cys Ala
                85                  90                  95

Lys His Ile Val Ser Glu Gln Gly Ile Thr Ala Trp Val Ala Trp Lys
            100                 105                 110

Ser His Cys Arg Asp His Asp Val Ser Ser Tyr Val Gln Gly Cys Thr
        115                 120                 125

Leu


<210> SEQ ID NO 111
<211> LENGTH: 129
<212> TYPE: PRT
<213> ORGANISM: Bos taurus

<400> SEQUENCE: 111

Lys Val Phe Glu Arg Cys Glu Leu Ala Arg Thr Leu Lys Lys Leu Gly
1               5                   10                  15

Leu Asp Gly Tyr Lys Gly Val Ser Leu Ala Asn Trp Leu Cys Leu Thr
            20                  25                  30

Lys Trp Glu Ser Ser Tyr Asn Thr Lys Ala Thr Asn Tyr Asn Pro Gly
        35                  40                  45

Ser Glu Ser Thr Asp Tyr Gly Ile Phe Gln Ile Asn Ser Lys Trp Trp
    50                  55                  60

Cys Asn Asp Gly Lys Thr Pro Asn Ala Val Asp Gly Cys His Val Ser
65                  70                  75                  80

Cys Ser Glu Leu Met Glu Asn Asp Ile Ala Lys Ala Val Ala Cys Ala
                85                  90                  95

Lys Gln Ile Val Ser Glu Gln Gly Ile Thr Ala Trp Val Ala Trp Lys
            100                 105                 110

Ser His Cys Arg Asp His Asp Val Ser Ser Tyr Val Glu Gly Cys Thr
        115                 120                 125

Leu


<210> SEQ ID NO 112
<211> LENGTH: 129
<212> TYPE: PRT
<213> ORGANISM: Ovis aries

<400> SEQUENCE: 112

Lys Val Phe Glu Arg Cys Glu Leu Ala Arg Thr Leu Lys Glu Leu Gly
1               5                   10                  15

Leu Asp Gly Tyr Lys Gly Val Ser Leu Ala Asn Trp Leu Cys Leu Thr
            20                  25                  30

Lys Trp Glu Ser Ser Tyr Asn Thr Lys Ala Thr Asn Tyr Asn Pro Gly
        35                  40                  45

Ser Glu Ser Thr Asp Tyr Gly Ile Phe Gln Ile Asn Ser Lys Trp Trp
    50                  55                  60

Cys Asn Asp Gly Lys Thr Pro Asn Ala Val Asp Gly Cys His Val Ser
65                  70                  75                  80
```

-continued

```
Cys Ser Glu Leu Met Glu Asn Asn Ile Ala Lys Ala Val Ala Cys Ala
                 85                  90                  95

Lys His Ile Val Ser Glu Gln Gly Ile Thr Ala Trp Val Ala Trp Lys
            100                 105                 110

Ser His Cys Arg Asp His Asp Val Ser Ser Tyr Val Glu Gly Cys Ser
        115                 120                 125

Leu


<210> SEQ ID NO 113
<211> LENGTH: 129
<212> TYPE: PRT
<213> ORGANISM: Ovis aries

<400> SEQUENCE: 113

Lys Val Phe Glu Arg Cys Glu Leu Ala Arg Thr Leu Lys Glu Leu Gly
  1               5                  10                  15

Leu Asp Gly Tyr Lys Gly Val Ser Leu Ala Asn Trp Leu Cys Leu Thr
            20                  25                  30

Lys Trp Glu Ser Ser Tyr Asn Thr Lys Ala Thr Asn Tyr Asn Pro Gly
        35                  40                  45

Ser Glu Ser Thr Asp Tyr Gly Ile Phe Gln Ile Asn Ser Lys Trp Trp
     50                  55                  60

Cys Asn Asp Gly Lys Thr Pro Asn Ala Val Asp Gly Cys His Val Ser
 65                  70                  75                  80

Cys Ser Glu Leu Met Glu Asn Asn Ile Ala Lys Ala Val Ala Cys Ala
                 85                  90                  95

Lys His Ile Val Ser Glu Gln Gly Ile Thr Ala Trp Val Ala Trp Lys
            100                 105                 110

Ser His Cys Arg Asp His Asp Val Ser Ser Tyr Val Glu Gly Cys Ser
        115                 120                 125

Leu


<210> SEQ ID NO 114
<211> LENGTH: 129
<212> TYPE: PRT
<213> ORGANISM: Cervus elaphus

<400> SEQUENCE: 114

Lys Val Phe Glu Arg Cys Glu Leu Ala Arg Thr Leu Lys Glu Leu Gly
  1               5                  10                  15

Leu Asp Gly Tyr Lys Gly Val Ser Leu Ala Asn Trp Leu Cys Leu Thr
            20                  25                  30

Lys Trp Glu Ser Ser Tyr Asn Thr Lys Ala Thr Asn Tyr Asn Pro Gly
        35                  40                  45

Ser Glu Ser Thr Asp Tyr Gly Ile Phe Gln Ile Asn Ser Lys Trp Trp
     50                  55                  60

Cys Asp Asp Gly Lys Thr Pro Asn Ala Val Asp Gly Cys His Val Ala
 65                  70                  75                  80

Cys Ser Glu Leu Met Glu Asn Asn Ile Asp Lys Ala Val Thr Cys Ala
                 85                  90                  95

Lys Gln Ile Val Arg Glu Gln Gly Ile Thr Ala Trp Val Ala Trp Lys
            100                 105                 110

Ser His Cys Arg Gly His Asp Val Ser Ser Tyr Val Glu Gly Cys Thr
        115                 120                 125

Leu
```

-continued

<210> SEQ ID NO 115
<211> LENGTH: 129
<212> TYPE: PRT
<213> ORGANISM: Bos taurus

<400> SEQUENCE: 115

```
Lys Thr Phe Lys Arg Cys Glu Leu Ala Lys Thr Leu Lys Asn Leu Gly
  1               5                  10                  15

Leu Ala Gly Tyr Lys Gly Val Ser Leu Ala Asn Trp Met Cys Leu Ala
             20                  25                  30

Lys Gly Glu Ser Asn Tyr Asn Thr Gln Ala Lys Asn Tyr Asn Pro Gly
         35                  40                  45

Ser Lys Ser Thr Asp Tyr Gly Ile Phe Gln Ile Asn Ser Lys Trp Trp
     50                  55                  60

Cys Asn Asp Gly Lys Thr Pro Lys Ala Val Asn Gly Cys Gly Val Ser
 65                  70                  75                  80

Cys Ser Ala Leu Leu Lys Asp Asp Ile Thr Gln Ala Val Ala Cys Ala
                 85                  90                  95

Lys Lys Ile Val Ser Gln Gln Gly Ile Thr Ala Trp Val Ala Trp Lys
            100                 105                 110

Asn Lys Cys Arg Asn Arg Asp Leu Thr Ser Tyr Val Lys Gly Cys Gly
        115                 120                 125

Val
```

<210> SEQ ID NO 116
<211> LENGTH: 128
<212> TYPE: PRT
<213> ORGANISM: Sus scrofa

<400> SEQUENCE: 116

```
Lys Val Tyr Asp Arg Cys Glu Phe Ala Arg Ile Leu Lys Lys Ser Gly
  1               5                  10                  15

Met Asp Gly Tyr Arg Gly Val Ser Leu Ala Asn Trp Tyr Cys Leu Ala
             20                  25                  30

Lys Trp Glu Ser Asp Phe Asn Thr Lys Ala Ile Asn Arg Asn Val Gly
         35                  40                  45

Ser Thr Asp Tyr Gly Ile Phe Gln Ile Asn Ser Arg Tyr Trp Cys Asn
     50                  55                  60

Asp Gly Lys Thr Pro Lys Ala Val Asn Ala Cys His Ile Ser Cys Lys
 65                  70                  75                  80

Val Leu Leu Asp Asp Asp Leu Ser Gln Asp Ile Glu Cys Ala Lys Arg
                 85                  90                  95

Val Val Arg Asp Pro Gln Gly Ile Lys Ala Trp Val Ala Trp Arg Thr
            100                 105                 110

His Cys Gln Asn Lys Asp Val Ser Gln Tyr Ile Arg Gly Cys Lys Leu
        115                 120                 125
```

<210> SEQ ID NO 117
<211> LENGTH: 128
<212> TYPE: PRT
<213> ORGANISM: Sus scrofa

<400> SEQUENCE: 117

```
Lys Val Tyr Asp Arg Cys Glu Phe Ala Arg Ile Leu Lys Lys Ser Gly
  1               5                  10                  15

Met Asp Gly Tyr Arg Gly Val Ser Leu Ala Asn Trp Val Cys Leu Ala
             20                  25                  30
```

```
Lys Trp Glu Ser Asp Phe Asn Thr Lys Ala Ile Asn His Asn Val Gly
        35                  40                  45

Ser Thr Asp Tyr Gly Ile Phe Gln Ile Asn Ser Arg Tyr Trp Cys Asn
    50                  55                  60

Asp Gly Lys Thr Pro Lys Ala Val Asn Ala Cys His Ile Ser Cys Lys
65                  70                  75                  80

Val Leu Leu Asp Asp Asp Leu Ser Gln Asp Ile Glu Cys Ala Lys Arg
                85                  90                  95

Val Val Arg Asp Pro Leu Gly Val Lys Ala Trp Val Ala Trp Arg Ala
            100                 105                 110

His Cys Gln Asn Lys Asp Val Ser Gln Tyr Ile Arg Gly Cys Lys Leu
        115                 120                 125


<210> SEQ ID NO 118
<211> LENGTH: 130
<212> TYPE: PRT
<213> ORGANISM: Sus scrofa

<400> SEQUENCE: 118

Lys Val Tyr Asp Arg Cys Glu Phe Ala Arg Ile Leu Lys Lys Ser Gly
1               5                   10                  15

Met Asp Gly Tyr Arg Gly Val Ser Leu Ala Asn Trp Val Cys Leu Ala
            20                  25                  30

Lys Trp Glu Ser Asn Phe Asn Thr Lys Ala Thr Asn Tyr Asn Pro Gly
        35                  40                  45

Ser Gln Ser Thr Asp Tyr Gly Ile Phe Gln Ile Asn Ser Arg Tyr Trp
    50                  55                  60

Cys Asn Asp Gly Lys Thr Pro Lys Ala Val Asn Ala Cys His Ile Ser
65                  70                  75                  80

Cys Lys Val Leu Leu Asp Asp Asp Leu Ser Gln Asp Ile Glu Cys Ala
                85                  90                  95

Lys Arg Val Val Arg Asp Pro Gln Gly Ile Lys Ala Trp Val Ala Trp
            100                 105                 110

Lys Ala His Cys Gln Asn Lys Asp Val Ser Gln Tyr Ile Arg Gly Cys
        115                 120                 125

Lys Leu
    130


<210> SEQ ID NO 119
<211> LENGTH: 129
<212> TYPE: PRT
<213> ORGANISM: Rattus norvegicus

<400> SEQUENCE: 119

Lys Ile Tyr Glu Arg Cys Gln Phe Ala Arg Thr Leu Lys Arg Asn Gly
1               5                   10                  15

Met Ser Gly Tyr Tyr Gly Val Ser Leu Ala Asp Trp Val Cys Leu Ala
            20                  25                  30

Gln His Glu Ser Asn Tyr Asn Thr Gln Ala Arg Asn Tyr Asn Pro Gly
        35                  40                  45

Asp Gln Ser Thr Asp Tyr Gly Ile Phe Gln Ile Asn Ser Tyr Trp Cys
    50                  55                  60

Asn Asp Gly Lys Thr Pro Arg Ala Lys Asn Ala Cys Gly Ile Pro Cys
65                  70                  75                  80

Ser Ala Leu Leu Gln Asp Asp Ile Thr Gln Ala Ile Ala Cys Ala Lys
                85                  90                  95
```

-continued

```
Arg Val Val Arg Asp Pro Gln Gly Ile Arg Ala Trp Val Ala Trp Gln
            100                 105                 110

Arg His Cys Lys Asn Arg Asp Leu Ser Gly Tyr Ile Arg Asn Cys Gly
        115                 120                 125

Val


<210> SEQ ID NO 120
<211> LENGTH: 130
<212> TYPE: PRT
<213> ORGANISM: Mus musculus

<400> SEQUENCE: 120

Lys Val Tyr Glu Arg Cys Glu Phe Ala Arg Thr Leu Lys Arg Asn Gly
  1               5                  10                  15

Met Ala Gly Tyr Tyr Gly Val Ser Leu Ala Asp Trp Val Cys Leu Ala
            20                  25                  30

Gln His Glu Ser Asn Tyr Asn Thr Arg Ala Thr Asn Tyr Asn Arg Gly
        35                  40                  45

Asp Gln Ser Thr Asp Tyr Gly Ile Phe Gln Ile Asn Ser Arg Tyr Trp
    50                  55                  60

Cys Asn Asp Gly Lys Thr Pro Thr Ala Val Asn Ala Cys Gly Ile Asn
 65                  70                  75                  80

Cys Ser Ala Leu Leu Gln Asp Asp Ile Thr Ala Ala Ile Gln Cys Ala
                 85                  90                  95

Lys Arg Val Val Arg Asp Pro Gln Gly Ile Arg Ala Trp Val Ala Trp
            100                 105                 110

Arg Ala His Cys Gln Asn Arg Asp Leu Ser Gln Tyr Ile Arg Asn Cys
        115                 120                 125

Gly Val
    130


<210> SEQ ID NO 121
<211> LENGTH: 130
<212> TYPE: PRT
<213> ORGANISM: Mus musculus

<400> SEQUENCE: 121

Lys Val Tyr Asn Arg Cys Glu Leu Ala Arg Ile Leu Lys Arg Asn Gly
  1               5                  10                  15

Met Asp Gly Tyr Arg Gly Val Lys Leu Ala Asp Trp Val Cys Leu Ala
            20                  25                  30

Gln His Glu Ser Asn Tyr Asn Thr Arg Ala Thr Asn Tyr Asn Arg Gly
        35                  40                  45

Asp Arg Ser Thr Asp Tyr Gly Ile Phe Gln Ile Asn Ser Arg Tyr Trp
    50                  55                  60

Cys Asn Asp Gly Lys Thr Pro Arg Ser Lys Asn Ala Cys Gly Ile Asn
 65                  70                  75                  80

Cys Ser Ala Leu Leu Gln Asp Asp Ile Thr Ala Ala Ile Gln Cys Ala
                 85                  90                  95

Lys Arg Val Val Arg Asp Pro Gln Gly Ile Arg Ala Trp Val Ala Trp
            100                 105                 110

Arg Thr Gln Cys Gln Asn Arg Asp Leu Ser Gln Tyr Ile Arg Asn Cys
        115                 120                 125

Gly Val
    130
```

-continued

<210> SEQ ID NO 122
<211> LENGTH: 128
<212> TYPE: PRT
<213> ORGANISM: Rattus norvegicus

<400> SEQUENCE: 122

Lys Val Phe Lys His Cys Glu Leu Ala Arg Ile Leu Arg Ser Ser Ala
1 5 10 15

Gly Tyr Arg Gly Val Ser Leu Glu Asn Trp Met Cys Met Ala Gln His
20 25 30

Glu Ser Asn Phe Asp Thr Glu Ala Ile Asn Tyr Asn Ser Thr Asp Gln
35 40 45

Ser Thr Asp Tyr Gly Ile Phe Gln Ile Asn Ser Arg Tyr Trp Cys Asn
50 55 60

Asp Gly Lys Thr Pro Arg Ala Val Asn Ala Cys Gly Ile Pro Cys Ser
65 70 75 80

Ala Leu Leu Gln Asp Asp Ile Thr Gln Ala Ile Gln Cys Ala Lys Arg
85 90 95

Val Val Arg Asp Pro Gln Gly Ile Arg Ala Trp Val Ala Trp Gln Arg
100 105 110

His Cys Gln Asn Arg Asp Leu Ser Gly Tyr Ile Arg Asn Cys Gly Val
115 120 125

<210> SEQ ID NO 123
<211> LENGTH: 130
<212> TYPE: PRT
<213> ORGANISM: Canis familiaris

<400> SEQUENCE: 123

Lys Ile Phe Glu Arg Cys Glu Leu Ala Arg Thr Leu Lys Asn Leu Gly
1 5 10 15

Leu Ala Gly Tyr Lys Gly Val Ser Leu Ala Asn Trp Val Cys Leu Ala
20 25 30

Lys Trp Glu Ser Asn Tyr Asn Thr Arg Ala Thr Asn Tyr Asn Pro Gly
35 40 45

Ser Lys Ser Thr Asp Tyr Gly Ile Phe Gln Ile Asn Ser Arg Tyr Trp
50 55 60

Cys Asn Asp Gly Lys Thr Pro Arg Ala Val Asn Ala Cys His Ile Ser
65 70 75 80

Cys Ser Ala Leu Leu Gln Asp Asp Ile Thr Gln Ala Val Ala Cys Ala
85 90 95

Lys Arg Val Val Ser Asp Pro Asn Gly Ile Arg Ala Trp Val Ala Trp
100 105 110

Arg Ala His Cys Glu Asn Arg Asp Val Ser Gln Tyr Val Arg Asn Cys
115 120 125

Gly Val
130

<210> SEQ ID NO 124
<211> LENGTH: 130
<212> TYPE: PRT
<213> ORGANISM: Oryctolagus cuniculus

<400> SEQUENCE: 124

Lys Ile Tyr Glu Arg Cys Glu Leu Ala Arg Thr Leu Lys Lys Leu Gly
1 5 10 15

Leu Asp Gly Tyr Lys Gly Val Ser Leu Ala Asn Trp Met Cys Leu Ala

-continued

```
            20                  25                  30

Lys Trp Glu Ser Ser Tyr Asn Thr Arg Ala Thr Asn Tyr Asn Pro Gly
        35                  40                  45

Asp Lys Ser Thr Asp Tyr Gly Ile Phe Gln Ile Asn Ser Arg Tyr Trp
    50                  55                  60

Cys Asn Asp Gly Lys Thr Pro Arg Ala Val Asn Ala Cys His Ile Pro
 65                  70                  75                  80

Cys Ser Asp Leu Leu Lys Asp Asp Ile Thr Gln Ala Val Ala Cys Ala
                 85                  90                  95

Lys Arg Val Val Ser Asp Pro Gln Gly Ile Arg Ala Trp Val Ala Trp
            100                 105                 110

Arg Asn His Cys Gln Asn Gln Asp Leu Thr Pro Tyr Ile Arg Gly Cys
        115                 120                 125

Gly Val
    130


<210> SEQ ID NO 125
<211> LENGTH: 130
<212> TYPE: PRT
<213> ORGANISM: Cebus apella

<400> SEQUENCE: 125

Lys Ile Phe Glu Arg Cys Glu Leu Ala Arg Thr Leu Lys Arg Leu Gly
  1               5                  10                  15

Leu Asp Gly Tyr Arg Gly Ile Ser Leu Ala Asn Trp Val Cys Leu Ala
            20                  25                  30

Lys Trp Glu Ser Asp Tyr Asn Thr Gln Ala Thr Asn Tyr Asn Pro Gly
        35                  40                  45

Asp Gln Ser Thr Asp Tyr Gly Ile Phe Gln Ile Asn Ser His Tyr Trp
    50                  55                  60

Cys Asn Asn Gly Lys Thr Pro Gly Ala Val Asn Ala Cys Arg Ile Ser
 65                  70                  75                  80

Cys Asn Ala Leu Leu Gln Asp Asn Ile Ala Asp Ala Val Thr Cys Ala
                 85                  90                  95

Lys Arg Val Val Arg Asp Pro Gln Gly Ile Arg Ala Trp Val Ala Trp
            100                 105                 110

Arg Asn His Cys Gln Asn Arg Asp Val Ser Gln Tyr Val Gln Gly Cys
        115                 120                 125

Gly Val
    130


<210> SEQ ID NO 126
<211> LENGTH: 130
<212> TYPE: PRT
<213> ORGANISM: Cebus apella

<400> SEQUENCE: 126

Lys Ile Phe Glu Arg Cys Glu Leu Ala Arg Thr Leu Lys Arg Leu Gly
  1               5                  10                  15

Leu Asp Gly Tyr Arg Gly Ile Ser Leu Ala Asn Trp Val Cys Leu Ala
            20                  25                  30

Lys Trp Glu Ser Asp Tyr Asn Thr Gln Ala Thr Asn Tyr Asn Pro Gly
        35                  40                  45

Asp Gln Ser Thr Asp Tyr Gly Ile Phe Gln Ile Asn Ser His Tyr Trp
    50                  55                  60

Cys Asn Asn Gly Lys Thr Pro Gly Ala Val Asn Ala Cys His Ile Ser
```

-continued

```
 65                  70                  75                  80

Cys Asn Ala Leu Leu Gln Asp Asn Ile Ala Asp Ala Val Thr Cys Ala
                 85                  90                  95

Lys Arg Val Val Arg Asp Pro Gln Gly Ile Arg Ala Trp Val Ala Trp
            100                 105                 110

Arg Asn His Cys His Asn Arg Asp Val Ser Gln Tyr Val Gln Gly Cys
        115                 120                 125

Gly Val
    130


<210> SEQ ID NO 127
<211> LENGTH: 130
<212> TYPE: PRT
<213> ORGANISM: Felis sp.

<400> SEQUENCE: 127

Lys Ile Phe Glu Arg Cys Glu Leu Ala Arg Thr Leu Lys Arg Leu Gly
  1               5                  10                  15

Leu Asp Gly Tyr Arg Gly Ile Ser Leu Ala Asn Trp Val Cys Leu Ala
             20                  25                  30

Lys Trp Glu Ser Gly Tyr Asn Thr Gln Ala Thr Asn Tyr Asn Pro Gly
         35                  40                  45

Asp Gln Ser Thr Asp Tyr Gly Ile Phe Gln Ile Asn Ser His Tyr Trp
     50                  55                  60

Cys Asn Asn Gly Lys Thr Pro Gly Ala Val Asn Ala Cys His Ile Ser
 65                  70                  75                  80

Cys Asn Ala Leu Leu Gln Asp Asn Ile Ala Asp Ala Val Thr Cys Ala
                 85                  90                  95

Lys Arg Val Val Arg Asp Pro Gln Gly Ile Arg Ala Trp Val Ala Trp
            100                 105                 110

Arg Asn His Cys Gln Asn Arg Asp Val Ser Gln Tyr Val Gln Gly Cys
        115                 120                 125

Gly Val
    130


<210> SEQ ID NO 128
<211> LENGTH: 130
<212> TYPE: PRT
<213> ORGANISM: Macaca mulatta

<400> SEQUENCE: 128

Lys Ile Phe Glu Arg Cys Glu Leu Ala Arg Thr Leu Lys Arg Leu Gly
  1               5                  10                  15

Leu Asp Gly Tyr Arg Gly Ile Ser Leu Ala Asn Trp Val Cys Leu Ala
             20                  25                  30

Lys Trp Glu Ser Asn Tyr Asn Thr Gln Ala Thr Asn Tyr Asn Pro Gly
         35                  40                  45

Asp Gln Ser Thr Asp Tyr Gly Ile Phe Gln Ile Asn Ser His Tyr Trp
     50                  55                  60

Cys Asn Asn Gly Lys Thr Pro Gly Ala Val Asn Ala Cys His Ile Ser
 65                  70                  75                  80

Cys Asn Ala Leu Leu Gln Asp Asn Ile Ala Asp Ala Val Thr Cys Ala
                 85                  90                  95

Lys Arg Val Val Ser Asp Pro Gln Gly Ile Arg Ala Trp Val Ala Trp
            100                 105                 110

Arg Asn His Cys Gln Asn Arg Asp Val Ser Gln Tyr Val Gln Gly Cys
```

-continued

```
        115                 120                 125

Gly Val
    130


<210> SEQ ID NO 129
<211> LENGTH: 130
<212> TYPE: PRT
<213> ORGANISM: Papio sp.

<400> SEQUENCE: 129

Lys Ile Phe Glu Arg Cys Glu Leu Ala Arg Thr Leu Lys Arg Leu Gly
  1               5                  10                  15

Leu Asp Gly Tyr Arg Gly Ile Ser Leu Ala Asn Trp Val Cys Leu Ala
             20                  25                  30

Lys Trp Glu Ser Asp Tyr Asn Thr Gln Ala Thr Asn Tyr Asn Pro Gly
         35                  40                  45

Asp Gln Ser Thr Asp Tyr Gly Ile Phe Gln Ile Asn Ser His Tyr Trp
     50                  55                  60

Cys Asn Asn Gly Lys Thr Pro Gly Ala Val Asn Ala Cys His Ile Ser
 65                  70                  75                  80

Cys Asn Ala Leu Leu Gln Asp Asn Ile Ala Asp Ala Val Thr Cys Ala
                 85                  90                  95

Lys Arg Val Val Ser Asp Pro Gln Gly Ile Arg Ala Trp Val Ala Trp
            100                 105                 110

Glu Asn His Cys Gln Asn Arg Asp Val Ser Gln Tyr Val Gln Gly Cys
        115                 120                 125

Gly Val
    130


<210> SEQ ID NO 130
<211> LENGTH: 130
<212> TYPE: PRT
<213> ORGANISM: Callithrix jacchus

<400> SEQUENCE: 130

Lys Val Phe Glu Arg Cys Glu Leu Ala Arg Thr Leu Lys Arg Phe Gly
  1               5                  10                  15

Leu Asp Gly Tyr Arg Gly Ile Ser Leu Ala Asn Trp Met Cys Leu Ala
             20                  25                  30

Lys Trp Glu Ser Asp Tyr Asn Thr Arg Ala Thr Asn Tyr Asn Pro Gly
         35                  40                  45

Asp Gln Ser Thr Asp Tyr Gly Ile Phe Gln Ile Asn Ser His Tyr Trp
     50                  55                  60

Cys Asn Asn Gly Arg Thr Pro Gly Ala Val Asn Ala Cys His Ile Ser
 65                  70                  75                  80

Cys Asn Ala Leu Leu Gln Asp Asp Ile Thr Glu Ala Val Ala Cys Ala
                 85                  90                  95

Lys Arg Val Val Arg Asp Pro Gln Gly Ile Arg Ala Trp Val Ala Trp
            100                 105                 110

Lys Ala His Cys Gln Asn Arg Asp Val Ser Gln Tyr Val Gln Gly Cys
        115                 120                 125

Gly Val
    130


<210> SEQ ID NO 131
<211> LENGTH: 130
<212> TYPE: PRT
```

-continued

<213> ORGANISM: Tamarindus indica

<400> SEQUENCE: 131

```
Lys Val Phe Glu Arg Cys Glu Leu Ala Arg Thr Leu Lys Arg Phe Gly
  1               5                  10                  15

Leu Asp Gly Tyr Arg Gly Ile Ser Leu Ala Asn Trp Met Cys Leu Ala
             20                  25                  30

Lys Trp Glu Ser Asp Tyr Asn Thr Arg Ala Thr Asn Tyr Asn Pro Gly
         35                  40                  45

Asp Gln Ser Thr Asp Tyr Gly Ile Phe Gln Ile Asn Ser His Tyr Trp
     50                  55                  60

Cys Asn Asn Gly Arg Thr Pro Gly Ala Val Asn Ala Cys His Ile Ser
 65                  70                  75                  80

Cys Asn Ala Leu Leu Gln Asp Asp Ile Thr Glu Ala Val Ala Cys Ala
                 85                  90                  95

Lys Arg Val Val Arg Asp Pro Gln Gly Ile Arg Ala Trp Val Ala Trp
            100                 105                 110

Lys Ala His Cys Gln Asn Arg Asp Val Ser Gln Tyr Ile Gln Gly Cys
        115                 120                 125

Gly Val
    130
```

<210> SEQ ID NO 132
<211> LENGTH: 130
<212> TYPE: PRT
<213> ORGANISM: Saimiri sp.

<400> SEQUENCE: 132

```
Lys Val Phe Glu Arg Cys Glu Leu Ala Arg Thr Leu Lys Arg Leu Gly
  1               5                  10                  15

Leu Asp Gly Tyr Arg Gly Ile Ser Leu Ala Asn Trp Met Cys Leu Ala
             20                  25                  30

Lys Trp Glu Ser Asp Tyr Asn Thr Arg Ala Thr Asn Tyr Asn Pro Gly
         35                  40                  45

Asp Gln Ser Thr Asp Tyr Gly Ile Phe Gln Ile Asn Ser His Tyr Trp
     50                  55                  60

Cys Asn Asn Gly Arg Thr Pro Gly Ala Val Asn Ala Cys His Ile Ser
 65                  70                  75                  80

Cys Asn Ala Leu Leu Gln Asp Asp Ile Thr Gln Ala Val Ala Cys Ala
                 85                  90                  95

Lys Arg Val Val Arg Asp Pro Gln Gly Ile Arg Ala Trp Val Ala Trp
            100                 105                 110

Lys Ala His Cys Gln Asn Arg Asp Val Ser Gln Tyr Val Gln Gly Cys
        115                 120                 125

Gly Val
    130
```

<210> SEQ ID NO 133
<211> LENGTH: 130
<212> TYPE: PRT
<213> ORGANISM: Gorilla gorilla

<400> SEQUENCE: 133

```
Lys Val Phe Glu Arg Cys Glu Leu Ala Arg Thr Leu Lys Arg Leu Gly
  1               5                  10                  15

Met Asp Gly Tyr Arg Gly Ile Ser Leu Ala Asn Trp Met Cys Leu Ala
             20                  25                  30
```

-continued

```
Lys Trp Glu Ser Gly Tyr Asn Thr Arg Ala Thr Asn Tyr Asn Pro Gly
        35                  40                  45

Asp Gln Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys His Leu Ser
65                  70                  75                  80

Cys Ser Ala Leu Leu Gln Asp Asn Ile Ala Asp Ala Val Ala Cys Ala
                85                  90                  95

Lys Arg Val Val Arg Asp Pro Gln Gly Ile Arg Ala Trp Val Ala Trp
            100                 105                 110

Arg Asn Arg Cys Gln Asn Arg Asp Val Arg Gln Tyr Val Gln Gly Cys
        115                 120                 125

Gly Val
    130


<210> SEQ ID NO 134
<211> LENGTH: 130
<212> TYPE: PRT
<213> ORGANISM: Homo sapiens

<400> SEQUENCE: 134

Lys Val Phe Glu Arg Cys Glu Leu Ala Arg Thr Leu Lys Arg Leu Gly
1               5                   10                  15

Met Asp Gly Tyr Arg Gly Ile Ser Leu Ala Asn Trp Met Cys Leu Ala
            20                  25                  30

Lys Trp Glu Ser Gly Tyr Asn Thr Arg Ala Thr Asn Tyr Asn Ala Gly
        35                  40                  45

Asp Arg Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys His Leu Ser
65                  70                  75                  80

Cys Ser Ala Leu Leu Gln Asp Asn Ile Ala Asp Ala Val Ala Cys Ala
                85                  90                  95

Lys Arg Val Val Arg Asp Pro Gln Gly Ile Arg Ala Trp Val Ala Trp
            100                 105                 110

Arg Asn Arg Cys Gln Asn Arg Asp Val Arg Gln Tyr Val Gln Gly Cys
        115                 120                 125

Gly Val
    130


<210> SEQ ID NO 135
<211> LENGTH: 130
<212> TYPE: PRT
<213> ORGANISM: Pongo pygmaeus

<400> SEQUENCE: 135

Lys Val Phe Glu Arg Cys Glu Leu Ala Arg Thr Leu Lys Arg Leu Gly
1               5                   10                  15

Met Asp Gly Tyr Arg Gly Ile Ser Leu Ala Asn Trp Met Cys Leu Ala
            20                  25                  30

Lys Trp Glu Ser Gly Tyr Asn Thr Arg Ala Thr Asn Tyr Asn Ala Gly
        35                  40                  45

Asp Arg Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys His Leu Ser
65                  70                  75                  80
```

-continued

```
Cys Ser Ala Leu Leu Gln Asp Asn Ile Ala Asp Ala Val Ala Cys Ala
                85                  90                  95

Lys Arg Val Val Arg Asp Pro Gln Gly Ile Arg Ala Trp Val Ala Trp
            100                 105                 110

Arg Asn Arg Cys Gln Asn Arg Asp Val Arg Gln Tyr Val Gln Gly Cys
        115                 120                 125

Gly Val
    130


<210> SEQ ID NO 136
<211> LENGTH: 130
<212> TYPE: PRT
<213> ORGANISM: Gibbon sp.

<400> SEQUENCE: 136

Lys Val Phe Glu Arg Cys Glu Leu Ala Arg Thr Leu Lys Arg Leu Gly
  1               5                  10                  15

Met Asp Gly Tyr Arg Gly Ile Ser Leu Ala Asn Trp Met Cys Leu Ala
             20                  25                  30

Lys Trp Glu Ser Gly Tyr Asn Thr Arg Ala Thr Asn Tyr Asn Pro Gly
         35                  40                  45

Asp Arg Ser Thr Asp Tyr Gly Ile Phe Gln Ile Asn Ser Arg Tyr Trp
     50                  55                  60

Cys Asn Asp Gly Lys Thr Pro Gly Ala Val Asn Ala Cys His Leu Ser
 65                  70                  75                  80

Cys Asn Ala Leu Leu Gln Ser Asn Ile Ala Asp Ala Val Ala Cys Ala
                85                  90                  95

Lys Arg Val Val Arg Asp Pro Gln Gly Ile Arg Ala Trp Val Ala Trp
            100                 105                 110

Arg Asn Arg Cys Gln Asn Arg Asp Leu Arg Gln Tyr Ile Gln Gly Cys
        115                 120                 125

Gly Val
    130


<210> SEQ ID NO 137
<211> LENGTH: 130
<212> TYPE: PRT
<213> ORGANISM: Colobus sp.

<400> SEQUENCE: 137

Lys Val Phe Glu Arg Cys Glu Leu Ala Arg Thr Leu Lys Arg Leu Gly
  1               5                  10                  15

Met Asp Gly Tyr Arg Gly Ile Ser Leu Ala Asn Trp Met Cys Leu Ala
             20                  25                  30

Lys Trp Glu Ser Gly Tyr Asn Thr Arg Ala Thr Asn Tyr Asn Pro Gly
         35                  40                  45

Asp Arg Ser Thr Asp Tyr Gly Ile Phe Gln Ile Asn Ser Arg Tyr Trp
     50                  55                  60

Cys Asn Asp Gly Lys Thr Pro Gly Ala Val Asn Ala Cys His Ile Ser
 65                  70                  75                  80

Cys Asn Ala Leu Leu Gln Asn Asn Ile Ala Asp Ala Val Ala Cys Ala
                85                  90                  95

Lys Arg Val Val Ser Asp Pro Gln Gly Ile Arg Ala Trp Val Ala Trp
            100                 105                 110

Lys Lys His Cys Gln Asn Arg Asp Val Ser Gln Tyr Val Glu Gly Cys
        115                 120                 125
```

-continued

```
Gly Val
    130


<210> SEQ ID NO 138
<211> LENGTH: 130
<212> TYPE: PRT
<213> ORGANISM: Cebus apella

<400> SEQUENCE: 138

Lys Ile Phe Glu Arg Cys Glu Leu Ala Arg Thr Leu Lys Lys Leu Gly
  1               5                  10                  15

Leu Asp Gly Tyr Lys Gly Val Ser Leu Ala Asn Trp Val Cys Leu Ala
             20                  25                  30

Lys Trp Glu Ser Gly Tyr Asn Thr Asp Ala Thr Asn Tyr Asn Pro Gly
         35                  40                  45

Asp Glu Ser Thr Asp Tyr Gly Ile Phe Gln Ile Asn Ser Arg Tyr Trp
     50                  55                  60

Cys Asn Asn Gly Lys Thr Pro Gly Ala Val Asp Ala Cys His Ile Ser
 65                  70                  75                  80

Cys Ser Ala Leu Leu Gln Asn Asn Ile Ala Asp Ala Val Ala Cys Ala
                 85                  90                  95

Lys Arg Val Val Ser Asp Pro Gln Gly Ile Arg Ala Trp Val Ala Trp
            100                 105                 110

Arg Asn His Cys Gln Asn Arg Asp Val Ser Gln Tyr Val Lys Gly Cys
        115                 120                 125

Gly Val
    130


<210> SEQ ID NO 139
<211> LENGTH: 130
<212> TYPE: PRT
<213> ORGANISM: Cebus apella

<400> SEQUENCE: 139

Lys Ile Phe Glu Arg Cys Glu Leu Ala Arg Thr Leu Lys Lys Leu Gly
  1               5                  10                  15

Leu Asp Gly Tyr Lys Gly Val Ser Leu Ala Asn Trp Val Cys Leu Ala
             20                  25                  30

Lys Trp Glu Ser Gly Tyr Asn Thr Glu Ala Thr Asn Tyr Asn Pro Gly
         35                  40                  45

Asp Glu Ser Thr Asp Tyr Gly Ile Phe Gln Ile Asn Ser Arg Tyr Trp
     50                  55                  60

Cys Asn Asn Gly Lys Thr Pro Gly Ala Val Asp Ala Cys His Ile Ser
 65                  70                  75                  80

Cys Ser Ala Leu Leu Gln Asn Asn Ile Ala Asp Ala Val Ala Cys Ala
                 85                  90                  95

Lys Arg Val Val Ser Asp Pro Gln Gly Ile Arg Ala Trp Val Ala Trp
            100                 105                 110

Arg Asn His Cys Gln Asn Lys Asp Val Ser Gln Tyr Val Lys Gly Cys
        115                 120                 125

Gly Val
    130


<210> SEQ ID NO 140
<211> LENGTH: 130
<212> TYPE: PRT
<213> ORGANISM: Cebus apella
```

```
<400> SEQUENCE: 140

Lys Ile Phe Glu Arg Cys Glu Leu Ala Arg Thr Leu Lys Lys Leu Gly
 1               5                  10                  15

Leu Asp Gly Tyr Lys Gly Val Ser Leu Ala Asn Trp Val Cys Leu Ala
            20                  25                  30

Lys Trp Glu Ser Gly Tyr Asn Thr Glu Ala Thr Asn Tyr Asn Pro Gly
        35                  40                  45

Asp Glu Ser Thr Asp Tyr Gly Ile Phe Gln Ile Asn Ser Arg Tyr Trp
    50                  55                  60

Cys Asn Asn Gly Lys Thr Pro Gly Ala Val Asp Ala Cys His Ile Ser
65                  70                  75                  80

Cys Ser Ala Leu Leu Gln Asn Asn Ile Ala Asp Ala Val Ala Cys Ala
                85                  90                  95

Lys Arg Val Val Ser Asp Pro Gln Gly Ile Arg Ala Trp Val Ala Trp
            100                 105                 110

Arg Asn His Cys Gln Asn Lys Asp Val Ser Gln Tyr Val Lys Gly Cys
        115                 120                 125

Gly Val
    130


<210> SEQ ID NO 141
<211> LENGTH: 130
<212> TYPE: PRT
<213> ORGANISM: Cebus apella

<400> SEQUENCE: 141

Lys Ile Phe Glu Arg Cys Glu Leu Ala Arg Thr Leu Lys Lys Leu Gly
 1               5                  10                  15

Leu Asp Gly Tyr Lys Gly Val Ser Leu Ala Asn Trp Val Cys Leu Ala
            20                  25                  30

Lys Trp Glu Ser Gly Tyr Asn Thr Glu Ala Thr Asn Tyr Asn Pro Gly
        35                  40                  45

Asp Glu Ser Thr Asp Tyr Gly Ile Phe Gln Ile Asn Ser Arg Tyr Trp
    50                  55                  60

Cys Asn Asn Gly Lys Thr Pro Gly Ala Val Asp Ala Cys His Ile Ser
65                  70                  75                  80

Cys Ser Ala Leu Leu Gln Asn Asn Ile Ala Asp Ala Val Ala Cys Ala
                85                  90                  95

Lys Arg Val Val Ser Asp Pro Gln Gly Val Arg Ala Trp Val Ala Trp
            100                 105                 110

Arg Asn His Cys Gln Asn Lys Asp Val Ser Gln Tyr Val Lys Gly Cys
        115                 120                 125

Gly Val
    130


<210> SEQ ID NO 142
<211> LENGTH: 130
<212> TYPE: PRT
<213> ORGANISM: Ovis aries

<400> SEQUENCE: 142

Lys Val Phe Glu Arg Cys Glu Leu Ala Arg Thr Leu Lys Arg Phe Gly
 1               5                  10                  15

Met Asp Gly Phe Arg Gly Ile Ser Leu Ala Asn Trp Met Gly Leu Ala
            20                  25                  30
```

-continued

Arg Trp Glu Ser Ser Tyr Asn Thr Gln Ala Thr Asn Tyr Asn Ser Gly
35 40 45

Asp Arg Ser Thr Asp Tyr Gly Ile Phe Gln Ile Asn Ser His Trp Trp
50 55 60

Cys Asn Asp Gly Lys Thr Pro Gly Ala Val Asn Ala Cys His Ile Pro
65 70 75 80

Cys Ser Ala Leu Leu Gln Asp Asp Ile Thr Gln Ala Val Ala Cys Ala
85 90 95

Lys Arg Val Val Ser Asp Pro Gln Gly Ile Arg Ala Trp Val Ala Trp
100 105 110

Arg Ser His Cys Gln Asn Gln Asp Leu Thr Ser Tyr Ile Gln Gly Cys
115 120 125

Gly Val
130

<210> SEQ ID NO 143
<211> LENGTH: 130
<212> TYPE: PRT
<213> ORGANISM: Bos taurus

<400> SEQUENCE: 143

Lys Val Phe Glu Arg Cys Glu Leu Ala Arg Ser Leu Lys Arg Phe Gly
1 5 10 15

Met Asp Asn Phe Arg Gly Ile Ser Leu Ala Asn Trp Met Cys Leu Ala
20 25 30

Arg Trp Glu Ser Asn Tyr Asn Thr Gln Ala Thr Asn Tyr Asn Ala Gly
35 40 45

Asp Gln Ser Thr Asp Tyr Gly Ile Phe Gln Ile Asn Ser His Trp Trp
50 55 60

Cys Asn Asp Gly Lys Thr Pro Gly Ala Val Asn Ala Cys His Leu Pro
65 70 75 80

Cys Gly Ala Leu Leu Gln Asp Asp Ile Thr Gln Ala Val Ala Cys Thr
85 90 95

Lys Arg Asp Val Ser Asp Pro Gln Gly Ile Arg Ala Trp Val Ala Trp
100 105 110

Arg Ser His Cys Gln Asn Gln Asp Leu Thr Ser Tyr Ile Gln Gly Cys
115 120 125

Gly Val
130

<210> SEQ ID NO 144
<211> LENGTH: 128
<212> TYPE: PRT
<213> ORGANISM: Camelus bactrianus

<400> SEQUENCE: 144

Lys Val Trp Glu Arg Cys Ala Arg Lys Leu Lys Glu Leu Gly Met Asp
1 5 10 15

Gly Tyr Arg Gly Val Ser Leu Ala Asn Trp Met Cys Leu Thr Lys Trp
20 25 30

Glu Ser Asp Tyr Asn Thr Asp Ala Thr Asn Tyr Asn Pro Ser Ser Glu
35 40 45

Ser Thr Asp Tyr Gly Ile Phe Gln Ile Asn Ser Arg Tyr Trp Cys Asn
50 55 60

Asn Gly Lys Thr Pro His Ala Val Asn Gly Cys Gly Ile Asn Cys Asn
65 70 75 80

-continued

```
Val Leu Leu Glu Asp Asp Ile Thr Lys Ala Val Gln Cys Ala Lys Arg
                85                  90                  95

Val Val Arg Asp Pro Gln Gly Val Arg Ala Trp Val Ala Trp Lys Asn
            100                 105                 110

His Cys Glu Gly His Asp Val Glu Gln Tyr Val Glu Gly Cys Asp Leu
        115                 120                 125
```

<210> SEQ ID NO 145
<211> LENGTH: 129
<212> TYPE: PRT
<213> ORGANISM: Didelphis albiventris

<400> SEQUENCE: 145

```
Lys Arg Met Glu Arg Cys Glu Phe Ala Arg Arg Ile Lys Gln Leu His
  1               5                  10                  15

Leu Asp Gly Tyr His Gln Ile Ser Leu Ala Asn Trp Val Cys Leu Ala
            20                  25                  30

Gln Trp Glu Ser Gly Phe Asp Thr Lys Ala Thr Asn Tyr Asn Pro Gly
        35                  40                  45

Asp Gln Ser Thr Asp Tyr Gly Ile Leu Gln Ile Asn Ser His Tyr Trp
    50                  55                  60

Cys Asp Asp Gly Lys Thr Pro His Ala Ala Asn Glu Cys Lys Val Arg
 65                  70                  75                  80

Cys Ser Glu Leu Gln Glu Asp Asp Leu Val Lys Ala Val Asn Cys Ala
                85                  90                  95

Lys Lys Ile Val Asp Gln Gln Gly Ile Arg Ala Trp Val Ala Trp Arg
            100                 105                 110

Asn Lys Cys Glu Gly Lys Asp Leu Ser Lys Tyr Leu Glu Gly Cys His
        115                 120                 125

Leu
```

<210> SEQ ID NO 146
<211> LENGTH: 129
<212> TYPE: PRT
<213> ORGANISM: Salmo sp.

<400> SEQUENCE: 146

```
Lys Val Tyr Asp Arg Cys Glu Leu Ala Arg Ala Leu Lys Ala Ser Gly
  1               5                  10                  15

Met Asp Gly Tyr Ala Gly Asn Ser Leu Pro Asn Trp Val Cys Leu Ser
            20                  25                  30

Lys Trp Glu Ser Ser Tyr Asn Thr Gln Ala Thr Asn Arg Asn Thr Asp
        35                  40                  45

Gly Ser Thr Asp Tyr Gly Ile Phe Gln Ile Asn Ser Arg Tyr Trp Cys
    50                  55                  60

Asp Asp Gly Arg Thr Pro Gly Ala Lys Asn Val Cys Gly Ile His Cys
 65                  70                  75                  80

Ser Gln Leu Leu Thr Asp Asp Leu Thr Val Ala Ile Arg Cys Ala Lys
                85                  90                  95

Arg Val Val Leu Asp Pro Asn Gly Ile Gly Ala Trp Val Ala Trp Arg
            100                 105                 110

Leu His Cys Gln Asn Gln Asp Leu Arg Ser Tyr Val Ala Gly Cys Gly
        115                 120                 125

Val
```

<210> SEQ ID NO 147

-continued

```
<211> LENGTH: 128
<212> TYPE: PRT
<213> ORGANISM: Platichthys sp.

<400> SEQUENCE: 147

Arg Val Tyr Glu Arg Cys Glu Trp Ala Arg Leu Leu Arg Asn Gln Gly
  1               5                  10                  15

Met Asp Gly Tyr Arg Gly Ile Ser Leu Ala Asn Trp Val Cys Leu Thr
             20                  25                  30

Glu Trp Glu Ser His Tyr Asn Thr Arg Ala Thr Asn His Asn Thr Asp
         35                  40                  45

Gly Ser Thr Asp Tyr Gly Ile Phe Gln Ile Asn Ser Arg Trp Trp Cys
     50                  55                  60

Asn Asp Ser Gln Thr Pro Thr Ser Asn Ala Cys Asn Ile Arg Cys Ser
 65                  70                  75                  80

Glu Leu Leu Thr Asp Asp Val Ile Val Ala Ile Lys Cys Ala Lys Arg
                 85                  90                  95

Val Val Arg Asp Pro Asn Gly Ile Gly Ala Trp Val Ala Trp Arg Gln
            100                 105                 110

His Cys Gln Gly Gln Asp Leu Ser Ser Tyr Leu Ala Gly Cys Gly Leu
        115                 120                 125


<210> SEQ ID NO 148
<211> LENGTH: 128
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 148

Lys Val Phe Glu Arg Cys Glu Trp Ala Arg Leu Leu Lys Arg Asn Gly
  1               5                  10                  15

Met Ser Asn Tyr Arg Gly Ile Ser Leu Ala Asp Trp Val Cys Leu Ser
             20                  25                  30

Gln Trp Glu Ser Ser Tyr Asn Thr Arg Ala Thr Asn Arg Asn Thr Asp
         35                  40                  45

Gly Ser Thr Asp Tyr Gly Ile Phe Gln Ile Asn Ser Arg Trp Trp Cys
     50                  55                  60

Asp Asn Gly Gln Thr Pro Thr Ser Asn Ala Cys Gly Ile Ser Cys Ser
 65                  70                  75                  80

Ala Leu Leu Thr Asp Asp Val Gly Ala Ala Ile Ile Cys Ala Lys His
                 85                  90                  95

Val Val Arg Asp Pro Asn Gly Ile Gly Ala Trp Val Ala Trp Lys Arg
            100                 105                 110

His Cys Gln Gly Gln Asp Leu Ser Ser Tyr Val Ala Gly Cys Gly Val
        115                 120                 125


<210> SEQ ID NO 149
<211> LENGTH: 129
<212> TYPE: PRT
<213> ORGANISM: Canis familiaris

<400> SEQUENCE: 149

Lys Ile Phe Ser Lys Cys Glu Leu Ala Arg Lys Leu Lys Ser Met Gly
  1               5                  10                  15

Met Asp Gly Phe His Gly Tyr Ser Leu Ala Asn Trp Val Cys Met Ala
             20                  25                  30
```

-continued

```
Glu Tyr Glu Ser Asn Phe Asn Thr Gln Ala Phe Asn Gly Arg Asn Ser
        35                  40                  45

Asn Gly Ser Ser Asp Tyr Gly Ile Phe Gln Leu Asn Ser Lys Trp Trp
    50                  55                  60

Cys Lys Ser Asn Ser His Ser Ser Ala Asn Ala Cys Asn Ile Asn Cys
65                  70                  75                  80

Ser Lys Phe Leu Asp Asp Asn Ile Asp Asp Asp Ile Ala Cys Ala Lys
                85                  90                  95

Arg Trp Trp Lys Asp Pro Asn Gly Met Ser Ala Trp Val Ala Trp Val
            100                 105                 110

Lys His Cys Lys Gly Lys Asp Leu Ser Lys Tyr Leu Ala Ser Cys Asn
        115                 120                 125

Leu


<210> SEQ ID NO 150
<211> LENGTH: 129
<212> TYPE: PRT
<213> ORGANISM: Equus caballus

<400> SEQUENCE: 150

Lys Val Phe Ser Lys Cys Glu Leu Ala His Lys Leu Lys Ala Gln Glu
  1               5                  10                  15

Met Asp Gly Phe Gly Gly Tyr Ser Leu Ala Asn Trp Val Cys Met Ala
            20                  25                  30

Glu Tyr Glu Ser Asn Phe Asn Thr Arg Ala Phe Asn Gly Lys Asn Ala
        35                  40                  45

Asn Gly Ser Ser Asp Tyr Gly Leu Phe Gln Leu Asn Asn Lys Trp Trp
    50                  55                  60

Cys Lys Asp Asn Lys Arg Ser Ser Ser Asn Ala Cys Asn Ile Met Cys
65                  70                  75                  80

Ser Lys Leu Leu Asp Glu Asn Ile Asp Asp Ile Ser Cys Ala Lys
                85                  90                  95

Arg Val Val Arg Asp Pro Lys Gly Met Ser Ala Trp Lys Ala Trp Val
            100                 105                 110

Lys His Cys Lys Asp Lys Asp Leu Ser Glu Tyr Leu Ala Ser Cys Asn
        115                 120                 125

Leu


<210> SEQ ID NO 151
<211> LENGTH: 129
<212> TYPE: PRT
<213> ORGANISM: Equus asinus

<400> SEQUENCE: 151

Lys Val Phe Ser Lys Cys Glu Leu Ala His Lys Leu Lys Ala Gln Glu
  1               5                  10                  15

Met Asp Gly Phe Gly Gly Tyr Ser Leu Ala Asn Trp Val Cys Met Ala
            20                  25                  30

Glu Tyr Glu Ser Asn Phe Asn Thr Arg Ala Phe Asn Gly Lys Asn Ala
        35                  40                  45

Asn Gly Ser Tyr Asp Tyr Gly Leu Phe Gln Leu Asn Ser Lys Trp Trp
    50                  55                  60

Cys Lys Asp Asn Lys Arg Ser Ser Ser Asn Ala Cys Asn Ile Met Cys
65                  70                  75                  80

Ser Lys Leu Leu Asp Asp Asn Ile Asp Asp Asp Ile Ser Cys Ala Lys
                85                  90                  95
```

-continued

```
Arg Val Val Arg Asp Pro Lys Gly Met Ser Ala Trp Lys Ala Trp Val
            100                 105                 110

Lys His Cys Lys Asp Lys Asp Leu Ser Glu Tyr Leu Ala Ser Cys Asn
        115                 120                 125

Leu


<210> SEQ ID NO 152
<211> LENGTH: 125
<212> TYPE: PRT
<213> ORGANISM: Tachyglossus aculeatus

<400> SEQUENCE: 152

Lys Ile Leu Lys Lys Gln Glu Leu Cys Lys Asn Leu Val Ala Gln Gly
  1               5                  10                  15

Met Asn Gly Tyr Gln His Ile Thr Leu Pro Asn Trp Val Cys Thr Ala
             20                  25                  30

Phe His Glu Ser Ser Tyr Asn Thr Arg Ala Thr Asn His Asn Thr Asp
         35                  40                  45

Gly Ser Thr Asp Tyr Gly Ile Leu Gln Ile Asn Ser Arg Tyr Trp Cys
     50                  55                  60

His Asp Gly Lys Thr Pro Gly Ser Lys Asn Ala Cys Asn Ile Ser Cys
 65                  70                  75                  80

Ser Lys Leu Leu Asp Asp Asp Ile Thr Asp Asp Leu Lys Cys Ala Lys
                 85                  90                  95

Lys Ile Ala Gly Glu Ala Lys Gly Leu Thr Pro Trp Val Ala Trp Lys
            100                 105                 110

Ser Lys Cys Arg Gly His Asp Leu Ser Lys Phe Lys Cys
        115                 120                 125


<210> SEQ ID NO 153
<211> LENGTH: 129
<212> TYPE: PRT
<213> ORGANISM: Homo sapiens

<400> SEQUENCE: 153

Lys Ile Tyr Thr Arg Cys Lys Leu Ala Lys Ile Phe Ser Arg Ala Gly
  1               5                  10                  15

Leu Asp Asn Tyr Trp Gly Phe Ser Leu Gly Asn Trp Ile Cys Met Ala
             20                  25                  30

Tyr Tyr Glu Ser Gly Tyr Asn Thr Thr Ala Gln Thr Val Leu Asp Asp
         35                  40                  45

Gly Ser Ile Asp Tyr Gly Ile Phe Gln Ile Asn Ser Phe Ala Trp Cys
     50                  55                  60

Arg Arg Gly Lys Leu Lys Glu Asn Asn His Cys His Val Ala Cys Ser
 65                  70                  75                  80

Ala Leu Ile Thr Asp Asp Leu Thr Asp Ala Ile Ile Cys Ala Arg Lys
                 85                  90                  95

Ile Val Lys Glu Thr Gln Gly Met Asn Tyr His Gln Gly Trp Lys Lys
            100                 105                 110

His Cys Glu Gly Arg Asp Leu Ser Glu Trp Lys Lys Gly Cys Glu Val
        115                 120                 125

Ser


<210> SEQ ID NO 154
<211> LENGTH: 129
<212> TYPE: PRT
```

<213> ORGANISM: Mus musculus

<400> SEQUENCE: 154

```
Lys Ile Tyr Thr Arg Cys Lys Leu Ala Lys Ile Phe Ala Lys Ala Gly
  1               5                  10                  15

Leu Asp Asn Tyr Gly Gly Phe Ala Leu Gly Asn Trp Leu Cys Met Ala
             20                  25                  30

Tyr Tyr Glu Ser His Tyr Asn Thr Thr Ala Glu Asn Val Leu Glu Asp
         35                  40                  45

Gly Ser Thr Asp Tyr Gly Ile Phe Gln Ile Asn Ser Phe Thr Trp Cys
     50                  55                  60

Arg Asn Ala Arg Lys His Gln Lys Asn His Cys His Val Ala Cys Ser
 65                  70                  75                  80

Ala Leu Ile Thr Asp Asp Leu Thr Asp Ala Ile Leu Cys Ala Lys Lys
                 85                  90                  95

Ile Val Lys Glu Thr Gln Gly Met Asn Tyr His Gln Gly Trp Lys Lys
            100                 105                 110

Asn Cys Glu Asn Lys Asp Met Ser Glu Trp Lys Arg Gly Cys Glu Val
        115                 120                 125

Ser
```

<210> SEQ ID NO 155
<211> LENGTH: 127
<212> TYPE: PRT
<213> ORGANISM: Columba sp.

<400> SEQUENCE: 155

```
Lys Asp Ile Pro Arg Cys Glu Leu Val Lys Ile Leu Arg Arg His Gly
  1               5                  10                  15

Phe Glu Gly Phe Val Gly Lys Thr Val Ala Asn Trp Val Cys Leu Val
             20                  25                  30

Lys His Glu Ser Gly Tyr Arg Thr Thr Ala Phe Asn Asn Asn Gly Pro
         35                  40                  45

Asn Ser Arg Asp Tyr Gly Ile Phe Gln Ile Asn Ser Lys Tyr Trp Cys
     50                  55                  60

Asn Asp Gly Lys Thr Arg Gly Ser Lys Asn Ala Cys Asn Ile Asn Cys
 65                  70                  75                  80

Ser Lys Leu Arg Asp Asp Asn Ile Ala Asp Asp Ile Gln Cys Ala Lys
                 85                  90                  95

Lys Ile Ala Arg Glu Ala Arg Gly Leu Thr Pro Trp Val Ala Trp Lys
            100                 105                 110

Lys Tyr Cys Gln Gly Lys Asp Leu Ser Ser Tyr Val Arg Gly Cys
        115                 120                 125
```

<210> SEQ ID NO 156
<211> LENGTH: 118
<212> TYPE: PRT
<213> ORGANISM: Opisthocomus hoazin

<400> SEQUENCE: 156

```
Val Lys Ile Leu Arg Glu His Gly Phe Glu Gly Phe Glu Gly Thr Thr
  1               5                  10                  15

Ile Ala Asp Trp Ile Cys Leu Val Gln His Glu Ser Asp Tyr Asn Thr
             20                  25                  30

Glu Ala Tyr Asn Asn Asn Gly Pro Ser Arg Asp Tyr Gly Ile Phe Gln
         35                  40                  45
```

-continued

```
Ile Asn Ser Lys Tyr Trp Cys Asn Asp Gly Lys Thr Ser Gly Ala Val
     50                  55                  60

Asp Gly Cys His Ile Ser Cys Ser Glu Leu Met Thr Asn Asp Leu Glu
 65                  70                  75                  80

Asp Asp Ile Lys Cys Ala Lys Lys Ile Ala Arg Asp Ala His Gly Leu
                 85                  90                  95

Thr Pro Trp Tyr Gly Trp Lys Asn His Cys Glu Gly Arg Asp Leu Ser
            100                 105                 110

Ser Tyr Val Lys Gly Cys
        115


<210> SEQ ID NO 157
<211> LENGTH: 125
<212> TYPE: PRT
<213> ORGANISM: Mus musculus

<400> SEQUENCE: 157

Arg Cys Ser Leu Ala Lys Ile Leu Tyr Glu Glu Asp Leu Asp Gly Phe
  1               5                  10                  15

Glu Gly Tyr Ser Leu Pro Asp Trp Leu Cys Leu Ala Phe Val Glu Ser
            20                  25                  30

Asn Phe Asn Ile Ser Lys Val Asn Glu Asn Val Asp Gly Ser Phe Asp
        35                  40                  45

Tyr Gly Ile Phe Gln Ile Asn Ser Arg Tyr Trp Cys Asn Asp Tyr Gln
     50                  55                  60

Ser His Ser Glu Asn Phe Cys His Val Asp Cys Gln Glu Leu Leu Ser
 65                  70                  75                  80

Pro Asn Leu Ile Ser Thr Ile His Cys Ala Lys Lys Ile Val Ser Gly
                 85                  90                  95

Pro Gly Gly Met Lys Asn Trp Val Glu Trp Lys Leu His Cys Leu Gly
            100                 105                 110

Arg Pro Leu Ser Tyr Trp Met Thr Gly Cys His Leu Gly
        115                 120                 125


<210> SEQ ID NO 158
<211> LENGTH: 118
<212> TYPE: PRT
<213> ORGANISM: Anopheles sp.

<400> SEQUENCE: 158

Lys Thr Phe Gly Lys Cys Glu Leu Ala Lys Ala Asn Asn Gly Ile Ala
  1               5                  10                  15

Lys Ala Ser Leu Pro Asp Trp Val Cys Leu Val Gln Asn Glu Ser Ala
            20                  25                  30

Phe Ser Thr Ser Ala Thr Asn Lys Asn Lys Asn Gly Ser Thr Asp Tyr
        35                  40                  45

Gly Ile Phe Gln Ile Asn Asn Lys Tyr Trp Cys Asp Ser Gly Tyr Gly
     50                  55                  60

Ser Asn Asp Cys Lys Ile Ala Cys Lys Asn Leu Leu Asn Asp Asp Ile
 65                  70                  75                  80

Thr Asp Asp Ile Lys Cys Ala Lys Leu Ile His Lys Arg His Gly Phe
                 85                  90                  95

Asn Ala Trp Tyr Gly Trp Lys Asn His Cys Asn Gly Lys Lys Leu Pro
            100                 105                 110

Asn Val Ser Ser Cys Phe
        115
```

-continued

<210> SEQ ID NO 159
<211> LENGTH: 119
<212> TYPE: PRT
<213> ORGANISM: Bombix mori

<400> SEQUENCE: 159

```
Lys Thr Phe Thr Arg Cys Gly Leu Val His Glu Leu Arg Lys His Gly
  1               5                  10                  15

Phe Glu Glu Asn Leu Met Arg Asn Trp Val Cys Leu Val Glu His Glu
             20                  25                  30

Ser Ser Arg Asp Thr Ser Lys Thr Asn Thr Asn Arg Asn Gly Ser Lys
         35                  40                  45

Asp Tyr Gly Leu Phe Gln Ile Asn Asp Arg Tyr Trp Cys Ser Lys Gly
     50                  55                  60

Ala Ser Pro Gly Lys Asp Cys Asn Val Lys Cys Ser Asp Leu Leu Thr
 65                  70                  75                  80

Asp Asp Ile Thr Lys Ala Ala Lys Cys Ala Lys Lys Ile Tyr Lys Arg
                 85                  90                  95

His Arg Phe Asp Ala Trp Tyr Gly Trp Lys Asn His Cys Gln Gly Ser
            100                 105                 110

Leu Pro Asp Ile Ser Ser Cys
        115
```

<210> SEQ ID NO 160
<211> LENGTH: 120
<212> TYPE: PRT
<213> ORGANISM: Cecropia sp.

<400> SEQUENCE: 160

```
Lys Arg Phe Thr Arg Cys Gly Leu Val Gln Glu Leu Arg Arg Leu Gly
  1               5                  10                  15

Phe Asp Glu Thr Leu Met Ser Asn Trp Val Cys Leu Val Glu Asn Glu
             20                  25                  30

Ser Gly Arg Phe Thr Asp Lys Ile Gly Lys Val Asn Lys Asn Gly Ser
         35                  40                  45

Arg Asp Tyr Gly Leu Phe Gln Ile Asn Asp Lys Tyr Trp Cys Ser Lys
     50                  55                  60

Gly Thr Thr Pro Gly Lys Asp Cys Asn Val Thr Cys Asn Gln Leu Leu
 65                  70                  75                  80

Thr Asp Asp Ile Ser Val Ala Ala Thr Cys Ala Lys Lys Ile Tyr Lys
                 85                  90                  95

Arg His Lys Phe Asp Ala Trp Tyr Gly Trp Lys Asn His Cys Gln His
            100                 105                 110

Gly Leu Pro Asp Ile Ser Asp Cys
        115                 120
```

<210> SEQ ID NO 161
<211> LENGTH: 120
<212> TYPE: PRT
<213> ORGANISM: Bombyx mori

<400> SEQUENCE: 161

```
Lys Arg Phe Thr Arg Cys Gly Leu Val Gln Glu Leu Arg Arg Gln Gly
  1               5                  10                  15

Phe Asp Glu Ser Leu Met Ser Asn Trp Val Cys Leu Val Glu Asn Glu
             20                  25                  30

Ser Gly Arg Phe Thr Asp Lys Ile Gly Lys Val Asn Lys Asn Gly Ser
```

-continued

```
        35                  40                  45

Arg Asp Tyr Gly Leu Phe Gln Ile Asn Asp Lys Tyr Trp Cys Ser Thr
     50                  55                  60

Gly Ser Thr Pro Gly Lys Asp Cys His Val Thr Cys Asn Gln Leu Leu
 65                  70                  75                  80

Thr Asp Asp Ile Ser Val Ala Ala Thr Cys Ala Lys Lys Ile Tyr Lys
                 85                  90                  95

Arg His Lys Phe Asp Ala Trp Tyr Gly Trp Lys Asn His Cys Gln His
            100                 105                 110

Gly Leu Pro Asp Ile Ser Asp Cys
        115                 120


<210> SEQ ID NO 162
<211> LENGTH: 120
<212> TYPE: PRT
<213> ORGANISM: Pieris sp.

<400> SEQUENCE: 162

Lys Tyr Phe Ala Thr Asn Cys Glu Leu Val His Glu Leu Arg Arg Gln
  1               5                  10                  15

Gly Phe Pro Glu Asp Lys Met Arg Asp Trp Val Cys Leu Ile Gln Asn
             20                  25                  30

Glu Ser Gly Arg Asn Thr Ser Lys Met Gly Thr Ile Asn Lys Asn Gly
        35                  40                  45

Ser Arg Asp Tyr Gly Leu Phe Gln Ile Asn Asp Lys Tyr Trp Cys Ser
     50                  55                  60

Lys Thr Ser Thr Pro Gly Lys Asp Cys Asn Val Thr Cys Ala Glu Met
 65                  70                  75                  80

Leu Leu Asp Ile Thr Lys Ala Ser Lys Cys Ala Lys Lys Ile Tyr Lys
                 85                  90                  95

Arg His Lys Phe Gln Ala Trp Tyr Gly Trp Arg Asn His Cys Gln Gly
            100                 105                 110

Thr Leu Pro Asp Ile Ser Lys Cys
        115                 120


<210> SEQ ID NO 163
<211> LENGTH: 120
<212> TYPE: PRT
<213> ORGANISM: Manduca sexta

<400> SEQUENCE: 163

Lys His Phe Ser Arg Cys Glu Leu Val His Glu Leu Arg Arg Gln Gly
  1               5                  10                  15

Phe Pro Glu Asn Leu Met Arg Asp Trp Val Cys Leu Val Glu Asn Glu
             20                  25                  30

Ser Ser Arg Tyr Thr Asp Lys Val Gly Arg Val Asn Lys Asn Gly Ser
        35                  40                  45

Arg Asp Tyr Gly Leu Phe Gln Ile Asn Asp Lys Tyr Trp Cys Ser Asn
     50                  55                  60

Gly Ser Thr Pro Gly Lys Asp Cys Asn Val Lys Cys Ser Asp Leu Leu
 65                  70                  75                  80

Ile Asp Asp Ile Thr Lys Ala Ser Thr Cys Ala Lys Lys Ile Tyr Lys
                 85                  90                  95

Arg His Lys Phe Gln Ala Trp Tyr Gly Trp Arg Asn His Cys Gln Gly
            100                 105                 110

Ser Leu Pro Asp Ile Ser Ser Cys
```

-continued

```
        115                 120

<210> SEQ ID NO 164
<211> LENGTH: 122
<212> TYPE: PRT
<213> ORGANISM: Hyphantria cunea

<400> SEQUENCE: 164

Lys Tyr Tyr Ser Thr Arg Cys Asp Leu Val Arg Glu Leu Arg Lys Gln
  1               5                  10                  15

Gly Phe Pro Glu Asn Gln Met Gly Asp Trp Val Cys Leu Val Glu Asn
             20                  25                  30

Glu Ser Gly Arg Lys Thr Asp Lys Val Gly Pro Val Asn Lys Asn Gly
         35                  40                  45

Ser Lys Asp Tyr Gly Leu Phe Gln Ile Asn Asp Lys Tyr Trp Cys Ser
     50                  55                  60

Asn Thr Arg Thr Pro Gly Lys Asp Cys Asn Val Thr Cys Ala Asp Leu
 65                  70                  75                  80

Leu Leu Asp Asp Ile Thr Lys Ala Ser Thr Cys Ala Lys Lys Ile Phe
                 85                  90                  95

Lys Arg His Asn Phe Arg Ala Trp Tyr Gly Trp Arg Asn His Cys Asp
            100                 105                 110

Gly Lys Thr Leu Pro Asp Thr Ser Asn Cys
        115                 120

<210> SEQ ID NO 165
<211> LENGTH: 1087
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 165

gctatttctt tgttttttg agcacgtaaa acggcgccat ctcctttgaa ggctttcctg     60

cgccgggagc gcccatgtag cgaacggagt tactgtctat cagctcgtac agctctttct    120

cgtgcggtgc cttcgattgc tccgaggaca caagcgagag ttcgacaatt ccgtcttcac    180

gtaccatcca cgtaccgcga taggtaagag gagaaggtgc cgacttcttc tcaagggcaa    240

gctctacctt ttgcgcagtg ccatccgcgt tgaacgtcac agtcgtatcg attcccgggc    300

aatcggccgc aggtagcgta ccccgaaaga tacctccctt caacgcgcac tctacctttt    360

ccgctttggc cttcccggcg tgcggacaca cggttgtgca cgagacacag gatccacgcg    420

gaaccagatc cgattttgga ggatggtcgc caccaccaaa cgtggcttgc cagccctgca    480

aaggccatgc tatatacttg ctggatttca agtacttatc aatttgtggg atagcttcaa    540

tacgtttttt aaaacaaact aattttggga acgcatccag gcacattggg tccatgtata    600

aaacaacatc aagagcgtca tacaacatga agtcaggatg ggttacatga tcaccattta    660

aatatgtttt atgacataaa cgatcttcga acattttcag catttcaggt agcttgctaa    720

gaaaatcaac tttgagagtt tcaaagtctt tactatatgc aattctcgaa acaccgtatc    780

taatatccaa aaccgctcct tcaagcattg aaatctctgc acgctctttt ggacaaccac    840

ccaacatgtt gtgcttgtca gctatataac gtatgatggc catagactgt gttaatttaa    900

catcaccatc aatataataa ggaagattgg gaaactccaa acccaattca aactttttgt    960

ttcgccattt atcaccttca tcgcgctcat acaaatgctc ttcatatttt tcttcaagat   1020
```

-continued

```
attccaaaag aagtcgagtg ggttgcacaa ggcccttaat tttccaataa cctagtatag   1080

gggacat                                                             1087


<210> SEQ ID NO 166
<211> LENGTH: 143
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 166

Met Val Ser Cys Thr Thr Val Cys Pro His Ala Gly Lys Ala Lys Ala
1               5                   10                  15

Glu Lys Val Glu Cys Ala Leu Lys Gly Gly Ile Phe Arg Gly Thr Leu
            20                  25                  30

Pro Ala Ala Asp Cys Pro Gly Ile Asp Thr Thr Val Thr Phe Asn Ala
        35                  40                  45

Asp Gly Thr Ala Gln Lys Val Glu Leu Ala Leu Glu Lys Lys Ser Ala
    50                  55                  60

Pro Ser Pro Leu Thr Tyr Arg Gly Thr Trp Met Val Arg Glu Asp Gly
65                  70                  75                  80

Ile Val Glu Leu Ser Leu Val Ser Ser Glu Gln Ser Lys Ala Pro His
                85                  90                  95

Glu Lys Glu Leu Tyr Glu Leu Ile Asp Ser Asn Ser Val Arg Tyr Met
            100                 105                 110

Gly Ala Pro Gly Ala Gly Lys Pro Ser Lys Glu Met Ala Pro Phe Tyr
        115                 120                 125

Val Leu Lys Lys Thr Lys Lys Leu Glu His His His His His His
    130                 135                 140


<210> SEQ ID NO 167
<211> LENGTH: 157
<212> TYPE: PRT
<213> ORGANISM: Escherichia coli

<400> SEQUENCE: 167

Met Gly Arg Ile Ser Ser Gly Gly Met Met Phe Lys Ala Ile Thr Thr
1               5                   10                  15

Val Ala Ala Leu Val Ile Ala Thr Ser Ala Asn Ala Gln Asp Asp Leu
            20                  25                  30

Thr Ile Ser Ser Leu Ala Lys Gly Glu Thr Thr Lys Ala Ala Phe Asn
        35                  40                  45

Gln Met Val Gln Gly His Lys Leu Pro Ala Trp Val Met Lys Gly Gly
    50                  55                  60

Thr Tyr Thr Pro Ala Gln Thr Val Thr Leu Gly Asp Glu Thr Tyr Gln
65                  70                  75                  80

Val Met Ser Ala Cys Lys Pro His Asp Cys Gly Ser Gln Arg Ile Ala
                85                  90                  95

Val Asn Trp Ser Glu Lys Ser Asn Gln Met Thr Gly Leu Phe Ser Thr
            100                 105                 110

Ile Asp Glu Lys Thr Ser Gln Glu Lys Leu Thr Trp Leu Asn Val Asn
        115                 120                 125

Asp Ala Leu Ser Ile Asp Gly Lys Thr Val Leu Phe Ala Ala Leu Thr
    130                 135                 140

Gly Ser Leu Glu Asn His Pro Asp Gly Phe Asn Phe Lys
145                 150                 155
```

```
<210> SEQ ID NO 168
<211> LENGTH: 156
<212> TYPE: PRT
<213> ORGANISM: Treponema pallidum

<400> SEQUENCE: 168

Met Lys Gly Ser Val Arg Ala Leu Cys Ala Phe Leu Gly Val Gly Ala
1               5                   10                  15

Leu Gly Ser Ala Leu Cys Val Ser Cys Thr Thr Val Cys Pro His Ala
            20                  25                  30

Gly Lys Ala Lys Ala Glu Lys Val Glu Cys Ala Leu Lys Gly Gly Ile
        35                  40                  45

Phe Arg Gly Thr Leu Pro Ala Ala Asp Cys Pro Gly Ile Asp Thr Thr
    50                  55                  60

Val Thr Phe Asn Ala Asp Gly Thr Ala Gln Lys Val Glu Leu Ala Leu
65                  70                  75                  80

Glu Lys Lys Ser Ala Pro Ser Pro Leu Thr Tyr Arg Gly Thr Trp Met
                85                  90                  95

Val Arg Glu Asp Gly Ile Val Glu Leu Ser Leu Val Ser Ser Glu Gln
            100                 105                 110

Ser Lys Ala Pro His Glu Lys Glu Leu Tyr Glu Leu Ile Asp Ser Asn
        115                 120                 125

Ser Val Arg Tyr Met Gly Ala Pro Gly Ala Gly Lys Pro Ser Lys Glu
    130                 135                 140

Met Ala Pro Phe Tyr Val Leu Lys Lys Thr Lys Lys
145                 150                 155


<210> SEQ ID NO 169
<211> LENGTH: 155
<212> TYPE: PRT
<213> ORGANISM: Artificial Sequence
<220> FEATURE:
<223> OTHER INFORMATION: Description of Artificial Sequence: Synthetic
      protein
<220> FEATURE:
<221> NAME/KEY: MOD_RES
<222> LOCATION: (48)..(48)
<223> OTHER INFORMATION: X is a change V/I
<220> FEATURE:
<221> NAME/KEY: MOD_RES
<222> LOCATION: (74)..(74)
<223> OTHER INFORMATION: X is a conservative change D/E or
      semiconservative change D/N
<220> FEATURE:
<221> NAME/KEY: MOD_RES
<222> LOCATION: (77)..(77)
<223> OTHER INFORMATION: X is a conservative change D/E or
      semiconservative change D/N
<220> FEATURE:
<221> NAME/KEY: MOD_RES
<222> LOCATION: (112)..(112)
<223> OTHER INFORMATION: X is a conservative change D/E or
      semiconservative change D/N
<220> FEATURE:
<221> NAME/KEY: MOD_RES
<222> LOCATION: (127)..(127)
<223> OTHER INFORMATION: X is a conservative change D/E or
      semiconservative change D/N

<400> SEQUENCE: 169

Met Lys Gly Gly Gly Arg Ala Leu Cys Ala Ile Leu Gly Val Ala Ala
1               5                   10                  15

Leu Gly Ile Ala Leu Cys Ala Met Ala Gln Asp Asp Cys Pro His Ala
            20                  25                  30
```

-continued

```
Gly Leu Ala Lys Ala Glu Lys Thr Glu Ala Ala Leu Asn Gln Gly Xaa
        35                  40                  45

Gln Arg Gly Lys Leu Pro Ala Ala Asp Cys Lys Gly Gly Asp Thr Thr
    50                  55                  60

Pro Ala Gln Asn Ala Asp Gly Gly Ala Xaa Lys Tyr Xaa Leu Ala Leu
65                  70                  75                  80

Ala Cys Lys Pro Ala Asp Cys Gly Ser Gln Arg Gly Ala Trp Met Trp
                85                  90                  95

Arg Glu Asp Gly Asn Gln Glu Leu Gly Leu Phe Ser Ser Glu Glu Xaa
            100                 105                 110

Glu Lys Ala Pro Gln Glu Lys Leu Thr Glu Leu Asn Asp Asn Xaa Ala
        115                 120                 125

Leu Arg Ile Asp Gly Ala Pro Gly Ala Gly Ala Ala Leu Lys Glu Met
    130                 135                 140

Ala Glu Asn His Pro Asp Gly Lys Asn Lys Lys
145                 150                 155


<210> SEQ ID NO 170
<211> LENGTH: 92
<212> TYPE: PRT
<213> ORGANISM: Human herpesvirus 1

<400> SEQUENCE: 170

Met Ser Leu Arg Ala Val Trp His Leu Gly Leu Leu Gly Ser Leu Val
1               5                   10                  15

Gly Ala Val Leu Ala Ala Thr His Arg Gly Pro Ala Ala Asn Thr Thr
            20                  25                  30

Asp Pro Leu Thr His Ala Pro Val Ser Pro His Pro Ser Pro Leu Gly
        35                  40                  45

Gly Phe Ala Val Pro Leu Val Val Gly Gly Leu Cys Ala Val Val Leu
    50                  55                  60

Gly Ala Ala Cys Leu Leu Glu Leu Leu Arg Arg Thr Cys Arg Gly Trp
65                  70                  75                  80

Gly Arg Tyr His Pro Tyr Met Asp Pro Val Val Val
                85                  90


<210> SEQ ID NO 171
<211> LENGTH: 92
<212> TYPE: PRT
<213> ORGANISM: Human herpesvirus 2

<400> SEQUENCE: 171

Met Asp Arg Tyr Ala Val Arg Thr Trp Gly Ile Val Gly Ile Leu Gly
1               5                   10                  15

Cys Ala Ala Val Gly Ala Ala Pro Thr Gly Pro Ala Ser Asp Thr Thr
            20                  25                  30

Asn Ala Thr Ala Arg Leu Pro Thr His Pro Pro Leu Ile Arg Ser Gly
        35                  40                  45

Gly Phe Ala Val Pro Leu Ile Val Gly Gly Leu Cys Leu Met Ile Leu
    50                  55                  60

Gly Met Ala Cys Leu Leu Glu Val Leu Arg Arg Leu Gly Arg Glu Leu
65                  70                  75                  80

Ala Arg Cys Cys Pro His Ala Gly Gln Phe Ala Pro
                85                  90


<210> SEQ ID NO 172
```

-continued

<211> LENGTH: 92
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (30)..(30)
<223> OTHER INFORMATION: Asn or Asp
<220> FEATURE:
<221> NAME/KEY: MOD_RES
<222> LOCATION: (33)..(33)
<223> OTHER INFORMATION: Asn or Asp
<220> FEATURE:
<221> NAME/KEY: MOD_RES
<222> LOCATION: (55)..(55)
<223> OTHER INFORMATION: Ile or Val
<220> FEATURE:
<221> NAME/KEY: MOD_RES
<222> LOCATION: (63)..(63)
<223> OTHER INFORMATION: Ile or Val

<400> SEQUENCE: 172

Met Asp Arg Arg Ala Val Arg His Leu Gly Ile Leu Gly Ile Leu Gly
1 5 10 15

Cys Ala Ala Leu Ala Ala Ala His Arg Gly Pro Ala Ala Xaa Thr Thr
20 25 30

Xaa Ala Leu Ala Arg Ala Pro Thr His Pro His Leu Ile Arg Leu Gly
35 40 45

Gly Phe Ala Val Pro Leu Xaa Val Gly Gly Leu Cys Ala Met Xaa Leu
50 55 60

Gly Ala Ala Cys Leu Leu Glu Leu Leu Arg Arg Leu Cys Arg Glu Leu
65 70 75 80

Ala Arg Cys Cys Pro His Ala Asp Gln Phe Ala Pro
85 90

<210> SEQ ID NO 173
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 173

Gly Arg Tyr His Pro Tyr Met Asp Pro Val Val Val
1 5 10

<210> SEQ ID NO 174
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 174

Ala Arg Cys Cys Pro His Ala Gly Gln Phe Ala Pro
1 5 10

<210> SEQ ID NO 175
<211> LENGTH: 16
<212> TYPE: PRT
<213> ORGANISM: Artificial Sequence
<220> FEATURE:
<223> OTHER INFORMATION: Description of Artificial Sequence: Synthetic peptide -continued

```
<220> FEATURE:
<221> NAME/KEY: MOD_RES
<222> LOCATION: (2)..(4)
<223> OTHER INFORMATION: any amino acid or is absent; region may
      encompass 0-3 residues
<220> FEATURE:
<221> NAME/KEY: MOD_RES
<222> LOCATION: (6)..(15)
<223> OTHER INFORMATION: any amino acid or is absent; region may
      encompass 0-10 residues

<400> SEQUENCE: 175

Cys Xaa Xaa Xaa His Xaa Xaa Xaa Xaa Xaa Xaa Xaa Xaa Xaa Xaa Cys
1               5                   10                  15


<210> SEQ ID NO 176
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: any amino acid or is absent; region may
      encompass 0-3 residues
<220> FEATURE:
<221> NAME/KEY: MOD_RES
<222> LOCATION: (7)..(20)
<223> OTHER INFORMATION: any amino acid or is absent; region may
      encompass 0-14 residues

<400> SEQUENCE: 176

Cys Xaa Xaa Xaa Pro His Xaa Xaa Xaa Xaa Xaa Xaa Xaa Xaa Xaa Xaa
1               5                   10                  15

Xaa Xaa Xaa Xaa Cys
            20


<210> SEQ ID NO 177
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(6)
<223> OTHER INFORMATION: any amino acid or is absent; region may
      encompass 0-5 residues
<220> FEATURE:
<221> NAME/KEY: MOD_RES
<222> LOCATION: (7)..(7)
<223> OTHER INFORMATION: Lys, Arg, or His
<220> FEATURE:
<221> NAME/KEY: MOD_RES
<222> LOCATION: (8)..(8)
<223> OTHER INFORMATION: Ala or Gly
<220> FEATURE:
<221> NAME/KEY: MOD_RES
<222> LOCATION: (9)..(9)
<223> OTHER INFORMATION: Lys, Arg, or His
<220> FEATURE:
<221> NAME/KEY: MOD_RES
<222> LOCATION: (10)..(11)
<223> OTHER INFORMATION: any amino acid or is absent; region may
      encompass 0-2 residues
<220> FEATURE:
<221> NAME/KEY: MOD_RES
<222> LOCATION: (12)..(12)
<223> OTHER INFORMATION: Lys or Arg
<220> FEATURE:
<221> NAME/KEY: MOD_RES
```

-continued

<222> LOCATION: (13)..(13)
<223> OTHER INFORMATION: any amino acid or is absent
<220> FEATURE:
<221> NAME/KEY: MOD_RES
<222> LOCATION: (14)..(14)
<223> OTHER INFORMATION: Glu, Asp, Gln, or Asn

<400> SEQUENCE: 177

Cys Xaa Xaa Xaa Xaa Xaa Xaa Xaa Xaa Xaa Xaa Xaa Xaa Xaa Cys
1 5 10 15

<210> SEQ ID NO 178
<211> LENGTH: 15
<212> TYPE: PRT
<213> ORGANISM: Artificial Sequence Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(6)
<223> OTHER INFORMATION: any amino acid or not present; region may encompass 0-5 residues
<220> FEATURE:
<221> NAME/KEY: MOD_RES
<222> LOCATION: (7)..(7)
<223> OTHER INFORMATION: Lys, Arg, or His
<220> FEATURE:
<221> NAME/KEY: MOD_RES
<222> LOCATION: (8)..(8)
<223> OTHER INFORMATION: Ala or Gly
<220> FEATURE:
<221> NAME/KEY: MOD_RES
<222> LOCATION: (9)..(9)
<223> OTHER INFORMATION: Lys, Arg, or His
<220> FEATURE:
<221> NAME/KEY: MOD_RES
<222> LOCATION: (10)..(11)
<223> OTHER INFORMATION: any amino acid or not present; region may encompass 0-2 residues
<220> FEATURE:
<221> NAME/KEY: MOD_RES
<222> LOCATION: (12)..(12)
<223> OTHER INFORMATION: Lys or Arg
<220> FEATURE:
<221> NAME/KEY: MOD_RES
<222> LOCATION: (13)..(13)
<223> OTHER INFORMATION: any amino acid or is absent
<220> FEATURE:
<221> NAME/KEY: MOD_RES
<222> LOCATION: (14)..(14)
<223> OTHER INFORMATION: Glu, Asp, Gln, or Asn

<400> SEQUENCE: 178

Cys Xaa Xaa Xaa Xaa Xaa Xaa Xaa Xaa Xaa Xaa Xaa Xaa Xaa Cys
1 5 10 15

<210> SEQ ID NO 179
<211> LENGTH: 17
<212> TYPE: PRT
<213> ORGANISM: Haemophilus ducreyi

<400> SEQUENCE: 179

Cys Pro His Tyr Pro Glu Gly Gln Gly Glu Tyr Gln Gln Lys Cys Asp
1 5 10 15

Cys

<210> SEQ ID NO 180
<211> LENGTH: 15
<212> TYPE: PRT
<213> ORGANISM: Haemophilus influenzae -continued

<400> SEQUENCE: 180

Cys Pro His His Ser Glu Gly Lys Gly Glu Tyr Lys Glu Asp Cys
1 5 10 15

<210> SEQ ID NO 181
<211> LENGTH: 18
<212> TYPE: PRT
<213> ORGANISM: Salmonella typhi

<400> SEQUENCE: 181

Cys Pro His His Pro Gln Gly Ser Ile Glu Glu Phe Arg Gln Val Cys
1 5 10 15

Asp Cys

<210> SEQ ID NO 182
<211> LENGTH: 18
<212> TYPE: PRT
<213> ORGANISM: Vibrio cholerae

<400> SEQUENCE: 182

Cys Pro His His Ala Glu His Gly Ile Gly Gln Tyr Lys Glu Glu Cys
1 5 10 15

Asp Cys

<210> SEQ ID NO 183
<211> LENGTH: 16
<212> TYPE: PRT
<213> ORGANISM: Vibrio vulnificus

<400> SEQUENCE: 183

Cys Pro His His Ala Glu His Gly Val Gly Asp Tyr Lys Gln Asp Cys
1 5 10 15

<210> SEQ ID NO 184
<211> LENGTH: 14
<212> TYPE: PRT
<213> ORGANISM: Porphyromonas gingivalis

<400> SEQUENCE: 184

Cys Gly His His Gly Asn Thr Asn Gln Lys Ser Ser Asp Cys
1 5 10

<210> SEQ ID NO 185
<211> LENGTH: 9
<212> TYPE: PRT
<213> ORGANISM: Helicobacter pylori

<400> SEQUENCE: 185

Cys Arg His Ala Pro Glu Glu Asn Cys
1 5

<210> SEQ ID NO 186
<211> LENGTH: 9
<212> TYPE: PRT
<213> ORGANISM: Neisseria meningitidis

<400> SEQUENCE: 186

Cys Pro His Thr Asp Ala Asp Asn Cys
1 5

<210> SEQ ID NO 187
<211> LENGTH: 9
<212> TYPE: PRT

-continued

<213> ORGANISM: Neisseria meningitidis

<400> SEQUENCE: 187

Cys Pro His Thr Asp Ala Asp Asn Cys
1 5

<210> SEQ ID NO 188
<211> LENGTH: 9
<212> TYPE: PRT
<213> ORGANISM: Coxiella burnetii

<400> SEQUENCE: 188

Cys Pro His Ala Pro Gln Ala Asn Cys
1 5

<210> SEQ ID NO 189
<211> LENGTH: 9
<212> TYPE: PRT
<213> ORGANISM: Bordetella pertussis

<400> SEQUENCE: 189

Cys Pro His Gly Pro Asp Asp Gly Cys
1 5

<210> SEQ ID NO 190
<211> LENGTH: 13
<212> TYPE: PRT
<213> ORGANISM: Treponema denticola

<400> SEQUENCE: 190

Cys Pro His Cys Gly Arg Phe Phe Ala Ser Val Arg Cys
1 5 10

<210> SEQ ID NO 191
<211> LENGTH: 15
<212> TYPE: PRT
<213> ORGANISM: Bacteroides thetaiotaomicron

<400> SEQUENCE: 191

Cys Pro His Ser Gly Lys Arg Arg Met Leu Leu Asn Leu Leu Cys
1 5 10 15

<210> SEQ ID NO 192
<211> LENGTH: 7
<212> TYPE: PRT
<213> ORGANISM: Legionella pneumophila

<400> SEQUENCE: 192

Cys Pro His Tyr Gln Met Cys
1 5

<210> SEQ ID NO 193
<211> LENGTH: 11
<212> TYPE: PRT
<213> ORGANISM: Staphylococcus aureus

<400> SEQUENCE: 193

Cys Pro His Ala Asp Gly Arg Arg Val Ile Cys
1 5 10

<210> SEQ ID NO 194
<211> LENGTH: 13
<212> TYPE: PRT
<213> ORGANISM: Neisseria gonorrhoeae -continued

<400> SEQUENCE: 194

```
Cys Pro His Pro Arg Pro Arg Arg Arg Gln Gly Arg Cys
1               5                   10
```

<210> SEQ ID NO 195
<211> LENGTH: 20
<212> TYPE: PRT
<213> ORGANISM: Escherichia coli

<400> SEQUENCE: 195

```
Val Met Ser Ala Cys Lys Pro His Asp Cys Gly Ser Gln Arg Ile Ala
1               5                   10                  15

Val Met Trp Ser
            20
```

<210> SEQ ID NO 196
<211> LENGTH: 21
<212> TYPE: PRT
<213> ORGANISM: Pseudomonas aeruginosa

<400> SEQUENCE: 196

```
Val Leu Ala Asn Ser Cys Lys Pro His Asp Cys Gly Asn Asn Arg Leu
1               5                   10                  15

Leu Val Ala Phe Arg
            20
```

<210> SEQ ID NO 197
<211> LENGTH: 20
<212> TYPE: PRT
<213> ORGANISM: Yersinia pestis

<400> SEQUENCE: 197

```
Val Gly Ser Leu Cys Lys Pro His Asp Cys Ser Asn Asn Phe Met Trp
1               5                   10                  15

Val Ala Phe Ser
            20
```

<210> SEQ ID NO 198
<211> LENGTH: 28
<212> TYPE: PRT
<213> ORGANISM: Treponema pallidum

<400> SEQUENCE: 198

```
Val Ser Cys Thr Thr Val Cys Pro His Ala Gly Lys Ala Lys Ala Glu
1               5                   10                  15

Lys Val Glu Cys Ala Leu Lys Gly Gly Ile Phe Arg
            20                  25
```

<210> SEQ ID NO 199
<211> LENGTH: 25
<212> TYPE: PRT
<213> ORGANISM: Homo sapiens

<400> SEQUENCE: 199

```
Val Thr Ile Gln Asn Trp Cys Lys Arg Gly Arg Lys Gln Cys Lys Thr
1               5                   10                  15

His Pro His Phe Val Ile Pro Tyr Arg
            20                  25
```

<210> SEQ ID NO 200
<211> LENGTH: 25
<212> TYPE: PRT

-continued

<213> ORGANISM: Homo sapiens

<400> SEQUENCE: 200

Val Thr Ile Gln Asn Trp Cys Lys Arg Gly Arg Lys Gln Cys Lys Thr
1 5 10 15

His Pro His Phe Val Ile Pro Tyr Arg
20 25

<210> SEQ ID NO 201
<211> LENGTH: 25
<212> TYPE: PRT
<213> ORGANISM: Homo sapiens

<400> SEQUENCE: 201

Val Thr Ile Gln Asn Trp Cys Lys Arg Gly Arg Lys Gln Cys Lys Thr
1 5 10 15

His Pro His Phe Val Ile Pro Tyr Arg
20 25

<210> SEQ ID NO 202
<211> LENGTH: 12
<212> TYPE: PRT
<213> ORGANISM: Homo sapiens

<400> SEQUENCE: 202

Cys Pro Leu Pro Arg Gly Arg Ala Arg Trp Gln Cys
1 5 10

<210> SEQ ID NO 203
<211> LENGTH: 8
<212> TYPE: PRT
<213> ORGANISM: Fugu rubripes

<400> SEQUENCE: 203

Cys Lys Lys Gly Arg Lys Gln Cys
1 5

<210> SEQ ID NO 204
<211> LENGTH: 8
<212> TYPE: PRT
<213> ORGANISM: Homo sapiens

<400> SEQUENCE: 204

Cys Lys Arg Gly Arg Lys Gln Cys
1 5

<210> SEQ ID NO 205
<211> LENGTH: 8
<212> TYPE: PRT
<213> ORGANISM: Macaca fascicularis

<400> SEQUENCE: 205

Cys Lys Arg Gly Arg Lys Gln Cys
1 5

<210> SEQ ID NO 206
<211> LENGTH: 8
<212> TYPE: PRT
<213> ORGANISM: Mus musculus

<400> SEQUENCE: 206

Cys Lys Arg Gly Arg Lys Gln Cys
1 5

-continued

<210> SEQ ID NO 207
<211> LENGTH: 8
<212> TYPE: PRT
<213> ORGANISM: Rattus norvegicus

<400> SEQUENCE: 207

Cys Lys Arg Gly Arg Lys Gln Cys
1               5

<210> SEQ ID NO 208
<211> LENGTH: 8
<212> TYPE: PRT
<213> ORGANISM: Tetraodon fluviatilis

<400> SEQUENCE: 208

Cys Lys Lys Gly Arg Lys Gln Cys
1               5

<210> SEQ ID NO 209
<211> LENGTH: 8
<212> TYPE: PRT
<213> ORGANISM: Cauliflower mosaic virus

<400> SEQUENCE: 209

Cys Pro Lys Gly Lys Lys Asp Cys
1               5

<210> SEQ ID NO 210
<211> LENGTH: 12
<212> TYPE: PRT
<213> ORGANISM: Homo sapiens

<400> SEQUENCE: 210

Cys Lys Leu Gly Arg Gly Lys Cys Arg Lys Glu Cys
1               5                   10

<210> SEQ ID NO 211
<211> LENGTH: 10
<212> TYPE: PRT
<213> ORGANISM: Ralstonia solanacearum

<400> SEQUENCE: 211

Cys Phe Pro Arg Gly Lys Arg Ser Glu Cys
1               5                   10

<210> SEQ ID NO 212
<211> LENGTH: 14
<212> TYPE: PRT
<213> ORGANISM: Baboon endogenous virus

<400> SEQUENCE: 212

Cys Ala Tyr Cys Lys Glu Arg Gly His Trp Ile Lys Asp Cys
1               5                   10

<210> SEQ ID NO 213
<211> LENGTH: 14
<212> TYPE: PRT
<213> ORGANISM: Caprine arthritis-encephalitis virus

<400> SEQUENCE: 213

Cys His Asn Cys Gly Lys Arg Gly His Met Gln Lys Glu Cys
1               5                   10

<210> SEQ ID NO 214

-continued

<211> LENGTH: 14
<212> TYPE: PRT
<213> ORGANISM: Feline leukemia virus

<400> SEQUENCE: 214

Cys Ala Tyr Cys Lys Glu Lys Gly His Trp Val Arg Asp Cys
1 5 10

<210> SEQ ID NO 215
<211> LENGTH: 14
<212> TYPE: PRT
<213> ORGANISM: Gibbon leukemia virus

<400> SEQUENCE: 215

Cys Ala Tyr Cys Lys Glu Lys Gly His Trp Ala Arg Glu Cys
1 5 10

<210> SEQ ID NO 216
<211> LENGTH: 14
<212> TYPE: PRT
<213> ORGANISM: Simian Mason-Pfizer virus

<400> SEQUENCE: 216

Cys Phe Lys Cys Gly Lys Lys Gly His Phe Ala Lys Asn Cys
1 5 10

<210> SEQ ID NO 217
<211> LENGTH: 14
<212> TYPE: PRT
<213> ORGANISM: Ovine lentivirus

<400> SEQUENCE: 217

Cys His His Cys Gly Lys Arg Gly His Met Gln Lys Asp Cys
1 5 10

<210> SEQ ID NO 218
<211> LENGTH: 14
<212> TYPE: PRT
<213> ORGANISM: Visna virus

<400> SEQUENCE: 218

Cys His His Cys Gly Lys Arg Gly His Met Gln Lys Asp Cys
1 5 10

<210> SEQ ID NO 219
<211> LENGTH: 11
<212> TYPE: PRT
<213> ORGANISM: Vibrio cholerae

<400> SEQUENCE: 219

Cys Ser Gly Lys Gly Arg Val Ala Arg Asp Cys
1 5 10

<210> SEQ ID NO 220
<211> LENGTH: 11
<212> TYPE: PRT
<213> ORGANISM: Vibrio parahaemolyticus

<400> SEQUENCE: 220

Cys Gly Ser Lys Gly Arg Val Asp Lys Asp Cys
1 5 10

<210> SEQ ID NO 221
<211> LENGTH: 11
<212> TYPE: PRT

-continued

<213> ORGANISM: Vibrio vulnificus

<400> SEQUENCE: 221

Cys Gly Ser Lys Gly Arg Val Asp Lys Asp Cys
1 5 10

<210> SEQ ID NO 222
<211> LENGTH: 13
<212> TYPE: PRT
<213> ORGANISM: Homo sapiens

<400> SEQUENCE: 222

Cys Glu Asp His Arg Gly Arg Met Val Lys His Gln Cys
1 5 10

<210> SEQ ID NO 223
<211> LENGTH: 14
<212> TYPE: PRT
<213> ORGANISM: Homo sapiens

<400> SEQUENCE: 223

Cys Phe Asp Ser Leu Lys Gly Arg Cys Thr Arg Glu Asn Cys
1 5 10

<210> SEQ ID NO 224
<211> LENGTH: 9
<212> TYPE: PRT
<213> ORGANISM: Sindbis virus

<400> SEQUENCE: 224

Cys Ala Cys Lys Ala Arg Arg Glu Cys
1 5

<210> SEQ ID NO 225
<211> LENGTH: 11
<212> TYPE: PRT
<213> ORGANISM: Homo sapiens

<400> SEQUENCE: 225

Cys Tyr Ser Lys Gly Lys Ser Lys Glu Glu Cys
1 5 10

<210> SEQ ID NO 226
<211> LENGTH: 11
<212> TYPE: PRT
<213> ORGANISM: Homo sapiens

<400> SEQUENCE: 226

Cys Arg Met Lys Gly Lys His Lys Asp Glu Cys
1 5 10

<210> SEQ ID NO 227
<211> LENGTH: 11
<212> TYPE: PRT
<213> ORGANISM: Mus musculus

<400> SEQUENCE: 227

Cys Arg Met Lys Gly Lys His Lys Asp Glu Cys
1 5 10

<210> SEQ ID NO 228
<211> LENGTH: 14
<212> TYPE: PRT
<213> ORGANISM: Treponema pallidum -continued

<400> SEQUENCE: 228

Cys Pro His Ala Gly Lys Ala Lys Ala Glu Lys Val Glu Cys
1 5 10

<210> SEQ ID NO 229
<211> LENGTH: 12
<212> TYPE: PRT
<213> ORGANISM: Homo sapiens

<400> SEQUENCE: 229

Cys Phe Lys Cys Gly Ala Arg Ala His Lys Glu Cys
1 5 10

<210> SEQ ID NO 230
<211> LENGTH: 12
<212> TYPE: PRT
<213> ORGANISM: Homo sapiens

<400> SEQUENCE: 230

Cys Arg Asp Leu Pro Lys Gly Arg Lys Arg Asp Cys
1 5 10

<210> SEQ ID NO 231
<211> LENGTH: 12
<212> TYPE: PRT
<213> ORGANISM: Brachydanio rerio

<400> SEQUENCE: 231

Cys Gln His Gln Phe Arg Gly His Arg Trp Asn Cys
1 5 10

<210> SEQ ID NO 232
<211> LENGTH: 12
<212> TYPE: PRT
<213> ORGANISM: Homo sapiens

<400> SEQUENCE: 232

Cys Gln His Gln Phe Arg Gly Arg Arg Trp Asn Cys
1 5 10

<210> SEQ ID NO 233
<211> LENGTH: 12
<212> TYPE: PRT
<213> ORGANISM: Mus musculus

<400> SEQUENCE: 233

Cys Gln His Gln Phe Arg Gly Arg Arg Trp Asn Cys
1 5 10

<210> SEQ ID NO 234
<211> LENGTH: 12
<212> TYPE: PRT
<213> ORGANISM: Homo sapiens

<400> SEQUENCE: 234

Cys Gln His Gln Phe Arg Gly Arg Arg Trp Asn Cys
1 5 10

<210> SEQ ID NO 235
<211> LENGTH: 14
<212> TYPE: PRT
<213> ORGANISM: Human immunodeficiency virus type 1

<400> SEQUENCE: 235

-continued

Cys Trp Lys Cys Gly Lys Lys Gly His Gln Met Lys Asp Cys
1 5 10

<210> SEQ ID NO 236
<211> LENGTH: 8
<212> TYPE: PRT
<213> ORGANISM: Narke japonica

<400> SEQUENCE: 236

Cys Lys Lys Gly Arg Lys Gln Cys
1 5

<210> SEQ ID NO 237
<211> LENGTH: 13
<212> TYPE: PRT
<213> ORGANISM: Treponema pallidum

<400> SEQUENCE: 237

Cys Val Arg Arg Thr Ile Arg Ala Arg Arg Pro Gln Cys
1 5 10

<210> SEQ ID NO 238
<211> LENGTH: 14
<212> TYPE: PRT
<213> ORGANISM: Homo sapiens

<400> SEQUENCE: 238

Cys Phe Asp Ser Leu Lys Gly Arg Cys Ser Arg Glu Asn Cys
1 5 10

<210> SEQ ID NO 239
<211> LENGTH: 14
<212> TYPE: PRT
<213> ORGANISM: Homo sapiens

<400> SEQUENCE: 239

Cys Lys Lys Cys Gly Cys Lys Gly His Phe Ala Lys Asp Cys
1 5 10

<210> SEQ ID NO 240
<211> LENGTH: 14
<212> TYPE: PRT
<213> ORGANISM: Human immunodeficiency virus type 1
<220> FEATURE:
<221> NAME/KEY: MOD_RES
<222> LOCATION: (7)..(7)
<223> OTHER INFORMATION: Variable amino acid

<400> SEQUENCE: 240

Cys Trp Lys Cys Gly Lys Xaa Gly His Gln Met Lys Asp Cys
1 5 10

<210> SEQ ID NO 241
<211> LENGTH: 8
<212> TYPE: PRT
<213> ORGANISM: Canis familiaris

<400> SEQUENCE: 241

Cys Lys Lys Gly Arg Lys Gln Cys
1 5

<210> SEQ ID NO 242
<211> LENGTH: 14
<212> TYPE: PRT
<213> ORGANISM: Small ruminant lentivirus -continued

<400> SEQUENCE: 242

Cys His His Cys Gly Lys Arg Gly His Met Gln Lys Asp Cys
1               5                   10

<210> SEQ ID NO 243
<211> LENGTH: 14
<212> TYPE: PRT
<213> ORGANISM: Porcine endogenous retrovirus

<400> SEQUENCE: 243

Cys Ala Tyr Cys Lys Glu Lys Gly His Trp Ala Arg Asp Cys
1               5                   10

<210> SEQ ID NO 244
<211> LENGTH: 14
<212> TYPE: PRT
<213> ORGANISM: Human immunodeficiency virus type 1
<220> FEATURE:
<221> NAME/KEY: MOD_RES
<222> LOCATION: (5)..(5)
<223> OTHER INFORMATION: Variable amino acid
<220> FEATURE:
<221> NAME/KEY: MOD_RES
<222> LOCATION: (7)..(7)
<223> OTHER INFORMATION: Variable amino acid

<400> SEQUENCE: 244

Cys Trp Lys Cys Xaa Lys Xaa Gly His Gln Met Lys Asp Cys
1               5                   10

<210> SEQ ID NO 245
<211> LENGTH: 12
<212> TYPE: PRT
<213> ORGANISM: Human immunodeficiency virus type 1

<400> SEQUENCE: 245

Cys Gly Arg Glu Arg Gly His Leu Ala Arg Asn Cys
1               5                   10

<210> SEQ ID NO 246
<211> LENGTH: 8
<212> TYPE: PRT
<213> ORGANISM: Xenopus laevis

<400> SEQUENCE: 246

Cys Lys Arg Gly Lys Lys Gln Cys
1               5

<210> SEQ ID NO 247
<211> LENGTH: 8
<212> TYPE: PRT
<213> ORGANISM: Xenopus laevis

<400> SEQUENCE: 247

Cys Lys Lys Gly Lys Lys Gln Cys
1               5

<210> SEQ ID NO 248
<211> LENGTH: 12
<212> TYPE: PRT
<213> ORGANISM: Leptospira interrogans

<400> SEQUENCE: 248

Cys Asp Trp Tyr Glu Lys Gly Lys Lys Met Glu Cys
1               5                   10

-continued

<210> SEQ ID NO 249
<211> LENGTH: 14
<212> TYPE: PRT
<213> ORGANISM: Human immunodeficiency virus type 1
<220> FEATURE:
<221> NAME/KEY: MOD_RES
<222> LOCATION: (7)..(7)
<223> OTHER INFORMATION: Variable amino acid

<400> SEQUENCE: 249

Cys Trp Lys Tyr Gly Lys Xaa Gly His Gln Met Lys Asp Cys
1               5                   10

<210> SEQ ID NO 250
<211> LENGTH: 11
<212> TYPE: PRT
<213> ORGANISM: Vibrio vulnificus

<400> SEQUENCE: 250

Cys Gly Ser Lys Gly Arg Val Asp Lys Asp Cys
1               5                   10

<210> SEQ ID NO 251
<211> LENGTH: 14
<212> TYPE: PRT
<213> ORGANISM: Anopheles gambiae

<400> SEQUENCE: 251

Cys His Asn Cys Phe Arg Lys Gly His Leu Ala Arg Asn Cys
1               5                   10

<210> SEQ ID NO 252
<211> LENGTH: 14
<212> TYPE: PRT
<213> ORGANISM: Anopheles gambiae

<400> SEQUENCE: 252

Cys His Asn Cys Gly Lys Lys Gly His Met Lys Lys Asp Cys
1               5                   10

<210> SEQ ID NO 253
<211> LENGTH: 14
<212> TYPE: PRT
<213> ORGANISM: Anopheles gambiae

<400> SEQUENCE: 253

Cys His Asn Cys Leu Arg Lys Gly His Leu Ala Arg Asn Cys
1               5                   10

<210> SEQ ID NO 254
<211> LENGTH: 11
<212> TYPE: PRT
<213> ORGANISM: Plasmodium yoelii

<400> SEQUENCE: 254

Cys Glu Tyr Glu Lys Ala Lys Glu Lys Asn Cys
1               5                   10

<210> SEQ ID NO 255
<211> LENGTH: 12
<212> TYPE: PRT
<213> ORGANISM: Plasmodium yoelii

<400> SEQUENCE: 255

Cys Asp Phe His Gly His Ser Ser Lys Tyr Asn Cys

-continued

```
1               5                   10


<210> SEQ ID NO 256
<211> LENGTH: 14
<212> TYPE: PRT
<213> ORGANISM: Plasmodium yoelii

<400> SEQUENCE: 256

Cys His Met Cys Gly Lys Lys Gly His Ser Ile Lys Asn Cys
1               5                   10


<210> SEQ ID NO 257
<211> LENGTH: 9
<212> TYPE: PRT
<213> ORGANISM: Plasmodium yoelii

<400> SEQUENCE: 257

Cys Lys Lys Gly Arg Lys Leu Asp Cys
1               5


<210> SEQ ID NO 258
<211> LENGTH: 14
<212> TYPE: PRT
<213> ORGANISM: Plasmodium yoelii

<400> SEQUENCE: 258

Cys Ser Tyr Ile Asp His Gly Lys Ser Gly Lys Asn Asn Cys
1               5                   10


<210> SEQ ID NO 259
<211> LENGTH: 11
<212> TYPE: PRT
<213> ORGANISM: Plasmodium yoelii

<400> SEQUENCE: 259

Cys Val Lys Glu Asn Lys Ala Lys Lys Asn Cys
1               5                   10


<210> SEQ ID NO 260
<211> LENGTH: 9
<212> TYPE: PRT
<213> ORGANISM: Helicobacter hepaticus

<400> SEQUENCE: 260

Cys Gln Lys Gly Lys Leu Lys Gln Cys
1               5


<210> SEQ ID NO 261
<211> LENGTH: 12
<212> TYPE: PRT
<213> ORGANISM: Trypanosoma brucei

<400> SEQUENCE: 261

Cys Thr Thr His Asn Phe Arg Gly Arg Lys Glu Cys
1               5                   10


<210> SEQ ID NO 262
<211> LENGTH: 14
<212> TYPE: PRT
<213> ORGANISM: Human immunodeficiency virus type 1
<220> FEATURE:
<221> NAME/KEY: MOD_RES
<222> LOCATION: (8)..(8)
<223> OTHER INFORMATION: Variable amino acid

<400> SEQUENCE: 262
```

-continued

Cys Phe Asn Cys Gly Lys Arg Xaa His Leu Ala Arg Asn Cys
1 5 10

<210> SEQ ID NO 263
<211> LENGTH: 9
<212> TYPE: PRT
<213> ORGANISM: Kyzylagach virus

<400> SEQUENCE: 263

Cys Thr Cys Lys Ala Arg Arg Glu Cys
1 5

<210> SEQ ID NO 264
<211> LENGTH: 9
<212> TYPE: PRT
<213> ORGANISM: Babanki virus

<400> SEQUENCE: 264

Cys Ala Cys Lys Ala Arg Arg Glu Cys
1 5

<210> SEQ ID NO 265
<211> LENGTH: 8
<212> TYPE: PRT
<213> ORGANISM: Highlands J virus

<400> SEQUENCE: 265

Cys Leu Lys Ala Arg Arg Asp Cys
1 5

<210> SEQ ID NO 266
<211> LENGTH: 8
<212> TYPE: PRT
<213> ORGANISM: Fort Morgan virus

<400> SEQUENCE: 266

Cys Leu Cys Arg Ala Arg Asp Cys
1 5

<210> SEQ ID NO 267
<211> LENGTH: 9
<212> TYPE: PRT
<213> ORGANISM: Buggy Creek virus

<400> SEQUENCE: 267

Cys Leu Cys Arg Ala Arg Arg Asp Cys
1 5

<210> SEQ ID NO 268
<211> LENGTH: 14
<212> TYPE: PRT
<213> ORGANISM: Homo sapiens

<400> SEQUENCE: 268

Cys Phe Asp Ser Leu Lys Gly Arg Cys Ser Arg Glu Asn Cys
1 5 10

<210> SEQ ID NO 269
<211> LENGTH: 14
<212> TYPE: PRT
<213> ORGANISM: Homo sapiens

<400> SEQUENCE: 269

Cys Phe Asp Ser Leu Lys Gly Arg Cys Ser Arg Glu Asn Cys

-continued 1 5 10

<210> SEQ ID NO 270
<211> LENGTH: 11
<212> TYPE: PRT
<213> ORGANISM: Homo sapiens

<400> SEQUENCE: 270

Cys Pro Pro Trp Arg Gly Arg Arg Glu Gln Cys
1 5 10

<210> SEQ ID NO 271
<211> LENGTH: 13
<212> TYPE: PRT
<213> ORGANISM: Homo sapiens

<400> SEQUENCE: 271

Cys Asp Ala Cys Leu Gly Lys Gly Lys Lys Asn Glu Cys
1 5 10

<210> SEQ ID NO 272
<211> LENGTH: 12
<212> TYPE: PRT
<213> ORGANISM: Homo sapiens

<400> SEQUENCE: 272

Cys Arg Tyr Met Asn Pro Arg Ala Arg Lys Asn Cys
1 5 10

<210> SEQ ID NO 273
<211> LENGTH: 13
<212> TYPE: PRT
<213> ORGANISM: Homo sapiens

<400> SEQUENCE: 273

Cys Glu Asp His Arg Gly Arg Met Val Lys His Gln Cys
1 5 10

<210> SEQ ID NO 274
<211> LENGTH: 12
<212> TYPE: PRT
<213> ORGANISM: Simian immunodeficiency virus

<400> SEQUENCE: 274

Cys Arg Asp Ser Asp Tyr Arg Gly His Lys Asn Cys
1 5 10

<210> SEQ ID NO 275
<211> LENGTH: 12
<212> TYPE: PRT
<213> ORGANISM: Vibrio parahaemolyticus

<400> SEQUENCE: 275

Cys Asn Lys Lys Leu Gly Lys Gly Lys Lys Glu Cys
1 5 10

<210> SEQ ID NO 276
<211> LENGTH: 14
<212> TYPE: PRT
<213> ORGANISM: Human immunodeficiency virus type 1

<400> SEQUENCE: 276

Cys Phe Asn Cys Gly Lys Lys Gly His Leu Ala Arg Asn Cys
1 5 10

-continued

<210> SEQ ID NO 277
<211> LENGTH: 14
<212> TYPE: PRT
<213> ORGANISM: Human immunodeficiency virus type 1

<400> SEQUENCE: 277

Cys Phe Asn Tyr Gly Lys Lys Gly His Leu Ala Arg Asn Cys
1 5 10

<210> SEQ ID NO 278
<211> LENGTH: 12
<212> TYPE: PRT
<213> ORGANISM: Leptospira interrogans

<400> SEQUENCE: 278

Cys Asp Trp Tyr Glu Lys Gly Lys Lys Met Glu Cys
1 5 10

<210> SEQ ID NO 279
<211> LENGTH: 14
<212> TYPE: PRT
<213> ORGANISM: Brucella melitensis

<400> SEQUENCE: 279

Cys Ala His Ala Arg Ser Lys Gly His Ile Lys Asp Asn Cys
1 5 10

<210> SEQ ID NO 280
<211> LENGTH: 14
<212> TYPE: PRT
<213> ORGANISM: Human immunodeficiency virus type 1

<400> SEQUENCE: 280

Cys Trp Lys Cys Gly Arg Lys Gly His Gln Met Lys Asp Cys
1 5 10

<210> SEQ ID NO 281
<211> LENGTH: 14
<212> TYPE: PRT
<213> ORGANISM: Human immunodeficiency virus type 1

<400> SEQUENCE: 281

Cys Phe Asn Cys Gly Arg Lys Gly His Leu Ala Arg Asn Cys
1 5 10

<210> SEQ ID NO 282
<211> LENGTH: 14
<212> TYPE: PRT
<213> ORGANISM: Human immunodeficiency virus type 1
<220> FEATURE:
<221> NAME/KEY: MOD_RES
<222> LOCATION: (7)..(7)
<223> OTHER INFORMATION: Variable amino acid

<400> SEQUENCE: 282

Cys Trp Lys Cys Gly Lys Xaa Gly His Gln Met Lys Asp Cys
1 5 10

<210> SEQ ID NO 283
<211> LENGTH: 13
<212> TYPE: PRT
<213> ORGANISM: Human immunodeficiency virus type 1

<400> SEQUENCE: 283

Cys Ile Pro Pro Asp Gln Lys Gly Lys Met Lys Asn Cys

-continued 1 5 10

<210> SEQ ID NO 284
<211> LENGTH: 12
<212> TYPE: PRT
<213> ORGANISM: Simian immunodeficiency virus

<400> SEQUENCE: 284

Cys Arg Asp Phe Asp Tyr Arg Gly His Lys Asp Cys
1 5 10

<210> SEQ ID NO 285
<211> LENGTH: 14
<212> TYPE: PRT
<213> ORGANISM: Trypanosoma cruzi

<400> SEQUENCE: 285

Cys Tyr Val Cys Gly Glu Lys Gly His Leu Ala Arg Asp Cys
1 5 10

<210> SEQ ID NO 286
<211> LENGTH: 14
<212> TYPE: PRT
<213> ORGANISM: Homo sapiens

<400> SEQUENCE: 286

Cys Phe Asp Ser Leu Lys Gly Arg Cys Ser Arg Glu Asn Cys
1 5 10

<210> SEQ ID NO 287
<211> LENGTH: 14
<212> TYPE: PRT
<213> ORGANISM: Human immunodeficiency virus type 1
<220> FEATURE:
<221> NAME/KEY: MOD_RES
<222> LOCATION: (7)..(7)
<223> OTHER INFORMATION: Variable amino acid

<400> SEQUENCE: 287

Cys Phe Asn Cys Gly Lys Xaa Gly His Leu Ala Arg Asn Cys
1 5 10

<210> SEQ ID NO 288
<211> LENGTH: 14
<212> TYPE: PRT
<213> ORGANISM: Human immunodeficiency virus type 1
<220> FEATURE:
<221> NAME/KEY: MOD_RES
<222> LOCATION: (4)..(4)
<223> OTHER INFORMATION: Variable amino acid
<220> FEATURE:
<221> NAME/KEY: MOD_RES
<222> LOCATION: (7)..(7)
<223> OTHER INFORMATION: Variable amino acid

<400> SEQUENCE: 288

Cys Phe Asn Xaa Gly Lys Xaa Gly His Ile Ala Arg Asn Cys
1 5 10

<210> SEQ ID NO 289
<211> LENGTH: 14
<212> TYPE: PRT
<213> ORGANISM: Human immunodeficiency virus type 1
<220> FEATURE:
<221> NAME/KEY: MOD_RES
<222> LOCATION: (7)..(7)
<223> OTHER INFORMATION: Variable amino acid -continued

<400> SEQUENCE: 289

Cys Phe Asn Cys Gly Lys Xaa Gly His Leu Ala Arg Asn Cys
1               5                   10

<210> SEQ ID NO 290
<211> LENGTH: 14
<212> TYPE: PRT
<213> ORGANISM: Human immunodeficiency virus type 1
<220> FEATURE:
<221> NAME/KEY: MOD_RES
<222> LOCATION: (6)..(6)
<223> OTHER INFORMATION: Variable amino acid
<220> FEATURE:
<221> NAME/KEY: MOD_RES
<222> LOCATION: (7)..(7)
<223> OTHER INFORMATION: Variable amino acid

<400> SEQUENCE: 290

Cys Phe Asn Cys Gly Xaa Xaa Gly His Ile Ala Lys Asn Cys
1               5                   10

<210> SEQ ID NO 291
<211> LENGTH: 14
<212> TYPE: PRT
<213> ORGANISM: Human immunodeficiency virus type 1
<220> FEATURE:
<221> NAME/KEY: MOD_RES
<222> LOCATION: (7)..(7)
<223> OTHER INFORMATION: Variable amino acid

<400> SEQUENCE: 291

Cys Phe Asn Cys Gly Lys Xaa Gly His Ile Ala Lys Asn Cys
1               5                   10

<210> SEQ ID NO 292
<211> LENGTH: 14
<212> TYPE: PRT
<213> ORGANISM: Human immunodeficiency virus type 1
<220> FEATURE:
<221> NAME/KEY: MOD_RES
<222> LOCATION: (7)..(7)
<223> OTHER INFORMATION: Variable amino acid

<400> SEQUENCE: 292

Cys Phe Asn Cys Gly Lys Xaa Gly His Leu Ala Arg Asn Cys
1               5                   10

<210> SEQ ID NO 293
<211> LENGTH: 14
<212> TYPE: PRT
<213> ORGANISM: Human immunodeficiency virus type 1
<220> FEATURE:
<221> NAME/KEY: MOD_RES
<222> LOCATION: (7)..(7)
<223> OTHER INFORMATION: Variable amino acid

<400> SEQUENCE: 293

Cys Phe Asn Cys Gly Lys Xaa Gly His Ile Ala Arg Asn Cys
1               5                   10

<210> SEQ ID NO 294
<211> LENGTH: 12
<212> TYPE: PRT
<213> ORGANISM: Trypanosoma brucei

<400> SEQUENCE: 294

Cys Thr Thr His Asn Phe Arg Gly Arg Lys Glu Cys
1               5                   10

-continued

<210> SEQ ID NO 295
<211> LENGTH: 148
<212> TYPE: PRT
<213> ORGANISM: Homo sapiens

<400> SEQUENCE: 295

```
Met Lys Ala Leu Ile Val Leu Gly Leu Val Leu Leu Ser Val Thr Val
1               5                   10                  15

Gln Gly Lys Val Phe Glu Arg Cys Glu Leu Ala Arg Thr Leu Lys Arg
            20                  25                  30

Leu Gly Met Asp Gly Tyr Arg Gly Ile Ser Leu Ala Asn Trp Met Cys
        35                  40                  45

Leu Ala Lys Trp Glu Ser Gly Tyr Asn Thr Arg Ala Thr Asn Tyr Asn
    50                  55                  60

Ala Gly Asp Arg Ser Thr Asp Tyr Gly Ile Phe Gln Ile Asn Ser Arg
65                  70                  75                  80

Tyr Trp Cys Asn Asp Gly Lys Thr Pro Gly Ala Val Asn Ala Cys His
                85                  90                  95

Leu Ser Cys Ser Ala Leu Leu Gln Asp Asn Ile Ala Asp Ala Val Ala
            100                 105                 110

Cys Ala Lys Arg Val Val Arg Asp Pro Gln Gly Ile Arg Ala Trp Val
        115                 120                 125

Ala Trp Arg Asn Arg Cys Gln Asn Arg Asp Val Arg Gln Tyr Val Gln
    130                 135                 140

Gly Cys Gly Val
145
```

<210> SEQ ID NO 296
<211> LENGTH: 147
<212> TYPE: PRT
<213> ORGANISM: Gallus gallus

<400> SEQUENCE: 296

```
Met Arg Ser Leu Leu Ile Leu Val Leu Cys Phe Leu Pro Leu Ala Ala
1               5                   10                  15

Leu Gly Lys Val Phe Gly Arg Cys Glu Leu Ala Ala Ala Met Lys Arg
            20                  25                  30

His Gly Leu Asp Asn Tyr Arg Gly Tyr Ser Leu Gly Asn Trp Val Cys
        35                  40                  45

Ala Ala Lys Phe Glu Ser Asn Phe Asn Thr Gln Ala Thr Asn Arg Asn
    50                  55                  60

Thr Asp Gly Ser Thr Asp Tyr Gly Ile Leu Gln Ile Asn Ser Arg Trp
65                  70                  75                  80

Trp Cys Asn Asp Gly Arg Thr Pro Gly Ser Arg Asn Leu Cys Asn Ile
                85                  90                  95

Pro Cys Ser Ala Leu Leu Ser Ser Asp Ile Thr Ala Ser Val Asn Cys
            100                 105                 110

Ala Lys Lys Ile Val Ser Asp Gly Asn Gly Met Asn Ala Trp Val Ala
        115                 120                 125

Trp Arg Asn Arg Cys Lys Gly Thr Asp Val Gln Ala Trp Ile Arg Gly
    130                 135                 140

Cys Arg Leu
145
```

<210> SEQ ID NO 297

-continued

```
<211> LENGTH: 215
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 297

Met Val Ser Ala Leu Arg Gly Ala Pro Leu Ile Arg Val His Ser Ser
1               5                   10                  15

Pro Val Ser Ser Pro Ser Val Ser Gly Pro Arg Arg Leu Val Ser Cys
            20                  25                  30

Leu Ser Ser Gln Ser Ser Ala Leu Ser Gln Ser Gly Gly Gly Ser Thr
        35                  40                  45

Ser Ala Ala Gly Ile Glu Ala Arg Ser Arg Ala Leu Arg Arg Arg Trp
    50                  55                  60

Cys Pro Ala Gly Ile Met Leu Leu Ala Leu Val Cys Leu Leu Ser Cys
65                  70                  75                  80

Leu Leu Pro Ser Ser Glu Ala Lys Leu Tyr Gly Arg Cys Glu Leu Ala
                85                  90                  95

Arg Val Leu His Asp Phe Gly Leu Asp Gly Tyr Arg Gly Tyr Ser Leu
            100                 105                 110

Ala Asp Trp Val Cys Leu Ala Tyr Phe Thr Ser Gly Phe Asn Ala Ala
        115                 120                 125

Ala Leu Asp Tyr Glu Ala Asp Gly Ser Thr Asn Asn Gly Ile Phe Gln
    130                 135                 140

Ile Asn Ser Arg Arg Trp Cys Ser Asn Leu Thr Pro Asn Val Pro Asn
145                 150                 155                 160

Val Cys Arg Met Tyr Cys Ser Asp Leu Leu Asn Pro Asn Leu Lys Asp
                165                 170                 175

Thr Val Ile Cys Ala Met Lys Ile Thr Gln Glu Pro Gln Gly Leu Gly
            180                 185                 190

Tyr Trp Glu Ala Trp Arg His His Cys Gln Gly Lys Asp Leu Thr Glu
        195                 200                 205

Trp Val Asp Gly Cys Asp Phe
    210                 215


<210> SEQ ID NO 298
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298

ccgtgtgtcc ggccgggaag gc                                              22


<210> SEQ ID NO 299
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299

gccttcccgg cggccggaca cacgg                                           25


<210> SEQ ID NO 300
```

-continued

```
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300

aatcgaaggc accggccgag aaagagctgt acg                              33


<210> SEQ ID NO 301
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301

cgtacagctc tttctcggcc ggtgccttcg att                              33
```

COMPOSITIONS AND KITS FOR DETECTING PATHOGEN INFECTION

REFERENCE TO RELATED APPLICATIONS

This application claims the benefit of International Application No. PCT/ES2004/000581, filed Dec. 23, 2004, which claims priority to European Patent Application No. EP 03 380 307.3, filed Dec. 23, 2003, the entire contents of each of which are incorporated by reference into the present application.

FIELD OF THE INVENTION

The present invention generally features diagnostic and therapeutic compositions and methods derived from the characterization of the binding of a lysozyme polypeptide to a *Treponema pallidum* P17 polypeptide (Tp17) or Tp17-like polypeptides. In addition, the invention provides methods and compositions for increasing or decreasing the binding between a lysozyme and a TP-17 or a TP-17 like polypeptide.

BACKGROUND OF THE INVENTION

Syphilis is a disease caused by *Treponema pallidum* (hereinafter also referred to as "Tp") infection. The diagnosis of syphilis is generally made by an immunoassay of anti-Tp antibody in the blood using, for example, the *Treponema pallidum* Hemagglutination Test (TPHA), the Fluorescent *Treponema* Antibody Absorption Test (FTA-ABS) and/or the *Treponema pallidum* Immobilization Test (TPI), as well as enzyme-linked immuno sorbent assay (ELISA) and Western Blot systems. These tests detect antibodies that react with Tp or antigen preparations from Tp, such as the Tp antigens Tp15, Tp17, and Tp47, for example. The TPI test involves a microscopic assessment of the extent to which complement activating antibodies in a patient's serum inhibit the mobility of Tp. This test is not generally used as a diagnostic due to its high cost. The TPHA test involves agglutination of patient serum antibodies with erythrocytes to which the Tp sonicate antigen is bound. The FTA-ABS test involves indirect immunofluorescence microscopy to detect the binding of specific antibodies in patient serum to Tp attached to a solid support via a fluorescent-labelled secondary antibody. Although these assays are widely used, they lack the sensitivity required for detecting early stage or low level infection, when Tp antibody levels in the body fluids are very low.

In addition, the popular use of individual recombinant or purified Tp antigens in existing immunoassays for syphilis does not account for the binding by some antibodies to complexes formed between Tp antigens and other antigens (i.e., Tp antigen binding partners) normally present in the subject's body fluid. Existing immunoassays thus fail to detect such antibodies in the absence of the Tp antigen binding partner, which results in some instances in low sensitivity or false negative assay results. A need therefore exists for pathogen diagnostic assays with improved sensitivity, which detect antibodies that bind to pathogen antigen/binding partner complexes.

SUMMARY OF THE INVENTION

The invention provides compositions and methods for the detection and treatment of a pathogen infection. The invention generally relates to the discovery that the *Treponema pallidum* polypeptide, Tp17, binds to lysozyme, an anti-microbial peptide produced by the host, and inhibits lysozyme's anti-microbial activity. The binding site on Tp17 for lysozyme and the binding site on lysozyme for Tp17 were identified. Comparisons of TP17 sequences required for binding and inhibiting lysozyme with related proteins provided for the identification of lysozyme binding consensus sequences that are conserved among many different pathogens, including Herpes Simplex viruses, suggesting that TP17-related polypeptide binding to lysozyme provides a general mechanism for inhibiting a host immune response. Accordingly, the invention also provides for the identification of mutant lysozyme polypeptides containing mutations that interfere with or destabilize TP17 binding. Such polypeptides, or fragments thereof, useful in preventing or treating a pathogen infection. In addition, the invention provides for improved diagnostic assays based on the detection of antibodies that bind to a Tp17-lysozyme complex.

The identification of a lysozyme binding motif on Tp17, as well as the identification of lysozyme binding motif consensus sequences shared by other pathogen-derived proteins, also provides useful compositions and methods for the detection or inhibition of lysozyme, as well as the detection of specific pathogens and inhibition of the corresponding infections besides syphilis. In addition, pathogen-derived polypeptides are useful in the diagnosis, prophylaxis, and treatment of a number of diseases, including diseases related to aberrant lysozyme activity. Those polypeptides also provide a useful affinity tag for use in protein purification using inexpensive lysozyme affinity chromatography.

In one aspect, the invention generally features a fragment of a substantially pure Tp17-like polypeptide containing at least a lysozyme binding motif containing an amino acid sequence of $Xaa_n$ Pro His $Xaa_n$ (SEQ ID NO:1), where Xaa is any amino acid and n is at least one and the fragment is capable of binding a lysozyme polypeptide and where the motif is not CKPHDC (SEQ ID NO:24). In one embodiment, the fragment is between about 4 amino acids and about 200 amino acids (e.g., 5, 10, 25, 50, 75, 100, 125, 150, 175) of a Tp17-like polypeptide. In another embodiment, the fragment is less than about 30 or 100 amino acids of a Tp17-like polypeptide. In another embodiment, the fragment is capable of substantially inhibiting an enzymatic activity or an anti-microbial activity of the lysozyme. In yet another embodiment, the lysozyme binding motif contains an amino acid consensus sequence CS1: Cys $Xaa_1$ $Xaa_2$ $Xaa_3$ Pro His $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$ Cys (SEQ ID NO:2), where $Xaa_1$, $Xaa_2$, $Xaa_3$, $Xaa_4$, $Xaa_5$, $Xaa_6$, $Xaa_7$, $Xaa_8$, $Xaa_9$, $Xaa_{10}$, $Xaa_{11}$, $Xaa_{12}$, or $Xaa_{13}$ is any amino acid, is absent, or is a peptide bond.

In related aspects, the invention features a substantially pure nucleic acid molecule encoding the fragment of the previous aspect, a vector containing the nucleic acid molecule, and a host cell containing such a vector.

In another aspect, the invention features a substantially pure mutant lysozyme polypeptide containing at least one amino acid mutation that reduces binding between the mutant lysozyme polypeptide and a Tp17-like polypeptide (e.g., reduces binding by 5%, 10%, 25%, 50%, 75%, 85%, or 95% relative to wild-type binding), where the mutant lysozyme polypeptide retains at least 50%, 60%, 75%, 85%, or 95% of the anti-microbial activity of a corresponding wild-type lysozyme polypeptide. In one embodiment, the mutation reduces binding between the mutant lysozyme polypeptide and a Tp17-like polypeptide by at least 5% relative to wild-type lysozyme polypeptide binding. In another embodiment, the mutation affects a surface charge in the corresponding wild-type polypeptide. In other embodiments, the mutation is in a positively charged amino acid residue, is in a negatively charged amino acid residue, or is in a hydrophobic amino acid residue of a wild-type lysozyme polypeptide that contacts a Tp17-like polypeptide. In other embodiments, the mutation is of at least one, two, three, four, or more amino acid positions selected from the group consisting of Lys19, Arg23, Lys51, Gly 55, Asn57, Arg131, Asn132 and Arg133 of human lysozyme or is present at a corresponding position in a lysozyme derived from another species (e.g., prokaryotic, eukaryotic, mammalian).

In a related aspect, the invention features a substantially pure nucleic acid molecule encoding the lysozyme polypeptide of the previous aspect, a vector containing such a nucleic acid molecule, and a host cell containing this vector.

In yet another aspect, the invention features a composition containing a substantially pure Tp17-like polypeptide and a substantially pure lysozyme polypeptide, where the Tp17-like polypeptide is not an Ivy polypeptide. In one embodiment, the lysozyme is exogenous. In one embodiment, the composition further contains carrier particles (e.g., red blood cells, polypeptide aggregate particles, polymeric particles, inorganic particles, paramagnetic particles, and yeast cells).

In yet another aspect, the invention features a method for detecting an immune response against a pathogen in a subject. The method involves (a) contacting a biological sample from the subject with an exogenous lysozyme and a Tp17-like polypeptide; and (b) detecting antibody binding to the Tp17-like polypeptide or to a Tp17-like polypeptide-lysozyme polypeptide complex.

In yet another aspect, the invention features a method for enhancing the sensitivity of a diagnostic assay for detecting an immune response against a pathogen. The method involves adding a lysozyme polypeptide to the diagnostic assay (e.g., an agglutination assay), where the addition of the lysozyme polypeptide increases the assay's sensitivity by at least 5%.

In various embodiments of the previous aspects, the lysozyme polypeptide is contacted with the Tp17-like polypeptide prior to, during, or after contacting the biological sample. In other embodiments, the assay is an immunoassay (e.g., enzyme-linked immunoabsorbent assay (ELISA), Western blot, immunoagglutination assay, radioimmunoassay, turbidimetric assay, nephelometric assay, immunochromatographic assay, chemiluminescent assay, and fluorescent assay). In other embodiments, the biological sample is selected from the group consisting of blood, serum, plasma, tears, saliva, sputum, nasal fluid, ear fluid, genital fluid, breast fluid, milk, colostrum, placental fluid, perspiration, synovial fluid, ascites fluid, gastrointestinal fluid, exudate, transudate, pleural fluid, pericardial fluid, amniotic fluid, cerebrospinal fluid, bile, gastric fluid, semen, fecal material, upper airway fluid, peritoneal fluid, fluid harvested from a site of inflammation, fluid harvested from a pooled collection site, bronchial lavage, urine, biopsy material, aqueous humor, material from the forestomach of a ruminant animal, nucleated cell sample, any fluid associated with a mucosal surface, hair, and skin. In one preferred embodiment, the method is used to diagnose syphilis.

In another aspect, the invention features a composition for detecting a pathogen in a sample, the composition containing a lysozyme polypeptide fragment containing the amino acid sequence Xaa Xaa Xaa Xaa Xaa Xaa Cys Xaa Xaa Xaa Xaa Xaa Xaa Xaa Xaa Xaa Xaa Xaa Xaa Xaa Xaa Xaa Xaa Xaa Xaa Xaa Xaa Xaa Trp Xaa Cys Xaa Xaa Xaa Xaa Glu Ser Xaa Xaa Xaa Thr Xaa Xaa Xaa Xaa Xaa Xaa Xaa Xaa Xaa Ser Xaa Asp Tyr Gly Xaa Xaa Gln Ile Asn Xaa Xaa Xaa Trp Cys Xaa Xaa Xaa Xaa Xaa Xaa Xaa Xaa Xaa Xaa Xaa Cys Xaa Xaa Xaa Cys Xaa Xaa Leu Xaa Xaa Xaa Xaa Xaa Xaa Xaa Xaa Cys Ala Lys Xaa Xaa Xaa Xaa Xaa Xaa Xaa Xaa Xaa Xaa Xaa Trp Xaa Xaa Trp Xaa Xaa Xaa Cys Xaa Xaa Xaa Xaa Xaa Xaa Xaa Xaa Xaa Cys Xaa Xaa Xaa (SEQ ID NO:28), where Xaa is any amino acid or is absent, where the fragment is capable of binding to a Tp17-like polypeptide.

In yet another aspect, the invention features a method for detecting or identifying a pathogen or pathogen polypeptide. The method involves (a) contacting a sample with a lysozyme polypeptide fragment containing the amino acid sequence:

```
                                        (SEQ ID NO: 28)
     Xaa Xaa Xaa Xaa Xaa Xaa Cys Xaa Xaa Xaa Xaa

Xaa Xaa Xaa Xaa Xaa Xaa Xaa Xaa Xaa Xaa Xaa

Xaa Xaa Xaa Xaa Xaa Trp Xaa Cys Xaa Xaa Xaa Xaa

Glu Ser Xaa Xaa Xaa Thr Xaa Xaa Xaa Xaa Xaa

Xaa Xaa Xaa Xaa Ser Xaa Asp Tyr Gly Xaa Xaa Gln

Ile Asn Xaa Xaa Xaa Trp Cys Xaa Xaa Xaa Xaa

Xaa Xaa Xaa Xaa Xaa Xaa Cys Xaa Xaa Xaa Cys Xaa

Xaa Leu Xaa Xaa Xaa Xaa Xaa Xaa Xaa Xaa Cys Ala

Lys Xaa Xaa Xaa Xaa Xaa Xaa Xaa Xaa Xaa Xaa Xaa

Trp Xaa Xaa Trp Xaa Xaa Xaa Cys Xaa Xaa Xaa Xaa

Xaa Xaa Xaa Xaa Xaa Cys Xaa Xaa Xaa,
```

where Xaa is any amino acid or is absent, under conditions that permit binding; and (2) detecting binding of the lysozyme polypeptide to a polypeptide in the sample, where the binding indicates the presence of a pathogen or pathogen polypeptide in the sample. In another embodiment, the invention further involves determining the sequence of the polypeptide bound to the lysozyme polypeptide. In some embodiments, the lysozyme polypeptide contains a sequence derived from a human lysozyme polypeptide.

In another aspect, the invention features a method for detecting lysozyme in a sample, the method involves (a) contacting the sample with a Tp17-like polypeptide bound to a solid support; and (b) detecting binding of the polypeptide to a polypeptide in the sample, where the binding indicates lysozyme is present in the sample (e.g., a biological fluid, a cell culture, a body sample, a water sample, a fluid sample, a food, a medicine, or a pathogen culture). In one embodiment, the method further involves removing lysozyme from the sample through the binding.

In another aspect, the invention features a kit for detecting an immune response to a pathogen containing a Tp17-like polypeptide and a lysozyme polypeptide.

In another aspect, the invention features a kit for detecting a pathogen in a sample containing a labeled lysozyme polypeptide containing SEQ ID NO:28.

In another aspect, the invention features a fusion polypeptide containing at least a fragment of a Tp17-like polypeptide lysozyme binding motif fused to a second amino acid sequence with which it is not naturally linked. In one embodiment, the fusion polypeptide is fixed to a solid support. In another embodiment, the motif is at a terminus of the fusion polypeptide. In another embodiment, the fusion polypeptide is capable of reducing a lysozyme anti-microbial activity.

In another aspect, the invention features a method for isolating a fusion polypeptide, the method containing the steps of: (a) providing the fusion polypeptide of the previous aspect; (b) contacting the fusion polypeptide with a lysozyme polypeptide, where the lysozyme is affixed to a solid support, under conditions that permit binding of the fusion polypeptide to the lysozyme polypeptide; and (c) eluting the fusion polypeptide from the lysozyme polypeptide.

In another aspect, the invention features a method for identifying a candidate compound that increases lysozyme antimicrobial activity. The method involves detecting a reduction in binding between a lysozyme polypeptide and a polypeptide containing a lysozyme binding motif in the presence of the candidate compound. In one embodiment, the candidate compound reduces binding of a lysozyme binding motif to a catalytic glutamic acid that corresponds to Glu53 of human lysozyme.

In another aspect, the invention features a method for identifying a mutant lysozyme polypeptide having increased antimicrobial activity. The method involves (a) providing a lysozyme polypeptide containing at least one mutation in the amino acid sequence of the polypeptide relative to a wild-type lysozyme sequence; and (b) detecting a reduction in binding between the mutant lysozyme polypeptide and a Tp17-like polypeptides.

In yet another aspect, the invention features a method for treating or preventing a pathogen infection in a subject in need thereof. The method involves administering an effective amount of a mutant lysozyme polypeptide containing an amino acid mutation to a subject, where the mutation reduces binding between the lysozyme polypeptide and a Tp17-like polypeptide.

In another aspect, the invention features a method for treating or preventing a pathogen infection in a subject in need thereof. The method involves administering an effective amount of a mutant Tp17-like polypeptide containing an amino acid mutation to the subject, where the administration of the mutant Tp17-like polypeptide reduces the binding between a pathogen-expressed Tp17-like polypeptide and an endogenous lysozyme polypeptide.

In another aspect, the invention features a vaccine that increases an immune response in a subject in need thereof, the composition containing at least one of the gJ and gD glycoproteins from Herpes Simplex-2 virus.

In another aspect, the invention features a vaccine that increases an immune response in a subject in need thereof, the composition containing a lysozyme binding polypeptide.

In another aspect, the invention features a vaccine that increases an immune response in a subject in need thereof, the composition containing a lysozyme polypeptide and a polypeptide containing a lysozyme binding motif.

In another aspect, the invention features a method of diagnosing a Herpes Simplex Virus type-2 infection in a subject. The method involves detecting the presence of a gJ protein lysozyme binding motif in a sample from the subject. In one embodiment, the lysozyme binding motif is detected in a lysozyme binding assay. In another embodiment, the lysozyme binding motif is detected in an immunoassay.

In another aspect, the invention features a method for reducing lysozyme enzymatic activity in a sample. The method involves contacting a sample with a Tp17-like polypeptide under conditions that permit binding of the polypeptide to the lysozyme, where the Tp17-like polypeptide does not contain an Ivy protein.

In another aspect, the invention features a method for reducing lysozyme enzymatic activity in a subject. The method involves administering to the subject an effective amount of a Tp17-like polypeptide or fragment thereof.

In various embodiments of the previous aspects, the polypeptide is Herpes Simplex Virus Type 2 glycoprotein J. In other embodiments of the previous aspects, the method is used to treat or prevent a disease selected from the group consisting of cancer, Alzheimer's disease, renal amyloidosis, leukemia, Crohn's disease, and allergy.

In another aspect, the invention features a fragment of a substantially pure Tp17-like polypeptide containing at least a lysozyme binding motif containing an amino acid sequence Cys $Xaa_1$ $Xaa_2$ $Xaa_3$ His $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$ Cys (SEQ ID NO: 175), where Xaa is any amino acid or is absent and the fragment is capable of binding a lysozyme polypeptide. In one embodiment, the fragment is derived from *Porphyromonas gingivalis* or *Helicobacter pylori*.

In another aspect, the invention features a fragment of a substantially pure APP-like polypeptide containing at least a lysozyme binding motif containing an amino acid sequence of Cys $Xaa_1$ $Xaa_2$ $Xaa_3$ $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$ Cys, where $Xaa_1$ $Xaa_2$, $Xaa_3$, $Xaa_4$ and $Xaa_5$ are any amino acid or are absent, $Xaa_6$ is amino acid K, R or H, $Xaa_7$ is A or G, $Xaa_8$ is K, R, or H, $Xaa_9$ and $Xaa_{10}$ are any amino acid or are absent, $Xaa_{11}$ is amino acid K or R, $Xaa_{12}$ is any amino acid or is absent, and $Xaa_{13}$ is amino acid E, D, Q or N (SEQ ID NO:177). In one embodiment, the APP-like polypeptide is the β-amyloid precursor protein. In another embodiment, the fragment is substantially a fragment of a human β-amyloid precursor protein.

In related aspects, the invention features nucleic acids encoding the fragments of the previous aspect, vectors containing the nucleic acids, and host cells containing such vectors.

In another aspect, the invention features a composition containing an APP-like polypeptide and a substantially pure lysozyme polypeptide.

In another aspect, the invention features a method of diagnosing Alzheimer's disease in a subject. The method involves detecting the presence in a biological sample (serum sample, a cerebrospinal fluid sample, or a tissue sample) from the subject of a complex between an APP-like polypeptide and a lysozyme polypeptide. In one embodiment, method involves an immunoassay.

In another aspect, the invention features a method of diagnosing Alzheimer's disease by detecting the presence of an antibody that binds to a complex between an APP-like polypeptide and a lysozyme polypeptide.

In another aspect, the invention features a method for identifying a candidate compound that modulates binding between the APP-like polypeptide and a lysozyme polypeptide. The method involves detecting a reduction in binding between the Tp17-like polypeptide and the lysozyme polypeptide in the presence of the candidate compound.

In another aspect, the invention features a Tp17-like polypeptide containing at least a lysozyme binding motif having an amino acid sequence of $Xaa_n$ Pro His $Xaa_n$ (SEQ ID NO:1), where Xaa is any amino acid and n is at least one and the fragment is capable of binding SLLP1. In one embodiment, the fragment is between about 4 amino acids and about 200 amino acids of a Tp17-like polypeptide. In one embodiment, the motif contains the amino acid consensus sequence CS1: Cys $Xaa_1$ $Xaa_2$ $Xaa_3$ Pro His $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$ Cys (SEQ ID NO:2), where $Xaa_1$, $Xaa_2$, $Xaa_3$, $Xaa_4$, $Xaa_5$, $Xaa_6$, $Xaa_7$, $Xaa_8$, $Xaa_9$, $Xaa_{10}$, $Xaa_{11}$, $Xaa_{12}$, or $Xaa_{13}$ is any amino acid, is absent, or is a peptide bond.

In related aspects, the invention features a substantially pure nucleic acid molecule encoding the fragment of the previous aspect, a vector containing the nucleic acid molecule, and a host cell containing the vector.

In another aspect, the invention features a substantially pure mutant SLLP1 polypeptide containing at least one amino acid mutation that reduces binding between the mutant SLLP1 polypeptide and a Tp17-like polypeptide relative to a wild-type SLLP1 polypeptide.

In another aspect, the invention features a substantially pure mutant SLLP1 polypeptide containing at least one amino acid mutation that increases the enzymatic activity of the mutant SLLP1 polypeptide relative to a wild-type SLLP1 polypeptide. In one embodiment, the enzymatic activity includes an antimicrobial activity.

In another aspect, the invention features a method for modulating fertility in a subject in need thereof. The method involves administering an effective amount of a mutant SLLP1 polypeptide containing at least one amino acid mutation to the subject, where the administration of the mutant SLLP1 polypeptide alters the binding between a Tp17-like polypeptide and an endogenous SLLP1 polypeptide such that the subject's fertility is modulated.

In another aspect, the invention features a method for modulating fertility in a subject in need thereof. The method involves administering an effective amount of a Tp17-like polypeptide to the subject, where the administration of the Tp17-like polypeptide reduces the binding between an endogenous SLLP1 polypeptide and a cognate receptor at an egg cell surface, such that the subject's fertility is modulated.

In yet another aspect, the invention features a method for identifying a candidate compound that modulates human fertility. The method involves detecting a reduction in binding between a SLLP1 polypeptide and a polypeptide containing a lysozyme binding motif in the presence of the candidate compound.

In another aspect, the invention features a method for treating or preventing a sexually transmitted pathogen infection in a subject. The method involves administering an effective amount of a mutant SLLP1 polypeptide containing at least one amino acid mutation to a subject, where the mutation reduces binding between an endogenous SLLP1 polypeptide and a pathogen-expressed Tp17-like polypeptide.

In another aspect, the invention features a method for treating or preventing a sexually transmitted pathogen infection in a subject. The method involves administering an effective amount of a Tp17-like polypeptide to the subject, where the administration of the Tp17-like polypeptide reduces the binding between a pathogen-expressed Tp17-like polypeptide and an endogenous SLLP1 polypeptide.

In another aspect, the invention features a method for identifying a candidate compound useful for the treatment or prevention of a sexually transmitted pathogen infection. The method involves (a) contacting a SLLP1 polypeptide and a Tp17-like polypeptide with a candidate compound; and (b) detecting a reduction in binding between the lysozyme polypeptide and the pathogen expressed Tp17-like polypeptide in the presence of the candidate compound.

In another aspect, the invention features a method for reducing SLLP1 binding to a sexually transmitted pathogen-expressed Tp17-like protein in a subject. The method involves administering to the subject an effective amount of a Tp17-like polypeptide or a lysozyme polypeptide, or a fragment thereof.

In another aspect, the invention features a contraceptive composition containing a Tp17-like polypeptide that interferes with SLLP1 binding during a fertilization process.

In another aspect, the invention features a pharmaceutical composition for preventing or treating a sexually transmitted pathogen infection, the composition containing a Tp17-like polypeptide that interferes with SLLP1 binding during an infection process.

In another aspect, the invention features a pharmaceutical composition for use as an anti-microbial containing at least an effective amount of bacteriophage T4 lysozyme and papain or bacitracin. In one embodiment, pharmaceutical composition of the previous aspect, where the composition contains bacteriophage T4 lysozyme, papain, and bacitracin. In one embodiment, the amount of T4 lysozyme present in a unit dose is between 2 mg and 100 mg (e.g., 5, 10, 20, 30, 40, 50, 60, 70, 80, or 90). Preferably, the amount of T4 lysozyme present in a unit dose is 5 mg. In another embodiment, the amount of papain present in a unit dose is 2 mg. the amount of bacitracin present is 3 mg per unit dose. In another embodiment, composition is an oral formulation (e.g., a buccal tablet).

In another aspect, the invention features a method of treating a pathogen infection in a subject involves administering to a subject diagnosed as having a pathogen infection a pharmaceutical composition containing bacteriophage T4 lysozyme and papain or bacitracin. In one embodiment, the pharmaceutical composition contains bacteriophage T4 lysozyme, papain, and bacitracin. In another embodiment, the pharmaceutical composition is in an oral formulation.

In various embodiments of any of the above aspects, the Tp17-like polypeptide is derived from a pathogen selected from the group consisting of a bacteria, a virus, a parasite, a plasmid, a prion, a mycoplasma, and a mycotic agent.

In other embodiments of any of the previous aspects, the pathogen is *Escherichia coli, Pseudomonas aeruginosa, Pseudomonas putida, Yersinia pestis, Shigella flexnerii, Treponema denticola, Vibrio cholerae, Vibrio vulnificus, Vibrio parahemolyticus, Chlamydia pneumoniae, Chlamydia trachomatis, Staphylococcus aureus, Staphylococcus epidermidis, Streptococcus pneumoniae, Streptococcus agalactiae, Streptococcus mutans, Streptococcus pyogenes, Enterococcus faecalis, Bordetella bronchiseptica, Bordetella pertussis, Bordetella parapertussis, Helicobacter hepaticus, Helicobacter pylori, Salmonella typhimurium, Ralstonia solanacearum, Xanthomonas campestris, Pseudomonas syringae, Pasteurella multocida, Brucella melitensis, Brucella suis, Porphyromonas gingivalis*, Severe Acute Respiratory Syndrome (SARS) coronavirus, Respiratory Syncytial Virus, Hepatitis A virus, Hepatitis B virus, Hepatitis C virus, Rubella virus, *Toxoplasma gondii, Trypanozoma* spp., *Gardnerella vaginalis, Mycobacterium avium, Mycobacterium leprae, Mycobacterium paratuberculosis, Mycobacterium tuberculosis, Campylobacter jejuni, Helicobacter* spp., *Agrobacterium tumefaciens, Moraxella catarrhalis, Neisseria meningitidis, Neisseria gonorrhoeae, Haemophilus influenzae, Haemophilus ducreyii, Propionibacterium acnes, Listeria monocytogenes*, Herpes Simplex Virus type 2, Influenza virus, TACARIBE virus, Bluetongue virus, *Bacteroides thetaiotaomicron, Coxiella burnetti, Legionella pneumophila, Salmonella typhi*, Chimpanzee cytomegalovirus, Human cytomegalovirus, Human papilloma virus, Dengue virus, Foot and Mouth Disease, West Nile virus, Avian influenza virus, Human immunodeficiency virus, LdMNPV, *Plasmodium falciparum, Plasmodium ovale, Emeiria tenella, Eimeria acervulina, Giardia lamblia, Plasmodium yoelii* and pathogens carried by *Anopheles gambiae.*

In other embodiments of any of the previous aspects, the pathogen is *Treponema denticola, Bacteroides thetaiotaomicron, Coxiella burnetti, Haemophilus influenzae, Neisseria gonorrhoeae, Legionella pneumophila, Staphylococcus, aureus, and Salmonella typhi, Neisseria meningitidis* serogroup A and serogroup B, *Vibrio cholerae, Vibrio vulnificus, Haemophilus ducreyi*, and *Bordetella pertussis*. Preferably, the pathogen is *Treponema pallidum.*

In other embodiments of any of the previous aspects, the motif contains the amino acid consensus sequence CS2: $Xaa_1$ $Xaa_2$ Pro His $Xaa_3$ $Xaa_4$ (SEQ ID NO:3), where $Xaa_1$ is Cys, Lys, Val, Ala, or is absent; $Xaa_2$ is Ala, Cys, or Lys; $Xaa_3$ is Ala, Asp, or Glu, and $Xaa_4$ is Cys, Gly, or Lys. In other embodiments of any of the previous aspects, the Tp17-like polypeptide contains the sequence Cys $Xaa_1$ $Xaa_2$ $Xaa_3$ Pro His $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$ Cys (SEQ ID NO:2), where $Xaa_1$, $Xaa_2$, $Xaa_3$, $Xaa_4$, $Xaa_5$, $Xaa_6$, $Xaa_7$, $Xaa_8$, $Xaa_9$, $Xaa_{10}$, $Xaa_{11}$, $Xaa_{12}$, or $Xaa_{13}$ is any amino acid or is absent. In still other embodiments of any of the previous aspects, the motif contains an amino acid consensus sequence CS3: Xaa Cys Pro His Ala Gly (SEQ ID NO:25), where Xaa is Cys or Val. In yet other embodiments of any of the previous aspects, the motif is selected from the group consisting of CCPHAG (SEQ ID NO:4), VCPHAG (SEQ ID NO:5), VAPHDC (SEQ ID NO:6), KAPHDK (SEQ ID NO:7), VKPHDG (SEQ ID NO:8); KKPHAK (SEQ ID NO:9), KAPHEK (SEQ ID NO:10), KKPHAC (SEQ ID NO:11), VAPHAG (SEQ ID NO:12), VKPHAK (SEQ ID NO:13), VKPHAC (SEQ ID NO:14), VAPHEG (SEQ ID NO:15), VKPHEK (SEQ ID NO:16), VCPHEK (SEQ ID NO:17), CKPHAG (SEQ ID NO:18), ACPHAG (SEQ ID NO:19) or KCPHDC (SEQ ID NO:20), VKPHDK (SEQ ID NO:21), KKPHAG (SEQ ID NO:22), and CAPHEK (SEQ ID NO:23).

In various embodiments of any of the above aspects, the lysozyme polypeptide contains the following amino acid sequence:

```
                                       (SEQ ID NO: 28)
Xaa Xaa Xaa Xaa Xaa Xaa Cys Xaa Xaa Xaa Xaa Xaa

Xaa Xaa Xaa Xaa Xaa Xaa Xaa Xaa Xaa Xaa Xaa Xaa

Xaa Xaa Xaa Xaa Trp Xaa Cys Xaa Xaa Xaa Xaa Glu

Ser Xaa Xaa Xaa Thr Xaa Xaa Xaa Xaa Xaa Xaa Xaa

Xaa Xaa Xaa Ser Xaa Asp Tyr Gly Xaa Xaa Gln Ile

Asn Xaa Xaa Xaa Trp Cys Xaa Xaa Xaa Xaa Xaa Xaa

Xaa Xaa Xaa Xaa Xaa Cys Xaa Xaa Xaa Cys Xaa Xaa

Leu Xaa Xaa Xaa Xaa Xaa Xaa Xaa Xaa Cys Ala Lys

Xaa Xaa Xaa Xaa Xaa Xaa Xaa Xaa Xaa Xaa Xaa Trp

Xaa Xaa Trp Xaa Xaa Xaa Cys Xaa Xaa Xaa Xaa Xaa

Xaa Xaa Xaa Xaa Cys Xaa Xaa Xaa,
```

where Xaa is any amino acid or is absent.

In other embodiments of any of the previous aspects, the Tp17-like polypeptide or the lysozyme polypeptide, or a fragment thereof, is isolated from a biological sample, is a recombinant polypeptide, is fused to an affinity tag, is affixed to a solid support (e.g., a resin, a gel, a bead, a well, a column, a chip, a membrane, a matrix, a plate, and a filter device), is derived from a human polypeptide, is detectably labeled (e.g., labeled with a fluorophore, a fluorescent protein, a chromophore, a radioactive moiety, a luminiferous moiety, and an enzymatically active label). In still other embodiments, the lysozyme polypeptide and the Tp17-like polypeptide are present in a molecular ratio of between about 0.001 and about 1,000,000.

Compositions and methods of the invention are useful for identifying and/or quantifying antibodies to pathogens such as, for example, *Treponema pallidum, Escherichia coli* (e.g., *E. coli* O157:H7 and *E. coli* K1), *Pseudomonas aeruginosa, Pseudomonas putida, Yersinia pestis, Shigella flexnerii, Treponema denticola, Vibrio cholerae, Vibrio vulnificus, Vibrio parahemolyticus, Chlamydia pneumoniae, Staphylococcus aureus, Staphylococcus epidermidis, Streptococcus pneumoniae, Streptococcus agalactiae, Streptococcus mutans, Streptococcus pyogenes, Enterococcus faecalis, Bordetella bronchiseptica, Bordetella pertussis, Bordetella parapertussis, Helicobacter hepaticus, Salmonella typhimurium, Ralstonia solanacearum, Xanthomonas campestris, Pseudomonas syringae, Pasteurella multocida, Brucella melitensis, Brucella suis, Mycobacterium tuberculosis, Campylobacter jejuni, Helicobacter* spp., *Agrobacterium tumefaciens, Moraxella catarrhalis, Neisseria meningitidis, Neisseria gonorrhoeae, Haemophilus influenzae, Haemophilus ducreyii, Propionobacterium acnes, Listeria monocytogenes*, Herpes Simplex Virus type 2, Influenza virus, TACARIBE virus, Bluetongue virus, Chimpanzee cytomegalovirus, Human cytomegalovirus, Human papilloma virus, Dengue virus, Foot and Mouth Disease, Human immunodeficiency virus, LdMNPV, *Plasmodium falciparum, Plasmodium ovale, Emeiria tenella, Eimeria acervulina, Giardia lamblia, Plasmodium yoelii*, and pathogens carried by *Anopheles gambiae*. In another embodiment, pathogens such as *Mycobacterium paratuberculosis*, Ebola virus, Rift Valley Fever virus, Severe Acute Respiratory Syndrome (SARS) virus, Small Pox virus, *Bacillus anthracis, Leishmania* Spp., mycoplasma, rickettsia, fungi, and yeast are detected.

In another embodiment, the invention provides compositions for detecting anti-pathogen antibodies in a sample, comprising (a) a polypeptide comprising the amino acid sequence of TAPHRGLATLYNGDC (SEQ ID NO:26) or CSPEVGQMDC (SEQ ID NO:27), and (b) an a full-length lysozyme polypeptide or a fragment thereof.

In an embodiment, lysozyme (A) and Tp17-like polypeptides (B) are present in a molar ratio (A/B) of between about 0.001 and about 1,000,000. In a preferred embodiment, lysozyme (A) and Tp17-like polypeptides (B) are present in a molar ratio (A/B) of between about 0.01 and about 1,000,000. In another preferred embodiment, lysozyme (A) and Tp17-like polypeptides (B) are present in a molar ratio (A/B) of between about 0.1 and about 1,000,000. Most preferably, lysozyme (A) and Tp17-like polypeptides (B) are present in a molar ratio (A/B) of between about 1 and about 1000, between about 10 and about 1000, or between about 100 and about 1000.

The methods of the invention are used to diagnose diseases such as, for example, syphilis, HIV infection, genital herpes, bubonic plague, dysentery, shigellosis, dental caries, *E. coli* infection, cystic fibrosis, tuberculosis, cholerae, group A or group B streptococcal infections, staphylococcal infections, gastric ulcer, whooping cough, Enterococcal infections, chlamydiosis, brucellosis, otitis media, otitis interna, meningitis, influenza infection, malaria, Hepatitis B, and Hepatitis C virus infections. In another embodiment, the methods of the invention are used to diagnose salmonellosis, gonorrhea, vibriosis, colibacillosis, pneumonia, bronchitis, severe acute respiratory syndrome (SARS), and cytoplasmic storage diseases, such as lysosomal storage diseases.

The invention also provides methods for detecting lysozyme in a sample by contacting the sample with a Tp17-like polypeptide and detecting the binding of the Tp17-like polypeptide to the lysozyme. Lysozyme anti-microbial activity is reduced by contacting a sample with a Tp17-like polypeptide under conditions that permit binding of the Tp17-like polypeptide to the lysozyme. The sample may be a pathogen preparation, such as, for example, a bacteria, a virus, a parasite, a plasmid, a mycoplasma, a mycotic agent (e.g., fungus and yeast), and a prion preparation. The sample may also be a material that needs to be rendered free of lysozyme contamination, such as a biological sample (e.g., throat aspirate, hemoculture, cerebrospinal fluid), culture vessel, cell culture, cuvette, swab, clinical diagnostic apparatus or assay material, medical instrument, fluid, water, food, medicine, implant, or graft.

The methods of the invention may also be used for reducing lysozyme anti-microbial activity in a subject (e.g., an animal, such as human) by administering to the subject an effective amount of a Tp17-like polypeptide. The methods are used to treat or prevent diseases such as cancer, infectious disease, inflammatory disease, Alzheimer's disease, renal amyloidosis, leukemia, Crohn's disease, and allergy, which are associated with increased lysozyme activity over normal levels.

In another aspect, the invention provides compositions for detecting a pathogen in a sample, comprising a ligand, or a binding partner, capable of binding to a Tp17-like polypeptide. In an embodiment, the ligand comprises a lysozyme polypeptide, a monoclonal antibody, a polyclonal antibody, or an Fab fragment, or DNA or RNA aptamers, for example. In an embodiment, the ligand comprises a detection molecule.

In another aspect, the invention provides methods for detecting a pathogen in a sample by (1) contacting a sample with a ligand (e.g., a lysozyme polypeptide) capable of binding to a Tp17-like polypeptide under conditions that permit binding of the ligand to a pathogen or a pathogen polypeptide; and (2) detecting the binding of the ligand to the pathogen or pathogen polypeptide, if present, wherein such binding is indicative of the presence of the pathogen or pathogen polypeptide in the sample. In an embodiment, the ligand is labeled with a detection molecule, such as a fluorophore, a fluorescent protein, chromophore, radioactive moiety, luminiferous moiety or enzymatically active reporter.

In another aspect, the invention provides a kit comprising a Tp17-like polypeptide and a ligand capable of binding to the Tp17-like polypeptide. In an embodiment, the ligand is attached to a solid support such as a resin, bead, well, chip, column, gel, membrane, or filter device. In a preferred embodiment, the ligand is a lysozyme polypeptide.

In another aspect, the invention provides recombinant fusion proteins comprising a Tp17-like polypeptide linked to a polypeptide of interest. In an embodiment, the Tp17-like polypeptide is at the N or C terminus of the polypeptide of interest. In another embodiment, the Tp17-like polypeptide is between the N or C terminus of the polypeptide of interest. In an embodiment, the recombinant protein is capable of reducing lysozyme activity. The invention further provides methods of preparing the recombinant fusion proteins by linking the Tp17-like polypeptide to the polypeptide of interest. Yet further, the invention provides methods of using the recombinant fusion proteins to affinity purify a polypeptide of interest by (1) contacting a sample comprising a recombinant fusion polypeptide with lysozyme under conditions that permit the polypeptide to bind to lysozyme; (2) washing the sample; and (4) eluting the recombinant fusion polypeptide from the lysozyme. In an embodiment, the method comprises isolating the polypeptide of interest from the Tp17-like polypeptide. In an embodiment, the lysozyme is linked to a solid support.

In another aspect, the invention provides methods for treating or preventing a disease associated with a pathogen infection by administering to a subject in need thereof an effective amount of a lysozyme that is resistant to inhibition by a Tp17-like polypeptide.

In another aspect, the invention provides methods for treating or preventing a disease associated with a pathogen infection by administering to a subject in need thereof an effective amount of an reagent that inhibits the binding of a Tp17-like polypeptide to a lysozyme polypeptide. In one embodiment, the reagent inhibits binding of a Tp17-like polypeptide to the glutamic acid 53 of human or chicken lysozyme or to a corresponding amino acid residue in other species (numbering refers to the full-length human lysozyme sequence deposited under accession number NP_000230In another embodiment, the reagent is a peptide, chemical drug, antibody, nucleic acid, PNA, small interfering RNA, or bacteriophage, DNA aptamer, or RNA aptamer. In another embodiment, the reagent is a lysozyme ligand.

The invention also provides treatments or vaccines comprising at least one of the gJ and gD glycoproteins from Herpes Simplex-2 virus. The invention also provides vaccines comprising (a) a lysozyme ligand and/or (b) a lysozyme polypeptide.

By "Tp17-like polypeptide" is meant an amino acid sequence, or fragment thereof, that comprises a $Xaa_n$ Pro His $Xaa_n$ consensus sequence and that has the ability to bind to a lysozyme polypeptide or to inhibit a biological activity of lysozyme. Exemplary TP17-like polypeptides are provided in FIGS. 1 and 2. Tp17-like polypeptides include, but are not limited to, all variants, homologs, and mutants of Tp17, full length or fragments thereof, and fusion proteins containing any of the above as a material part. In some embodiments, a TP17-like polypeptide comprises a $Xaa_n$ Pro His $Xaa_n$ consensus sequence and is at least 50%, 75%, 85%, 95%, or 99% identical to TP17 (Genbank Accession No. P29722; SEQ ID NO:31) or a fragment thereof. In other embodiments, a "Tp17-like polypeptide" comprises the following consensus sequence: CX(1,5)[KRH][AG][KRH]X(0,2)[KR]X(0,1)[EDQN]C(SEQ ID No:178) and binds lysozyme.

By "mutant Tp17-like polypeptide" is meant a TP-17-like polypeptide having at least one amino acid change relative to the sequence of a naturally-occurring sequence. Such changes include, for example, amino acid substitutions, deletions, or insertions. In some embodiments, mutant Tp17-like polypeptide homologs, mutants, fragments, substitutions and modifications retain the ability to bind to lysozyme. In one preferred embodiment, such polypeptides bind lysozyme, but fail to inhibit its anti-microbial activity. FIG. 7 describes exemplary methods for targeted and random identification of polypeptide mutants.

By "Tp17-like nucleic acid molecule" or "mutant Tp17-like nucleic acid molecule" is meant a nucleic acid sequence encoding a Tp17-like or mutant Tp17-like polypeptide, respectively.

By "APP-like polypeptide" is meant a polypeptide that binds lysozyme and that contains the following consensus sequence:

CX(1,5)[KRH][AG][KRH]X(0,2)[KR]X(0,1)[EDQN]C (SEQ ID No:178).

By "lysozyme polypeptide" is meant an amino acid sequence comprising the following consensus sequence

```
                                      (SEQ ID NO: 28)
    Xaa Xaa Xaa Xaa Xaa Xaa Cys Xaa Xaa Xaa Xaa

Xaa Xaa Xaa Xaa Xaa Xaa Xaa Xaa Xaa Xaa Xaa Xaa

Xaa Xaa Xaa Xaa Xaa Trp Xaa Cys Xaa Xaa Xaa Xaa

Glu Ser Xaa Xaa Xaa Thr Xaa Xaa Xaa Xaa Xaa Xaa
```

-continued

```
Xaa Xaa Xaa Xaa Ser Xaa Asp Tyr Gly Xaa Xaa Gln

Ile Asn Xaa Xaa Xaa Trp Cys Xaa Xaa Xaa Xaa Xaa

Xaa Xaa Xaa Xaa Xaa Xaa Cys Xaa Xaa Xaa Cys Xaa

Xaa Leu Xaa Xaa Xaa Xaa Xaa Xaa Xaa Xaa Cys Ala

Lys Xaa Xaa Xaa Xaa Xaa Xaa Xaa Xaa Xaa Xaa Xaa

Trp Xaa Xaa Trp Xaa Xaa Xaa Cys Xaa Xaa Xaa Xaa

Xaa Xaa Xaa Xaa Xaa Cys Xaa Xaa Xaa,
```

and having anti-microbial activity or enzymatic activities. Exemplary lysozyme polypeptides are listed in FIGS. 3A-1 to 3A-3 and 3B-1 to 3B-3. In one preferred embodiment, a lysozyme polypeptide is at least 50%, 75%, 85%, 95%, or 99% identical to human lysozyme (Genbank Accession No. NP_000230 NP_783862, NP_15906, NP_898881, NP_653235, NP_65159, NP_776246, NP_995328, NP_002280).

By "mutant lysozyme polypeptide" is meant a lysozyme amino acid sequence containing at least one amino acid change relative to a naturally occurring lysozyme amino acid sequence.

By "lysozyme nucleic acid molecule" or "mutant lysozyme nucleic acid molecule" is meant a nucleic acid molecule encoding a lysozyme or mutant lysozyme polypeptide, respectively.

BRIEF DESCRIPTION OF THE DRAWINGS

The foregoing and other objects, features and advantages of the present invention, as well as the invention itself, will be more fully understood from the following description of preferred embodiments when read together with the accompanying drawings, in which:

FIGS. 1A-1 to 1A-3 and 1B illustrate the lysozyme binding sites on Tp17-like polypeptides from a number of bacteria, viruses, parasites and mammalian organisms and the 17 amino acid consensus sequence they define. In FIG. 1B, Tp17-related polypeptides from *T. denticola, B. thetaiotaomicron, C. burnetti, H. influenzae, N. meningitidis* serogroup A and serogroup B, *V. cholerae, V. vulnificus, H. ducreyi, S. typhi, L. pneumophila, S. aureus, N. gonorrhoeae*, and *B. pertussis* fit the following consensus sequence: Cys $Xaa_1$ $Xaa_2$ $Xaa_3$ Pro His $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ Cys (SEQ ID NO:176) wherein Xaa is any amino acid or is absent. The two remaining proteins from *P. gingivalis*, and *H. pylori* are grouped under the following consensus: sequence Cys $Xaa_1$ $Xaa_2$ $Xaa_3$ His $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$ Cys (SEQ ID NO: 175), wherein x is any amino acid or is absent. FIG. 1B is a table defining a lysozyme binding motif conserved among a variety of clinically relevant bacterial pathogens.

FIGS. 2A-C illustrate the lysozyme binding sites on Tp17-like polypeptides from a number of bacteria, viruses, parasites, insects and mammalian organisms and the 6 amino acid consensus sequence they define.

FIGS. 3A-1 to 3A-3 are an alignment of mature lysozyme sequences from a number of species. E35 and D53 in mature chicken lysozyme (or $D_{52}$ in mature human lysozyme) (▼) belong to the catalytic dyad and are conserved across all known lysozyme sequences. A consensus sequence is shown at the bottom of the alignment. Amino acid conservation is represented according to Risler comparison symbols (Risler et al. (1988) J. Mol. Biol. 204:1019). In that representation system, X represents any amino acid or no amino acid, upper case letters correspond to 100% amino acid conservation, lower-case letters correspond to a value of amino acid conservation comprised between 50% and 90%. Moreover, conservative changes shared by more than 50% of the sequences are represented using the following symbols $ corresponds to leucine or methionine, ! corresponds to isoleucine or valine, and # corresponds to asparagine or aspartic acid.

FIGS. 3B-1 to 3B-3 are a continuation of the alignment of mature lysozyme sequences presented in FIGS. 3A-1 to 3A-3. A consensus sequence is shown at the bottom of the alignment using the nomenclature described with respect to FIGS. 3A-1 to 3A-3.

FIGS. 6A-C illustrate the amino acid (SEQ ID NO:29) and nucleotide (SEQ ID NO:30) sequence of GST-Tp17 fusion protein. The sequences corresponding to the GST moiety and to Tp17 are represented in italics and bold, respectively. Numbered lines, SEQ ID NO: 30, represent the sense DNA strand; the antisense or RNA strand is below the sense strand.

FIG. 11A shows an alignment of the amino acid sequence of the IVY protein from *E. coli* with the amino acid sequence of Tp17 from *T. pallidum*. A consensus sequence is shown under the alignment. "#" identifies conservatives (Asp/Glu) and semi-conservatives (Asp/Asn) changes whereas "!" indicates Val/Ile changes.

FIG. 17A is a table illustrating the relative hemagglutination intensity corresponding to 10 human syphilitic sera (Syph71, 09-4, 09-3, HSP91, HSP17, HSP3, 4932, 5895, HG62, and HG82). Serum samples were combined with Tp17 (R) in the presence or absence of natural human lysozyme (LyzN) or recombinant human lysozyme (LyzR). Results are expressed as reciprocal dilution titers (e.g., 80 means positive at dilution 1/80).

FIG. 21A illustrates the improved sensitivity of a second generation ELISA syphilis assay in the presence of recombinant human lysozyme.

FIG. 21B illustrates the improved sensitivity of a third generation ELISA syphilis assay in the presence of recombinant human lysozyme.

FIG. 28A shows the inhibition of bacteriolytic activity of Lizipaina® (Boehringer Ingelheim) by both GST-Tp17 and Tp17-His at various molar ratios. FIG. 28B shows the inhibition of the bacteriolytic activity of Lizozima CHIESI (Laboratorio CHIESI) by GST-Tp17 at various molar ratios. The height of each bar indicates the detected enzymatic activity. A lysozyme control is on the far left side of the figure.

FIGS. 34A-1 to 34A-3 and 34B-1 to 34B-3 are tables showing an alignment of lysozyme binding/inhibitor proteins, their Genbank accession numbers, and the host species that the peptide is present in. These amino acid sequences were identified in silico using the CX(1,5)[KRH][AG][KRH]X(0,2)[KR]X(0,1)[EDQN]C peptide pattern (shown in FIG. 31) to search the Swiss-Prot and TrEMBL databases using the ScanProsite algorithm.

FIG. 37 shows an alignment of peptide sequences corresponding to human lysozyme (huLYS) and chicken lysozyme (chkLYS), as well as huLYS and human Sperm Lysosyme-Like (SLLP1) protein. This alignment shows that SLLP1 is closely related to both huLYS and chkLYS and support that Tp17 may bind to SLLP1.

DETAILED DESCRIPTION OF THE INVENTION

Figure 4:
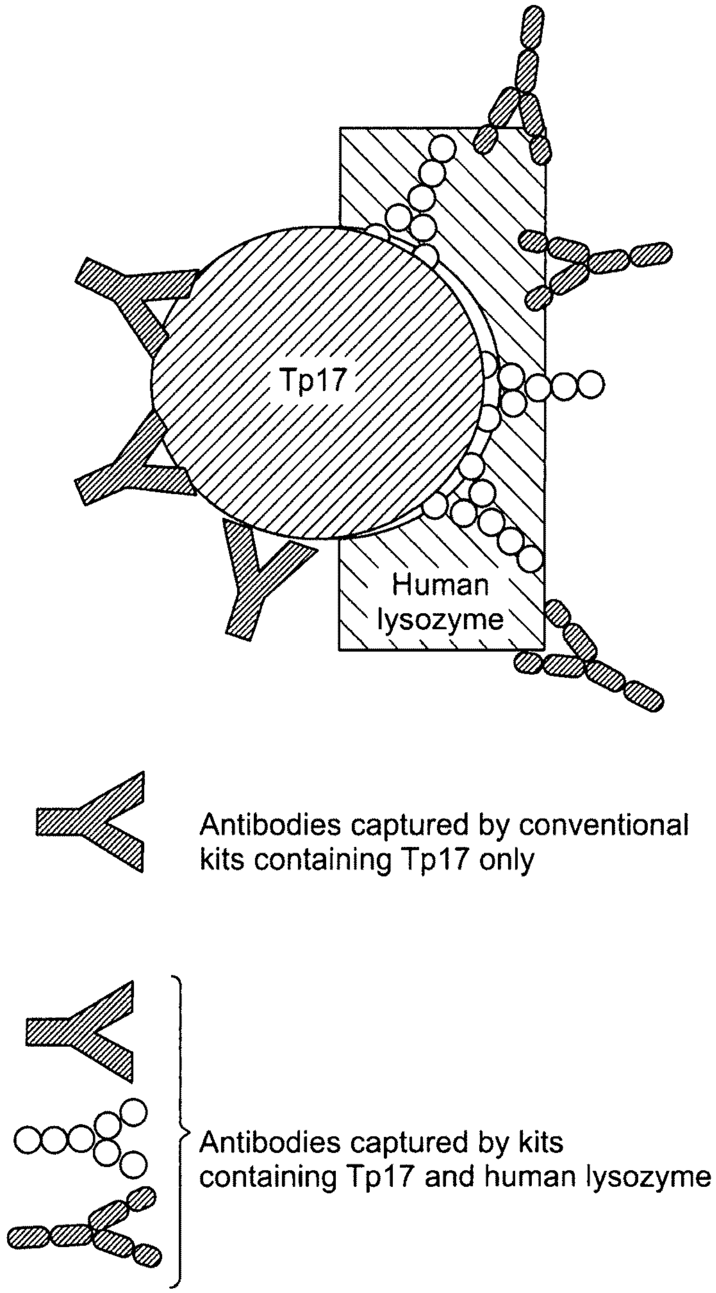
FIG. 4 illustrates an advantage of the present invention since conventional Tp17 antibody detection kits do not detect antibodies to the Tp17-lysozyme complex. In one embodiment, the invention features a kit containing a Tp17-like polypeptide and a lysozyme polypeptide. Such kits are capable of detecting antibodies to Tp17 alone, lysozyme alone, or a Tp17-lysozyme complex, if present.

In general, the invention features compositions and methods relating to the detection and treatment of subjects having a pathogen infection, such as *Treponema pallidum*. As described in more detail below, this invention is based, in part, on the discovery that a pathogen-expressed polypeptide, Tp17, binds to and inhibits lysozyme, a host-expressed antimicrobial polypeptide. Because many pathogens express Tp17-related proteins, this method of inhibiting a host immune response is likely to be conserved among a large number of pathogens. Accordingly, the invention provides for methods of treating or preventing a pathogen infection based on this observation. In addition, the invention provides for improved diagnostic assays based on the detection of antibodies that bind to a Tp17-lysozyme complex.

*Treponema pallidum* P17-Like Polypeptides

Compositions and methods of the invention comprise Treponema pallidum P17 (Tp17) polypeptide (Genbank Accession No. P29722; SEQ ID NO:31) and Tp17-like polypeptides. These polypeptides share certain structural similarities, as illustrated in FIGS. 1A-1 to 1A-3, 1B, and 2A-C collectively referred to herein as "Tp17-like polypeptides" and/or functional similarities, such as the ability to bind lysozyme or inhibit lysozyme enzymatic or anti-microbial activity. At least one and possibly two regions of Tp17 polypeptide (SEQ ID NO:31) bind to lysozyme: the polypeptide sequence VCPHAG (SEQ ID NO:5) at amino acid positions 28-33 and the polypeptide sequence KAPHEK (SEQ ID NO: 10) at amino acid positions 114-119. FIGS. 1A-1 to 1A-3 and 2A-C provide an alignment of exemplary Tp17-like polypeptides from a number of bacterial, viral, parasitic, and mammalian species, along with their accession numbers. In particular, the alignment shown in FIGS. 2A-C identifies an evolutionarily conserved consensus sequence, $Xaa_n$ Pro His $Xaa_n$, which is common to all TP17-like polypeptides.

In an embodiment, a Tp17-like polypeptide comprises the amino acid consensus sequence of $Xaa_n$ Pro His $Xaa_n$ (SEQ ID NO:1), wherein Xaa is any amino acid, is absent, or is a peptide bond, and n is at least one.

Referring now to FIGS. 1A-1 to 1A-3 and 1B, in another embodiment, the Tp17-like polypeptide comprises the amino acid consensus sequence CS1: Cys $Xaa_1$ $Xaa_2$ $Xaa_3$ Pro His $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$ Cys (SEQ ID NO:2), wherein $Xaa_1$, $Xaa_2$, $Xaa_3$, $Xaa_4$, $Xaa_5$, $Xaa_6$, $Xaa_7$, $Xaa_5$, $Xaa_9$, $Xaa_{10}$, $Xaa_{11}$, $Xaa_{12}$, or $Xaa_{13}$ is any amino acid, no amino acid, or a peptide bond. In a preferred embodiment, $Xaa_1$ is Lys, Gly, Ile, Arg, Leu, Ala, Ser, Thr, Gin, Asn, Phe, no amino acid, or a peptide bond; $Xaa_2$ is Thr, His, Cys, Gin, Asn, Be, Ser, Leu, no amino acid, or a peptide bond; $Xaa_3$ is His, Lys, no amino acid, or a peptide bond; $Xaa_4$ is Asn, Gly, Tyr, Leu, Ala, Cys, Glu, Thr, Arg, Met, Pro, Ile, Val, Phe, His, Gin, Lys, no amino acid, or a peptide bond; $Xaa_5$ is His, Arg, Asn, Leu, Ser, Lys, Glu, Gly, Pro, Ile, Thr, Cys, Trp, Val, Gln, Phe, Ala, Asp, no amino acid, or a peptide bond; $Xaa_6$ is Val, Cys, Ala, Asp, Ser, Pro, Gly, Glu, Lys, Leu, Gin, Ile, Tyr, Arg, Asn, Met, no amino acid, or a peptide bond; $Xaa_7$ is Asp, Glu, Ala, His, Val, Met, Pro, Lys, Arg, Cys, Asn, Gin, Phe, Leu, Ser, no amino acid, or a peptide bond; $Xaa_8$ is Gly, Asn, Ala, Be, Arg, Glu, Lys, Thr, Tyr, Pro, Asp, Leu, Ser, no amino acid, or a peptide bond; $Xaa_9$ is Leu, Arg, Phe, Ile, Ala, Pro, Asn, Gin, Lys, no amino acid, or a peptide bond; $Xaa_{10}$ is Val, Thr, Asp, Glu, Tyr, Arg, Ala, Trp, no amino acid, or a peptide bond; $Xaa_{11}$ is Pro, Asp, Lys, Asn, Gly, Thr, Be, no amino acid, or a peptide bond; $Xaa_{12}$ is Be, Val, Gly, Asp, Asn, Leu, no amino acid, or a peptide bond; and $Xaa_{13}$ is Asp, Glu, Cys, Thr, no amino acid, or a peptide bond. Also, a preferred Tp17-like polypeptide that does not strictly fit the consensus CS1 is the human immunodeficiency virus (HIV-1) Int protein with the related motif CSPEVGQMDC (SEQ ID NO:27) and the foot and mouth disease virus (FMDV) virus protein VP1 with the related motif TAPHRGLATLYNGDC (SEQ ID NO:26) (FIGS. 1A-1 to 1A-3).

Referring now to FIGS. 2A-C in another embodiment, the Tp17-like polypeptide comprises the amino acid consensus sequence CS2: $Xaa_1$ $Xaa_2$ Pro His $Xaa_3$ $Xaa_4$ (SEQ ID NO:3), wherein $Xaa_1$ is Cys, Lys, Val, Ala, no amino acid or a peptide bond; $Xaa_2$ is Ala, Cys, or Lys; $Xaa_3$ is Ala, Asp, or Glu, and $Xaa_4$ is Cys, Gly, or Lys. In a preferred embodiment, the Tp17-like polypeptide comprises the amino acid sequence CCPHAG (SEQ ID NO:4), VCPHAG (SEQ ID NO:5), VAPHDC (SEQ ID NO:6), KAPHDK (SEQ ID NO:7), VKPHDG (SEQ ID NO:8), KKPHAK (SEQ ID NO:9), KAPHEK (SEQ ID NO:10), KKPHAC (SEQ ID NO:11), VAPHAG (SEQ ID NO:12), VKPHAK (SEQ ID NO:13), VKPHAC (SEQ ID NO:14), VAPHEG (SEQ ID NO:15), VKPI-IEK (SEQ ID NO:16), VCPHEK (SEQ ID NO:17), CKPHAG (SEQ ID NO:18), ACPHAG (SEQ ID NO:19), KCPHDC (SEQ ID NO:20), VKPHDK (SEQ ID NO:21), KKPHAG (SEQ ID NO:22), or CAPHEK (SEQ ID NO:23).

In a preferred embodiment, the Tp17-like polypeptide comprises *Treponema pallidum* P17 protein or Herpes Simplex Virus Type 2 glycoprotein J.

In an embodiment, the Tp17-like polypeptide, as defined herein, does not comprise the Ivy protein. In another embodiment, the invention does not comprise a protein comprising CKPHDC (SEQ ID NO:24).

In another embodiment, the Tp17-like polypeptides comprise consensus sequence CS3, shared by Tp17 and Herpes simplex virus type 2 gJ protein, for example, corresponding to Xaa Cys Pro His Ala Gly (SEQ ID NO:25), wherein Xaa=Cys or Val.

Figure 7:
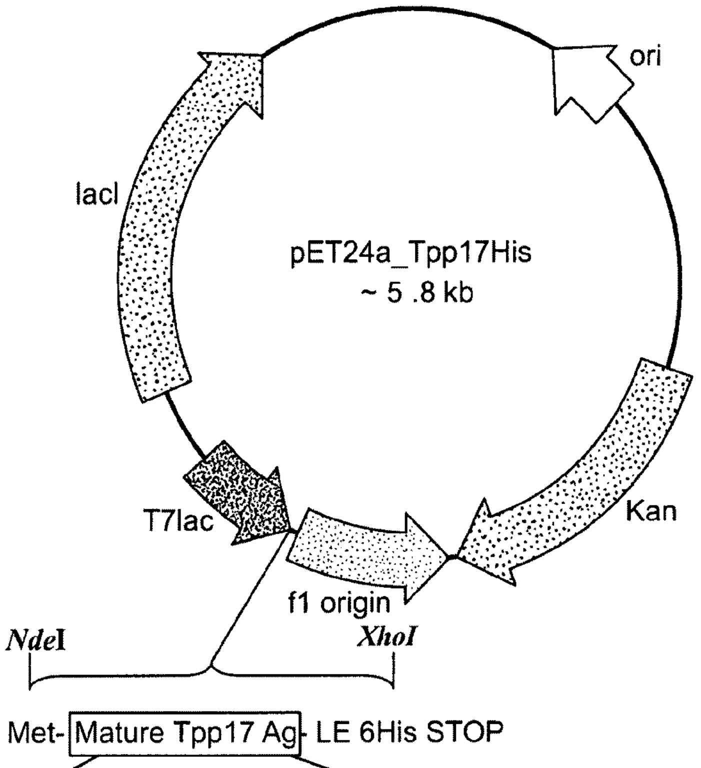
FIG. 7 illustrates the Tp17-HIS expression construct pET24a_Tpp17His. This vector derives from the pET24 expression vector (Novagen Inc., Madison, Wis.).

FIG. 7 describes exemplary methods for targeted and random identification of polypeptide mutants.

Lysozyme Molecules

Lysozyme causes the hydrolysis of bacterial cell walls. It is generally found in fluids contacting mucosal surfaces as well as other body fluids and constitutes a defense mechanism against bacterial infections. The enzyme cleaves the glycosidic bond between carbon number 1 of N-acetylmuramic acid and carbon number 4 of N-acetyl-D-glucosamine. In vivo, these two carbohydrates are polymerized to form a cell wall polysaccharide. Lysozyme has a multi-domain, mixed alpha and beta fold structure, containing four conserved disulfide bonds.

Lysozyme also has a strong antiviral effect against herpes simplex virus (HSV) and HIV type 1 (HIV-1). The formation of syncytia in cell monolayers infected with HSV is inhibited by hen egg-white lysozyme (Cisani et al. (1989) Microbios. 59:73-83). In addition, lysozyme enhances the anti-herpetic activity of glycyrrhizic acid in in vitro assays (Lampi et al. (2001) Antivir. Chem. Chemother. 12:125-131). In addition, anti-HIV-1 activity found in preparations of human chorionic gonadotrophin (hCG) has been attributed in part to lysozyme C (Lee-Huang et al. (1999) Proc. Natl. Acid. Sci. USA 96:2678-2681). In addition, an *E. coli* protein named Ivy was reported to bind and inhibit human and chicken lysozyme (Monchois et al. (2001) J. Biol. Chem. 276:18437-18441). The interactions between lysozyme and such pathogen proteins and the mechanism of their action are not clear in the prior art. As described herein, the characterization of the interaction between Tp17 antigen and lysozyme provides, at least in part, an explanation of how lysozyme interacts with pathogenic proteins and inhibits their activity.

Lysozyme levels are lower in patients suffering from HSV infection compared to healthy controls, suggesting that pathogen infection is associated with a decrease in lysozyme production or an inhibition of lysozyme activity. The instant invention provides, at least in part, an explanation of how lysozyme activity is inhibited by proteins produced by invading pathogenic viruses, suggesting a mechanism by which pathogenic viruses evade lysis by lysozyme by producing an inhibitor therefor. The instant invention therefore provides compositions and methods for relieving lysozyme inhibition in vitro and for the prevention or treatment of pathogen infection in vivo.

The compositions and methods of the invention comprise human lysozyme and polypeptides with sequence similarities thereto. FIGS. 3A-1 to 3A-3 and 3B-1 to 3B-3 provide an alignment of lysozyme polypeptides from a number of species, including duck, chicken, quail, guinea fowl, pheasant, peafowl, turkey, chachalaca, goat, sheep, cow, deer, pig, rat, mouse, dog, rabbit, monkey, grivet, rhesus monkey, baboon, marmoset, tamarmn, squirrel monkey, gorilla, human, orangutan, gibbon, colobus, langur, camel, possum, trout, flounder, fish, dog, horse, donkey, echidna, pigeon, hoatzin, anopheles, bombyx, cecropoia, silkmoth, trichoplusia, hornworm, and webworm. The alignment of the lysozyme proteins defines a lysozyme consensus sequence of:

```
                                        (SEQ ID NO: 28)
Xaa Xaa Xaa Xaa Xaa Xaa Cys Xaa Xaa Xaa Xaa Xaa

Xaa Xaa Xaa Xaa Xaa Xaa Xaa Xaa Xaa Xaa Xaa Xaa

Xaa Xaa Xaa Xaa Trp Xaa Cys Xaa Xaa Xaa Xaa Glu

Ser Xaa Xaa Xaa Thr Xaa Xaa Xaa Xaa Xaa Xaa Xaa

Xaa Xaa Xaa Ser Xaa Asp Tyr Gly Xaa Xaa Gln Ile

Asn Xaa Xaa Xaa Trp Cys Xaa Xaa Xaa Xaa Xaa Xaa

Xaa Xaa Xaa Xaa Xaa Cys Xaa Xaa Xaa Cys Xaa Xaa

Leu Xaa Xaa Xaa Xaa Xaa Xaa Xaa Xaa Cys Ala Lys

Xaa Xaa Xaa Xaa Xaa Xaa Xaa Xaa Xaa Xaa Xaa Trp

Xaa Xaa Trp Xaa Xaa Xaa Cys Xaa Xaa Xaa Xaa Xaa

Xaa Xaa Xaa Xaa Cys Xaa Xaa Xaa,
```

wherein Xaa is any amino acid or is absent. In an embodiment, the lysozyme consensus sequence comprises the sequence of

```
"XkXXXrCelaXX$kXXgXdgyXgXs$X#WvClaXXESXXnTXatnXnXXXgStDYGifQIN (SEQ ID NO: 32)

sXyWCndgktpXXXnXCX!XCsXLlXd#itXaCAKk!vXdXXgXXaWvaWkXhCXgXdlsX

yXXgCXXX",
```

where amino acid conservation is represented according to Risler comparisons symbols (Risler et al. (1988) J. Mol. Biol. 204:1019). In that representation system, X represents any amino acid or is absent, upper case letters correspond to 100% amino acid conservation, lower-case letters correspond to a value of amino acid conservation comprised between 50% and 90%. Moreover, conservative changes shared by more than 50% of the sequences are represented using the following symbols: $ corresponds to leucine or methionine, ! corresponds to isoleucine or valine, and # corresponds to asparagine or aspartic acid.

The term "lysozyme" or "lysozyme polypeptide" encompasses all homologs, mutants, full-length or fragments, substitutions and modifications thereof, including deletions and additions thereto. In an embodiment, a lysozyme polypeptide includes a mutation that decreases its ability to bind to or otherwise associate or interact with a Tp17-like polypeptide. As a result, the mutant lysozyme polypeptide is resistant to inhibition by a pathogen-expressed Tp17-like polypeptide. Example 7 describes exemplary methods for targeted and random identification of inhibition-resistant lysozyme mutants. Exogenous lysozyme is lysozyme that originates outside of, e.g., is not naturally occurring or occurs in a significantly lower concentration in, the sample or Tp17-like polypeptide preparation used in the methods of the invention. In an embodiment, exogenous lysozyme is lysozyme that is added to the sample or to the Tp17-like polypeptide to make up the compositions and methods of the invention.

Tp17-Like Polypeptide and Lysozyme Homologs, Mutants and Derivatives

The invention also provides purified or recombinant variants of a Tp17-like polypeptides or lysozyme polypeptide, including homologs, mutants, and derivatives. In some examples, recombinant mutant polypeptides contain specific mutations (e.g., missense mutations, insertions, deletions, or nonsense mutations) that inhibit the biological activity of the recombinant polypeptide relative to a native Tp17-like polypeptide or lysozyme polypeptide. Particularly advantageous Tp17-like mutant polypeptides bind lysozyme with an affinity that is equal to or greater than the affinity of a naturally-occurring polypeptide, but fail to inhibit the anti-microbial activity of lysozyme, such as its ability to cleave a pathogen-expressed polysacharide. Such Tp17-like mutant polypeptides are useful in treating or preventing a pathogen infection.

Particularly advantageous mutant lysozyme polypeptides of the invention are incapable of binding, or exhibit reduced binding to a Tp17-like polypeptide relative to a native lysozyme (FIG. 3). Preferably, binding, e.g., binding affinity or quantity, is reduced by at least 5%, 10%, 25%, 50%, 75%, 85%, 95%, or 100%. Other advantageous lysozyme polypeptides retain the ability to bind a Tp17-like polypeptide, but such binding does not inhibit the anti-microbial activity of the lysozyme polypeptide, such as its enzymatic activity.

Specific biological effects can be elicited by the use of a homolog, mutant, or derivative of limited function, e.g., with fewer side effects or greater therapeutic potency, relative to the use of a reference or a naturally occurring (i.e., a wild-type) form of a Tp17-like polypeptide or lysozyme polypeptide. Mutants of a Tp17-like polypeptide or lysozyme polypeptide can be generated by mutagenesis, for example, by introducing a discrete point mutation(s), an insertion, a deletion or other modifications and alterations. For instance, naturally occurring or laboratory induced mutations can generate mutant Tp17-like polypeptides or lysozyme polypeptides that retain substantially the same, or merely a subset, of the biological activity of the Tp17-like polypeptide or lysozyme polypeptide from which the mutant polypeptide was derived. Alternatively, antagonists forms of a Tp17-like polypeptide or lysozyme polypeptide can be generated. Such antagonists inhibit the function of a naturally occurring Tp17-like polypeptide or lysozyme polypeptide, by competitively binding to a naturally occurring ligand.

The purified or recombinant homologs of Tp17-like polypeptides or lysozyme polypeptides of the present invention also include naturally occurring homologs of the wild-type Tp17-like polypeptides or lysozyme polypeptides that are naturally resistant to proteolytic cleavage.

Tp17-like polypeptides or lysozyme polypeptides may also be chemically modified to create Tp17-like polypeptide or lysozyme polypeptide derivatives, respectively, by forming covalent or aggregate conjugates with other chemical moieties, such as glycosyl groups, lipids, phosphate, acetyl groups, and the like. Covalent derivatives of Tp17-like polypeptides or lysozyme polypeptides can be prepared by linking the chemical moieties to functional groups on amino acid side chains of the protein or at the N-terminus or at the C-terminus of the protein.

Modification of the structure of the Tp17-like polypeptides or lysozyme polypeptides (e.g., amino acid mutations) can be for such purposes as enhancing therapeutic or prophylactic efficacy, stability (e.g., ex vivo shelf life and resistance to proteolytic degradation), or post-translational modifications (e.g., to alter phosphorylation pattern of protein). Such modified or mutant Tp17-like polypeptides or lysozyme polypeptides, when designed to retain at least one activity of the naturally-occurring form of the Tp17-like polypeptides or lysozyme polypeptides, or to produce specific antagonists thereof, are considered functional equivalents of the Tp17-like polypeptides or lysozyme polypeptides described in more detail herein. Such modified Tp17-like polypeptides or lysozyme polypeptides can be produced, for instance, by amino acid substitution, deletion, or addition. The substitutional variant may be a substituted conserved amino acid or a substituted non-conserved amino acid.

For example, it is reasonable to expect that an isolated replacement of a leucine with an isoleucine or valine, an aspartate with a glutamate, a threonine with a serine, or a similar replacement of an amino acid with a structurally related amino acid (i.e., isosteric and/or isoelectric mutations) do not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. Whether a change in the amino acid sequence of a peptide results in a functional Tp17-like polypeptide or lysozyme polypeptide homolog (e.g., functional in the sense that the resulting polypeptide mimics or antagonizes the wild-type form) can be readily determined by assessing the ability of the variant peptide to produce a response in an assay or in cells in a fashion similar to the wild-type protein, or competitively inhibit such a response. Polypeptides in which more than one replacement has taken place can readily be tested in the same manner. Assays and reagents useful for testing such homologs are exemplified throughout the specification.

The term "polypeptide" thus includes naturally occurring peptides or proteins, as well as synthetic or recombinantly produced peptides or proteins. The polypeptide may encompass amino acid chains of any length, wherein the amino acid residues are linked by covalent peptide bonds. However, peptidomimetics of such polypeptides wherein amino acids and/or peptide bonds have been replaced by functional analogs are also encompassed by the invention. In accordance with the invention, an amino acid encompasses a non-naturally occurring amino acid analog.

This invention further contemplates a method for generating sets of combinatorial mutants of Tp17-like polypeptides or lysozyme polypeptides as well as truncation mutants, and is especially useful for identifying potential variant sequences (e.g., homologs). The purpose of screening such combinatorial libraries is to generate, for example, novel mutant Tp17-like polypeptides or mutant lysozyme polypeptides that can act as either agonists or antagonist, or alternatively, possess novel activities altogether. Thus, combinatorially-derived mutant polypeptides can be generated that have an increased potency relative to a naturally-occurring (wild-type) form of the polypeptide.

In another embodiment, the invention features isolated Tp17-like polypeptides or lysozyme polypeptides, preferably substantially pure preparations, e.g., of body-fluid derived or recombinantly produced polypeptides. The Tp17-like polypeptides or lysozyme polypeptides can comprise full length polypeptides or can comprise smaller fragments corresponding to one or more particular motifs/domains, or fragments comprising at least about 5, 6, 7, 8, 9, 10, 11, 12, 13, 14, 15, about 20, about 25, about 50, about 75, about 100, about 125, about 148, amino acids in length, for example.

Peptides may be produced by direct peptide synthesis using solid phase techniques (e.g., Stewart et al. (1969) Solid Phase Peptide Synthesis, WH Freeman Co. San Francisco; Merrifield (1963) J. Am. Chem. Soc. 85:2149-2154). In vitro protein synthesis may be performed by in vitro coupled transcription and translation, for example using a TnT® (Promega, Madison, Wis.) or RTS (Roche Applied Science, Barcelona, Spain) kits or using an automated approach, for example, using an Applied Biosystems 431 A Peptide Synthesizer (Perkin Elmer, Foster City, Calif.) according to the manufacturers instructions. Peptides may be made by one or more methods and chemically joined to produce a full length molecule.

The characterization of the lysozyme binding site on Tp17 and the consensus sequence of that binding site that is shared by a number of pathogen-derived Tp17-like polypeptides can be exploited to provide inhibitors of lysozyme/Tp17-like polypeptide binding and methods of making and using them as diagnostics (e.g., probes), prophylactics, or treatments for a number of pathogenic diseases or diseases characterized by altered lysozyme activity. Also, the invention provides natural and genetically modified variants of lysozymes, including homologs, mutants, and derivatives and methods of making them, that are unable to bind to Tp17-like polypeptides, which retain other lysozyme functions, such as peptidoglycan binding and hydrolysis for example, thereby escaping inhibition by the Tp17-like polypeptides. These non-wildtype lysozymes, including homologs, mutants and derivatives can be used to treat or prevent many pathogenic diseases, including syphilis, AIDS, and genital herpes.

The invention also provides Tp17-like mutant polypeptides that have altered lysozyme binding sequences, of and mutant lysozyme polypeptides that have altered Tp17-like polypeptide binding sequences. Preferably, these mutant polypeptides exhibit altered binding affinities. Particularly preferred are Tp17-like mutant polypeptides having an increase (e.g., 5%, 10%, 25%, 50%, 75%, or 100%) in their binding to lysozyme relative to a native Tp17-like polypeptide. Such mutant polypeptides compete with a native Tp17-like polypeptide for binding to lysozyme. Most preferred are Tp17-like mutant polypeptides that bind to lysozyme with at least native affinity, but that fail to inhibit a lysozyme anti-microbial activity, such as an enzymatic activity. Particularly preferred lysozyme mutant polypeptides have altered binding sites that reduce (e.g., 5%, 10%, 25%, 50%, 75%, or 100%) or eliminate binding to a Tp17-related polypeptide. Other preferred lysozyme mutant polypeptides bind a Tp17-related polypeptide, but such binding does not reduce or eliminate lysozyme anti-microbial activity.

Other alterations in a Tp17-related polypeptide or in a lysozyme polypeptide alter in vitro or in vivo function, for example, as effected by site-directed mutagenesis or combinatorial biochemistry. For example, lysozyme variants that have lost the ability to bind to peptidoglycan but retain the ability to bind to Tp17-like polypeptide are provided.

The invention further provides Tp17-like polypeptides that can be used to make fusion polypeptides with a polypeptide of interest, which can be inexpensively affinity purified using lysozyme (e.g., that is bound to a solid support, such as a resin, bead, well, chip, column, gel, membrane, or filter device).

The sequence information provided by the instant invention also provides specific probes for the identification of Tp17-like polypeptides using a lysozyme as a probe, or identification of lysozyme using a Tp17-like polypeptide as a probe. In addition, antibodies can be raised to sequences that define these binding sites using standard methods.

Methods for Improving Pathogen Infection Detection Methods

The instant invention also provides methods and compositions for improved detection of anti-pathogen antibodies in a sample, for example, as diagnosis of pathogen infection. While examples of such diagnostic methods may specifically relate to syphilis, one skilled in the art will understand that such methods are generally useful for detecting an immune response against virtually any pathogen that produces a Tp17-like polypeptide. The diagnostic methods of the invention involve the detection of an anti-pathogen antibody in a sample using reagents that include, among other things, lysozyme. Example 8 provides a description of an exemplary syphilis assay for anti-Tp17-like polypeptide antibodies. The above and other methods are discussed in more detail below.

Without being tied to any particular theory, it is likely that a syphilitic subject generates an immune response not only against an isolated Tp17 protein, but also against the Tp17 polypeptide/lysozyme complex. Contacting a biological sample from such a subject with lysozyme, allows for the detection of antibodies that recognize the Tp17/lysozyme complex, and increases the sensitivity of the syphilis diagnostic assay. Similarly, any pathogen diagnostic method that involves detection of an antibody that recognizes a Tp17-like protein/lysozyme complex is enhanced by the inclusion of lysozyme in the assay reagents. Preferably, the addition of lysozyme to an assay reagent increases the sensitivity of the diagnostic method by at least 5%, 10%, 25%, 50%, 75%, or even by as much as 85% or 95% relative to standard diagnostic methods.

Compositions and Methods for Detecting Anti-Pathogen Antibodies

The invention provides compositions and methods for detecting anti-pathogen antibodies in a sample that are indicative of the presence of, infection by, or immune response (e.g., humoral immune response) to a bacterial pathogen, such as, for example, *Treponema pallidum, Escherichia coli, Pseudomonas aeruginosa, Pseudomonas putida, Yersinia pestis, Shigella flexnerii, Treponema denticola, Vibrio cholerae, Vibrio vulnificus, Vibrio parahemolyticus, Chlamydia pneumoniae, Staphylococcus aureus, Staphylococcus epidermidis, Streptococcus pneumoniae, Streptococcus agalactiae, Streptococcus mutans, Streptococcus pyogenes, Enterococcus faecalis, Bordetella bronchiseptica, Bordetella pertussis, Bordetella parapertussis, Helicobacter hepaticus, Salmonella typhimurium, Ralstonia solanacearum, Xanthomonas campestris, Pseudomonas syringae, Pasteurella multocida, Brucella melitensis, Brucella suis, Mycobacterium tuberculosis, Campylobacter jejuni, Helicobacter* spp., and *Agrobacterium tumefaciens, Moraxella catarrhalis, Neisseria meningitidis, Neisseria gonorrhoeae, Haemophilus influenzae, Haemophilus ducreyii, Propionobacterium acnes, Listeria monocytogenes*. In addition, the composition is used to detect the presence of, infection by, or immune response (e.g., humoral immune response) to a viral pathogen, such as, for example, Coxsackie virus, Herpes Simplex Virus type 2, Influenza A virus, TACARIBE virus, Bluetongue virus, Chimpanzee cytomegalovirus, Hepatitis B, Hepatitis C virus, Human cytomegalovirus (HCMV), Human papilloma virus, Dengue virus, eastern equine encephalitis virus, Foot and Mouth Disease (HMD), Human immunodeficiency virus, Rubella virus, and LdMNPV. Further, the composition is used to detect the presence of, infection by, or immune response (e.g., humoral immune response) to a parasite, such as, for example, *Plasmodium falciparum, Plasmodium ovale, Emeiria tenella, Eimeria acervulina, Giardia lamblia, Plasmodium yoelii* and pathogens carried by *Anopheles gambiae*. In addition, the composition is used to detect the presence of, infection by, or immune response (e.g., humoral immune response) to Mycobacterium paratuberculosis, Ebola virus, Rift Valley Fever virus, Severe Acute Respiratory Syndrome (SARS) virus, Small Pox virus, *Bacillus anthracis, Leishmania* Spp., mycoplasma, rickettsia, fungi, or yeast. Such antibodies are identified, for example, by an assay that detects antibody binding to a Tp17-like polypeptide, a lysozyme polypeptide, a TP17-like polypeptide/lysozyme polypeptide complex, or a fragment thereof.

The Tp17-like polypeptide or lysozyme polypeptide may comprise an affinity tag, such as, for example, glutathione S-transferase (GST), 6-histidine tail (HIS), maltose binding protein, elastin-like peptide, or a Strep-Tag (IBA, Goettingen, Germany). The Tp17-like polypeptide, lysozyme, and/or Tp17-like polypeptide-lysozyme complex may be attached to a solid support such as a resin, bead, well, chip, column, gel, membrane, matrix, plate, or filter device. The use of a multiwell plate or a microchip is useful for the large scale testing of numerous samples or for testing a single sample in duplicate or for the presence of a number of pathogenic agents.

In one embodiment, the method of the invention comprises detecting binding, if present, of anti-pathogen antibodies present in the sample to (i) the Tp17-like polypeptide alone; (ii) the lysozyme alone; or (iii) the Tp17-like polypeptide-lysozyme complex. In one embodiment, the method comprises the steps of (a) contacting a sample with a Tp17-like polypeptide under conditions that permit binding of an antibody in the sample to the Tp17-like polypeptide; and (b) contacting the sample with a substantially pure, exogenous lysozyme under conditions that permit binding of an antibody to the lysozyme. The Tp17-like polypeptide and lysozyme may be bound to each other or otherwise associated such that an antibody can bind to both the Tp17-like polypeptide and lysozyme, e.g., a complex of the Tp17-like polypeptide and lysozyme. Binding of the antibody to the Tp17-like polypeptide, lysozyme, or their complex may occur at 15-25° C., or any temperature that allows binding of the antibody to the Tp17-like polypeptide and/or lysozyme.

In a preferred embodiment, the assay is an agglutination assay, such as, for example, a hemagglutination assay performed as described in Examples 8 and 9. The carrier particles used in the agglutination assay may be, for example, red blood cells, protein aggregate particles, polymeric particles, inorganic particles, paramagnetic particles, or yeast cells. In a preferred embodiment, hemagglutination is enhanced by at least about 0.1 to about 20 fold, about 0.3 to about 10 fold, or about 1 to about 10 fold, for example, preferably at least about 3-fold, by the addition of lysozyme. The lysozyme may be from the same species as the subject from which the assay sample is taken (e.g., human). The lysozyme is added to the Tp17-like polypeptide reagent, the dilution buffer, or any of the reagents or vessels used in the assay and may be added at any time, once or in installments, e.g., before, during or after the sample has contacted the remainder of the reagents or vessels of the assay. In a particular embodiment, exogenous lysozyme is present in a concentration range of about 1 femtogram/ml to about 999 milligrams/ml., lysozyme is present in a concentration range of about 1 nanogram/ml to about 999 micrograms/ml (e.g., 1, 10, 25, 50, 100, 250, 500, or 1000 nanograms or micrograms/ml).

In another embodiment, anti-pathogen antibodies are detected using an ELISA assay. Methods for carrying out ELISA assays are well known in the art. Briefly, for detecting the presence of antibodies to Tp17-like polypeptides in a sample, for example, a solid phase, such as an ELISA plate, is coated with a Tp17-like polypeptide alone, a combination of Tp17-like polypeptide and lysozyme, or lysozyme alone, in separate wells on a plate. After washing, a sample that may contain an anti-Tp17-like polypeptide antibody, an anti-Tp17-like polypeptide-lysozyme complex antibody, and/or anti-lysozyme antibody is added to the wells. The sample may be applied to several wells of the ELISA plate, and detected via direct labeling (if appropriate), by using a secondary binding partner for the anti-Tp17-like polypeptide antibody such as a rabbit anti-human IgG that has a detectable label, or by using a tertiary antibody or detection reagent (e.g., streptavidin-biotin or labeled protein A or protein G). Alternatively, detection can also be achieved using labeled Tp17-like polypeptide. If the specific antibodies are differentially labeled, detection of more than one antibody can occur in the same sample, for example in the same well of the ELISA plate. This can be accomplished through the use of labels that produce distinct signals that can be independently quantified, for example, by using dyes with different UV absorption maxima. The ELISA values for the variously treated wells can be compared to determine the presence of antibodies to Tp17-like polypeptide alone, Tp17-like polypeptide-lysozyme complex, and/or lysozyme alone. Any of the immunoassays described herein may be used in the practice of detecting antibodies to Tp17-like polypeptide and the Tp17-like polypeptide-lysozyme complex by the use of lysozyme which creates, either in the liquid or solid phase, Tp17-like polypeptide-lysozyme complexes that can bind to their cognate antibodies, according to standard methods.

Not to be limited to a particular theory, the assay is likely enhanced by the addition of lysozyme because the lysozyme forms complexes with the Tp17-like polypeptides, thereby forming substrate for binding with antibodies that bind only to the Tp17-lysozyme complex and not to Tp17-like polypeptide alone. Thus, by adding lysozyme to the assay, antibodies directed to the Tp17-like polypeptide alone, the lysozyme alone or the complex are detected in the sample (FIG. 4).

In an embodiment of the invention, the assay can be accomplished by using a natural purified or recombinant lysozyme that does not have peptidoglycan binding activity (e.g., a lysozyme mutant) so that binding of the lysozyme to the Tp17-like polypeptide is enriched. This selective binding can be achieved, for example, by site-directed mutagenesis of lysozyme, or other methods known in the art, for example, as described in Example 7.

In another embodiment, the lysozyme molecule can be altered to remove its ability to bind to a Tp17-like polypeptide, so that the resulting mutant is resistant to inhibition by a Tp17-like polypeptide. Such mutants may display an enhanced antimicrobial activity against pathogens equipped with Tp17-like polypeptide virulence factors. Mutations localized in the lysozyme coding sequence, selected so that acetyl muramidase and/or antimicrobial activities are not affected, destabilize the lysozymes/inhibitor interaction and confer resistance to inhibition by pathogen proteins such as the *T. pallidum* Tp17 antigen or members of the Ivy family. Such mutant lysozymes represent novel and interesting compositions for the treatment of infectious diseases. In addition, given their improved potency and spectrum of activity, they are superior to the chicken lysozyme presently used in commercially available medicinal preparations.

Compositions and Methods for Inhibiting Lysozyme Activity In Vitro

In another aspect, the invention provides compositions and methods for reducing lysozyme activity in a sample by contacting a sample with a Tp17-like polypeptide, or fragment thereof, where the Tp17-like polypeptide binds to and inhibits lysozyme activity in the sample. The treatment is useful for any sample that requires inactivation or neutralization of lysozyme, such as, for example, a preparation of a pharmaceutical fluid for human administration, a cell culture fluid, a food, a medicine, water, or other fluid or agent for ingestion, an implant, a graft, or any other preparation in which lysozyme is not desired or is harmful. The compositions and methods of the invention are suitable for small or large scale treatment of water supplies, for example. The compositions and methods may be used to inhibit lysozymes on a material that is supposed to be free of lysozyme contamination, or for which inhibition of lysozyme activity is desired, such as a biological sample, culture vessel, cuvette, swab, clinical diagnostic apparatus or assay material, medical instrument, cell culture, throat aspirate, cerebospinal fluid sample, or hemoculture. In some embodiments, the Tp17-like polypeptide or lysozyme binding fragment is fixed to a solid support and the lysozyme present in the sample is bound to the TP17-like polypeptide.

In an embodiment, material from the forestomach of a ruminant animal may be tested or treated using the methods and compositions of the invention. This material includes bacteria, yeast, fungus, and protozoan cells, for example. This flora controls the degradation and the assimilation of nutrients in ruminants. In an embodiment, the inhibition of lysozyme by a Tp17-like polypeptide, or the inhibition of a Tp17-like polypeptide by lysozyme, may alter the assimilation rate of nutrients and be advantageous in certain circumstances.

The sample may also be a bacterial sample, such that the recovery of a pathogen extract is enhanced by inhibiting cell lysis.

In addition, the invention is useful for identifying a bacteria by determining the extent to which lysozyme in the presence of a Tp17-like polypeptide of predetermined sequence can inhibit bacterial cell lysis. For example, the methods of the invention may be used to distinguish between HSV-1 infection and HSV-2 infection (see Example 6).

Method for Reducing Lysozyme Activity In Vivo

The identification of the lysozyme binding motif on Tp17-like polypeptides also provides compositions and methods (e.g., therapeutic or prophylactic, including vaccine) for inhibiting, inactivating or neutralizing lysozyme activity in an animal, such as a mammal, bird or fish. Tp17-like polypeptides comprising the lysozyme binding motif can be used to block Tp17-like polypeptide binding to lysozyme. The invention therefore provides a method for reducing lysozyme activity in an animal by administering an effective amount of a Tp17-like polypeptide. Such a method can be used to treat or prevent diseases such as cancer, infectious diseases, inflammatory diseases, Alzheimer's disease, renal amyloidosis, leukemia, Crohn's disease, and allergy.

Methods for Detecting Pathogens and Tp17-like Polypeptide Ligands

The compositions and methods of the invention may also be used for detecting a pathogen in a sample. Compositions comprising a ligand capable of binding to a Tp17-like polypeptide, such as lysozyme polypeptide or a molecule that can compete with lysozyme binding, may be used. Alternatively, the ligand may be a monoclonal antibody, a polyclonal antibody, or an Fab fragment that binds to the Tp17-like polypeptide.

The ligands may be detected directly, e.g., linked to a detection molecule, such as a fluorophore, a fluorescent protein, chromophore, radioactive moiety, luminiferous moiety or enzymatically active reporter or label. Exemplary detection molecules are well known in the art, for example, fluorescein conjugates, horseradish peroxidase conjugates, alkaline phosphatase conjugates and isoluminol conjugates. In this embodiment of the invention, a sample is contacted with lysozyme or with another Tp17-like ligand under conditions that permit binding of the ligand to a pathogen or a pathogen polypeptide and the binding of the lysozyme to the pathogen or pathogen polypeptide, if present, is detected. Such binding is indicative of the presence of the pathogen or pathogen polypeptide in the sample.

The compositions and methods of the invention are also useful for detecting the presence of lysozyme in a sample. A sample is contacted with a Tp17-like polypeptide and binding of the Tp17-like polypeptide to the lysozyme in the sample is detected.

Kits

The compositions and methods of the invention may be embodied in diagnostic or therapeutic kits containing at least one of a Tp17-like polypeptide, lysozyme, and a ligand therefore. Reagents necessary or useful for the administration, assay, or purification of the Tp17-like polypeptide or lysozyme polypeptide may also be included in the kit, such as reaction vessels (e.g., comprising a solid support, resin, bead, well, chip, column, gel, membrane, and filter device), control standards, or instruction manuals. Such diagnostic or therapeutic kits are useful for the diagnosis or treatment of a pathogen infection, such as syphilis or herpes, or for Alzheimer's disease.

Fusion Peptides and Affinity Chromatography

The Tp17-like polypeptides, or fragments thereof, of the invention are useful as affinity tags for use in affinity chromotography using lysozyme polypeptides, for example, that are linked to a solid support, such as a column. The invention therefore provides recombinant fusion proteins (e.g., Tp17 fusion proteins) comprising a first polypeptide sequence linked by a peptide bond to a second polypeptide sequence, wherein the first polypeptide sequence comprises a Tp17-like polypeptide and the second polypeptide sequence comprises an amino acid sequence of interest. In an embodiment, the first polypeptide sequence is not naturally linked to the second polypeptide sequence. The Tp17-like polypeptide acts as a purification cassette that is used to bind the polypeptide of interest to the lysozyme affinity column. The purification cassette can be positioned anywhere on the molecule, e.g., at the N terminus or the C terminus of the polypeptide of interest. Alternatively, the purification cassette can be positioned between the N terminus and the C terminus. The recombinant fusion polypeptide is prepared by linking a first polypeptide sequence by a peptide bond to a second polypeptide sequence, wherein the first polypeptide sequence comprises a Tp17-like polypeptide purification cassette and the second polypeptide sequence comprises an amino acid sequence of interest. The Tp17 fusion protein is then used in methods for purifying the polypeptide of interest by contacting a sample comprising the Tp17 fusion protein with lysozyme under conditions that permit the Tp17-like polypeptide to bind to lysozyme. The complex formed is then washed and the Tp17 fusion protein is eluted from the lysozyme and the protein of interest may be isolated from the purification cassette according to methods well known in the art. In one embodiment, the TP17-like polypeptide fragment is a 5, 10, 15, 20, 25, 50, 75, or 100 amino acid fragment that comprises at least a lysozyme-binding consensus sequence (e.g., SEQ ID NO:1).

Methods of Treating or Preventing Other Diseases

Lysozyme polypeptides are provided that do not bind to at least some Tp17-like polypeptides (e.g., inhibition of lysozymes functions) due to the presence of mutations. These mutations are targeted to residues that do not affect the catalytic activity of lysozyme. Such altered lysozyme polypeptides are made by standard methods (e.g., by site-directed or random mutagenesis as described herein). Such lysozymes are useful for avoiding inhibition by Tp17-like polypeptides and can be used to prevent or treat a pathogen infection. The invention also provides methods for inhibiting pathogen infection by administering an effective amount of a lysozyme polypeptide that cannot bind to Tp17-like polypeptides.

The invention also provides methods for identifying a reagent that inhibits the binding of a lysozyme inhibitor such as Tp17-like polypeptide to the E53 of a lysozyme (numbering refers to the full-length human lysozyme sequence deposited under accession number NP_000230). In a preferred embodiment, the reagent is a polypeptide, chemical, drug, antibody, nucleic acid, aptamer, or PNA. The inhibitor is, for example, any such molecule that prevents the binding of Tp17-like polypeptides to E53 of lysozyme.

Screening Assays

As discussed above, binding of a Tp17-like polypeptide to a lysozyme polypeptide may inhibit lysozyme anti-microbial activity. Based on this discovery, compositions of the invention are useful for the high-throughput low-cost screening of candidate compounds to identify those that increase or decrease binding between a Tp17-like polypeptide and a lysozyme polypeptide. Any number of methods are available and contemplated by this invention for carrying out screening assays to identify new candidate compounds that modulate the binding of a Tp17-like polypeptide and a lysozyme polypeptide.

In one embodiment, candidate compounds are screened for those that specifically bind a Tp17-like polypeptide or a lysozyme polypeptide. The efficacy of such a candidate compound is dependent upon its ability to interact with such a polypeptide or a functional equivalent thereof. Such an interaction can be readily assayed using any number of standard binding techniques and functional assays (e.g., those described in Ausubel et al., supra). In one embodiment, a candidate compound may be tested in vitro for its ability to specifically bind a polypeptide of the invention. In another embodiment, a candidate compound is tested for its ability to enhance the biological activity of a lysozyme polypeptide described herein, such as a Tp17-like polypeptide or a lysozyme polypeptide. The effect of the biological activity of the candidate compound on the Tp17-like polypeptide and/or the lysozyme polypeptide is assayed using any standard method, known to the skilled artisan, such as the assay described in Example 3.

In one particular example, a candidate compound that binds to a Tp17-like polypeptide or a lysozyme polypeptide is identified using a chromatography-based technique. For example, a recombinant polypeptide of the invention may be purified by standard techniques from cells engineered to express the polypeptide (e.g., those described herein) and may be immobilized on a column. A solution of candidate compounds is then passed through the column, and a compound that specifically interacts with a Tp17-like polypeptide or a lysozyme is identified on the basis of its ability to bind to the polypeptide and be immobilized on the column. To isolate the compound, the column is washed to remove non-specifically bound molecules, and the compound of interest is then released from the column and collected. Similar methods may be used to isolate a compound bound to a polypeptide microarray, for example, an array containing a plurality of Tp17-like lysozyme binding motifs. Compounds isolated by this method (or any other appropriate method) may, if desired, be further purified (e.g., by high performance liquid chromatography). In addition, these candidate compounds may be tested for their ability to modulate binding between a Tp17-like polypeptide and a lysozyme polypeptide. Binding may be altered, for example, by increasing or decreasing the number of complexed molecules, by altering the binding affinity, by altering the probability that a complex will form, or by competing with one or both molecules for binding. In other embodiments, the compound is assayed for its ability to increase lysozyme anti-microbial activity. In yet other embodiments, the compound is assayed for its ability to modulate the interaction between a polypeptide that contains a CX(1,5)[KRH][AG][KRH]X(0,2)[KR]X(0,1)[EDQN]C consensus motif (such as a β-amyloid precursor protein) and a lysozyme polypeptide.

Compounds isolated by this approach may be used, for example, as therapeutics to treat a pathogen infection, a lysozyme disorder, or Alzheimer's disease in a human patient. Compounds that are identified as binding to a polypeptide of the invention with an affinity constant less than or equal to 10 mM are considered particularly useful in the invention. Alternatively, any in vivo protein interaction detection system, for example, any two-hybrid assay may be utilized. Potential agonists and antagonists include organic molecules, peptides, peptide mimetics, polypeptides, nucleic acids, and antibodies that bind to a nucleic acid sequence or polypeptide of the invention, such as a Tp17-related polypeptide or a lysozyme polypeptide. For patient having a disorder characterized by Tp17-like polypeptide inhibition of lysozyme (e.g., a pathogen infection), compounds that inhibit Tp17-like polypeptide binding to lysozyme or that enhance a lysozyme anti-microbial activity or enzymatic activity are particularly useful. For patient having a disorder characterized by excessive lysozyme activity, a compound that binds to lysozyme and inhibits its activity, or that enhances binding between a Tp17-like polypeptide and lysozyme are particularly useful.

DNA sequences encoding the Tp17-like polypeptides and lysozyme polypeptides listed herein may also be used in the discovery and development of a therapeutic compound for the treatment of patients having a pathogen infection, lysozyme disorder, or Alzheimer's disease. The encoded proteins, upon expression, can be used as targets for the screening of drugs. Optionally, compounds identified in any of the above-described assays may be confirmed as useful in an in vivo assay for compounds that modulate binding between a Tp17-like polypeptide and a lysozyme polypeptide or that modulate the activity of a lysozyme polypeptide. Small molecules of the invention preferably have a molecular weight below 2,000 daltons, more preferably between 300 and 1,000 daltons, and most preferably between 400 and 700 daltons. It is preferred that these small molecules are organic molecules.

Test Compounds and Extracts

In general, compounds capable of modulating the binding of a Tp17-like polypeptide to a lysozyme polypeptide are identified from large libraries of both natural product or synthetic (or semi-synthetic) extracts or chemical libraries or from polypeptide or nucleic acid libraries, according to methods known in the art. Those skilled in the field of drug discovery and development will understand that the precise source of test extracts or compounds is not critical to the screening procedure(s) of the invention. Compounds used in screens may include known compounds (for example, known therapeutics used for other diseases or disorders). Alternatively, virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activity should be employed whenever possible.

When a crude extract is found to modulate the binding between a Tp17-like polypeptide and a lysozyme polypeptide, further fractionation of the positive lead extract is necessary to isolate chemical constituents responsible for the observed effect. Thus, the goal of the extraction, fractionation, and purification process is the careful characterization and identification of a chemical entity within the crude extract that alters the binding between a Tp17-like polypeptide and a lysozyme polypeptide. Methods of fractionation and purification of such heterogenous extracts are known in the art. If desired, compounds shown to be useful as therapeutics for the treatment of a pathogen infection of a lysozyme disorder are chemically modified according to methods known in the art.

Antibody Preparation

Suitable monoclonal antibodies for use in the immunoassays of the invention may be prepared by standard hybridoma methods, using differential binding assays to ensure that the antibodies are specific for a Tp17-like polypeptide, lysozyme, a Tp17-like polypeptide-lysozyme complex or other antigen of interest and do not show cross-reactivity, or show limited cross-reactivity between the related proteins. Alternatively, suitable monoclonal antibodies may be prepared using antibody engineering methods such as phage display. Methods for obtaining highly specific antibodies from antibody phage display libraries are known in the art, and several phage antibody libraries are commercially available from, for example, MorphoSys (Martinsried, Germany), Cambridge Antibody Technology (Cambridge, UK) and Dyax (Cambridge, Mass.). Suitable phage display methods are described, for example, in U.S. Pat. Nos. 6,300,064 and 5,969,108, which are hereby incorporated by reference in their entirety. See also, for example "Antibody Engineering," McCafferty et al. (Eds.)(IRL Press 1996) and references therein. Phage display antibody methods can use libraries of antibodies in the Fab or scFv format. Once the antibody heavy and light chain genes are recovered from the phage antibodies, antibodies in any suitable format may be prepared (e.g., whole antibodies, Fab, scFv, etc.).

Other antibody preparations may also be used, for example, Camelid antibodies, which contain only heavy immunoglobulin chains. See, for example, Muyldermans et al. (2001) J. Biotechnol. 74:277-302 and references therein.

Alternatively, polyclonal antibody preparations may be used for detection of antigens such as Tp17-like polypeptides, lysozyme, or other antigen of interest. Phage display methods also can be used to prepare reproducible populations of polyclonal antibodies. For example, an antibody library can be exhaustively depleted of clones that cross-react by absorption on other antigens bound to a solid surface, and then panned over a solid surface to identify antibodies that bind to the antigen of interest. The resulting population of clones can also be depleted of cross-reactive clones by absorption over surfaces bearing irrelevant proteins, such as bovine serum albumin, etc., using methods well known in the art. This results in identification of a population of antibodies that specifically bind to an antigen of interest.

Polyclonal antibodies specific for an antigen of interest may also be prepared using traditional animal-based methods. These antigens, such as, for example, peptides, can be conjugated at their N- or C-terminus to carrier proteins such as bovine serum albumin (BSA) or keyhole limpet hemocyanin (KLH) and used to immunize animals, such as rabbits, using well-known immunization regimes. Specific polyclonal antibodies can be obtained from the serum of the animal by, for example, affinity chromatography over a matrix containing the peptide used for immunization bound to a solid support. Again, for example, antisera raised against Tp17-like polypeptides can be adsorbed against other polypeptides bound to a solid support to remove any cross-reactive antibodies, and vice-versa.

Immunoassays

Any of a number of immunoassays may be used in the practice of the methods of the invention. For example, enzyme-linked immunosorbent assay (ELISA), agglutination assays, radioimmunoassays, turbidimetric assays, nephelometric assay, immunochromatography, chemiluminescence assays, and fluorescent assay. Such assays are well known in the art, and are described in detail herein (Andreotti et al. (2003) Biotechniques 35:850-859).

Methods for carrying out ELISA assays are well known in the art. Briefly, for detecting the presence of Tp17-like polypeptides in a sample, for example, a solid phase, such as an ELISA plate, is coated with lysozyme. After washing, a sample that may contain a Tp17-like polypeptide is added. The sample may be applied to several wells of the ELISA plate, and detected via direct labeling (if appropriate), by using an antibody to a Tp17-like polypeptide that is labeled, or by using secondary antibody and tertiary antibody or detection reagents (streptavidin-biotin) or labeled protein A or protein G. If the specific antibodies are differentially labeled, detection of more than one antigen can occur in the same sample, for example in the same well of the ELISA plate. This requires use of labels that produce distinct signals that can be independently quantified, for example, by using dyes with different UV absorption maxima. Useful dyes and spectra include, but are not limited to, ABTS (2,2'-azinobis (3-ethylben-thiazoline-b-sulphonic acid) chromogenic substrate for horseradish peroxidase (absorbs light at 410 nm) and TMB (3,3',5,5'-Tetramethyl benzidine) chromogenic substrate for horseradish peroxidase (absorbs light at 450 nm after the addition of 1M $H_2SO_4$.

Other known protein detection methods may be used in place of, or in addition to the above immunoassays. For example, when using antibodies against non-surface epitopes of proteins, enzyme or chemical (e.g., CNBr) digestion of the proteins prior to detection may be used. For example, a full length Tp17-like polypeptide could be obtained using a generic antibody that binds to a Tp17-like polypeptide, followed by enzymatic protein digestion and detection with Tp17-like polypeptide-specific antibodies. Improved methods for CNBr digestion of proteins are described in Kaiser et al. (1999) Anal. Biochem. 266:1-8.

Other methods that can be used include Western Blot, Far Western-Blot, immunohistochemistry, spot/slot blot techniques, protein chips, and biosensors. For Western Blot, for example, duplicate protein samples may be electrophoresed on an acrylamide gel and transferred to a membrane such as nitrocellulose or PVDF. One blot is detected with antibody for Tp17-like polypeptide and one blot is detected with antibody to a control protein. These primary antibodies are then detected, for example, with labeled secondary antibodies. Alternatively, antibodies specific for a protein of interest and a control protein are each labeled with a different fluorescent dye and are reacted with the same blot simultaneously. The fluorescence intensity of each dye is measured, and the ratio of the intensity indicates the ratio of the two proteins.

Figure 5:
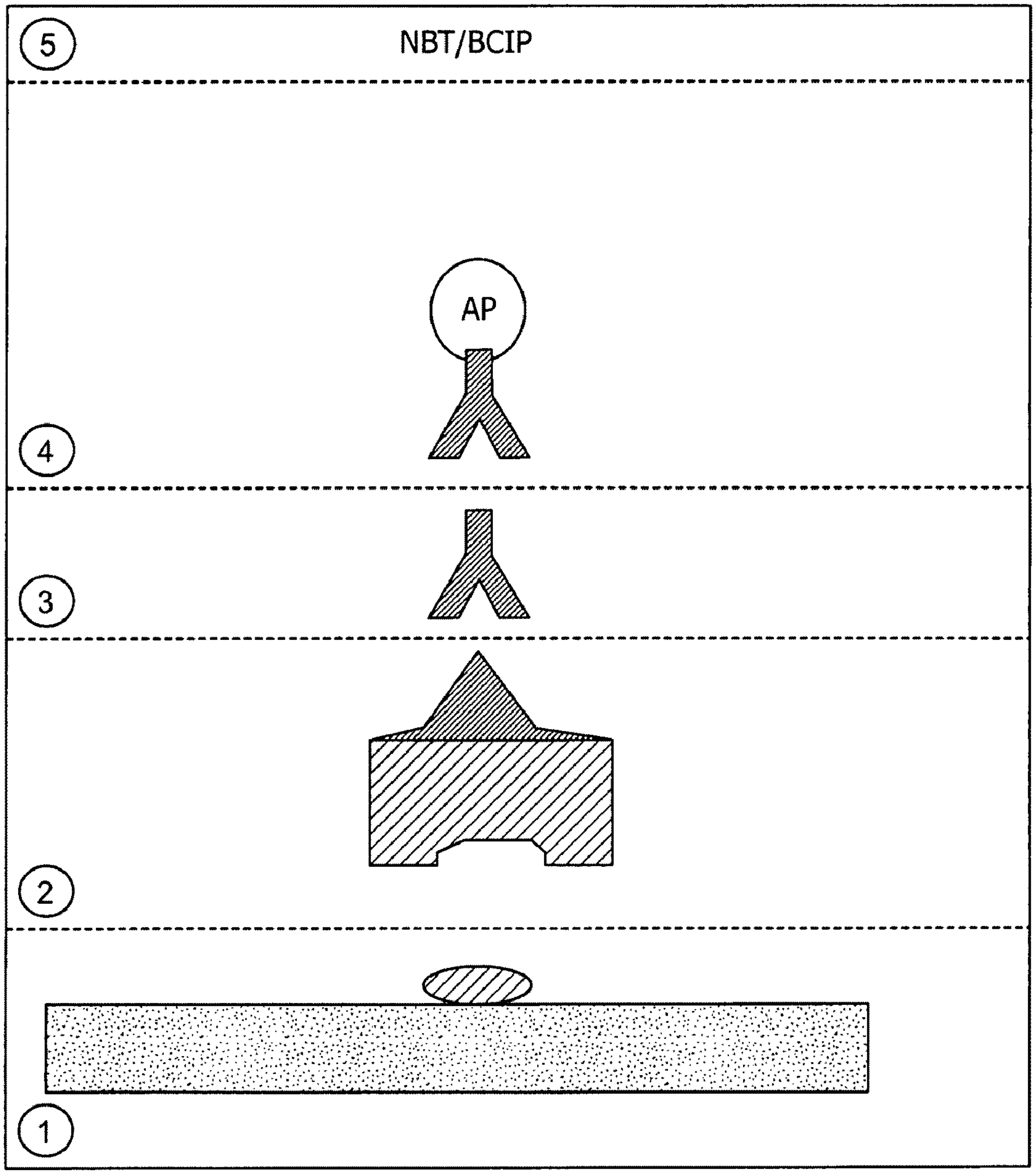
FIG. 5 illustrates a far western blot lysozyme-protein interaction assay comprising the following five steps: (1) immobilization of purified lysozyme onto a solid support; (2) probing of the solid support with a ligand for lysozyme (e.g., GST-Tp17); (3) binding of GST-Tp17 with goat anti-GST antibody; (4) binding of the goat antibody with an anti-goat alkaline phosphatase conjugate; and (5) staining with nitroblue tetra zolium/bromochloro indolyl phosphate alkaline phosphatase chromogenic substrate (NBT/BCIP).

A Far Western blot involves the immobilization of a protein to a solid support, probing of the support with a ligand likely to bind directly to protein and immunodetection of the bound protein-ligand. An exemplary Far Western blot is shown in FIG. 5 and described in detail in Example 2.

For immunohistochemistry, duplicate tissue sections may be treated with antibodies specific to a polypeptide of interest and a control polypeptide. These primary antibodies may be directly labeled or may be detected with suitable secondary antibodies. Staining intensity can be measured with a charge-coupled device (CCD) camera and the proteins quantitated. The ratio of the staining intensity indicates the ratio of the protein amounts. Alternatively, a single section can be stained with both antibodies if the antibodies have been labeled with different fluorescent labels.

Spot/slot blot techniques also are well known in the art. For example, identical amounts of a biological sample containing Tp17-like polypeptide antibody, Tp17-like polypeptide-lysozyme complex antibody, or lysozyme antibody may be directly spotted onto a membrane and detected with Tp17-like polypeptide, lysozyme, and/or the Tp17-like polypeptide-lysozyme complex, as described above. The probes may be labeled or a secondary ligand may be used.

Many types of biosensor-based methods are known in the art and may be used for detecting and quantitating anti-Tp17-like polypeptide antibodies, anti-Tp17-like polypeptide-lysozyme complex antibodies, or anti-lysozyme antibodies.

For example, samples containing antibodies specific to Tp17-like polypeptide and/or lysozyme may be bound to the surface of the biosensor such that when Tp17-like polypeptide and/or lysozyme binds to the coated surface a detectable change occurs in some property of the surface. Biosensors measure, for example, mass changes at the surface, changes in electrical properties, or changes in optical properties. Each of these methods are well known in the art and are suitable for use in the present methods.

Commercial biosensor-based methods are available from, for example, Biacore (Piscataway, N.J.) and are suitable for use in the present invention for detecting and quantitating changes in the levels of antibodies to Tp17-like polypeptide and/or lysozyme. See also, for example, the protein detection methods described in U.S. Pat. No. 6,225,047, the contents of which are hereby incorporated by reference in their entirety, and Davies et al. (1999) Biotechniques 27:1258-61. Commercial protein chip detection methods are available from Ciphergen (Fremont, Calif.). The invention can be scaled up to detect or differentiate between two or more pathogens, e.g., to determine if a strain of bacteria is a drug-resistant strain or is incapable of binding to or inhibiting lysozyme.

In another embodiment, any of the methods described herein may be competitive immunoassays, which are well known in the art. For example, a competitive sandwich immunoassay may be performed for measuring the level of antibody for a Tp17-like polypeptide and/or lysozyme in which known Tp17-like polypeptide antibodies are used to compete with the Tp17-like polypeptide antibody in the sample for binding to Tp17-like polypeptide. For example, serial dilutions of known Tp-like polypeptide antibodies may be incubated with the sample or with the Tp17-like polypeptide prior to addition to the assay.

Mass spectrometric methods for protein detection may also be used to detect and quantity changes in the levels of antibodies, or fragments thereof, to Tp17-like polypeptide and/or lysozyme in a sample, for example. See, for example, the methods described in U.S. Pat. Nos. 5,719,060; 5,894,063; and Shimizu et al. (2002) J. Chromatogr. B. Analyt. Technol. Biomed. Life Sci. 25:776:15-30; Kiernan et al. (2002) Anal. Biochem. 301:49-56; and Pramanik et al. (2002) Protein Sci. 11:2676-87. Mass spectrometry based protein detection methods are also available from Ciphergen (Fremont, Calif.).

Biological Sample

The sample analyzed or treated using any of the compositions and methods of the invention may comprise a body sample such as blood, serum, plasma, tears, saliva, nasal fluid, sputum, ear fluid, genital fluid, breast fluid, colostrum, milk, placental fluid, perspirate, synovial fluid, ascites fluid, cerebrospinal fluid, bile, gastric fluid, gastrointestinal fluid, exudate, transudate, pleural fluid, pericardial fluid, semen, fecal material, upper airway fluid, peritoneal fluid, fluid harvested from a site of inflammation or other immune response, fluid harvested from a pooled collection site, bronchial lavage, urine, aqueous humor, biopsy material, material from the forestomach of a ruminant animal, nucleated cell sample, fluid associated with a mucosal surface, for example. Alternatively, the compositions and methods according to the invention can be performed on dry cell samples (e.g., hair or skin) or biopsy samples of any tissue in which the genes of interest or antibodies are expressed or deposited.

Other Samples

As referred to herein, "sample" also means any diagnostic, experimental, or clinical sample that may be suspected to contain lysozyme or a Tp17-like polypeptide, or that otherwise requires testing or treatment for the presence of lysozyme or a Tp17-like polypeptide, or antibody thereto, such as a culture vessel, cuvette, swab, medical instrument (e.g., surgical instrument). A sample may also be a cell or fluid culture (e.g., throat aspirate, cerebrospinal fluid sample, hemoculture). A sample may be a pathogen preparation, such as, for example, a bacteria, a virus, a parasite, a plasmid, a mycoplasma, a mycotic agent (e.g., fungus, yeast), or prion preparation. The sample may be a liquid or solid agent, such as a food, a medicine, an implant, a graft, a tissue or cell culture medium, a water sample, or other solution, reagent or apparatus for which sterility is desired or required.

The compositions and methods can be used to diagnose or treat pathogen contamination or infection, e.g., pathogen-related diseases such as, for example, syphilis, HIV infection, genital herpes, bubonic plague, dysentery, shigellosis, dental caries, *E. coli* infection, cystic fibrosis, tuberculosis, cholerae, group A and group B streptococcal infections, staphylococcal infections, gastric ulcer, whooping cough, chlamydiosis, brucellosis, otitis media, meningitis, influenza infection, malaria, salmonellosis, gonorrhea, vibriosis, colibacillosis, pneumonia, bronchitis, Severe Acute Respiratory Syndrome. In an embodiment, the compositions and methods of the invention are useful in the diagnosis or treatment of cytoplasmic storage diseases such as lysosomal storage diseases.

In addition, the compositions and methods of the invention can be used to diagnose or treat diseases such as cancer, infectious disease, inflammatory disease, Alzheimer's disease, renal amyloidosis, leukemia, Crohn's disease, and allergy.

Administration

Inhibitors of Tp17-like polypeptides that compete with Tp17-like polypeptides for binding to lysozyme may be administered to a subject (e.g., a mammal, such as a human) in order to inhibit binding of a Tp17-like polypeptides to the lysozyme, so that lysozyme is able to combat the pathogenic agent. Alternatively, mutant lysozyme insensitive to inhibition by Tp17-like polypeptides may be administered.

Any technical means (e.g., chemical drugs, competitor peptides, antibodies, vectors, siRNA) that interferes with the union of lysozyme and its cognate inhibitors (e.g., such as Tp17-like polypeptide) may be used prophylactically or therapeutically to combat pathogenic disease caused by any pathogen that comprises such an inhibitor (e.g., syphilis, HIV infection, genital herpes, bubonic plague, dysentery, shigellosis, dental caries, *E. coli* infection, cystic fibrosis, tuberculosis, cholerae, group A and group B streptococcal infections, staphylococcal infections, gastric ulcer, whooping cough, Enterococcal infections, chlamydiosis, brucellosis, otitis media, meningitis, influenza infection, malaria, salmonellosis, gonorrhea, vibriosis, colibacillosis, pneumonia, bronchitis, and Severe Acute Respiratory Syndrome, for example. In an embodiment, the compositions and methods of the invention are useful in the prophylaxis or treatment of cytoplasmic storage diseases such as lysosomal storage diseases.

Alternatively, ligands that compete with lysozyme for binding with Tp17-like polypeptides may be administered to patients in order to inactivate lysozyme activity in patients that suffer from a disease related to over production of lysozyme or any disease or condition in which a decrease in lysozyme activity is desired.

Preparations for oral administration of inhibitors of Tp17-like polypeptide/lysozyme binding may be suitably formulated to give controlled release of the active compound. For buccal administration, the inhibitors may take the form of tablets or lozenges formulated in a conventional manner.

Alternatively, an area may be swabbed, sprayed or applied with inhibitors prior to obtaining a post-treatment sample (e.g., by scraping). For administration by inhalation, the inhibitors for use according to the methods of the invention is conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the inhibitors and a suitable powder base such as lactose or starch.

The inhibitors may be formulated for parenteral administration by injection, e.g., by bolus injection or continuous infusion. Formulations for injection may be presented in unit dosage form, e.g., in ampoules or in multi-dose containers, with an added preservative. The inhibitors may take such forms as suspensions, solutions or emulsions in oily or aqueous vehicles, and may contain formulatory agents such as suspending, stabilizing and/or dispersing agents. Alternatively, the inhibitors may be in powder form for constitution with a suitable vehicle, e.g., sterile pyrogen-free water, before use.

The inhibitors may also be formulated for rectal administration, inhibitors such as suppositories or retention enemas, e.g., containing conventional suppository bases such as cocoa butter or other glycerides.

The inhibitors may also be formulated as a depot preparation. For example, parenteral depot systems (PDS) are injected or implanted into the muscle or subcutaneous tissue and incorporated drug released in a controlled manner, allowing the adjustment of release rates over extended periods of time, ranging from several days up to one year. Such long acting formulations may be administered by implantation (e.g., subcutaneously or intramuscularly) or by intramuscular injection. The inhibitors may be formulated with suitable polymeric or hydrophobic materials (e.g., as an emulsion in an acceptable oil) or ion exchange resins, or as sparingly soluble derivatives, such as a sparingly soluble salt. Other suitable delivery systems include microspheres which offer the possibility of local noninvasive delivery of inhibitors over an extended period of time. This technology utilizes microspheres of precapillary size which can be injected via a coronary catheter into any selected part of the body, e.g., the eye, or other organs without causing inflammation or ischemia. The administered inhibitor is slowly released from these microspheres and taken up by surrounding tissue cells.

Systemic administration of the inhibitors can also be by transmucosal or transdermal means. For transmucosal or transdermal administration, penetrants appropriate to the barrier to be permeated are used in the formulation. Such penetrants are generally known in the art, and include, e.g., for transmucosal administration bile salts and fusidic acid derivatives. In addition, detergents may be used to facilitate permeation. Transmucosal administration may be through nasal sprays or using suppositories. For topical administration, the oligomers of the invention are formulated into ointments, salves, gels, or creams as generally known in the art. A wash solution may be used locally to treat an injury or inflammation to accelerate healing.

Cells

The invention may require cells for the preparation or testing of pathogen peptides, for example. Cultured primary or permanent animal or bacterial cell lines may be: primary cells (including, but not restricted to, monocytes, synoviocytes, fibroblasts, and endothelial cells) derived from the same subject as the fluid sample or derived from another individual; permanent cell lines from a range of tissue and organ origins (including, but not restricted to, cell lines available from public access repositories such as American Tissue Type Collection); or primary or permanent cell lines that have been stably transfected with "promoter-readout" constructs.

Bacterial cell culture techniques are well known in the art. For example, bacterial cells may be grown in 2XYT broth on a shaker at 37° C. Methods for growing bacteria transformed with a plasmid or virus may also include growth in selective agents such as ampicillin or other antibiotic. Preparations of cells and cell lysates, as well as purification of proteins and nucleic acids are also well known in the art.

The practice of the present invention can employ, unless otherwise indicated, conventional techniques of cell biology, cell culture, molecular biology, transgenic biology, microbiology, recombinant DNA, and immunology, which are within the skill of the art. Such techniques are explained fully in the literature. Molecular Cloning—A Laboratory Manual (1989), $2^{nd}$ Ed., Sambrook et al. (Eds.) Cold Spring Harbor Laboratory Press, Chapters 16 and 17; Hogan et al. (1986) Manipulating the Mouse Embryo: A Laboratory Manual, Cold Spring Harbor Laboratory Press, Cold Spring Harbor, N.Y.; U.S. Pat. No. 4,683,195; *DNA Cloning*, Volumes I and II (1985) Glover (Ed.); Oligonucleotide Synthesis (1984) Gait (Ed.); Nucleic Acid Hybridization (1984) Hames & Higgins (Eds.); Transcription and Translation (1984) Hames & Higgins (Eds.); Culture Of Animal Cells (1987) Freshney, Alan R. Liss, Inc.; Immobilized Cells And Enzymes (1986) IRL Press; Perbal (1984) A Practical Guide To Molecular Cloning; Methods In Enzymology (Academic Press, Inc., N.Y.); Gene Transfer Vectors For Mammalian Cells (1987) Miller and Calos (Eds.) Cold Spring Harbor Laboratory; Methods In Enzymology, Vols. 154 and 155, Wu et al. (Eds.) Academic Press Inc., N.Y.; Immunochemical Methods In Cell And Molecular Biology (1987) Mayer and Walker (Eds.) Academic Press, London; Handbook Of Experimental Immunology, Volumes I-IV (1986) Weir and Blackwell (Eds.).

The methods of the invention are useful therefore as a diagnostic and a prognostic tool, as a means for treating or immunizing against disease, for monitoring disease progression and resolution, for tracking the response, or lack thereof, to therapy, for evaluating the efficacy of alternative or concomitant medication; and for establishing the correct therapeutic dose of a medication. The methods of the invention may also be used, in the context of drug research and development, to assess the potential efficacy and side effects of investigational and approved drugs in biological samples collected in the course of animal testing and/or Phase I, II, III, and IV clinical trials and/or post-marketing studies. ExamplesPractice of the invention will be more fully understood from the following examples, which are presented herein for illustrative purposes only, and should not be construed as limiting the invention in any way.

Example 1

Chicken Lysozyme Copurifies With Recombinant Forms Of The *Treponema Pallidum* 17 kDa Antigen In the context of purifying *E. coli*-derived, recombinant *T. pallidum* Tp17 antigen (GST-Tp17 or Tp17-HIS), a protein reproducibly co-purified with Tp17. This "contaminant" protein, which had a molecular weight of 14 KDa and did not react with an anti-Tp17 polyclonal serum, was identified as chicken lysozyme as described below.

A protein fraction containing both entities (Tp17 and the "contaminant") was separated by PAGE-SDS, excised from the gel and subjected to N-terminal amino acid sequencing. The experiment yielded short N-terminal peptide sequences (6-7 amino acids) that matched perfectly with the expected sequence of the *T. pallidum* Tp17 antigen or chicken lysozyme, which was included in the cell paste resuspension buffer to facilitate bacterial cell lysis. These observations suggested that Tp17 interacts physically with chicken lysozyme. Experimental protocols corresponding to the purification of GST-Tp17 and Tp17-HIS, as well as microsequencing experiments, are presented below.

GST-Tp17 Chromatography

The recombinant *E. coli* DH5α containing pGEX2T-Tp17 (Akins et al. (1993) Infect. Immun. 61:1202-1210) (FIG. 6A-C) was grown in a 5 liter fermenter in 2×YT broth (Sambrook et al. (1989) Molecular Cloning: A Laboratory Manual $2^{nd}$, Chris Nolan (Ed.) Cold Spring Harbor Press.) with 100 μg/ml ampicillin (Roche Diagnostics, Barcelona, Spain). The culture was induced with 0.3 mM IPTG (Roche Diagnostics Mannheim, Germany) for four hours. Cells were harvested and resuspended in 50 mM Tris (pH 8.0), 85 mM NaCl, 2 mM EDTA, 1% Polyoxyethylene 10 tridecil ether, containing protease a inhibitor cocktail (1 ml/g of cell paste, Sigma-Aldrich, Madrid, Spain) and 0.5 mg/ml chicken lysozyme (Sigma-Aldrich, Madrid, Spain). After incubation for 50 minutes, cells were sonicated and centrifuged at 28,000 g. The recombinant GST-Tp17 was purified from the supernatant by ion exchange chromatography (Q Sepharose XL, Amersham Biosciences, Cerdanyola, Spain). The flowthrough was further purified by glutathione affinity chromatography (glutathione sepharose EF, Amersham, Cerdanyola, Spain). A 100 mM reduced glutathione buffer was used to elute the GST-Tp17. The fractions collected were analysed by gel electrophoresis. Another purification process was performed without using lysozyme following the same protocol.

Tp17-HIS Chromatography

The gene sequence encoding the mature Tp17 protein coding sequence (including residues 23 to 156 of the Tp17 sequence deposited under the NCBI accession number P29722) was PCR amplified using the pProExHT-Tp17 (Dr. Norgard, University of Dallas, Tex., USA) vector as a template. PCR amplification was performed using an Expand High Fidelity PCR system kit (Roche Diagnostics, Mannheim, Germany) and oligonucleotides P17-NdeI (5'-AGA TAT ACA TAT GGT CTC GTG CAC AAC CGT GTG TCC GCA CGC CGG GAA GGC CAA-3') (SEQ ID NO:33) and P17-rev1 (XhoI) (5'-ATG TAG CGA ACG GAG TTA-3') (SEQ ID NO:34) under the conditions recommended by the supplier (Roche Diagnostics, Mannheim, Germany). Thermal cycling conditions were as follows: a denaturation cycle (1 min. at 94° C.) followed by 30 amplification cycles (1 min. at 94° C., 1 min. at 55° C., 1 min. at 72° C.). The resulting PCR amplicon (≈300 bp) was purified using the Nucleotrap purification system (Macherey-Nagel, Düren, Germany). 1 μg of purified PCR fragment and 1 μg of purified pET24a plasmid were each digested with 10 units of NdeI and 10 units of XhoI using the conditions recommended by the supplier (Roche Diagnostics, Mannheim, Germany). Restricted fragments were separated through a 0.8% agarose gel (Sambrook et al. (1989)) and fragments corresponding to Tp17 (≈300 bp) and pET24a (≈5300 bp) vectors were excised and gel purified using the Nucleotrap purification system (Macherey-Nagel, Düren, Germany). Both fragments were ligated using T4 DNA ligase (Roche Diagnostics, Mannheim, Germany) using the conditions recommended by the supplier. The ligation reaction was then used to transform chemically competent *E. coli* TOP10 (Invitrogen SA, Barcelona Spain) and transformants were selected on LB plates (Sambrook et al. (1989)) supplemented with 100 μg/ml of ampicillin (Roche Diagnostics, Mannheim, Germany). Plasmid DNA was prepared from 10 individual clones and analyzed by restriction endonuclease digestion using NdeI and XhoI. Eight out of ten clones contained the correct pET24a-Tp17 recombinant plasmid. The sequence of one plasmid clone was verified by DNA sequencing (DNA Sequencing Facility, UAB, Barcelona, Spain) and was subsequently used to transform the *E. coli* BL21 (DE3) Rosetta (Novagen, Madison, Wis.) expression strain. The resulting strain was named EcBK633 (see FIG. 7).

The recombinant *E. coli* EcBK633 was grown in a 5 liter bioreactor in 2× YT broth with ampicillin (Roche Diagnostics, Mannheim, Germany). The culture was induced with 1 mM IPTG (Roche Diagnostics, Mannheim, Germany) for four hours. Cells were harvested and resuspended in 50 mM Tris (pH 8.5) containing protease inhibitors (Sigma-Aldrich Madrid, Spain) and 0.6 mg/ml chicken lysozyme (Sigma-Aldrich, Madrid, Spain). After incubation for 45 minutes, cells were sonicated and centrifuged at 30,100 g. The recombinant Tp17-HIS was purified from the supernatant by metal ion affinity chromatography, using nickel-charged resin (Chelating HP; Amersham, Cerdanyola, Spain) and a gradient elution 10-200 mM imidazole (Merck, Darhmstadt, Germany) and 500 mM imidazole as recommended by the supplier. The fractions collected were analyzed by gel electrophoresis and Western Blot.

Electrophoresis and Western Blot Analysis

Figure 8A:
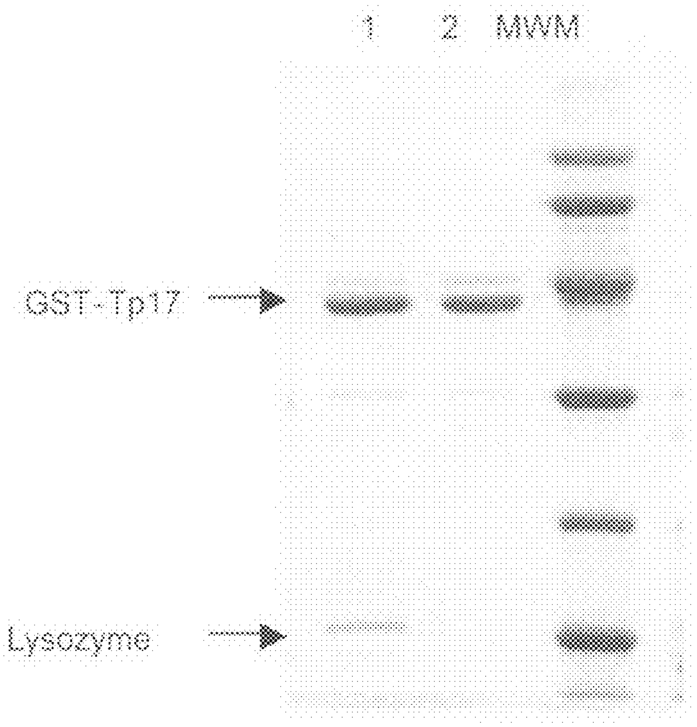
FIG. 8A is a Coomasie Brilliant Blue-stained gel of purified GST-Tp17 chromatographic fractions. Lane 1: purification process with added chicken lysozyme; lane 2: purification process without added chicken lysozyme; lane 3: MWM: molecular weight markers.
Figure 8B:
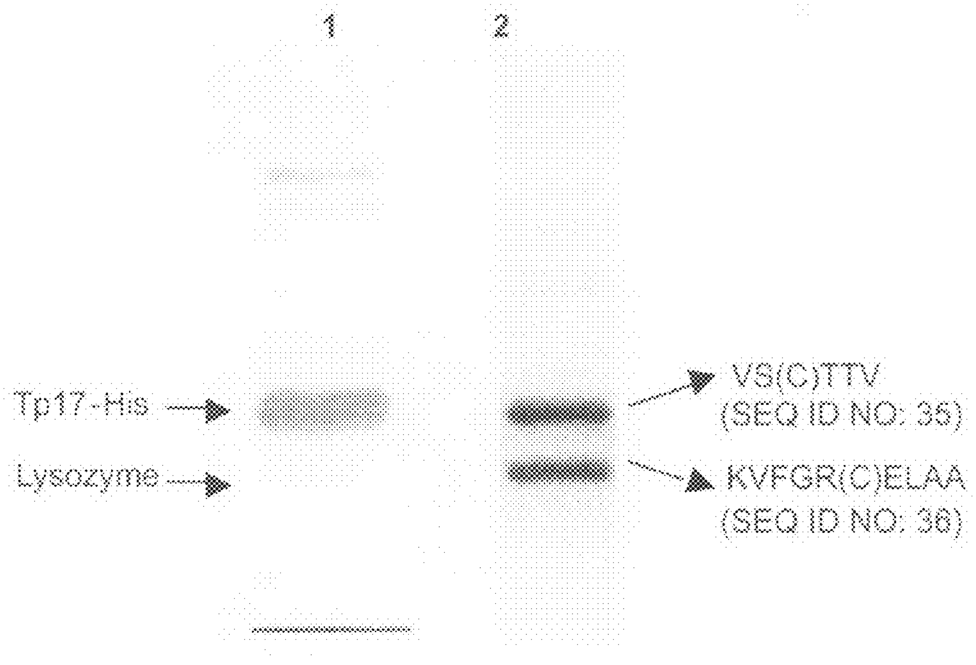
FIG. 8B is a Western Blot and Coomasie Brilliant Blue-stained gel of purified Tp17-HIS chromatographic fractions. Lane 1: Western blot using a syphilis positive human serum of proteins recovered from the purification process in the presence of added chicken lysozyme; lane 2: Coomasie Brilliant Blue staining of proteins recovered from the purification process in the presence of added chicken lysozyme. The peptide sequences obtained by N-terminal amino acid sequencing of the proteins recovered from the electrophoretic bands in lanes one and two are indicated.

The chromatographic fractions and protein molecular weight markers (See Blue Plus II™, Invitrogen, Barcelona, Spain) were separated electrophoretically through two identical 15% SDS-PAGE gels as described in Sambrook et al. (1989). Subsequently, one gel was stained with Coomasie Brilliant Blue R250 (Merck, Darhmstadt, Germany) in order to detect total protein. As shown in FIG. 8A, two major bands (14 kDa and 17 kDa) were observed in the fraction corresponding to the Tp17 purified protein. The proteins in the other gel were electro-transferred to an Immobilon™ P PVDF membrane (Millipore Corp., Bedford, Mass.) as recommended by the supplier. The membrane was then incubated for 1 hour at room temperature (18-22° C.) in 5 ml of Blotto™ (BioRad, Hercules, Calif.) containing PBS, 0.05% w/v Tween and 10% w/v of dried, non-fat skimmed milk (PBST). The membrane was then processed as follows: (1) three 10 minute washes with PBST, (2) 1 hour incubation at room temperature (18-22° C.) in the presence of 10 mls of a human serum from a patient with syphilis diluted 1/200 in Blotto™, (3) three 10 minute washes with PBST, (4) 1 hour incubation at room temperature with 10 mls an alkaline phosphatase-conjugate, rabbit-anti-human polyclonal serum (BioRad, Hercules, Calif., USA) diluted 1/2000 in PBST, (5) three 10 minute washes with PBST, and (6) a final incubation with 5 ml of NBT/BCIP alkaline phosphatase chromogenic substrate (Sigma-Aldrich, Madrid, Spain) until color development. As shown in FIG. 8B, this assay detects binding of the human IgG to the 17 kDa (Tp17-HIS) but not to the 14 kDa protein.

N-Terminal Sequencing

The chromatographic fraction containing the purified Tp17-HIS with the contaminant protein (14 kDa) and a protein molecular weight marker (SeeBlue Plus II™, Invitrogen SA, Barcelona, Spain) was separated electrophoretically through a 15% SDS-PAGE gel as described in Sambrook et al. (1989). Subsequently, the proteins in the gel were electro-transferred to an Immobilon™ P PVDF membrane (Millipore Corp., Bedford, Mass.) using the suppliers guidelines. The membrane was stained with Coomassie Brilliant Blue R250 and the two bands were cut and dried for sequencing analysis. The N-terminal analysis by automatic Edman degradation was performed in a Beckman LF3000 sequencer with a PTH-amino acid analyzer (System Gold, Beckman Coulter, Fullerton, Calif.).

The sequences obtained were:

| | |
|---|---|
| $_{NH2}$-VS(C)TTV$_{-COOH}$ | for the 17 KDa protein (SEQ ID NO: 35). |
| $_{NH2}$-KVFGR(C)ELAA$_{-COOH}$ | for the 14 KDa protein (SEQ ID NO: 36). |

As shown in FIG. 8B, the 17 kDa protein N-terminal sequence corresponded to the *Treponema pallidum* Tp17 and the 14 kDa protein sequence corresponded to the chicken lysozyme.

Example 2

Far Western Detection of Tp17 Binding to Chicken and Human Lysozyme

The observation that the *T. pallidum* 17 kDa (Tp17) protein antigen copurifies with chicken lysozyme strongly suggested a direct physical interaction between both proteins. In order to test this hypothesis, a Far-Western blot lysozyme-protein interaction assay was performed. The assay is summarized in FIG. 5 and comprises generally the following three steps: (1) immobilization of purified lysozyme onto a membrane; (2) probing of the membrane with a ligand likely to bind directly to the lysozyme; and (3) immunodetection of the bound lysozyme-ligand. A detailed experimental procedure is presented below.

Far Western Blotting Detection of Lysozyme-Tp17 Protein Interactions

Purified chicken egg white lysozyme and human breast milk lysozyme were purchased from Sigma-Aldrich (Madrid, Spain). Two series of aliquot fractions containing 1 μg, 5 μg, and 10 μg of purified lysozyme and a protein molecular weight marker (SeeBlue Plus II™, Invitrogen SA, Barcelona, Spain) were separated electrophoretically through a 4-12% SDS-PAGE gel using the conditions recommended by the supplier (Invitrogen). The gel was then processed for Western blotting as described in Sambrook et al. (1989) according to art known methods, and the proteins were electro-transferred to an Immobilon™ P PVDF membrane (Millipore Corp., Bedford, Mass.). The presence of lysozyme immobilized onto the PVDF membrane was assessed by staining for 1 minute with Ponceau S stain (Sigma-Aldrich, Madrid, Spain), and then destained by vigorous washing for 5 minutes with desionized water. The membrane was divided in two, each portion containing a protein ladder and three quantities of chicken or human lysozyme (1 μg, 5 μg and 10 μg per lane). Each membrane was then incubated for 16 hours at 4° C. in 5 ml of TBST (10 mM Tris-HCl, pH 8.0, 150 mM NaCl, 0.05% weight/vol. Tween 20™,) supplemented with 5% (weight/vol.) of non-fat skimmed dried SVELTESSE™milk (NESTLÉ, ESPAÑA, Barcelona, Spain) (to make TBST-milk). The membranes were then processed separately as follows: (1) three 1 minute washes with 10 mls TBST, (2) 1 hour incubation at room temperature (18-22° C.) in the presence of 10 mls of 100 mg/ml GST-Tp17 fusion protein (Akin et al. (1993)) or a control protein GST-Tp47, (Hsu et al. (1989) Infect. Immun. 57:196-203; Weigel et al. (1992) Infect. Immun. 60:1568-1576) (3) three 10 minute washes with 5 mls of TBST, (4) 30 minute incubation at room temperature with 10 mls of an anti-GST polyclonal goat serum (Amersham Biosciences, Cerdanyola, Spain) diluted 1/7500 with TBST-milk, (5) three 10 minute washes with 5 ml of TBST at room temperature, (6) 1 hour incubation at room temperature with 10 mls of an alkaline phosphatase-conjugate, rabbit-anti-goat polyclonal serum (Dako A/S, Glostrup, Denmark) diluted 1/5000 in TBST-milk, (7) three 10 minute washes with 5 ml of TBST and (8) 3 minutes incubation with 5 ml of Nitroblue tetra zolium/Bromo Chloro Indolyl Phosphate alkaline phosphatase chromogenic substrate (NBT/BCIP) (Sigma-Aldrich, Madrid, Spain) until color development.

Figure 9A:
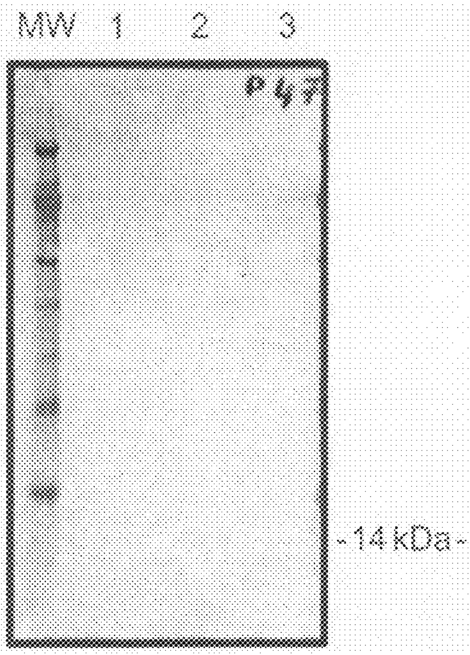
FIG. 9A illustrates the results from probing chicken lysozyme with GST-Tp47 in a far western blot assay. Lane MW: molecular weight markers; lane 1: 1 μg purified chicken lysozyme; lane 2: 5 μg purified chicken lysozyme; lane 3: 10 μg purified chicken lysozyme.
Figure 9B:
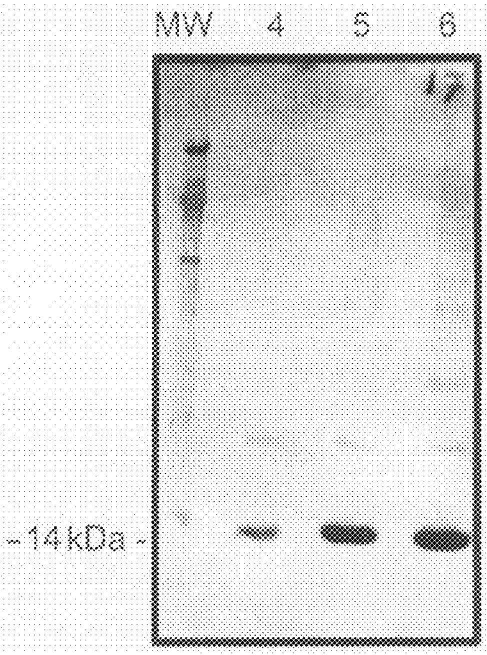
FIG. 9B illustrates the results from probing chicken lysozyme with GST-Tp17 in a far western blot assay. Lane MW: molecular weight markers; lane 4: 1 μg purified chicken lysozyme; lane 5: 5 μg purified chicken lysozyme; lane 6: 10 μg purified chicken lysozyme.
Figure 9C:
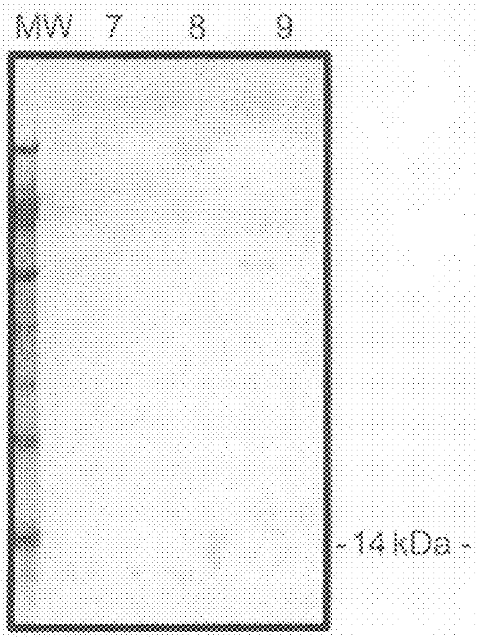
FIG. 9C illustrates the results from probing human lysozyme with GST-Tp47 in a far western blot assay. Lane MW: molecular weight markers; lane 7: 1 μg purified human lysozyme; lane 8: 5 μg purified human lysozyme; lane 9: 10 μg purified human lysozyme.
Figure 9D:
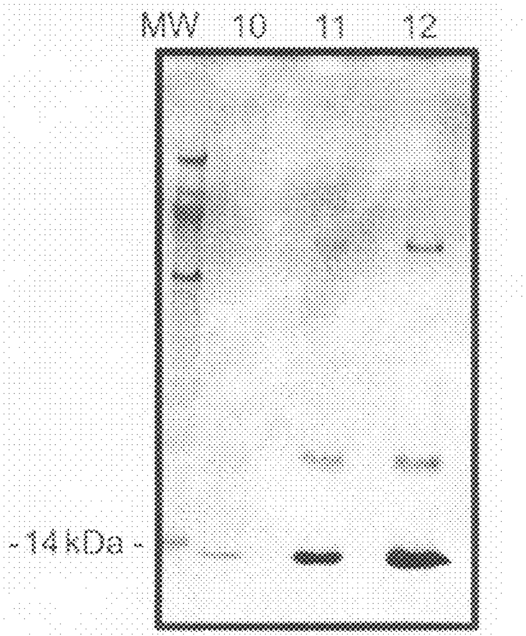
FIG. 9D illustrates the results from probing human lysozyme with GST-Tp17 in a far western blot assay. Lane MW: molecular weight markers; lane 10: 1 μg purified human lysozyme; lane 11: 5 μg purified human lysozyme; lane 12: 10 μg purified human lysozyme.

The above assay detected binding of the GST-Tp17 fusion protein to both chicken and human lysozyme (14 kDa band in FIGS. 9B and 9D, respectively). Moreover, the binding of GST-Tp17 to lysozyme is strong since it resisted numerous washings in the presence of detergent (0.05% Tween 20™). No signal was detected when the membrane was incubated with control GST-Tp47 antigen (FIGS. 9A and 9C), demonstrating that the interaction between Tp17 and lysozyme is specific and does not involve the GST moiety, which is shared by both GST-Tp17 and GST-Tp47. These results demonstrate that (i) the *T. pallidum* Tp17 antigen binds strongly and specifically to human and chicken lysozyme, and (ii) this property is contained between residues 22 to 156 of Tp17 (numbers relate to the Tp17 peptide sequence deposited under accession number P29722). This assay is used to characterize novel lysozyme binding proteins as well as to identify lysozyme mutants unable to bind lysozyme's cognate inhibitor. Conversely, this assay is used to screen for Tp17 mutants unable to bind or associate with lysozyme. This assay is also used to screen for substances (e.g., peptides, proteins, drugs, antibodies, nucleic acids, PNAs, etc.) that interfere with the binding of lysozyme to its cognate inhibitor.

Example 3

The *T. Pallidum* Tp17 Protein Antigen Inhibits The Antibacterial Activity Of Chicken And Human Lysozyme Lysozymes are well characterized antibacterial agents found on mucosal surfaces and in biological fluids. Due to their potent acetyl-muramidase enzymatic activity, lysozymes are capable of hydrolyzing cell wall peptidoglycan, thereby killing many pathogenic bacteria. The strong binding between Tp17 and human lysozyme suggested that this binding may alter the antibacterial activity of lysozyme. This hypothesis is consistent with the observation that (i) *T. pallidum* is a mucosal pathogen and (ii) it is in contact with human lysozyme in its ecological niche, throughout its infectious life cycle.

To test this hypothesis, the antibacterial activity of both human and chicken lysozyme, in the presence or absence of GST-Tp17, was assayed using an EnzCheck® lysozyme assay kit (Molecular Probes, Eugene, Oreg.). The assay comprises the use of Fluorescein-labeled *Micrococcus lysodeikticus* bacterial cells as a fluorescent substrate of lysozyme. In this Gram positive bacterium, the peptidoglycan layer is directly accessible to lysozyme, and has been Fluorescein-labeled such that fluorescence is naturally quenched. Upon lysozyme hydrolysis, quenching is relieved and fluorescein is released in a quantity that is proportional to lysozyme activity. The following experimental protocol was used.

Lysozyme Inhibition Assay

A typical 100 μl reaction consisted of 25 μl of lysozyme solution (10 units for chicken lysozyme or 50 units for human lysozyme, dissolved in deionized water), 25 μl of the test protein solution and 50 μl of a suspension of fluorescein-labeled *Micrococcus lysodeikticus* (50 μg/ml). The reaction was incubated for 45 minutes at 37° C. and the fluorescence was measured ($\lambda_{exc.}$=485 nm; $\lambda_{emi.}$=520 nm) using a fluorescence multi-well plate reader model FLx800 (Bio TEK instruments, Winoosky, Vt.) equipped with KC junior data acquisition software (Bio TEK Instruments, Winoosky, Vt.). Each experimental point was expressed as the mean and standard deviation corresponding to the reading of three independent wells. Wells containing 50 μl of deionized water and 50 μl of Fluorescein-labeled *Micrococcus lysodeikticus* suspension were used as a blank. Two fold serial dilutions of test protein were used to vary the concentration of the test protein from 83.5 to 1.3 μg/well.

Figure 10:
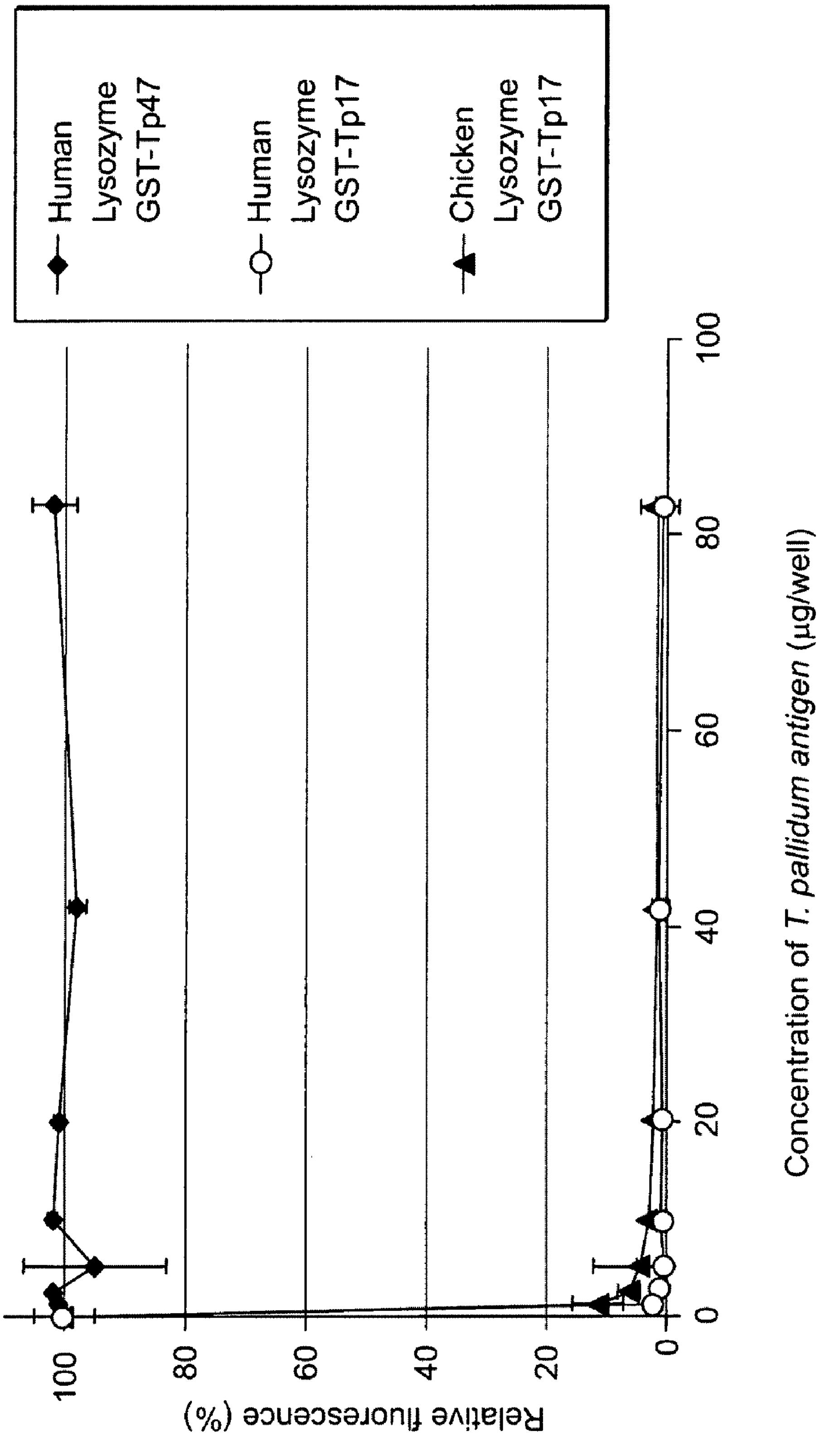
FIG. 10 shows a graphical representation of the effect of Tp17 polypeptide on lysozyme antibacterial activity. The concentration of GST-Tp17 in the presence of human (○) and chicken (▲) lysozyme was plotted versus relative fluorescence intensity. As a control, the concentration of GST-Tp47 in the presence of human (♦) lysozyme was also plotted versus relative fluorescence intensity.

As shown in FIG. 10, the acetyl muramidase activity of both human and chicken lysozyme was strongly inhibited (>85% of inhibition) by the addition of as little as 1.3 μg/well of the GST-Tp17 fusion protein. In contrast, the control GST-Tp47 fusion protein did not exert any inhibitory effect on either human or chicken lysozyme's acetyl muramidase enzymatic activity. These data demonstrate that Tp17 specifically inhibits the antibacterial activity of both chicken and human lysozymeand does not depend upon the GST moiety. Additionally, this assay is used to characterize novel lysozyme inhibitors as well as to identify lysozyme mutants unable to bind its cognate inhibitor and/or that is insensitive to inhibition by Tp17, Ivy, or other Tp17-like proteins. The assay also provides a useful screen for substances (e.g., peptides, proteins, drugs, antibodies, nucleic acids, or PNAs, etc.) that interfere with the inhibition of lysozyme's antibacterial activity.

Example 4

Structural Determinant Required For Binding Of *Escherichia Coli* Ivy To Chicken Lysozyme In order to identify the polypeptide region(s) involved in the binding of *T. pallidum* Tp17 to lysozyme and the inhibition of lysozyme acetyl muramidase activity, biological databases were searched for polypeptides previously described to bind to and inhibit the acetyl muramidase activity of lysozyme. A search through the National Institute of Health's PubMed database, using the terms "lysozyme" and "inhibitor" as key words, identified an *Escherichia coli* protein named Ivy (standing for inhibitor of vertebrate lysozyme), reported to bind and inhibit the acetyl muramidase activity of both human and chicken lysozyme (Monchois et al. (2001) J. Biol. Chem. 276:18437-18441)). This protein was of interest since (i) it is similar in size (14 kDa mature polypeptide) to mature Tp17 (15 kDa mature polypeptide) and (ii) a crystal structure of Ivy complexed to chicken lysozyme was available in the protein data bank PDB at the Research Collaboration for Structural Bioinformatics (RCSB) under the accession number 1GPQ. However, as represented in FIG. 11A, the Ivy protein shares less than 21% of amino acid sequence identity with Tp17 and no obvious peptide motif could be deduced from polypeptide sequence alignments. The Ivy/chicken lysozyme three dimensional crystal structure was examined for residues located at the interface between both molecules. The Cn3D three dimensional molecular structure viewer was used to analyze the molecular interactions between Ivy and chicken lysozyme. In the following examples, all the numbering refers and corresponds to the data archived under the following NCBI accession numbers: P00698 for chicken lysozyme, NP_000230 for human lysozyme, P45502 for *E. coli* Ivy, and P29722 for *T. pallidum* Tp17.

Figure 11B:
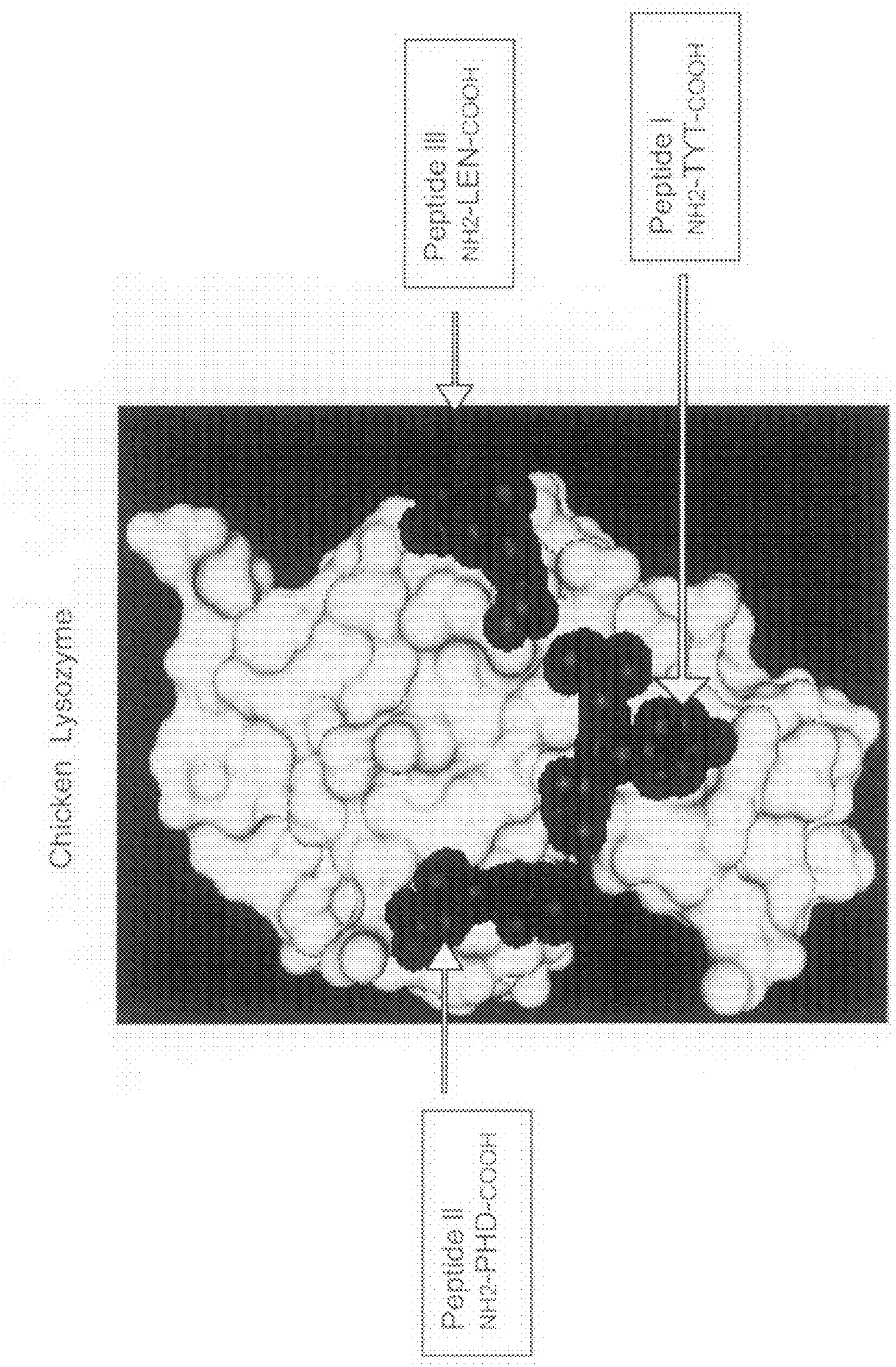
FIG. 11B illustrates the crystal structure of chicken lysozyme's three possible contact regions with *E. coli* IVY: proteini: peptides I, II, and III are indicated with dark shading.

As depicted in FIG. 11B, three zones of possible contact of chicken lysozyme with Ivy were identified. The corresponding peptide stretches are:

Peptide I: NH2-$_{52}$QGHKLPAWVMKGGTYTP$_{67}$-COOH (SEQ ID NO:37)

Peptide II: NH2$_{85}$-CKPHDCG$_{91}$-COOH (SEQ ID NO:38)

Peptide III: NH2$_{145}$-GSLENHPDGFN$_{155}$-COOH (SEQ ID NO:39)

Figure 14A:
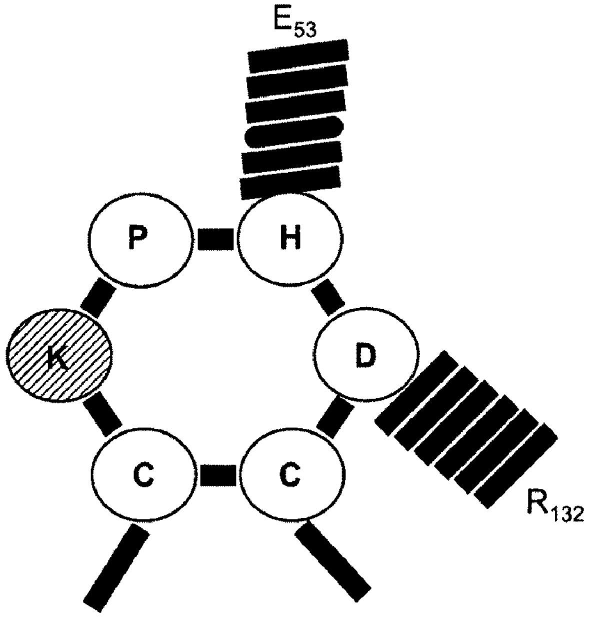
FIG. 14A illustrates the bridging of the two flanking cysteines of the *E. coli* IVY-chicken lysozyme binding site that brings the histidine and glutamic acid residues in close spatial proximity, in a configuration able to make contact with residues E53 and R132 of chicken lysozyme.

Peptide II displayed a finger-like structure composed of a cys-cys disulfide bridge closing at both ends a peptide loop comprising a KPHD motif (SEQ ID NO:40; FIG. 14A). A refined analysis of the amino acid present in this loop revealed two strong non-covalent, electrostatic interactions: between $H_{88\text{-}ivy}$ and $E_{53\text{-}chkcLys}$, and between $D_{89\text{-}ivy}$ and $R_{132\text{-}chkcLys}$.

Figure 12:
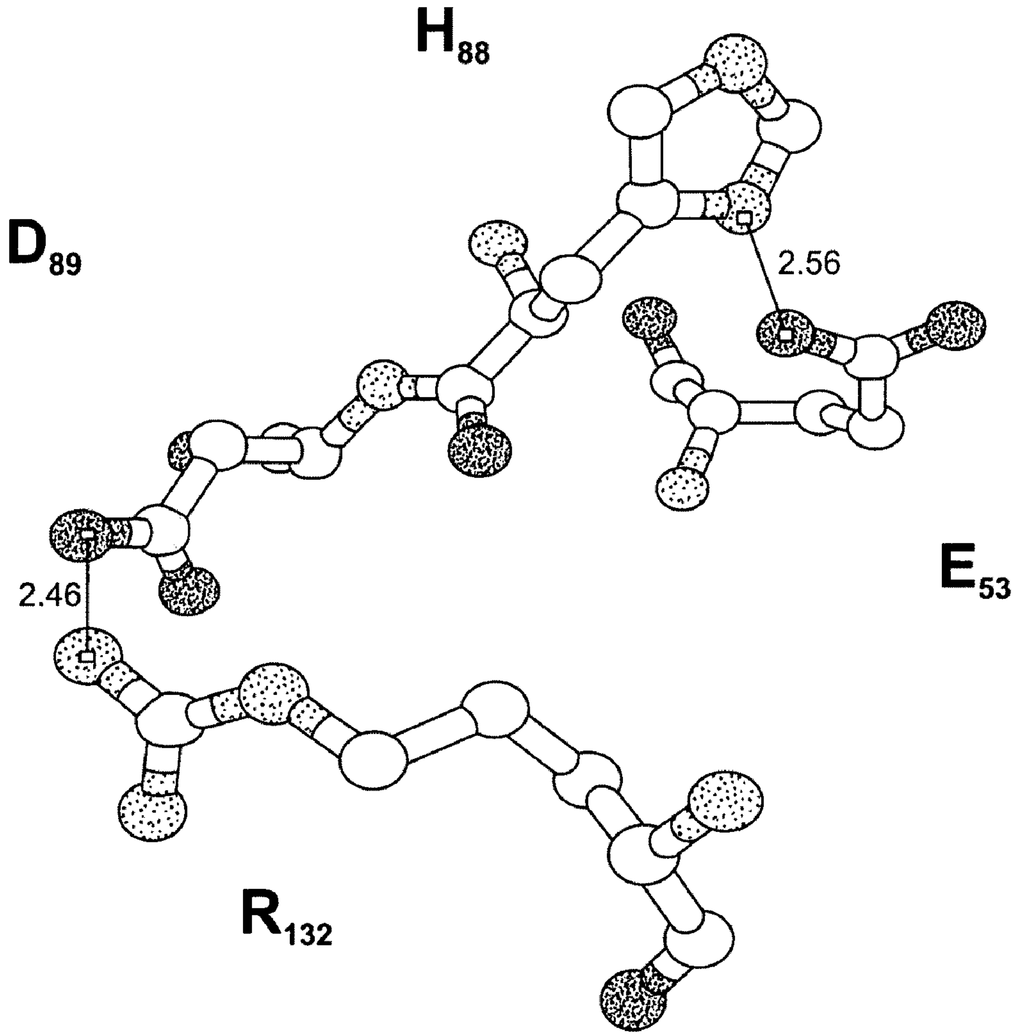
FIG. 12 illustrates atomic interactions between *E. coli* Ivy and chicken lysozyme, including the interaction between the nitrogen atom of H88-ivy and the oxygen atom of E53-chkcLys and between the oxygen atom of D89-ivy and the nitrogen atom of R132-chkcLy. The distance between atomic centers was 2.56 Å (1 angstrom=10-10 meter) in the H88-ivy/E53-chkcLys interaction and 2.46 Å in the D88-ivy/R132-chkcLys interaction.

The nitrogen atom of $H_{88\text{-}ivy}$ interacted with the oxygen atom of $E_{53\text{-}chkcLys}$ and the oxygen atom of $D_{89\text{-}ivy}$ interacted with the nitrogen atom of $R_{132\text{-}chkcLy}$ (FIG. 12). Using the 3-D Mol viewer computer software (Vector NTI suite 8.0, Informax, Frederick, Md.), the distance between atomic centers was measured at 2.56 Å (1 angstrom=$10^{-10}$ meter) in the $H_{88\text{-}ivy}/E_{53\text{-}ChkcLys}$ interaction and 2.46 Å in the $D_{89\text{-}ivy}/R_{132\text{-}chkcLys}$ interaction. The nature (electrostatic attraction between lateral chain residues) and the proximity (in the range 2.4-3.4 Å) of atomic centers indicated the presence of a particular class of non-covalent bond referred to as a "salt bridge." This observation was interesting because most salt bridges occur in relatively water-free depressions or at biomolecular interfaces where water is excluded. (Petsko et al. (2003) Protein Structure and Function. Lawrence and Robertson (Eds.) New Science Press Ltd., UK).

Figure 13B:
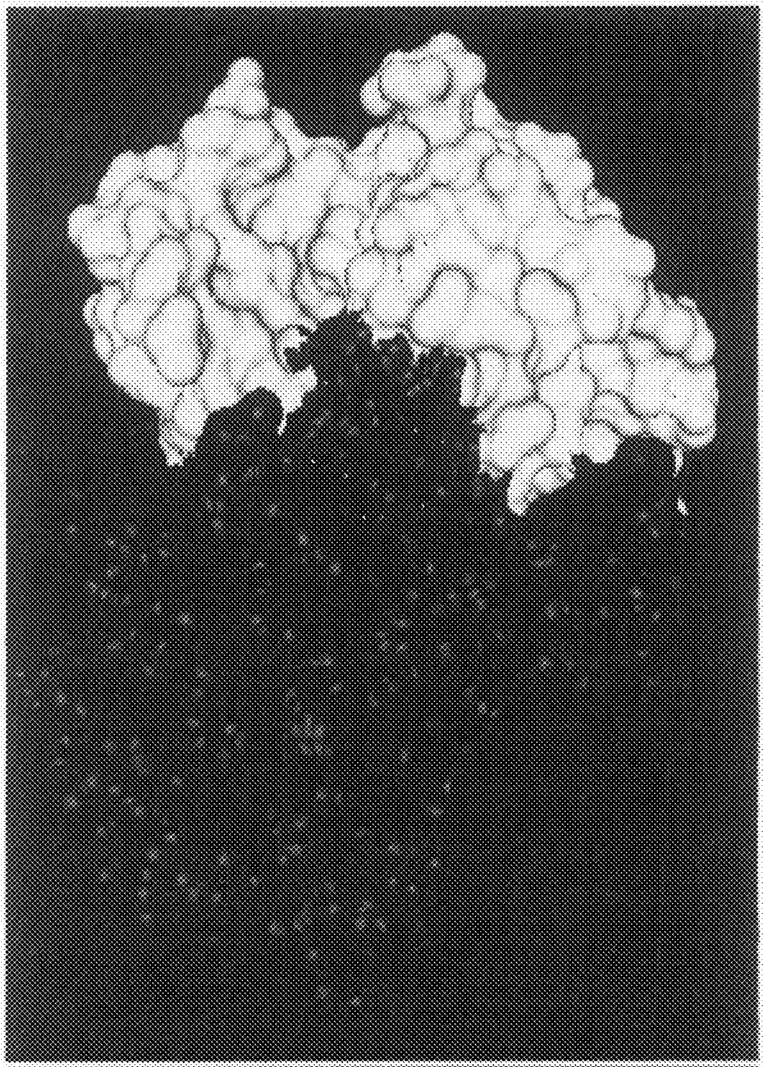
FIG. 13B illustrates the water accessible molecular surface of chicken lysozyme complexed to *E. coli* IVY. Amino acid residue $E_{53}$ is completely masked and poorly accessible to the solvent.
Figure 13A:
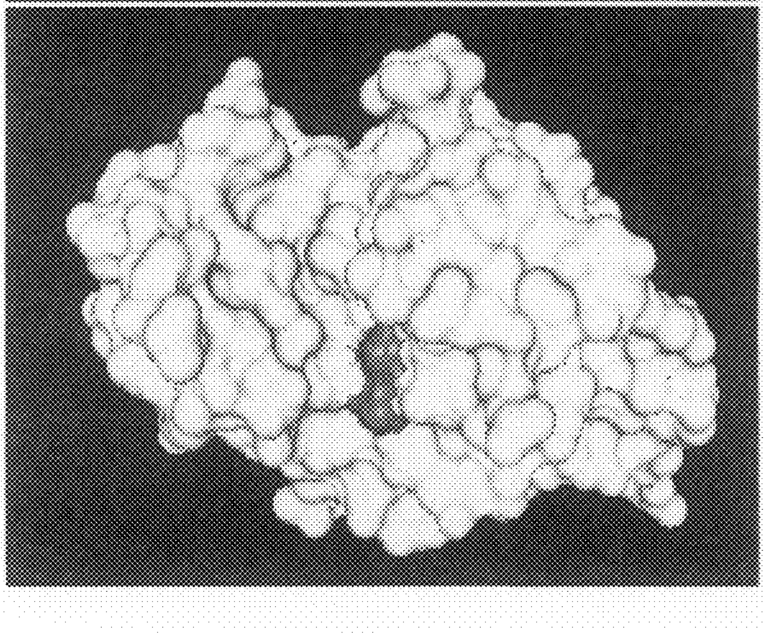
FIG. 13A illustrates the water accessible, molecular surface (light) of chicken lysozyme alone. The surface-exposed, water accessible region of amino acid residue E53 is shaded.
Figure 13D:
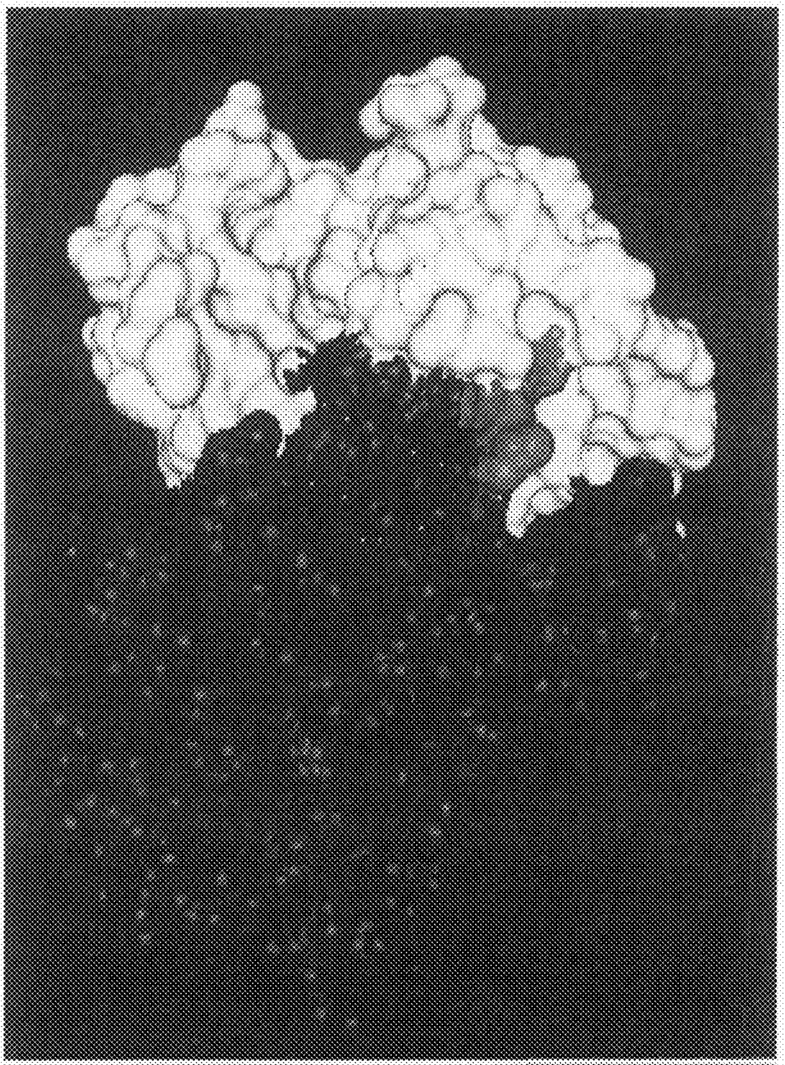
FIG. 13D illustrates the water accessible molecular surface of chicken lysozyme complexed to *E. coli* IVY. Amino acid residue R132 remains partially exposed to the solvent.
Figure 13C:
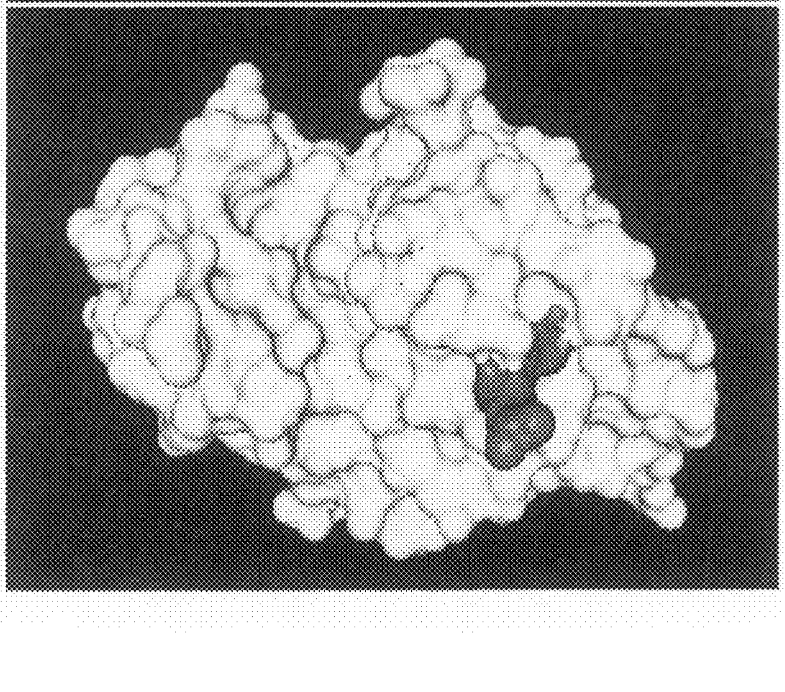
FIG. 13C illustrates the water accessible, molecular surface (light) of chicken lysozyme. The surface-exposed, water accessible region of amino acid residue R132 is shaded.

FIGS. 13A-13D illustrate that the salt bridge involving $D_{89\text{-}ivy}$≋$R_{132\text{-}chkcLys}$ was partially exposed to the water molecules of the solvent (FIGS. 13C and 13D), while the salt bridge involving $H_{88\text{-}ivy}$≋$E_{53\text{-}chkcLys}$ was completely buried and consequently protected from the solvent by the protein-protein interface (FIGS. 13A and 13B). Given that hydration of a salt bridge reduces its bonding strength, the $H_{88\text{-}ivy}$≋$E_{53\text{-}chkcLys}$ salt bridge is less likely to be broken by the solvent than the $D_{88\text{-}ivy}$≋$R_{53\text{-}chkcLys}$ salt bridge. Interestingly, FIGS. 13A and 13B also show that the $H_{88\text{-}ivy}$≋$E_{53\text{-}chkcLys}$ salt bridge blocked the accessibility to the glutamic acid 53 ($E_{53}$) of chicken lysozyme. Glutamic Acid number 53 ($E_{53}$) and Aspartic acid 71($D_{71}$) in the full length lysozyme sequence correspond to residues $E_{35}$ and $D_{53}$ of the mature lysozyme peptide chain. As depicted in FIGS. 3A-1 to 3A-3 and 3B-1 to 3B-3, $E_{53}$ together with $D_{53}$ in mature chicken lysozyme (or in human lysozyme) are conserved across all known lysozyme sequences and are thought to be the two catalytic residues required for the hydrolysis of the peptidoglycan (Malcolm et al. (1989) Proc. Natl. Acad. Sci. USA 86:133-7).

Taken together, these data demonstrate that Ivy establishes two salt bridges with lysozyme: one essential for the specificity and the stability of the interaction ($H_{88\text{-}ivy}$≋$E_{53\text{-}chkcLys}$) as well as for the inhibition of lysozyme antibacterial activity by steric hindrance, and the other ($D_{89\text{-}ivy}$ ≈ $R_{132\text{-}chkcLys}$) involved to a lesser extent in stabilizing the lysozyme/inhibitor interaction. Due to the strict conservation of residues $E_{35}$ and $D_{53}/D_{52}$ $D_{52}$ (numbering refers to the mature lysozyme sequence) across species, these observations demonstrate that Tp17 inhibits a wide range, if not all, lysozymes.

Example 5

Identification Of A Consensus Peptide Sequence Shared By Protein Inhibitors Of Mammalian Lysozymes Example 4 demonstrated that the peptide II sequence $_{NH2}$-CKPHDCG-$_{COOH}$ (SEQ ID NO:38) is necessary for binding to and inhibiting the enzymatic activity of chicken lysozyme. A detailed examination of the Tp17 polypeptide sequence identified two candidate sequences possibly mediating binding and inhibition of both chicken and human lysozyme. Both sequences, referred to as Tp17pep1 and Tp17pep2, are listed below:

```
Tp17_pep1:
NH2-29CPHAGKAKAEKVEC42-COOH          (SEQ ID NO: 41)

Tp17_pep2:
NH2-114KAPHEKE120-COOH              (SEQ ID NO: 42)
```

Figure 14B:
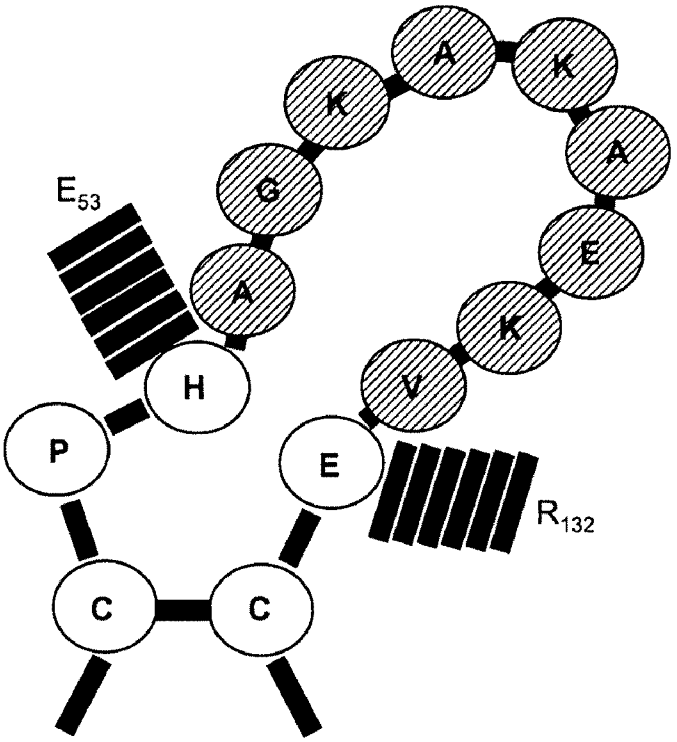
FIG. 14B illustrates the bridging of the two flanking cysteines of the *T. pallidum* Tp17-lysozyme binding site that likely brings the histidine and aspartic acid residues in close spatial proximity, possibly in a configuration able to make contact with residues $E_{53}$ and $R_{132}$ of lysozyme.

Tp17_pep1 is closely related to the $_{NH2\text{-}85}$CKPHDCG$_{91\text{-}COOH}$ motif (SEQ ID NO:38) of *E. coli* Ivy protein but differs by the presence of a nine amino acid stretch separating the histidine residue from the aspartic acid residue. As shown in FIG. 14B, and as found for the Ivy motif (FIG. 14A), bridging of the two flanking cysteines likely brings the critical histidine and aspartic acid residues in close spatial proximity, possibly in a configuration able to contact with residues $E_{53}$ and $R_{132}$ of lysozyme. Although the function of the possible 9 amino acid loop of Tp17 is presently unknown, its composition suggest that it is highly hydrophilic and probably immunogenic. Positively charged lysine residues contained in this 9 amino acid loop may contact directly with a negatively charged surface area of lysozyme, providing as well an additional anchorage point to strengthen the binding. By aligning the Tp17_pep1 peptide with the Ivy lysozyme binding motif, the consensus sequence $CX_1PHX_nX_2C$ (SEQ ID NO:43), wherein $X_1$ is at least one amino acid, is absent, or a peptide bond, $X_n$, is from zero to nine amino acids, or a peptide bond, and $X_2$ is glutamic acid or aspartic acid, was obtained.

Although lacking the two flanking cysteines, the Tp17_pep2 is also closely related to the $_{NH2}$-CKPHDCG-$_{COOH}$ motif SEQ ID NO:38 of the *E. coli* Ivy protein, since it shares the critical PH residues followed by an acid residue (D/E). Compiling structural data, bibliographic information and databases searches revealed a lysozyme binding consensus [CKVA][ACK]P H[AED][CGK](SEQ ID NO:3), written using the universal PROSITE peptide pattern syntax format.

Additional consensus sequences were determined and were written using the universal PROSITE peptide pattern syntax format, which is available through the Expert Protein Analysis System's SWISSProt database, as follows:

(a) $X_nPHX_n$ (SEQ ID NO:1), wherein $X_n$ is at least one amino acid.

(b) $CX_1X_2X_3PHX_4X_5X_6X_7X_8X_9X_{10}X_{11}X_{12}X_{13}C$ (SEQ ID NO:2), wherein $X_1$ to $X_{13}$ are any amino acid, no amino acid or a peptide bond.

(c) $X_1CPHAG$ (SEQ ID NO:25), wherein $X_1$ is C or V.

Preferred embodiments of Tp17-like polypeptides are illustrated in 1A-1 to 1A-3, 1B, and 2A-C.

Example 6

In Silico Identification Of Putative Lysozyme Binding Proteins & Inhibitors

Given the low overall peptide sequence conservation shared by *E. coli* Ivy and *T. pallidum* Tp17, previously undetected lysozyme binding motifs were likely present in the genome of other pathogenic organisms. To test this hypothesis, the consensus sequences defined in Example 5 were used to scan protein databases (Swiss-Prot, TrEMBL, TrEMBL-new and PDB) using the ScanProsite algorithm (http://us.expasy.orgtools/scanprosite/). FIGS. 1A-1 to 1A-3, 1B, and 2A-C illustrate that proteins containing a peptide stretch fitting within the consensus sequences were present in numerous human and animal pathogens.

Proteins from *T. denticola, B. thetaiotaomicron, C. burnetti, H. influenzae, N. meningitidis* serogroup A and serogroup B, *V cholerae, V. vulnificus, H. ducreyi, S. typhi, L. pneumophila, S. aureus, N. gonorrhoeae*, and *B. pertussis*, can be grouped into the following consensus sequence: CX(0,3)PHX(0,14), which corresponds to Cys $Xaa_1$ $Xaa_2$ $Xaa_3$ Pro His $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ NO:176), wherein Xaa is any amino acid or is absent.

Proteins (from *P. gingivalis* and *H. pylori*) are slightly atypical variants that could be grouped under the following consensus: CX(0,3)HX(0,10)C which corresponds to Cys $Xaa_1$ $Xaa_2$ $Xaa_3$ His $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$ Cys (SEQ ID NO: 175), wherein x is any amino acid or is absent.

Figure 15:
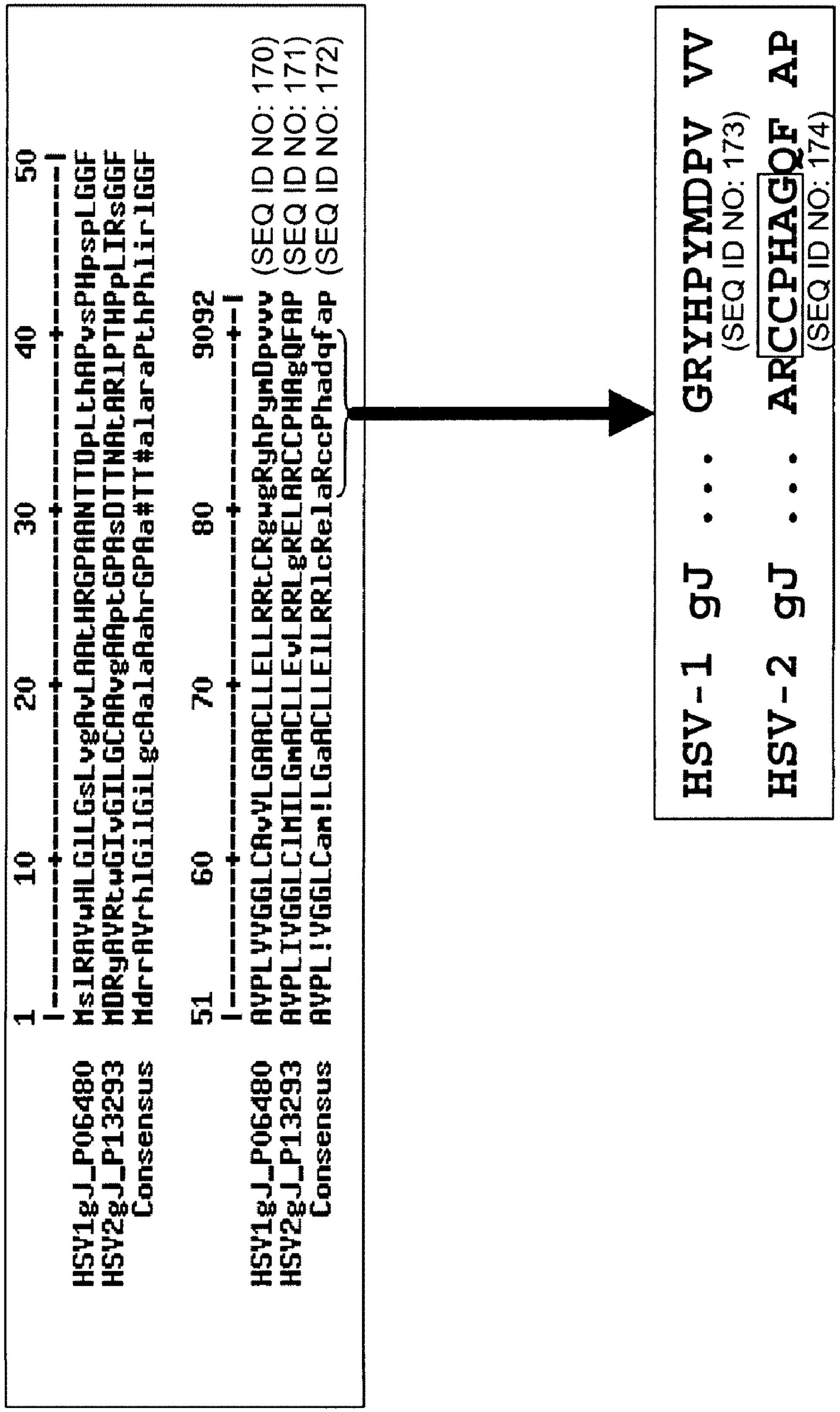
FIG. 15 illustrates an alignment of protein gJ from Herpes simplex virus type 1 (HSV1) and Herpes simplex virus type 2 (HSV2). A consensus sequence region is magnified under the alignment. The insert demonstrates that HSV1 gJ does not share the Tp17-like consensus sequence found in HSV2 gJ. "#" identifies semi-conservatives changes such as Asp/Asn.

This result is interesting since all of these organisms are mucosal pathogens during part or most of their infectious life cycle. Of particular interest was the presence of a consensus peptide motif in the carboxy terminus of the Herpes Simplex virus type 2 gJ glycoprotein. Although the function of this protein is presently unknown, it is encoded by the Us5 gene present in the unique short (Us) region of the virus. This region is known to contain most of the HSV proteins involved in virulence and mediating protein-protein interactions with human host proteins, supporting a role of gJ in the pathogenesis of HSV infection. Interestingly, several publications have documented that lysozyme has a strong inhibitory effect upon HSV2 infection and its clinical manifestations (Cisani et al. (1989) Microbios. 59:73-83; Oevermann et al. (2003) Antivir. Res. 59:23-33). The gJ protein from HSV-2 is also a lysozyme binding/inhibitor protein. Strikingly, the consensus lysozyme binding motif is absent from the closely related HSV-1 gJ protein (FIG. 15). This observation provides a possible explanation for clinical observations documenting a preferential but not exclusive tropism of HSV-1 for the orofacial region whereas HSV-2 is found most frequently in the lysozyme-rich, genital mucosa (Lowhagen et al. (2002) Acta Derm. Venereol. 82:118-21; Bruisten et al. (2003) Curr. Womens Health Report 3:288-98). In addition, it is intriguing to observe that two genital pathogens, one virus (HSV-2) and one bacteria (*T. pallidum*), share a common lysozyme inhibitory peptide sequence.

These observations demonstrate that gJ, alone or combined with human lysozyme, is useful for discriminating between HSV-1 and HSV-2 infections using differential serological or virological diagnostic assays. It also provides compositions and methods for treating Herpes simplex infections with lysozyme mutants that can escape inhibition by gJ and/or members of the Ivy and Tp17 families.

Example 7

Identification Of Point Mutations Destabilizing The Lysozyme/Inhibitor Protein-Protein Interaction It is widely recognized that protein-protein interactions depend upon structural and physicochemical complementarity. The irregularity and local heterogeneity of protein surfaces enables specific binding and association with ligands and provides a basis for the formation of quaternary structure. The fit between one protein surface and another depends upon more than their shape. It extends to the weak physicochemical bonds that hold complexes together: covalent bonding, hydrogen bonding, salt bridges, long range electrostatic interactions and Van der Waals interactions. This property of complementarity is universal, whether between a protein and a small molecule or between a protein and another kind of macromolecule (Petsko et al. (2003)).

Mutations localized in the lysozyme coding sequence, selected so that acetyl muramidase and antimicrobial activities are not affected, destabilize the lysozymes/inhibitor interaction and confer resistance to inhibition by pathogen proteins such as the *T. pallidum* Tp17 antigen or members of the Ivy family. In an embodiment, the mutant lysozyme substantially retains the desired anti-microbial activity (e.g., at least about 30%, 50%, or even 80%) of the corresponding wild-type lysozyme. Such mutant lysozymes represent novel and interesting tools for the treatment of infectious diseases. They are also substitutes for natural hen egg-derived chicken lysozyme used in commercially available medicinal preparations and have improved potency and spectrum of activity. A list of potential drugs likely to be improved by the use of such inhibition-resistant lysozyme mutants is given below:

| Marketed Drug | Pharmaceutical Company |
|---|---|
| LYSOPAINE ORL | Boehringer Ingelheim |
| LYSO-6 | UCB Health Care |
| GLOSSITHIASSE | Laboratoire Jolly-Jatel |
| CANTALENE | Laboratoire Cooper |
| HEXALYSE | Laboratoire Bouchara-Recordati |

Such lysozyme mutants are obtained using both targeted and random approaches.

Targeted Identification Of Inhibition-Resistant Lysozyme Mutants Deduced From Crystallographic Data Due to their elevated isoelectric point (pI), human lysozyme (theoritical pI=9.28) and chicken lysozyme (theoritical pI=9.32) exhibit a strong positive charge at physiological values of pH comprised between pH 3 and pH 7. All known lysozyme inhibitors have low pI values. For example, mature Ivy proteins (Monchois et al. (2001) J. Biol. Chem. 276:18437-18441) from *E. coli* (pI=5.51) and *P. aeruginosa* (pI=5.69), as well as the mature Sic protein protein (Fernie-King et al. (2002) Infect. Immun. 70:4908-4916) from *S. pneumoniae* (pI=4.39) are negatively charged at physiological pH. It was hypothesized that positively charged lysozyme residues that are present in the lysozyme/inhibitor contact area are attractive targets for mutagenesis. Producing a lysozyme mutant having a negatively charged contact area might produce an electrostratic repulsion preventing binding of the inhibitor. Since these mutations do not affect lysozyme catalytic residues, they are likely to produce active lysozyme mutants, uninhibited by pathogens.

The *E. coli* Ivy/chicken lysozyme crystal structure deposited under the PDB accession number 1GPQ, as well as the *P. aeruginosa* Ivy crystal structure deposited under the PDB accession number 1HKE, were inspected with a VNTI 3D molecular viewer. Critical residues were identified on each lysozyme and the following point mutations altering the binding of the inhibitor were made:

| Position in Human Lysozyme (NP_000230) | Position in Chicken Lysozyme (P00698) | Mutated to: |
|---|---|---|
| Mutation affecting lysozyme surface charge | | |
| $Lys_{19}$ | $Lys_{19}$ | Asp, Glu, or Gly |
| $Arg_{23}$ | $Arg_{23}$ | Asp, Glu, or Gly |
| $Lys_{51}$ | $Lys_{51}$ | Asp, Glu, or Gly |
| $Arg_{131}$ | $Arg_{130}$ | Asp, Glu, or Gly |
| $Arg_{133}$ | $Arg_{132}$ | Asp, Glu, or Gly |
| Mutation sterically hindering binding of the inhibitor | | |
| $Gly_{55}$ | $Asn_{55}$ | Phe, Trp or Tyr |
| $Asn_{57}$ | $Asn_{57}$ | Phe, Trp or Tyr |
| $Asn_{132}$ | $Asn_{131}$ | Phe, Trp or Tyr |

Introduction of Point Mutations By Site-Directed Mutagenesis:

Mutations are introduced using the QuikChange® Site-Directed Mutagenesis Kit, following the guidelines recommended by the supplier (Stratagene, La Jolla, Calif.). Briefly, the QuikChange® Site-Directed Mutagenesis Kit is used to make point mutations, switch amino acids, and delete or insert single or multiple amino acids. The QuikChange® site-directed mutagenesis method is performed using PfuTurbo® DNA polymerase and a temperature cycler. PfuTurbo® DNA polymerase replicates both plasmid strands with high fidelity and without displacing the mutant oligonucleotide primers. The basic procedure utilizes a supercoiled double-stranded DNA (dsDNA) vector with an insert of interest and two synthetic oligonucleotide primers containing the desired mutation. The oligonucleotide primers, each complementary to opposite strands of the vector, are extended during temperature cycling by PfuTurbo DNA polymerase. Incorporation of the oligonucleotide primers generates a mutated plasmid containing staggered nicks. Following temperature cycling, the product is treated with Dpn I. The Dpn I endonuclease (target sequence: 5'-Gm 6 ATC-3') is specific for methylated and hemimethylated DNA and is used to digest the parental DNA template and to select for mutation-containing synthesized DNA. DNA isolated from almost all *E. coli* strains is dam methylated and therefore susceptible to Dpn I digestion. The nicked vector DNA containing the desired mutations is then transformed into XLI-Blue supercompetent cells. The small amount of starting DNA template required to perform this method, the high fidelity of the PfuTurbo DNA polymerase, and the low number of thermal cycles all contribute to the high mutation efficiency and decreased potential for generating random mutations during the reaction.

Random Isolation Of Inhibition-Resistant Lysozyme Mutants Using PCR-Mediated Random Mutagenesis Followed By A Microbial Two-Hybrid Screening The two-hybrid system is based on the observation that many eukaryotic transcriptional activators consists of two physically discrete modular domains: the DNA-binding domain (DNA-BD) and the activation domain (AD). The DNA-BD binds to a specific promoter sequence and the AD directs the RNA polymerase II complex to transcribe the downstream gene conferring a selectable/screenable phenotype. The domains act as independent modules: neither alone can activate transcription, but each domain continues to function when fused to other proteins. Suitable commercial systems include the ready-to-use BacterioMatch® II Two-Hybrid System (Stratagene, La Jolla, Calif.) or the BD Matchmaker™ system (BD Biosciences Clontech, Palo Alto, Calif.

Lysozyme and Tp17, one fused to the AD and the other fused to DNA-BD, are expressed. If the two proteins interact, the DNA-BD and the AD domains are brought into close proximity and activate transcription of a reporter gene. Depending upon the host system used (e.g., bacterial, yeast or mammalian), interaction is detected by screening for observable physiological or structural change (e.g., color of the colony, emission of fluorescence, enzymatic activity, etc.). For example, AD and DNA-BD domains are fused with lysozyme and Tp17 respectively, transformed into an appropriate microbial host (e.g., bacteria or yeast), and the resulting transformants are screened for the appearance of blue colonies indicative of the activation of the reporter gene (e.g., beta-galactosidase). Once clones are obtained, plasmid DNA sequence bearing the human lysozyme open reading frame is subjected to extensive PCR-mediated random mutagenesis. The resulting transformants are visually screened for mutants that have lost the blue color and are likely to bear one or more mutations that impair the lysozyme/Tp17-like polypeptide interaction. Plasmid DNA from the corresponding clones is then extracted and sequenced.

Example 8

Human But Not Chicken Lysozyme Improves The Sensitivity Of Hemagglutination Kits Used For Syphilis Diagnostics Example 3 demonstrates that, in vitro, the *T. pallidum* 17 kDa protein Tp17 strongly binds to chicken and human lysozyme, and strongly inhibits the antibacterial activity of both lysozymes. The following experiment demonstrates that these binding and inhibition interactions also occur in vivo during the infection of human mucosal surfaces by *T. pallidum*. As a consequence of Tp17 binding to lysozyme, new epitopes are likely formed and exposed to the immune system. Syphilitic patients may raise an immune response against Tp17 epitopes as well as against epitopes shared by the Tp17-lysozyme complex or even lysozyme alone, as shown in FIG. 4. To test this, human or chicken lysozyme was added to the hemagglutination reagents used for a syphilis diagnostic assay in order to detect those antibodies generated against the complex, thereby improving the sensitivity of the assay. An increase in sensitivity of the syphilis assay was observed that was specific for human lysozyme.

Purified chicken egg white lysozyme (L-6876) and human breast milk lysozyme (L-6394) were obtained from Sigma-Aldrich (Madrid, Spain). An amount of chicken or human lysozyme sufficient to maintain the proportion: 3 μg lysozyme/1 μg Tp17 was added to a hemagglutination reagent (Biokit SA, Lliça d'Amunt, Spain) prepared as follows. Chicken red cells were tanned, fixed, and coated with GST-Tp17 (40 μg/ml) as previously described (Herbert et al. (1979) Passive Haemagglutination With Special Reference to the Tanned Cell Technique. Handbook of Experimental Immunology (vol. 1), pgs 20.1-22.20 (DMWeir (Ed.) Blackwell Scientific Publications (Oxford)); Stefen et al. (1951) J. Exp. Med. 93:107-120; Hirata (1968) J. Immunol. 100:641-46). One batch of GST-Tp17 coated, fixed chicken red cells (5 ml), was supplemented with 6 μl of purified chicken egg white lysozyme (100 μg/μl). Another batch of GST-Tp17 coated, fixed chicken red cells (1 ml), was supplemented with 120 μl of human breast milk lysozyme (1 μg/μl). Both lots of sensitized red cells were homogenized by magnetic stirring, for 30 minutes at room temperature. The sensitivity of each lot was then evaluated by performing a hemagglutination reaction using a set of human syphilis sera, characterized to give a borderline response with other commercial hemagglutination reagents.

The hemagglutination reaction was performed as follows. In a round-bottom microtiter plate (U-shaped), 25 μl of diluent (Syphagen TPHA, Biokit SA, Barcelona, Spain) was added to well 1, 100 μl to well 2 and 25 μl to each of wells 3 to 8. 25 μl of sample was added to well 1. The content of well 1 was mixed and 25 μl was transferred to well 2 and mixed. 25 μl from well 2 to well 3. Serial two-fold dilutions were then made through well 8. 25 μl from well 8 was discarded. 75 μl of hemagglutination reagent was added to wells 3-8 (the final sample dilutions were 1/80 to 1/2560). The contents of the wells were mixed using a shaker for at least 30 seconds. The plate was covered and incubated for 1 hour at room temperature. The results of the assay were read applying the following criteria. A result was scored positive either when a smooth mat of cells covering the entire bottom of the well or when a smooth mat of cells partially covering the bottom of the well and surrounded by a heavy ring of cells was observed. A result was scored negative either when a button of cells with a small central opening or when a button of cells with or without a very small hole in the center was observed. The titer of a sample corresponded to the highest dilution giving a positive reaction. The cut-off of this technique was 1/80.

Figures 16A, 16B:
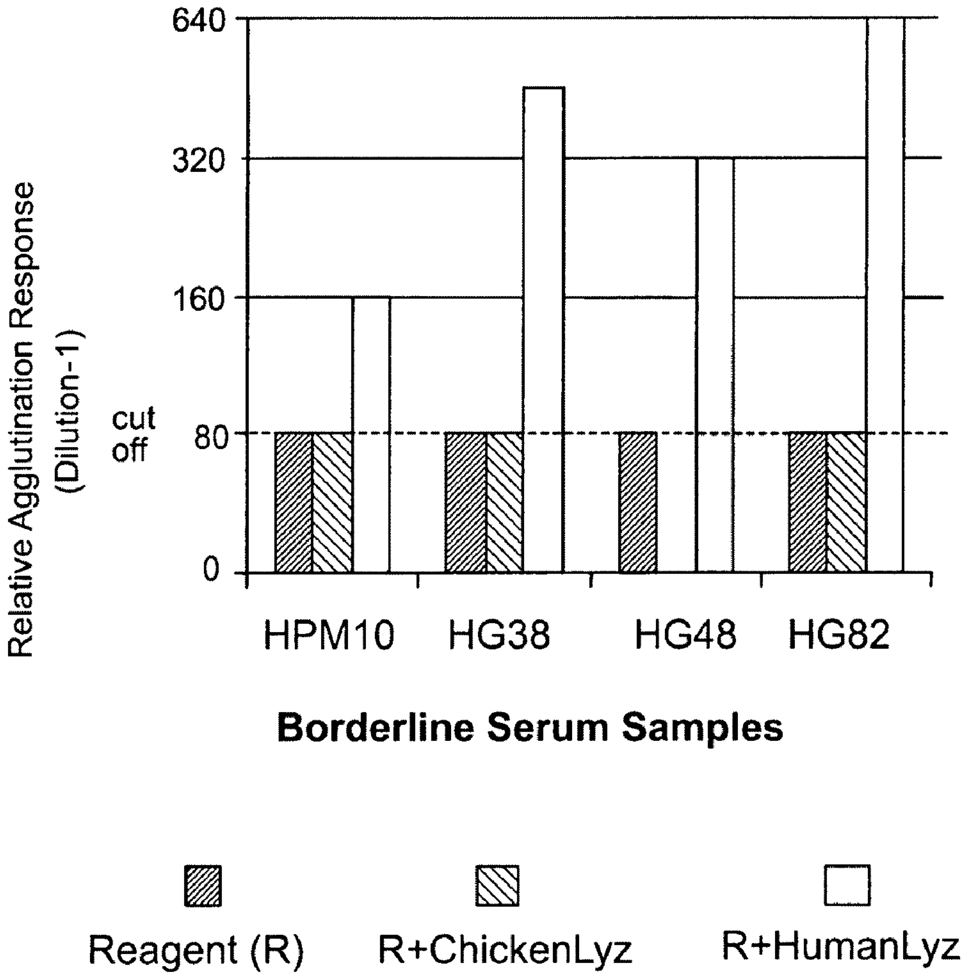
FIG. 16A is a table illustrating the relative hemagglutination intensity corresponding to 4 borderline human syphilitic sera (HPM10, HG38, HG48, and HG82). Serum samples were combined with Tp17 (R) in the presence or absence of chicken lysozyme (ChickenLyz) or human lysozyme (HumanLyz). Results are expressed as reciprocal dilution titers (e.g., 80 means positive at dilution 1/80).
FIG. 16B is a graphical representation of the hemagglutination results of FIG. 16A. Tp17 reagent without lysozyme (black bars); Tp17 reagent supplemented with chicken lysozyme (hatched bars); Tp17 reagent supplemented with human lysozyme (empty bars). Results are expressed as reciprocal dilution titers (e.g., 80 means positive at dilution 1/80).

As shown in FIGS. 16A and 16B, the addition of human lysozyme to the assay improves the intensity of hemagglutination (i.e., hemagglutination occurred at higher dilutions in the presence of human lysozyme compared to the absence of lysozyme) in a concentration dependent manner. This improvement appeared to be specific for human lysozyme because the addition of chicken lysozyme did not enhance the response. The addition of human lysozyme drastically improved the sensitivity of the syphilis hemagglutination reagent and allowed for the detection of antibodies that are not detected in kits presently in the market.

Example 9

Both Natural And Recombinant Human Lysozyme Improve The Sensitivity Of Hemagglutination Test Used For Syphilis Diagnostics Human breast milk is a natural source of human lysozyme. However, purifying lysozyme from this body fluid is tedious due to: (i) its low abundance, (ii) the difficulty in ensuring a regular and reproducible supply, (iii) the possible contamination with undetected pathogen, as well as (iv) social and ethical concerns. A recombinant source of human lysozyme is therefore preferred for use on an industrial scale. The potency of both natural human breast milk-derived lysozyme and recombinant human lysozyme derived from transgenic rice was compared.

Purified natural human breast milk lysozyme (L-6394; Sigma-Aldrich, Madrid, Spain) had 101,000 units/mg protein and a 10% lysozyme content. Purified recombinant human transgenic rice lysozyme (159-53LZ-90P; Ventria Bioscience, Sacramento, Calif.) had 187,000 units/mg protein and a 90% lysozyme content. The unit definition for both lysozymes is as follows. One unit produces an increment of the absorbance at 450 nm of 0.001 per minute at pH 6.24 at 25° C., using a suspension of *Micrococcus lysodeikticus* as substrate, in a 2.6 ml reaction mixture (1 cm light path) (Shugar et al. (1952) Biochem. Biophys. 8:302-309). In order for the results of the experiment to be comparable, the proportion 594 units of human lysozyme/μg GST-Tp17 of each was used. A hemoaggulutination reaction, as detailed in Example 8, was performed, adding an equivalent amount of either the natural or recombinant lysozyme to the hemagglutination syphilis reagent. The potency of both lysozymes was tested against positive and negative syphilis samples.

Figure 17B:
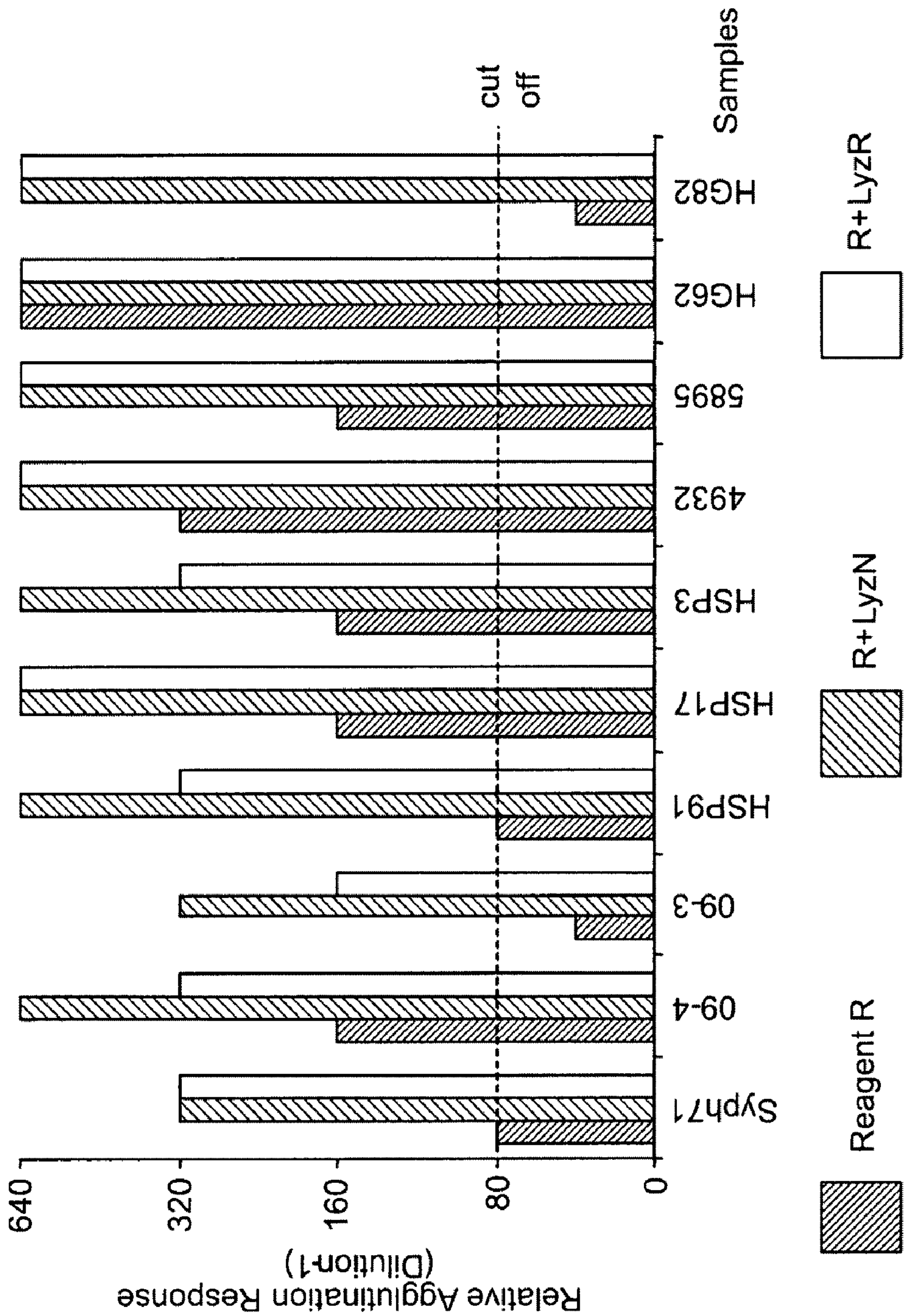
FIG. 17B is a graphical representation of the hemagglutination results of FIG. 17A. Tp17 reagent without lysozyme (black bars); Tp17 reagent supplemented with natural human lysozyme (checked bars); Tp17 reagent supplemented with recombinant human lysozyme (empty bars). Results are expressed as reciprocal dilution titers (e.g., 80 means positive at dilution 1/80).

As illustrated in FIGS. 17A and 17B, 6 out of the 10 samples tested showed an improvement in sensitivity of the assay with the addition of either natural (LysN) or recombinant (LysR) human lysozyme.

Figure 18A:
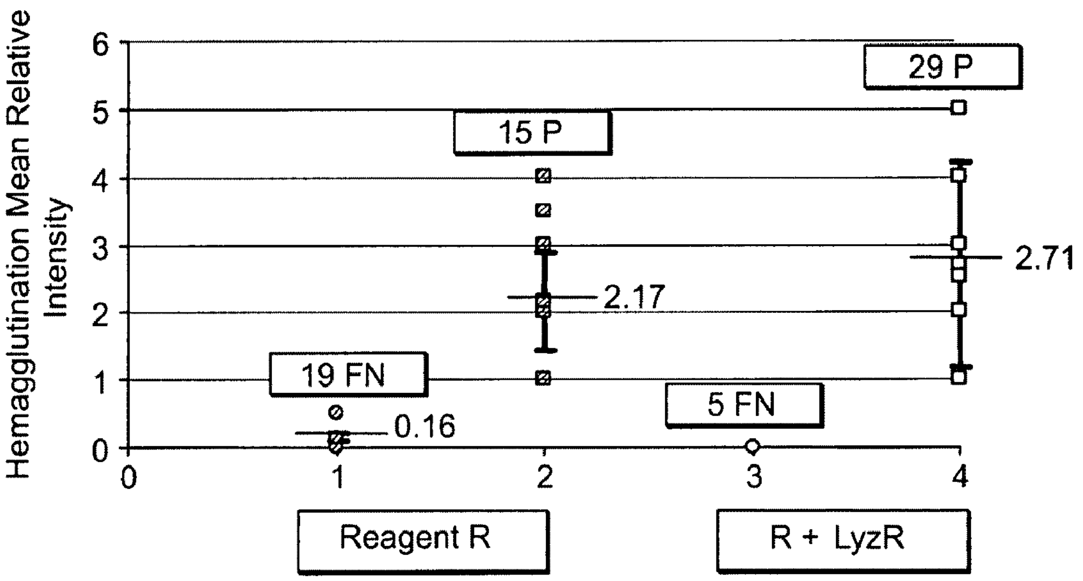
FIG. 18A illustrates the improvement of the relative intensity of hemagglutination with the addition of recombinant human lysozyme. A total of 34 sera were tested using either a Tp17 reagent (R) or Tp17 reagent supplemented with recombinant human lysozyme (R+LyzR). The results of the technique are given as the inverse of the last dilution that gave a positive agglutination. Each result was converted into a number (1/80 dilution is 1, 1/160 dilution is 2, etc.). The cut-off is at dilution 1/80 and a value lower than 1 is considered a negative result. FN and P respectively stand for False-negative and positive results, respectively.
Figure 18B:
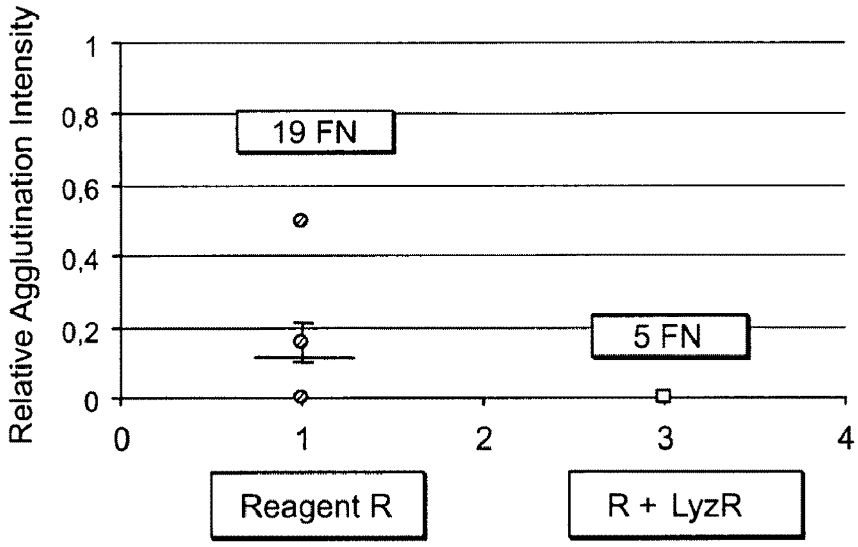
FIG. 18B illustrates the relative intensity of hemagglutination with the addition of recombinant human lysozyme on false negative serum samples using either Tp17 reagent (R) or Tp17 reagent supplemented with recombinant human lysozyme (R+LyzR). The intensity of the agglutination in the false negative samples is represented by a number between 0 and 1 (1 represents the cut-off of the hemagglutination technique).

FIG. 18A illustrates that the addition of recombinant human lysozyme to a hemagglutination syphilis reagent substantially improved the assay sensitivity. In an evaluation of 34 real positive samples, 14 of the 19 samples that tested negative using the reagent that did not contain lysozyme, were in fact positive when lysozyme was added to the reaction. As illustrated in FIG. 18B, the visual discrimination between a positive and negative reaction is simplified when recombinant human lysozyme is added to the reagent.

Figure 19:
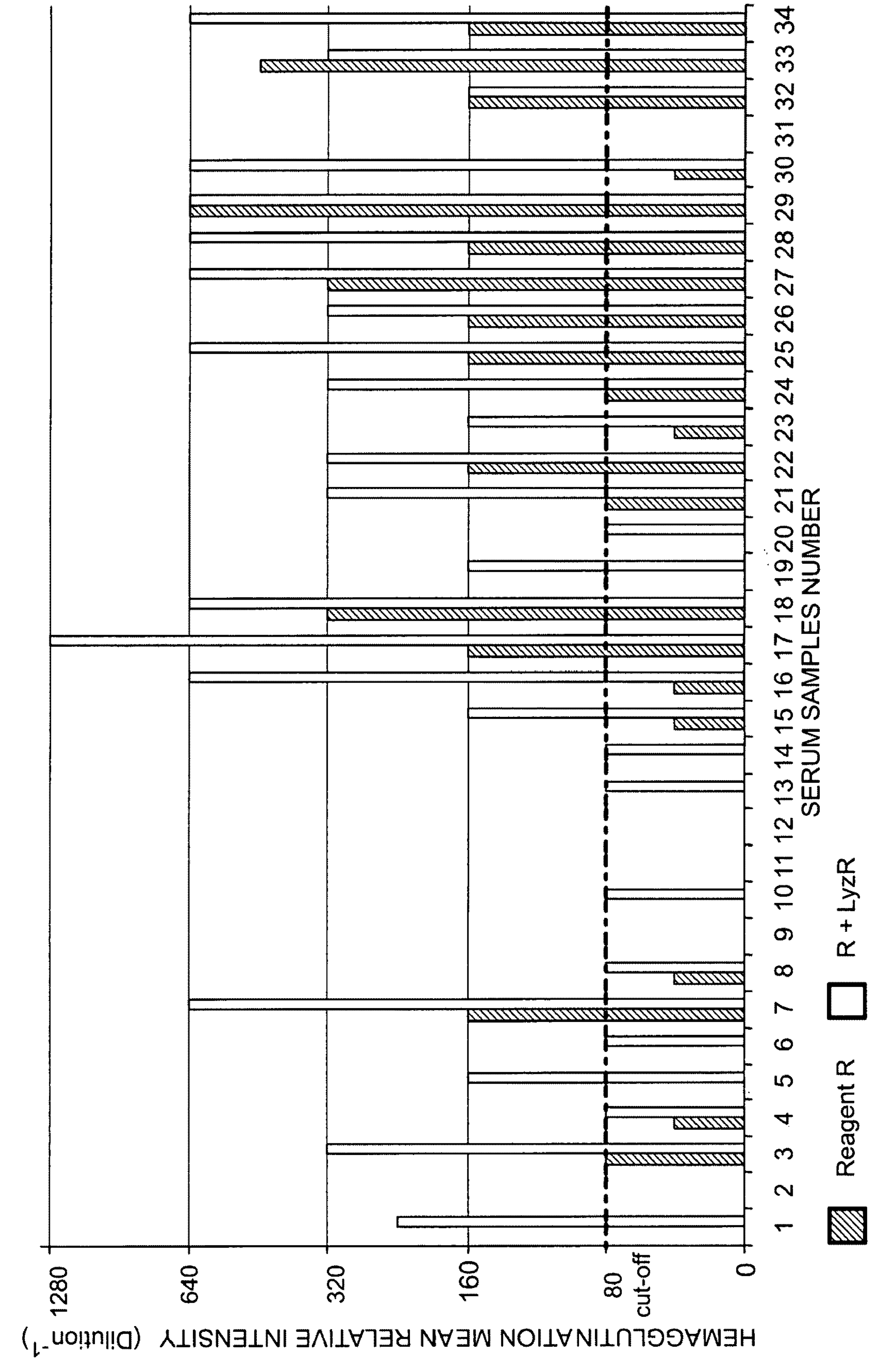
FIG. 19 illustrates an hemagglutination assay performed with 34 human sera. The assay was performed using a Tp17 reagent (black bars) or a Tp17 reagent supplemented with recombinant human lysozyme (empty bars). The result of the technique is given by the inverse of the last dilution that gave a positive agglutination. The cut-off is at dilution 1/80. Results are expressed as reciprocal dilution titers (e.g., 80 means positive at dilution 1/80).

FIG. 19 illustrates the performance (relative hemoaglutination intensity) of two hemagglutinantion reagents, with (reagent LysR) or without (reagent R) recombinant human lysozyme (LysR). In that experiment the LysR hemagglutination reagent out-performed the reagent R, displaying for all the sera tested (μ=34) a relative agglutination titer of between about 1- and about 2-fold higher.

Figure 20:
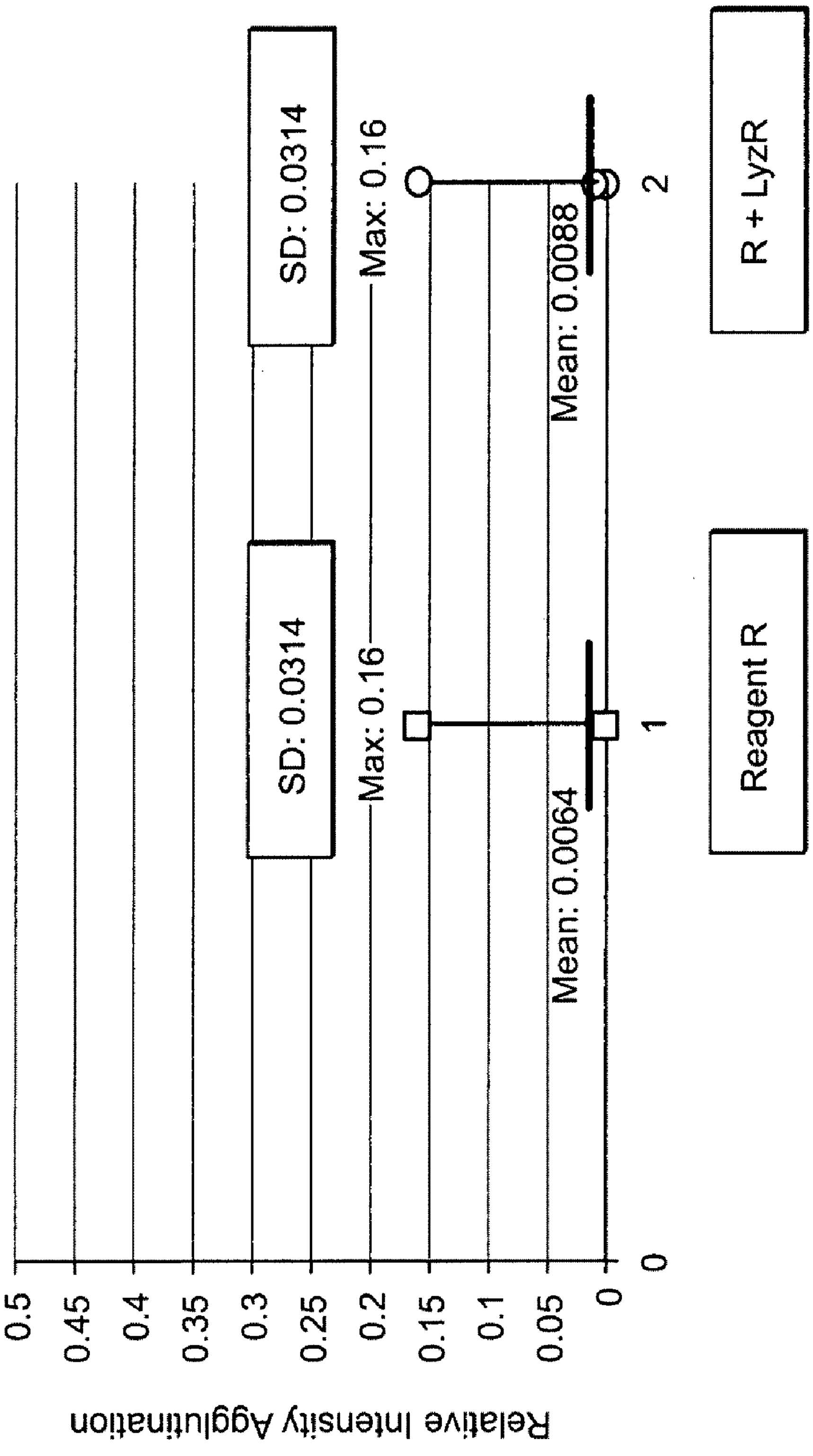
FIG. 20 illustrates the effect of lysozyme on the specificity of the hemagglutination assay on 200 Syphilis-negative blood bank serum samples using Tp17 reagent (R) or Tp17 reagent supplemented with recombinant human lysozyme (R+LyzR). The intensity of the agglutination in the negative samples is represented by a number between 0 and 0.5. SD, standard deviation.

FIG. 20 illustrates that the addition of recombinant human lysozyme (LysR) to a hemagglutination syphilis reagent does not give false positives results. In an evaluation of 200 blood bank samples the mean result and standard deviation between both reagents was very close. The potency of recombinant human lysozyme is thus equivalent to that of natural breast milk lysozyme. Recombinant lysozyme can therefore substitute for natural lysozyme for diagnostic applications.

Example 10

Human Lysozyme Improves the Sensitivity Of Enzyme-Linked Immunosorbent Assay (ELISA) Kits Used For Syphilis Diagnostics Syphilis screening is routinely performed using enzyme-linked immunosorbent assays (ELISA) kits. These kits detect the binding of anti-syphilis antibodies to *T. pallidum* antigens immobilized in the wells of a microtiter plate. Detection of the binding of anti-syphilis antibodies to the plate is normally carried out by means of either an enzyme-labeled antiserum directed against human Fc antibody chains (second generation kit) or an enzyme-labeled *T. pallidum* antigen (third generation kit).

Examples of such commercially available diagnostic reagents are listed below:

| Product name | Manufacturer | Kit Format |
|---|---|---|
| Bioelisa Syphilis | Biokit S. A. (Lliça d'Amunt, Spain) | 2nd generation |
| Bioelisa Syphilis 3.0 | Biokit S. A. (Lliça d'Amunt, Spain) | 3rd generation |
| ICE* Syphilis | Abbot Murex (Dartford, UK) | 3rd generation |
| Syphilis EIA480 | New Market Laboratories (Kentford, UK) | 3rd generation |
| Enzywell | Diesse (Siena, Italy) | 3rd generation |

Detection of Syphilis Antibodies Using A Second Generation Kit Format

All the reagents used in this study are provided by the commercial Bioelisa Syphilis 3.0 detection kit (Biokit S.A., Lliça d'Amunt, Spain). The protocol used is that recommended in the package insert of the kit. Briefly, serum or plasma samples are added to the wells of a microtiter plate. If antibodies specific for *T. pallidum* are present in the sample, they form stable complexes with the antigens on the well. After washing to remove the unbound material, a rabbit conjugate anti-human IgG and anti-human IgM labelled with horseradish peroxidase is added and, if the antigen/antibody complex is present, the conjugate binds to the complex. After a second wash, an enzyme substrate solution containing a chromogen is added. This solution develops a blue color if the sample is positive. The blue color changes to yellow after blocking the reaction with sulphuric acid. The intensity of color is proportional to the anti-*T. pallidum* antibody concentration in the sample. Wells containing negative samples remain colorless.

Detection Of Syphilis Antibodies Using A Third Generation Kit Format

All the reagents used in this study are provided by the commercial Bioelisa Syphilis 3.0 detection kit (Biokit S.A., Lliça d'Amunt, Spain). The protocol used is that recommended in the package insert of the kit. Briefly, the test is performed by incubating test specimens in the wells of a microtiter plate coated with *T. pallidum* proteins (e.g., recombinant Tp15, Tp17 or Tp47 antigens). The specific IgG and IgM antibodies present in the sample bind to the solid-phase antigens. Subsequently, the wells are washed to remove residual test sample and *T. pallidum* antigens conjugated with the enzyme peroxidase are added. The conjugate binds to the captured specific antibodies. After another washing to eliminate unbound material, a solution of enzyme substrate and chromogen is added. This solution develops a blue color if the sample contains anti-*T. pallidum* antibodies. The blue color changes to yellow after blocking the reaction with sulphuric acid. The intensity of color is proportional to the anti-*T. pallidum* antibody concentration in the sample.

Addition of Recombinant Human Lysozyme

For the second generation ELISA format, recombinant human lysozyme (Ventria Bioscience, Ventura, Calif.) was added at 2.86 μg/ml to the Bioelisa Syphilis 3.0 ELISA plates. For the third generation kit, recombinant human lysozyme was added either in the sample dilution buffer at a concentration of 10.8 μg/ml, or in the conjugate dilution buffer at a concentration of 1.08 μg/ml.

As represented in FIGS. 21A and 21B, when syphilis-positive human sera were tested with the Bioelisa Syphilis (second generation) and Bioelisa Syphilis 3.0 (third generation) ELISA reagents, a significant gain in signal intensity was detected in the presence of human lysozyme. The increase in signal intensity was in the range of about 20% when lysozyme was added to the plate and sera tested in the second generation format, and in the range of about 200% (for 3 out of 4 sera) when lysozyme was added both in the sample dilution buffer and in the conjugate dilution buffer and processed according to the third generation format. Interestingly, the addition of lysozyme does not modify the response of syphilis-negative human sera. These data demonstrate that human lysozyme increases the sensitivity of ELISA-based syphilis detection and screening.

Example 11

Purification of the Human Lysozyme/Tp17 Complex

The Human Lysozyme/Tp17 protein complex is highly antigenic, and, as described above, it is useful in diagnostic assay. Isolation of purified Human Lysozyme/Tp17 complex facilitates the performance of structural studies, such as protein crystallization and determination of the atomic structure via X-ray diffraction. Using the experimental procedures described below, mg quantities of purified Human Lysozyme/Tp17-HIS complex were obtained.

Isolation of Tp17-HIS Monomer and Tp17-HIS Dimers

Figure 22:
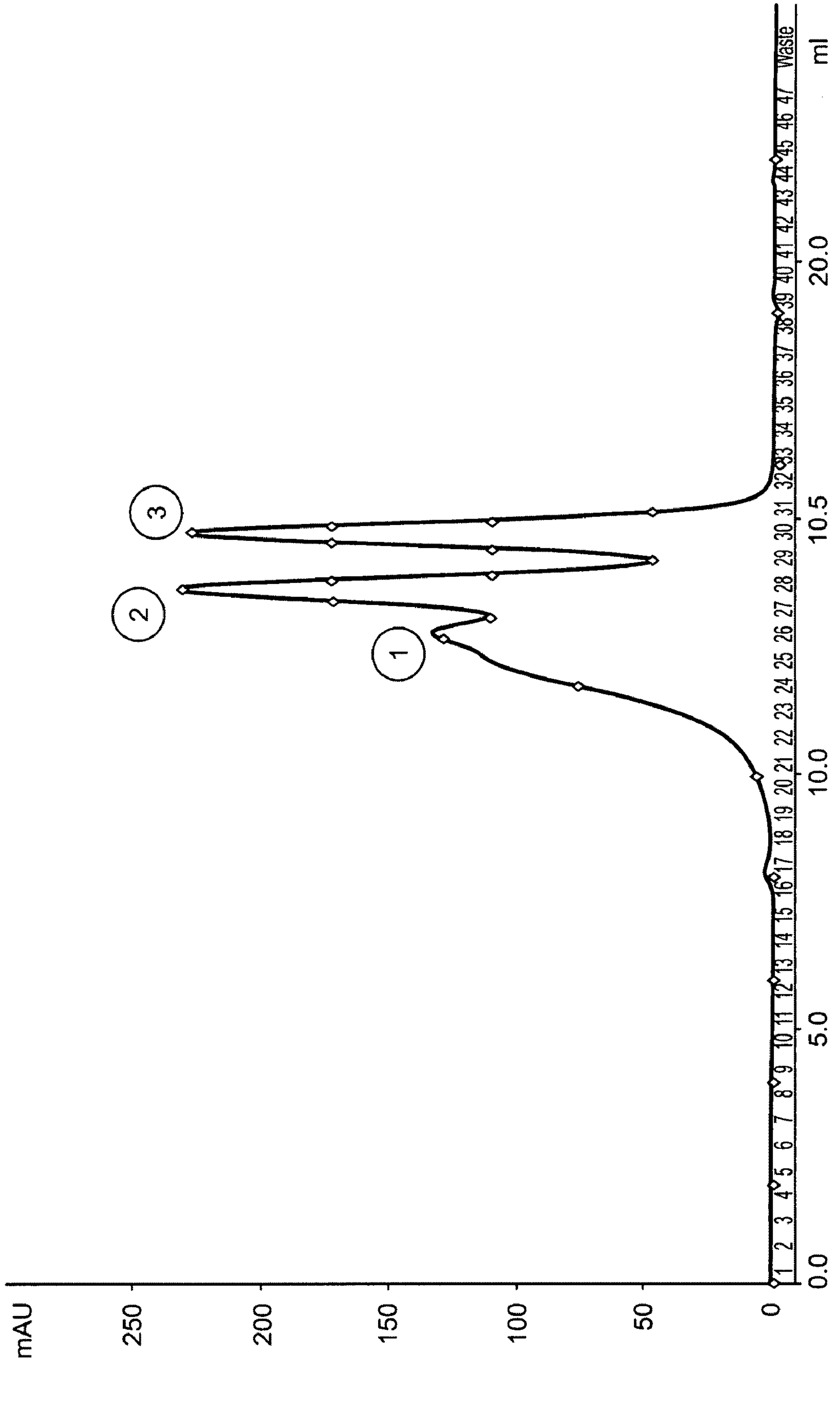
FIG. 22 shows a size-exclusion chromatographic separation of Tp17-His isoforms. Affinity purified Tp17-HIS is composed of three populations of molecules: monomeric Tp17-His (peak 3), dimeric Tp17-His (peak 2) and multimeric Tp17-His (peak 1).

Purified Tp17-His protein, obtained as described in example 1, was further purified via gel filtration chromatography in order to separate monomers and dimers from other aggregated forms (FIG. 22). An HR 16/50 column (1.6 cm diameter×60 cm height; Amersham Biosciences, Cerdanyola, Spain) filled with 100 ml of Superose 12 HR was equilibrated with two column volume of gel filtration buffer (Tris 20 mM NaCl 300 mM, pH8.0). A 2 ml sample containing 8 mg of Tp17-HIS fusion protein was then injected and chromatography was performed at a flow rate of 1-1.25 ml/min under a constant pressure of pressure 0.70 MPa. Fractions (1.5 ml) corresponding to Tp17-HIS monomers and Tp17-HIS dimers were collected from three consecutive chromatographic runs, and then were pooled into an 8 ml Tp17-HIS monomeric fraction and a 6 ml Tp17-HIS dimeric fraction.

Formation of the Tp17-HIS/Human Lysozyme Complex In Vitro

Figure 23:
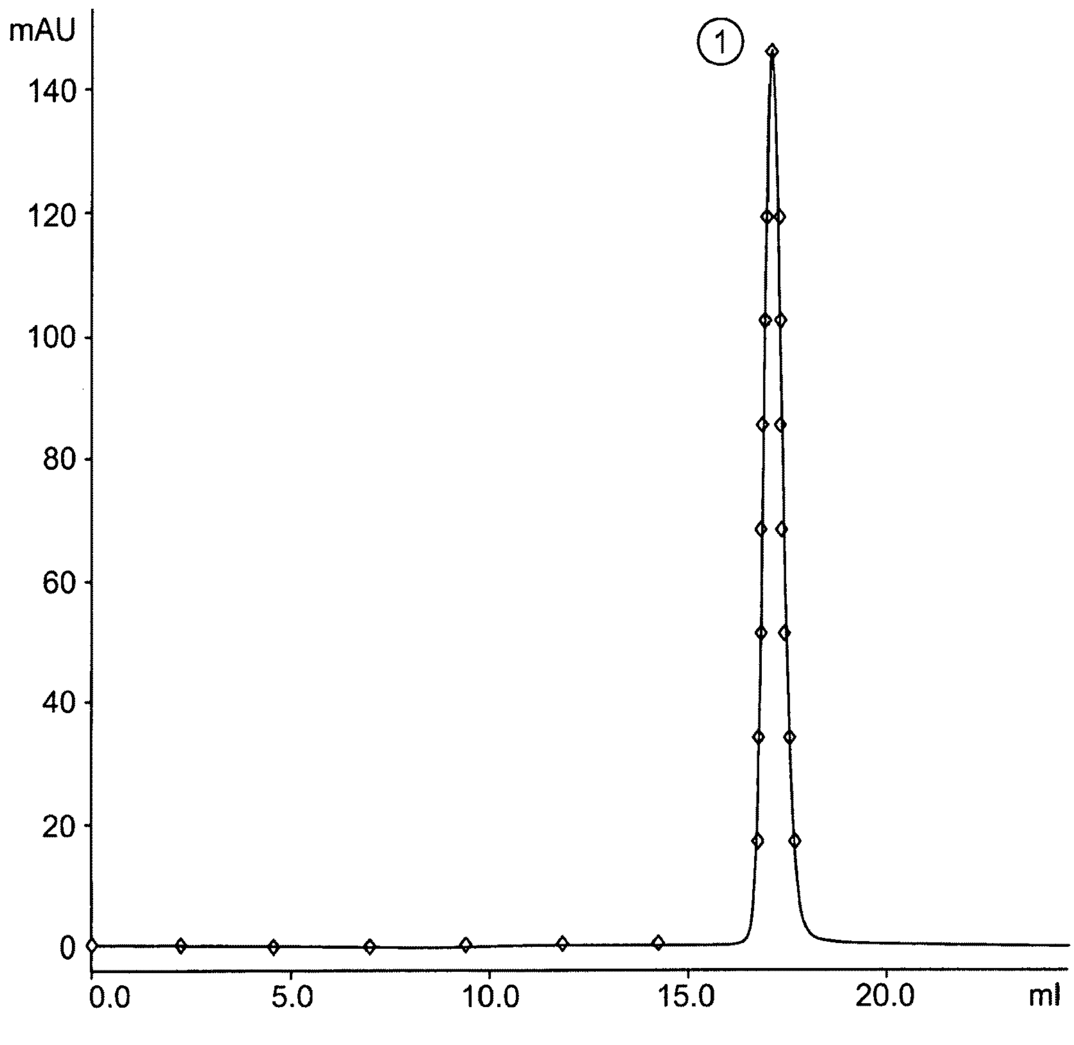
FIG. 23 shows a size-exclusion chromatographic separation of purified, recombinant human lysozyme (Ventria Biosciences, Sacramento, Calif., USA). Recombinant human Lysozyme is composed of a single, highly homogenous population of molecules (peak 1).

Recombinant human lysozyme (commercially obtained from Ventria Bioscience, Sacramento, Calif., USA) consisted of highly homogenous monomeric proteins as shown in by assay result depicted FIG. 23.

To form a complex in vitro, 3.8 mg of purified Tp17-HIS monomers and Tp17-HIS dimers were incubated separately for 30 minutes at 22° C. without agitation in the presence of a 2-fold molar excess of purified recombinant human lysozyme (Ventria Bioscience, Sacramento, Calif., USA).

Purification of the Tp17-HIS/Human Lysozyme Complex by Gel Filtration

Figure 24:
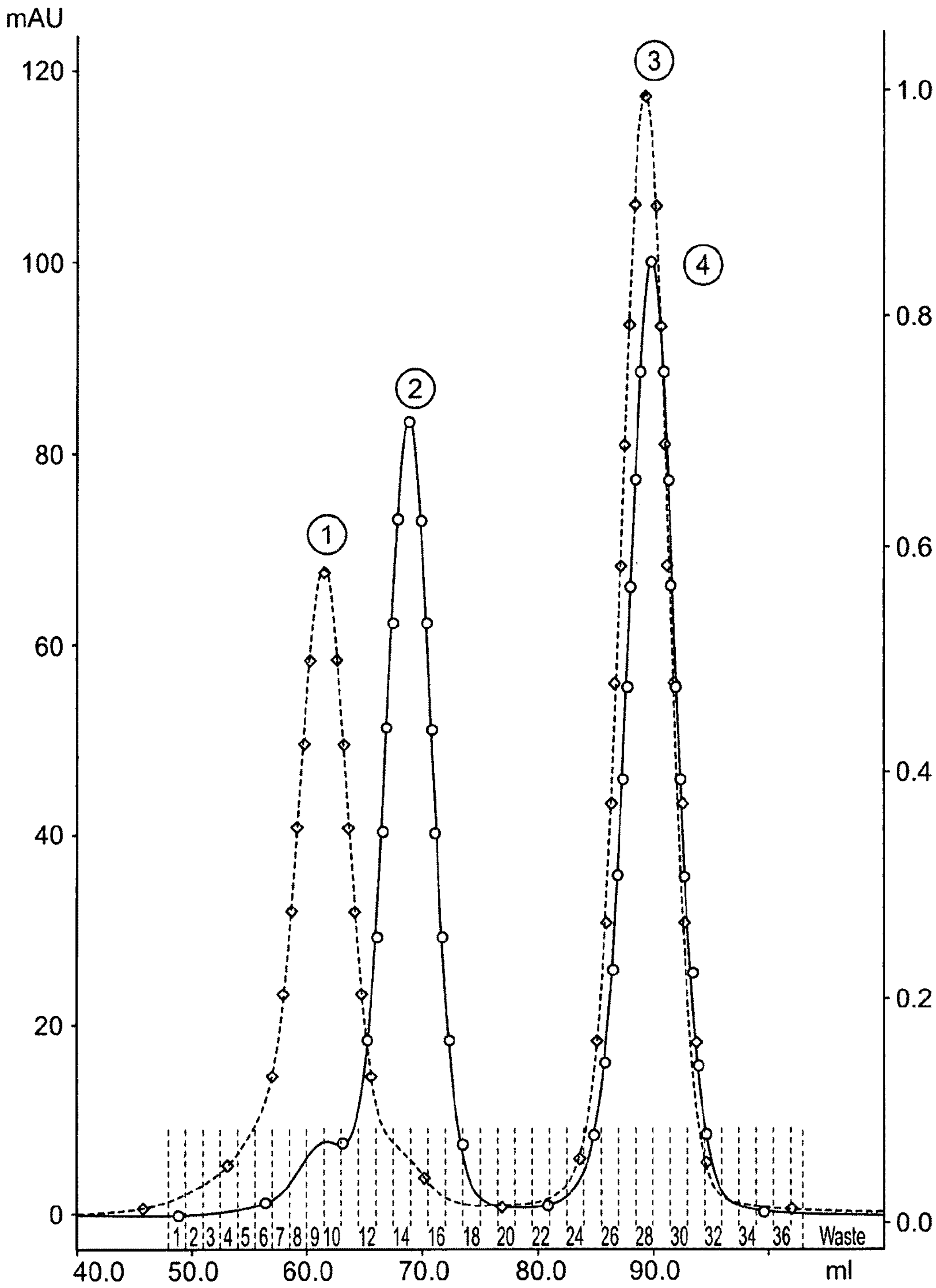
FIG. 24 shows a size-exclusion chromatographic separation of Tp17-His/huLYS complexes. The chromatographic profiles corresponding to huLYS complex with either monomeric Tp17-His (circles) or dimeric Tp17-His (diamonds) are represented. Peaks correspond to Tp17/huLYS protein complexes (peaks 1 & 2) or monomer (huLys & Tp17) excesses (peaks 3 & 4).

As shown in FIG. 24, the human lysozyme/Tp17 complexes were separated from non-assembled monomers by gel filtration through Superose 12 HR 16/50 gel as described above. The fractions corresponding to the Tp17-HIS/Human lysozyme peak were collected and concentrated using Centricon Plus 20 (UFC2LGC08, The Millipore Corporation, Bedford, Mass., USA) devices with a 10 kDa cut-off. Buffer was exchanged during centrifugal filtration by washing with three column volumes (10 ml) of Tris-HCl 10 mM, NaCl 50 mM, pH 8.0. Final samples of Tp17-$His_{monomers}$/human lysozyme and Tp17-$His_{dimers}$/human lysozyme were recovered at 1.62 mg/ml and 1.57 mg/ml, respectively. Final protein recovery yield was 60% for Tp17-$His_{monomers}$/human lysozyme complexes and 44% for Tp17-$His_{dimers}$/human lysozyme complexes.

Example 12

Method for Discovering Novel Tp17-Like Proteins

Tp17 and Tp17-like proteins share the capacity to bind human lysozyme. Based upon this observation, generic method were devised that provide for the detection of Tp17-like proteins in total protein extracts from pathogenic organisms. In one embodiment, human lysozyme conjugated with a detectable marker is hybridized to a protein sample. Binding of the lysozyme identifies a Tp17-like polypeptide in the sample.

Preparation of a Human Lysozyme-Horseraddish Peroxidase (HuLYS-POD) Conjugate

Human Lysozyme-Horseraddish Peroxidase conjugates were produced by mixing 9.72 mg of recombinant human lysozyme (159-53LZ-90P; Ventria Bioscience, Sacramento, Calif., USA) and 13.6 mg of activated peroxidase (POD) (1.428.861; Roche, Mannheim, Germany) in a total volume of 3.5 ml carbonate buffer (Sodium carbonate/-hydrogenocarbonate 50 mM, pH 9.55). The conjugation reaction was carried out for 2 hours at 25° C. in a water bath with manual agitation every 30 minutes. The reaction was terminated by the successive addition of 364 μl of Triethanolamine 2M (108379; Merck, Darmstadt, Germany), and 455 μl of Sodium borohydride (45,288-2; Sigma Aldrich Chemie, Steinheim, Germany) at a concentration of 4 mg/ml in deionized water. The resulting solution was agitated manually for 15 seconds and then incubated for 30 minutes at 2-8° C. Then, 227 μl of Triethanolamine 2M was added and the mixture was incubated for 2 hours at 2-8° C. Next, 91 μl of Glycine 1M (104201; Merck, Darmstadt, Germany) was added and the solution was dialysed for 15 hours against TSG buffer (Tris-HCl 20 mM, NaCl 150 mM, Glycine 10 mM, pH 7.5). The solution was then clarified by centrifugation for 30 minutes at 15.000 g. 4.5 ml of supernatant was recovered. 500 μl of BSA (Pentex Miles Inc., Kankakee, Ill., USA; 10% weight/volume in TSG buffer (Tris-HCl) and 25 μl of merthiolate-gentamycine sulfate were added to the conjugate. Merthiolate-gentamycine sulfate was prepared by dissolving 25 mg of Gentamycine sulfate (22191 E1; Jescuder, Terrassa, Spain) and 400 mg of Thimerosal (T-5125 Sigma, Saint Louis, Mo., USA) in 8.0 ml of fetal calf serum. The pH was then adjusted to pH 8.0 with sodium hydroxide (5M). The conjugate was then sterile filtered through Millex GV a 0.22 μm filter (SLGV R04 NL; The Millipore Corporation, Bedford, Mass., USA) and was stored protected from light at 2-8° C. until use.

Processing of the Protein Sample from the Pathogen

A 15 μl sample containing 2 to 20 μg of pathogen derived protein is mixed with 5 μl of NuPAGE® LDS loading buffer (4×) (Invitrogen, Carlsbad, Calif., USA) and immediately separated on a 4-12% NuPAGE® Novex Bis-Tris polyacrylamide gel (NPO323BOX; Invitrogen, Carlsbad, Calif., USA) using NuPAGE® MES SDS running buffer (1×) (NP0002; Invitrogen, Carlsbad, Calif., USA). The applied voltage is 165 Volts constant for 35 minutes. After allowing the proteins to migrate, the gel is recovered and incubated for 15 minutes in electrotransfer buffer (ET buffer: 25 mM Tris, 192 mM Glycine, 10% Methanol, no pH adjustment). The separated proteins on the gel are then electrophoretically transferred to an IMMOBILON® P membrane (IPVH00010; The Millipore Corporation, Bedford, Mass., USA). The membrane was prepared by rinsing once with methanol and twice with deionized water. For performing electrophoretic transfer, the applied voltage was held constant at 65 volts for one hour.

HuLYS-POD Protein Overlay Assay

After electrotransfer, the membrane is incubated 1 hour at 22° C. in TBST (Tris-HCl 10 mM pH8.0, NaCl 150 mM, Tween 20) supplemented by 5% (weight/volume) of SVELTESSE® skimmed milk (Nestlé España, Barcelona, Spain). The membrane is next rinsed with TBST and then incubated for 1 hour at 22° C. in TBST-milk containing the HuLYS-HRP conjugate, which is diluted 1/5000. After incubation the membrane is washed three times in TBST. Immunostaining is then achieved by immersing the membrane in 10 ml of 3,3',5,5'-Tetramethylbenzidine (TMB) (T0565; SIGMA-ALDRICH Inc., Saint-louis, Mo., USA) to visualize the proteins. As a positive control, a single band migrating at 17 kDa and corresponding to Ivy is detected in an *Escherichia coli* BL21 (DE3)cell extract.

Example 13

Gram-Positive Bacterial Pathogens Secretes Human Lysozyme Inhibitors

Gram positive bacteria lack an outer membrane and display to the culture medium a thick peptidoglycan layer. As a consequence, these bacteria are likely to be more sensitive to lysozyme killing than Gram negative bacteria. Thus, we hypothesized that Gram positive bacteria that are human pathogens possess lysozyme inhibitors. Due to the absence of an outer-membrane, these inhibitors may be present in the bacterial culture medium. As described below, we assayed for the presence of lysozyme inhibitors in the culture medium from eight clinically relevant Gram-positive bacterial species (*Enterococcus faecalis strain* CECT184, *Enterococcus faecium* strain ATCC10541, *Staphylococcus aureus* strain ATCC11632, *Staphylococcus epidermidis* strain ATCC 12228, *Streptococcus pneumoniae* strain ATCC49619, *Streptococcus pyogenes* strain CECT598, *Streptococcus agalactiae* strain CIP105451, and *Propionibacterium acnes* strain NMR-GF).

These strains were grown for 48 hours at 37° C. in cation-adjusted Mueller-Hinton broth (CAMHB). The bacterial cells were pelleted by centrifugation (20 minutes, 14.000 g, 4° C.) and 1 ml of supernatant was concentrated to a final volume of ≅200 μl using Microcon® YM-10 centrifugal filter devices (The Millipore Corporation, Bedford, Mass., USA). Fifteen μl of each supernatant concentrate was analyzed by SDS-PAGE electrophoresis using a NuPAGE® 4-12% gradient gel and then silver-stained (SilverXpress® kit) to visualize proteins according to the manufacturer's instructions (The Invitrogen company, Prat de Llobregat, Barcelona, Spain).

Figure 25:
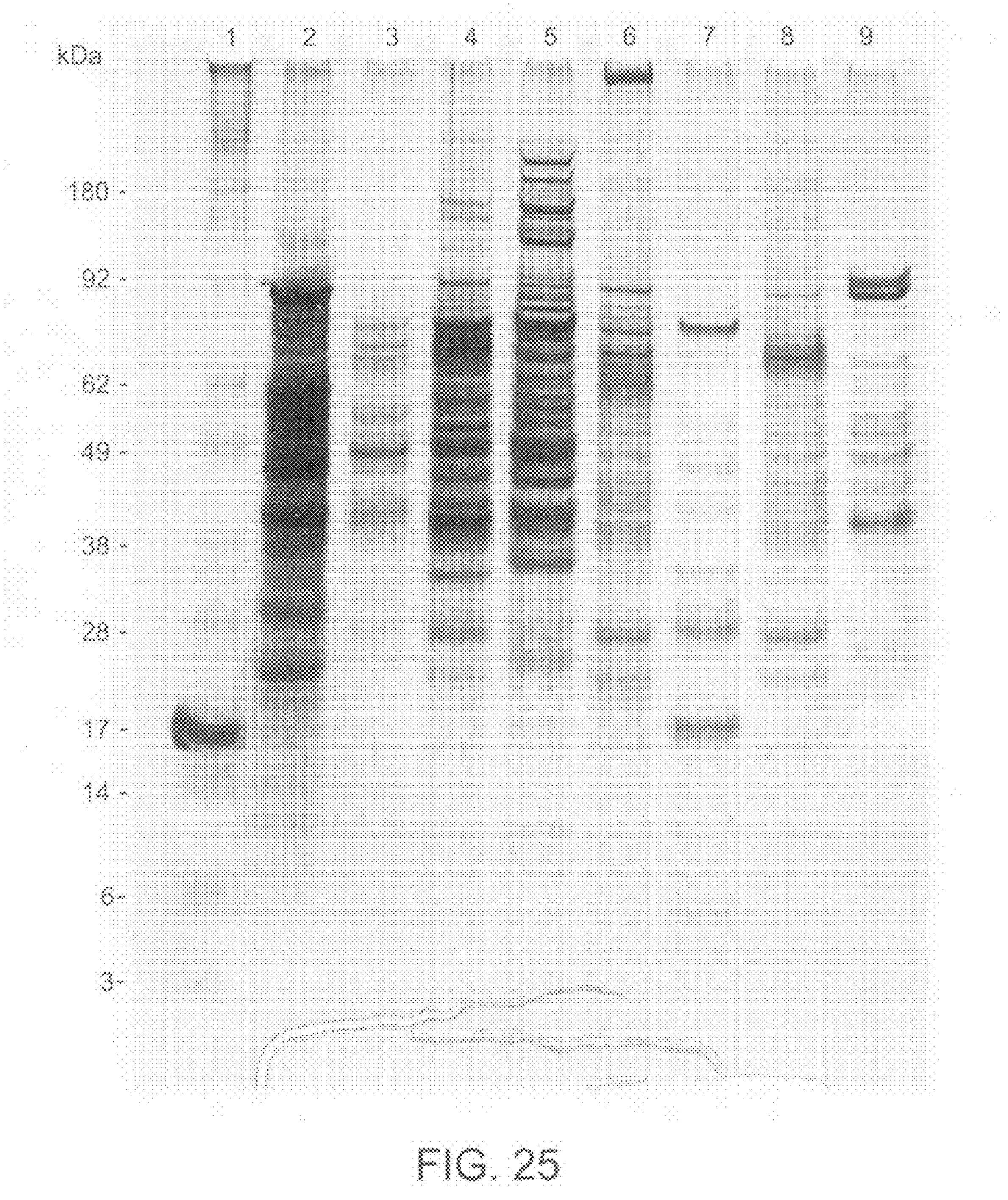
FIG. 25 shows an SDS-PAGE electrophoretic separation of concentrated (5×) bacterial culture supernatant and the detection of secreted bacterial proteins by silver staining. The following pathogens were analyzed: *Enterococcus faecalis* (lane 2), *Enterococcus faecium* (lane 3), *Staphylococcus aureus* (lane 4), *Streptococcus pneumoniae* (lane 5), *Streptococcus pyogenes* (lane 6), *Propionibacterium acnes* (lane 7), *Staphylococcus epidermidis* (lane 8), *Streptococcus agalactiae* (lane 9).
Figure 26:
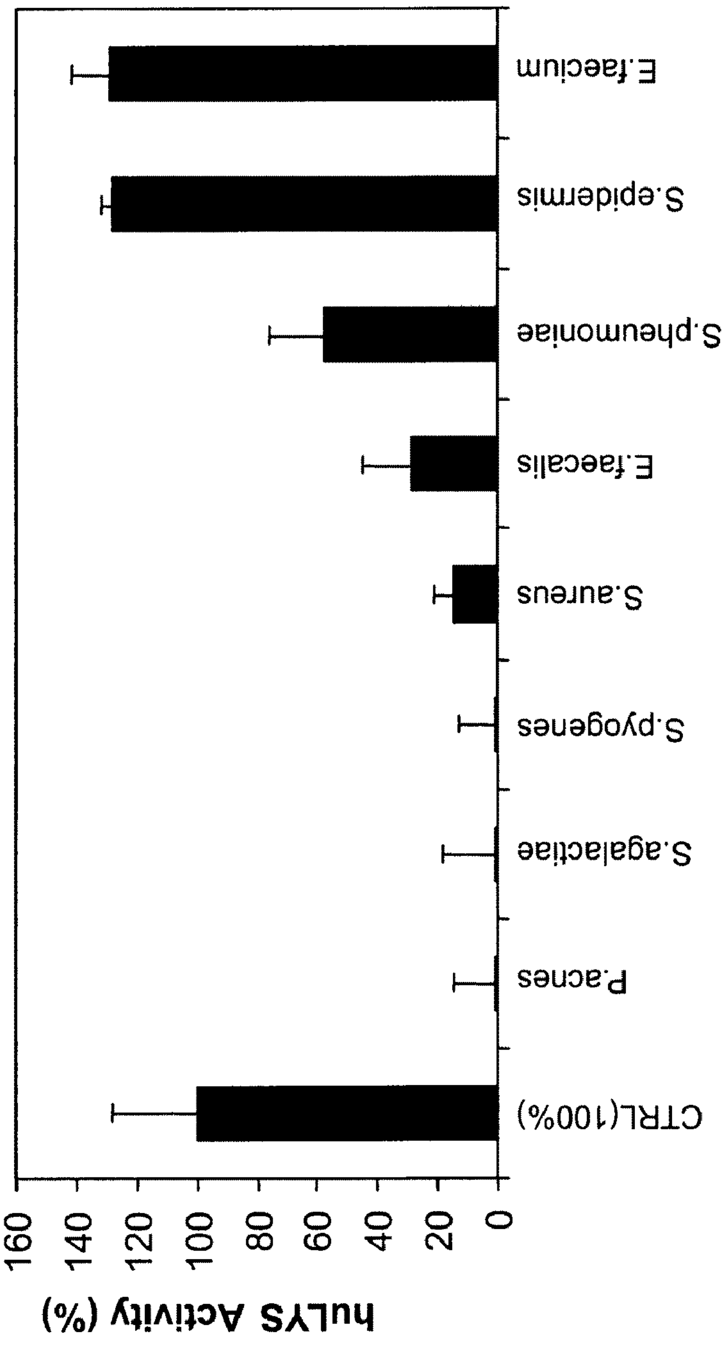
FIG. 26 is a bar graph showing human lysozyme enzymatic activity measured in the absence, or in presence of (5×) concentrated bacteria culture supernatant collected from the following eight bacterial species: *Propionibacterium acnes, Streptococcus agalactiae, Streptococcus pyogenes, Staphylococcus aureus, Enterococcus faecalis, Streptococcus pneumoniae, Staphylococcus epidermidis* and *Enterococcus faecium*. The height of each bar indicates the detected enzymatic activity. A lysozyme control is on the far left side of the figure.

As shown by the assay result depicted in FIG. 25, distinct protein patterns were detected for each of the eight bacterial species tested. The bacteriolytic activity of human lysozyme (1 unit) was determined in the absence, or in the presence of 10 μl of the concentrated supernatant corresponding to each of the eight bacterial species. The assay was carried out as previously described, using the EnzCheck® Lysozyme according to the manufacturer's instructions (Molecular Probes, Eugene, Oreg., USA). As shown in FIG. 26, complete inhibition of lysozyme enzymatic activity was observed in the presence of *Propionibacterium acnes, Streptococcus agalactiae*, and *Streptococcus pyogenes* concentrated supernatants. Partial inhibition was observed in the presence of *Staphylococcus aureus, Enterococcus faecalis*, and *Streptococcus pneumoniae* concentrated supernatents. No inhibition was detected in *Enterococcus faecium* and *Staphylococcus* epidermidis concentrated supernatants under these assay conditions.

These data demonstrate that uncharacterized inhibitors of human lysozyme are present in clinically-relevant Gram positive bacteria, which can be a potential source for discovering such inhibitors. These inhibitors represent novel and attractive targets for drugs and vaccines, as well as for novel diagnosis assay. These experiments also indicate that Gram positive bacteria can be used to screen for wild-type or mutant bacterially expressed lysozyme polypeptides that are resistant to Tp17-like polypeptide inhibition.

Example 14

Figure 27:
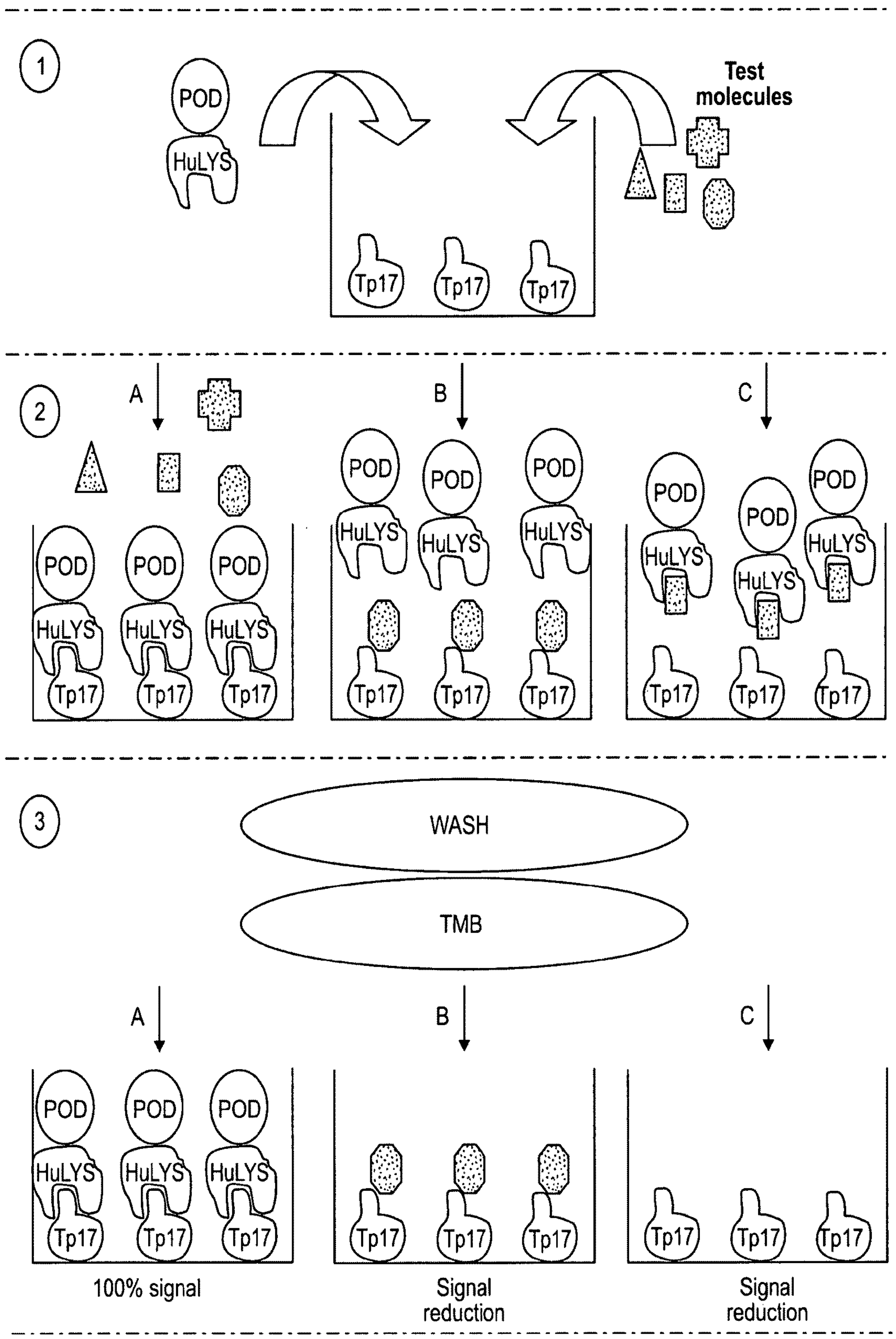
FIG. 27 is a schematic diagram showing the principle and design of a high throughput screening assay for the identification of candidate compounds capable of interfering with the formation of Tp17-like complexes with lysozyme. Step 1: Contacting a test sample with horseradish peroxidase (POD)-labeled huLYS and a Tp17-like polypeptide. Step 2: incubation of the test sample at 37° C. Step 3: Extensive washing, addition of POD substrate and signal detection.

Methods of Identifying Candidate Compounds that Inhibit Tp17/Lysozyme Complex Formation or Stability Tp17 and Tp17-like proteins are expressed by numerous human and animal pathogens (e.g., virus, bacteria, fungi, and protozoa). Drugs that interfere with the formation of and/or the stability of HuLYS/Tp17-like protein complexes are promising antimicrobial candidate compounds that can be used to prevent or treat a pathogen infection in a subject. In order to isolate such anti-microbial molecules, an in vitro screening test was devised as described below. It will be apparent to one skilled in the art that this test is useful for high throughput screening of biological extracts and chemical libraries. As shown in FIG. 27, an exemplary method involves the following steps:

Preparation of Reagents

PBS 10× was prepared by dissolving 29 g of $Na_2HPO_4$/12 $H_2O$, 2 g of $KH_2PO_4$ a 80 g of NaCl in 1 liter of distilled, apyrogenic water and adjusting the pH to pH 6.8 with sodium hydroxide (10M). BSA-Glycine solution was prepared by dissolving 10 g of BSA (81-003; Pentex Miles Inc., Kankakee, USA), 7.5 g of Glycine (500190; Merck, Darmstadt, Germany) and 1 g of sodium azide (6688; Merck, Darmstadt, Germany) in 1 liter of distilled water (MilliQ grade, The Millipore Corporation, Bedford, Mass., USA). The pH of the resulting solution was to pH 7.4 with NaOH (10M). ELISA wash buffer 10×, TMB chromogenic substrate and TMB dilution buffer are commercially available (BioELISA ANTI-HBS 96 wells kit, 3000-1101; biokit SA, Lliça d'Amunt, Spain). ELISA sample dilution buffer was obtained from BioELISA Syphilis 3.0 (3000-1148; biokit SA, Lliça d'Amunt, Spain).

Immobilization of Tp17 and/or Tp17-Like Protein on a Solid Substrate

Purified GST-Tp17 protein, produced as described in example 1, was resuspended in PBS 1× at a concentration of 0.4 μg/ml and 150 ill of that solution was dispensed in 96 wells microtiter plates (MaxiSorp™ Lockwell™; NUNC, Roskilde, Denmark) and incubated during 16 hours at room temperature (22° C.). Next, 100 μl of BSA-Glycine solution was added and incubated for 1 hour at 22° C. The wells were then emptied by aspiration and filled immediately with 200 μl of BSA-sucrose. Incubation was performed for 1 hour 30 minutes at 22° C. The liquid contents of each well was carefully aspired and the plates were then air-dried for 3 hours in a dry room (15% relative humidity) before being packaged in air-tight plastic bags.

Contacting Tp17 and/or Tp17-like with chemical(s) and HuLYS-POD

100 μl of candidate compound (dissolved at a concentration ranging from 10 ng/ml to 10 mg/ml in ELISA sample dilution buffer) is added to a microwell and incubated 15 minutes at 37° C. 50 μl of HuLYS-POD diluted 1/20.000 in ELISA sample dilution buffer is added to the well and incubated for an additional period of 15 minutes. The wells are then washed four times with wash buffer.

Color Development and Scoring of Candidate Compounds

100 μl of Horseradish peroxidase (POD) chromogenic substrate diluted in substrate dilution buffer is then added to each well and color development is stopped after 30 minutes after addition of 100 μl of $H_2SO_4$ 2M. In this experiment the average absorbance of three wells incubated without candidate compound is normalized to 100% value. Molecules or biological extracts able to reduce the binding of HuLYS-POD below at least 40%, 50%, 60%, 75%, 85%, 95%, or more are considered as "Hit" candidates as evidenced by respective reductions in the signal channel compared to the normalized value. Preferably binding is reduced below 85% relative to control wells not contacted with a candidate compound.

Example 15

Tp17 Inhibits Commercially Available Therapeutic Preparations of Lysozyme

Chicken Lysozyme is a potent antimicrobial enzyme active against both bacteria and viruses. Commercial preparations that contain Lysozyme as an active agent include, but are not limited to, LIZIPAINA® (Boehringer Ingleheim, San Cugat del Vallés, Spain) and LISOZIMA CHIESI (CHIESI ESPAÑA SA, Barcelona, Spain). Since the Tp17 protein was shown to inhibit the enzymatic antibacterial activity of purified chicken lysozyme in vitro, we postulated that Tp17 may also inhibit the antibacterial activity of LIZIPAINA® and LISOZIMA CHIESI. To test this hypothesis, one tablet of each drug, LIZIPAINA® (containing 5 mg chicken lysozyme per tablet) and LISOZIMA CHIESI (containing 250 mg chicken lysozyme per tablet), was resuspended in deionized water (The Millipore Corporation, Bedford, Mass., USA) to adjust the Lysozyme concentration to 4 μg/ml. These samples were then incubated in absence or in presence of increasing amount of either GST-Tp17 or Tp17-HIS. In this experiment the molar ratio between chicken lysozyme and its cognate inhibitor was varied from 1:5 to 1:50 for GST-Tp17 and from 1:16 to 1:160 for Tp17-HIS. After an incubation period of 5 minutes at 20° C. the samples were assayed for lysozyme enzymatic activity using the EnzCheck® Lysozyme assay kit (E-22013; Molecular Probes Inc., Eugene, Oreg., USA) as recommended by the supplier guidelines.

Figure 28A:
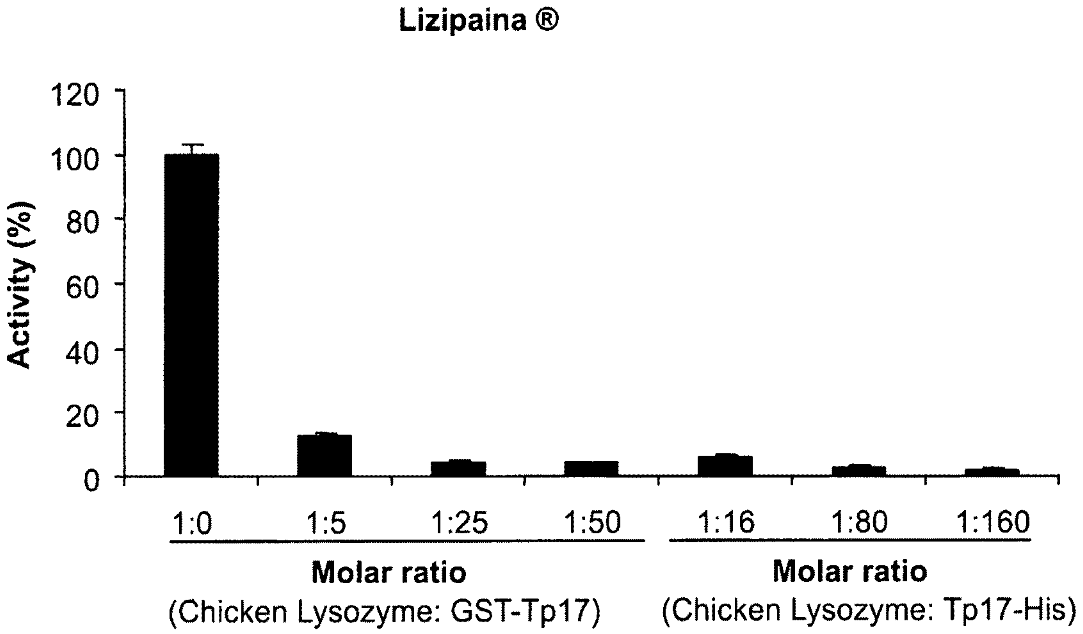
FIGS. 28A and 28B are bar graphs showing the inhibition of commercially available, therapeutic preparations of chicken lysozyme by Tp17.
Figure 28B:
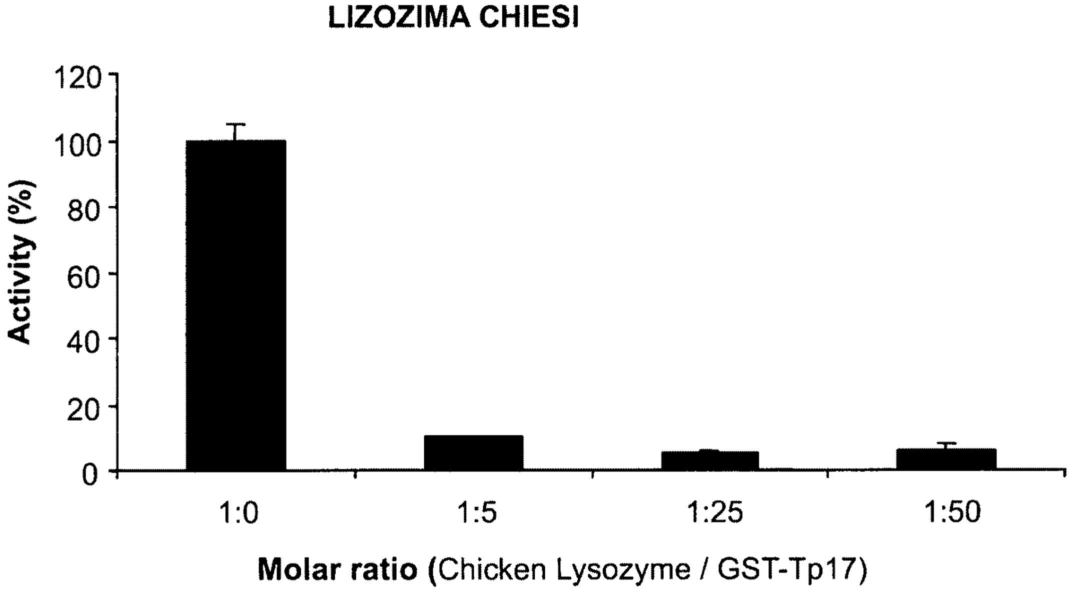

As reported in FIGS. 28A and 28B, both GST-Tp17 and Tp17-HIS strongly inhibited the enzymatic antibacterial activity of LIZIPAINA® and LISOZIMA CHIESI respectively. Thus, Tp17 and Tp17-like proteins are capable of inhibiting the enzymatic antibacterial activity of two commercially available antimicrobial drugs. It is likely that some of the therapeutic efficacy provided by LIZIPAINA®, LISOZIMA CHIESI, and related drugs is lost in vivo due to Tp17 and Tp17-like protein inhibition. As discussed above, Tp17 and Tp17-like proteins are widely expressed by bacterial, viral, fungal and parasite human pathogens. Consequently, lysozyme variants that are not subject to enzymatic inhibition by Tp17 and Tp17-like proteins are a promising class of novel antimicrobial drugs.

Example 16

The Antibacterial Activity of r-Lysozyme™ is not Inhibited by Tp17

In the search of a lysozyme variant able to resist the inhibition of Tp17 and Tp17-like proteins, we tested the commercially available rLysozyme™ (71110-5; Novagen® Merck-KGaA, Darmstadt, Germany). rLysozyme™ is a highly purified recombinant lysozyme that is recommended for the lysis of *E. coli* cells. The enzyme catalyzes the hydrolysis of N-Aetylmuramide linkages in the bacterial cell wall. The specific activity of rLysozyme solution (1,700,000 U/mg) is 250 times greater than that of chicken egg white lysozyme and therefore less enzyme is required to achieve *E. coli* Lysis. In addition, rLysozyme™ is optimally active at a physiological pH (6.0-8.0) that is compatible with Novagen's line of protein and nucleic acids extraction reagents.

Figure 29:
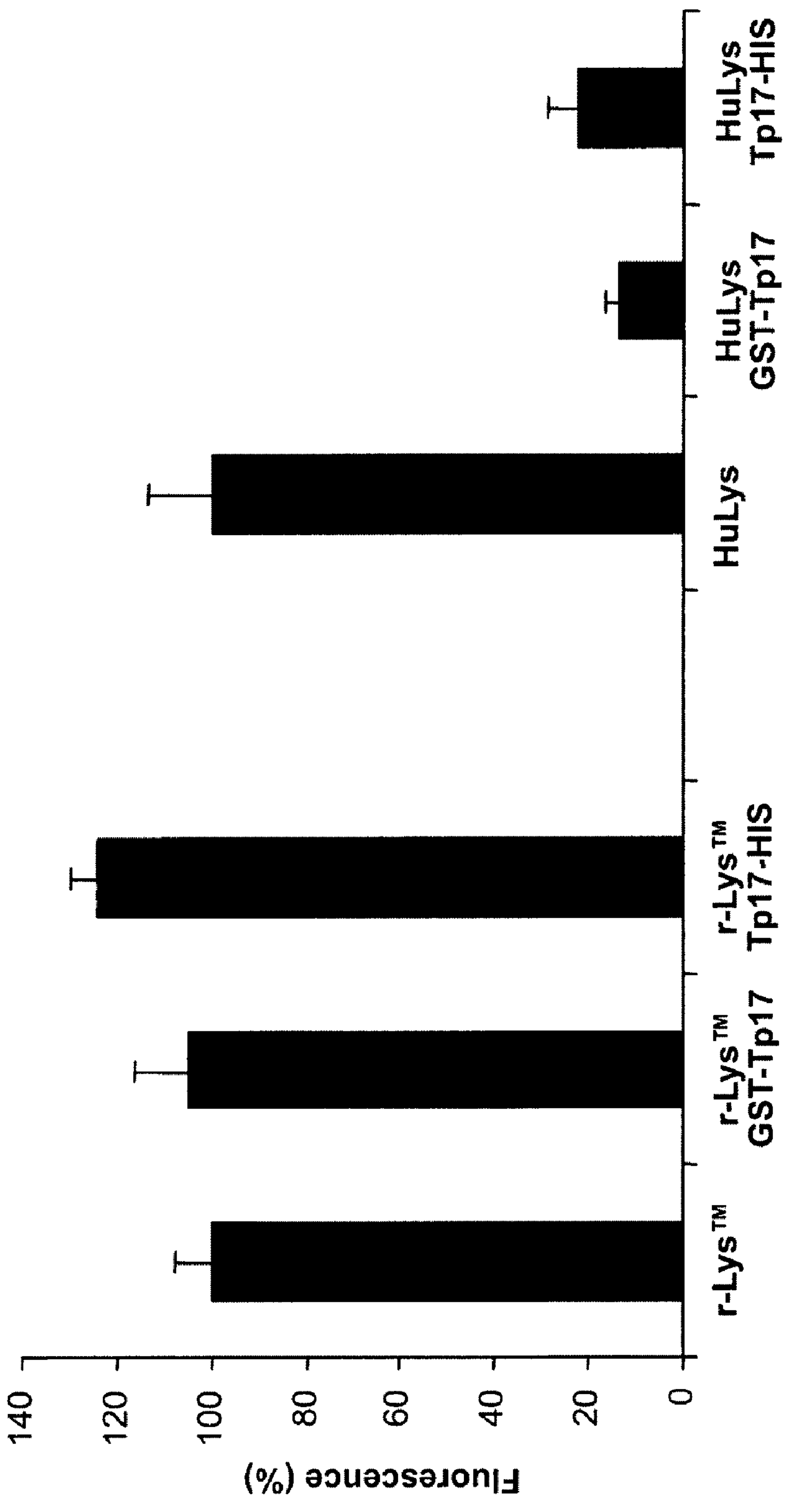
FIG. 29 is a bar graph showing that the bacteriolytic activity of r-Lysozyme™ (Novagen, VWR International, Mollet del Vallés, Spain) was not susceptible to inhibition by GST-Tp17 or Tp17-HIS, while the antibacterial activity of human lysozyme was strongly inhibited. The height of each bar indicates the detected fluorescence. An r-Lysozyme™ control and a human lysozyme (HuLys) control is present at the left of each experimental set.

In that context, we compared the antibacterial activity of human lysozyme (Ventria Bioscience, Sacramento, Calif., USA) and rLysozyme™ using the EnzCheck Lysozyme assay (E-22013; Molecular Probes, Eugene, Oreg.). We first determined that under the manufacturer's prescribed assay conditions, 1 unit of human lysozyme produced the same intensity of fluorescence as 230 units of rLysozyme™. Next, we measured the fluorescence intensity of either 1 unit of human lysozyme or 230 units of rLysozyme™, in the presence or absence of 10 μg of either GST-Tp17 or Tp17-HIS. As shown in FIG. 29, rLysozyme™ was not susceptible to the inhibition of GST-Tp17 or Tp17-HIS, while the antibacterial activity of human lysozyme was strongly inhibited. Interestingly, we reproducibly observed a slight increase (in the range of 20%) of the rLysozyme™ antibacterial activity in presence of Tp17. Taken together, these results suggest that rLysozyme™ is not susceptible to inhibition by Tp17 and possibly Tp-17 like proteins. As a consequence, rLysozyme™ represents a novel and promising antimicrobial drug that could eventually substitute for chicken lysozyme in various therapeutic preparations intended for human and animal use. Additionally, it can be used as an antiseptic and/or as a food preservative.

Example 17

Figure 30:
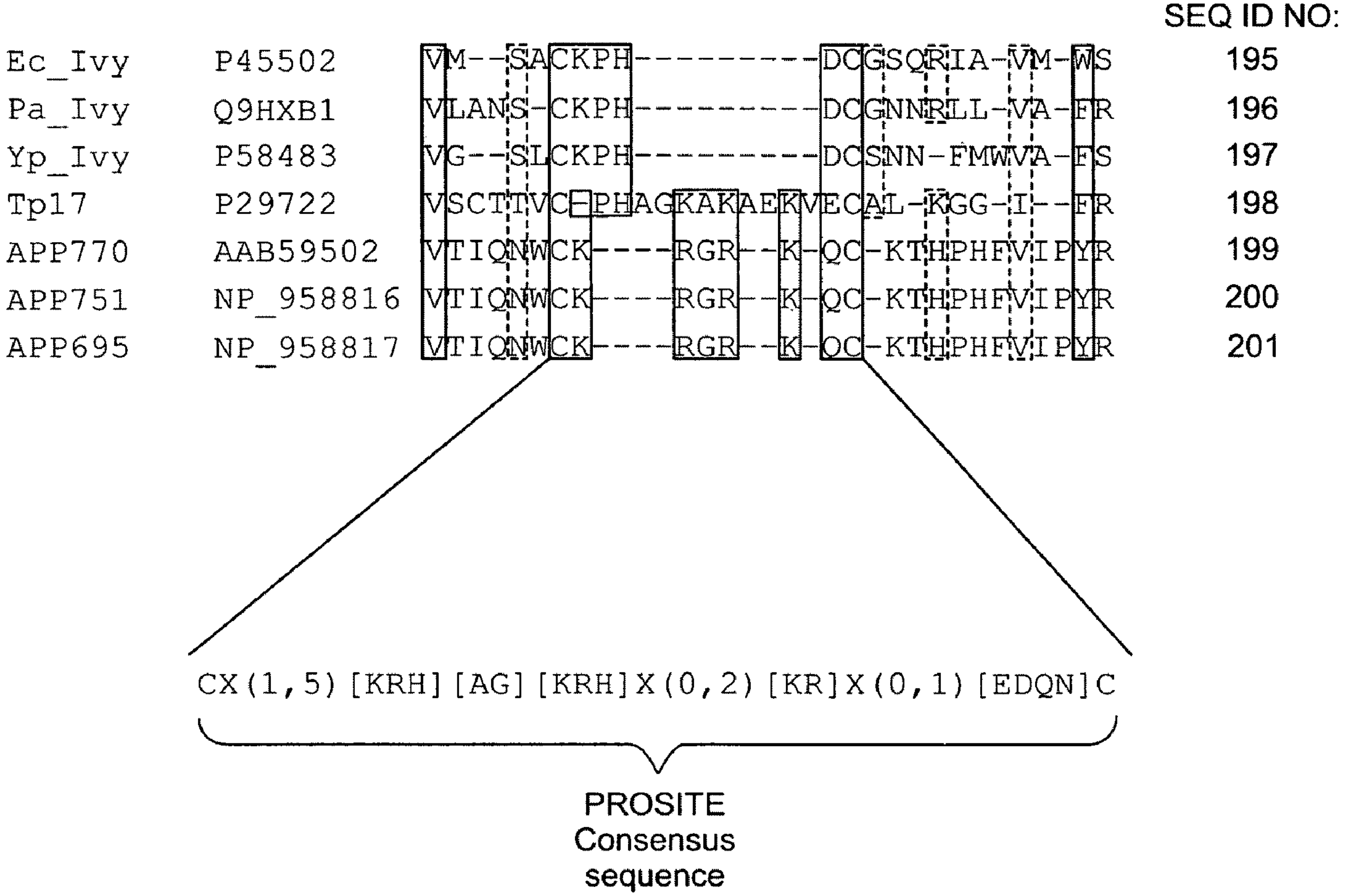
FIG. 30 shows sequence alignments of the lysozyme binding/inhibition sequences from *Escherichia coli* Ivy, *Pseudomonas aeruginosa* Ivy, *Yersinia pestis* Ivy, *Treponema pallidum* sp. *pallidum* Tp17 and the three isoforms (APP770, APP751 & APP695) of the human Beta amyloid precursor protein (β-APP). The Genbank accession number corresponding to each peptide sequence is indicated. The deduced consensus sequence is represented using the pattern syntax used in the PROSITE database.

The Alzheimer Precursor Protein (βAPP) Shares Structural Similarity With Tp17-Like Proteins Among the proteins that share extensive sequence similarity with Tp17 (see, for example, FIG. 1), we identified the human Beta Amyloid Precursor Protein (β-APP). This protein is of key medical and diagnostic interest since it is involved in the generation of amyloid deposition during Alzheimer disease. As shown in FIG. 30, we have discovered a well conserved peptide motif that is shared by members of the Ivy protein family, Tp17, and the three splicing isoforms of β-APP (APP770, APP751 & APP695). Manually performed multiple alignments allowed us to group all these peptide sequences under the following consensus:

CX(1,5)[KRH][AG][KRH]X(0,2)[KR]X(1,1)[EDQN]C (SEQ ID No: 178)

In this consensus, C, K, R, H, A, G, E, D, Q and N correspond to the one-letter amino acid code for Cysteine, Lysine, Arginine, Histidine, Alanine, Glycine, Glutamic acid, Aspartic acid, Glutamine, and Asparagine, respectively. The syntax rules are the one used in the PROSITE database. This consensus can also be represented as follows:

Cys $Xaa_1$ $Xaa_2$ $Xaa_3$ $Xaa_4$ $Xaa_5$ $Xaa_6$ (SEQ ID NO: 177)

$Xaa_7$ $Xaa_8$ $Xaa_9$ $Xaa_{10}$ $Xaa_{11}$ $Xaa_{12}$ $Xaa_{13}$ Cys where $Xaa_1$, $Xaa_2$, $Xaa_3$, $Xaa_4$ and $Xaa_5$ are any amino acid or are absent, $Xaa_6$ is amino acid K, R or H, $Xaa_7$ is A or G, $Xaa_8$ is K, R, or H, $Xaa_9$ and $Xaa_{10}$ are any amino acid or are absent, $Xaa_{11}$ is amino acid K or R, $Xaa_{12}$ is any amino acid or is absent, and $Xaa_{13}$ is amino acid E, D, Q or N.

Figure 31:
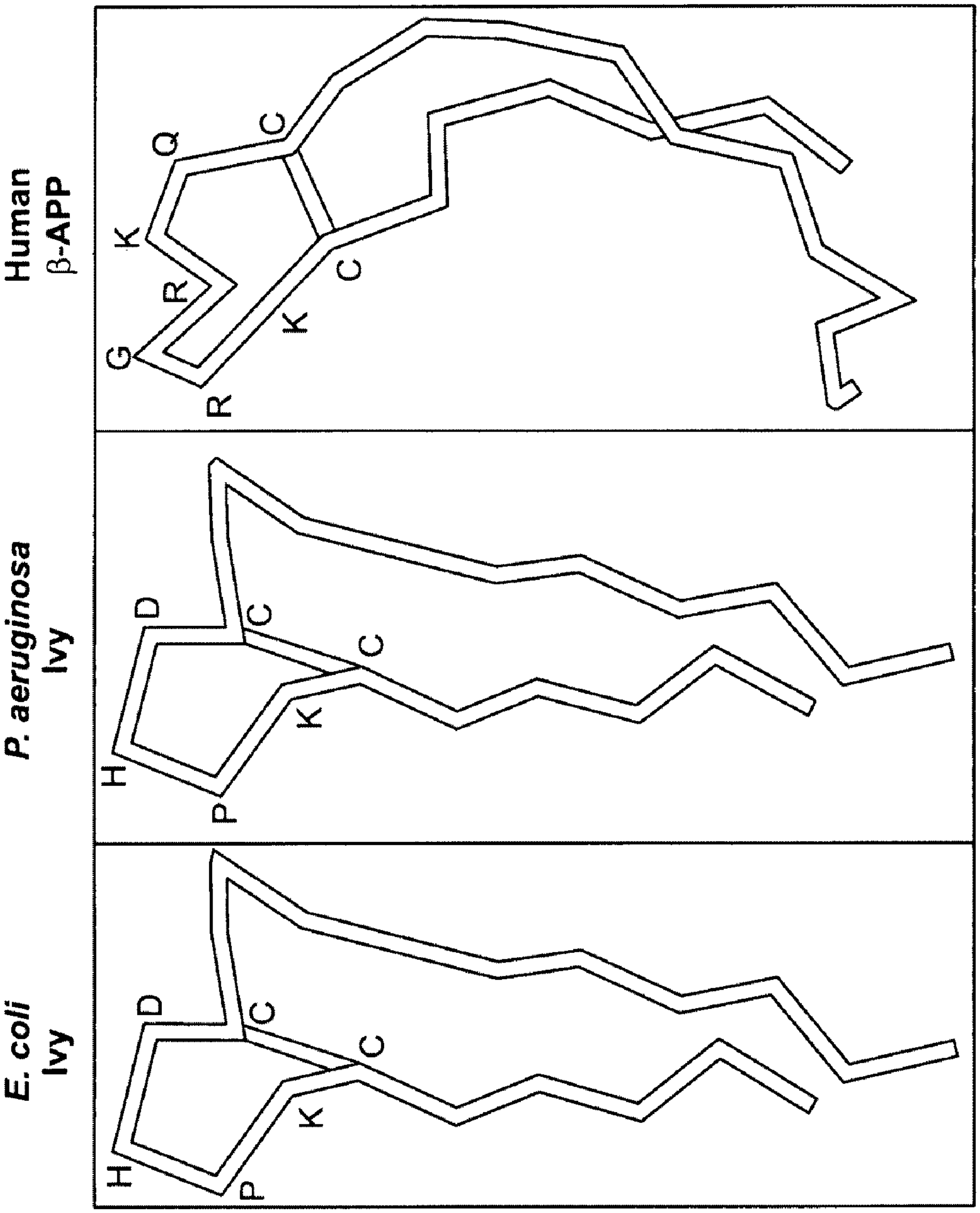
FIG. 31 shows 3D views of the lysozyme binding/inhibition domains of *Escherichia coli* Ivy, *Pseudomonas aeruginosa* Ivy and human β-APP.

For three of these proteins (Ivy from *E. coli*, Tp17, and *P. aeruginosa*), crystal structures were available. Using the Cn3D molecular viewer, we found that the related peptide stretches of each of the three proteins exhibited a conserved three dimensional organization. As shown in FIG. 31, all three form an extended beta sheet, displaying a disulfide bridged peptide loop. These proteins share a conserved three dimensional structural organization. All three molecules contain an extended beta sheet structure and an exposed disulfide-bridged peptide loop. This structural motif is conserved in all three isoforms (APP770, APP751 & APP695) of human β-APP protein. The 3D views were generated using Cn3D software, which is available on the National Center for Biotechnology's website and the following Protein Data Bank (PDB) atomic coordinates files: 1GPQ (*E. coli* Ivy), 1UUZ (*P. aeruginosa* Ivy) and 1MWP (*Homo sapiens* β-APP). These data suggest that Ivy, Tp17, and β-APP are structurally and functionally related.

Example 18

Human Lysozyme Binds to Immobilized Alzheimer Precursor Protein (βAPP)

Figure 32:
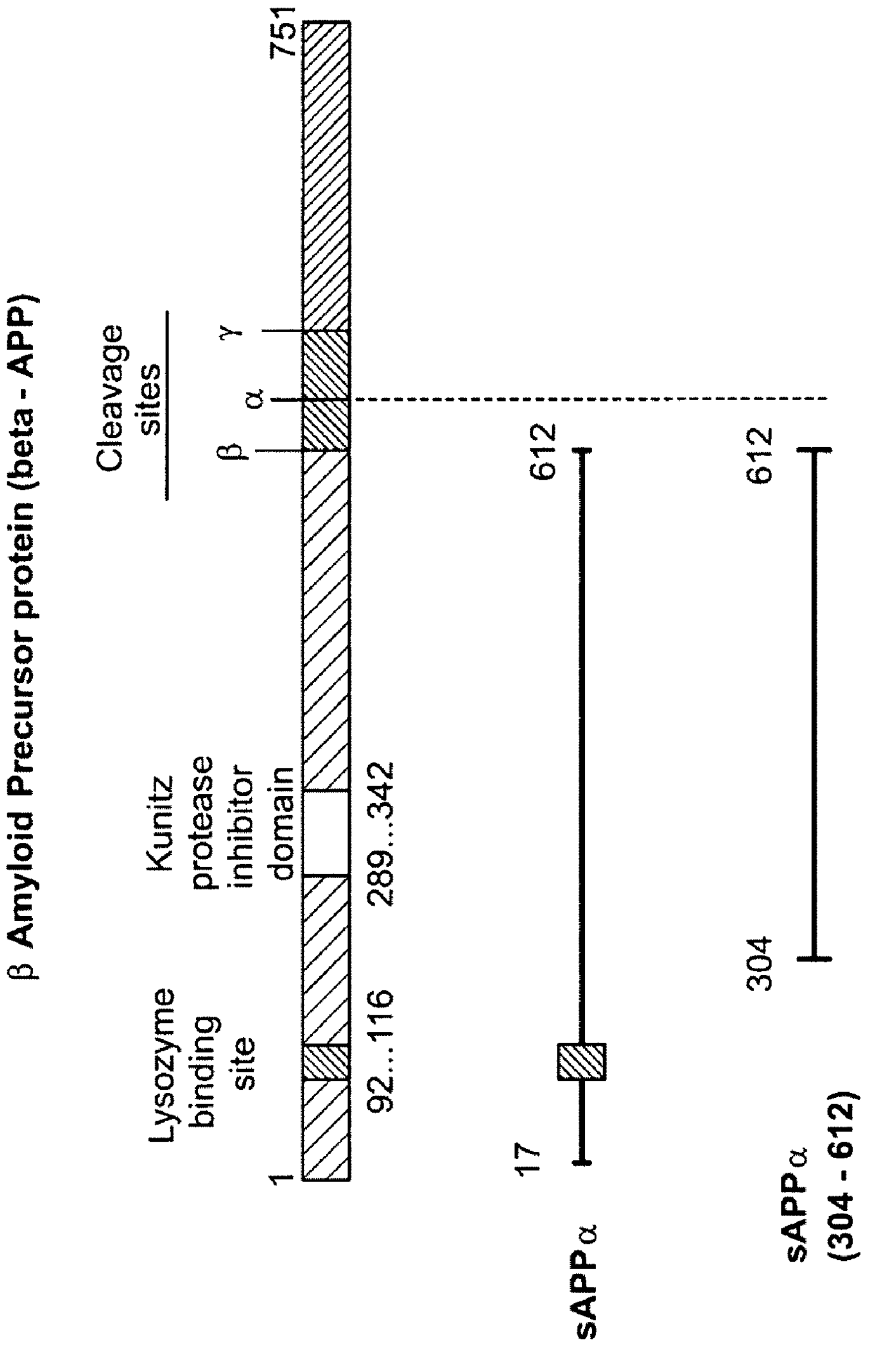
FIG. 32 is a schematic diagram showing the domain organization of sAPP and *Homo sapiens* Beta amyloid precursor protein (β-APP).

As shown in FIG. 32, the lysozyme binding site identified in β-APP lies at the extreme N-terminus of the protein and spans residues 92 to 116. The isoform APP751 (751 amino acid long) is an exemplary APP-like polypeptide. The conclusions drawn from this figure are also true for isoforms APP695 and APP770. The amino acid numbers refer to amino acid positions in the β-APP sequence deposited under Genbank accession number NP_958816. The lysozyme binding site is located between residues 92 to 116. Specifically, we used a longer fragment of β-APP derivative, called sAPPα and a shorter fragment called sAPPα (304-612): Both sAPPα and sAPPα (304-612) are derived from the APP695 isoform and consequently lack the kunitz protease inhibitor domain (residues 289 to 342 in APP770 and APP751).

Figure 33:
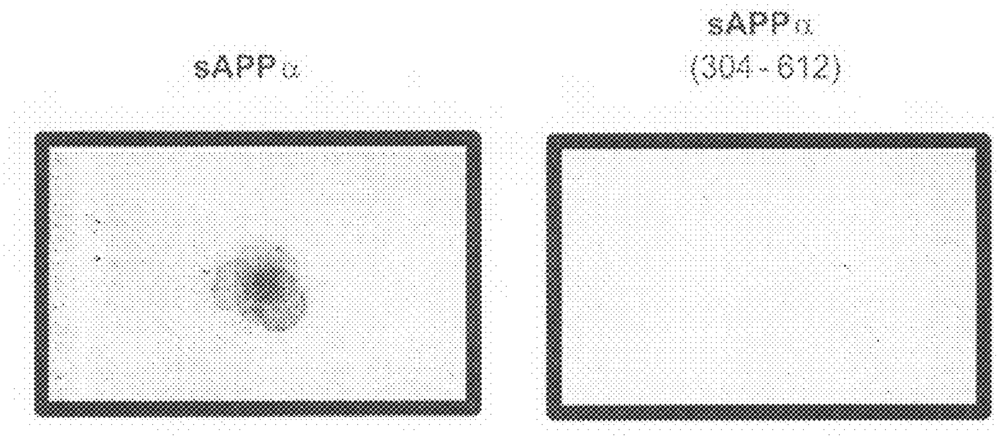
FIG. 33 shows the detection of horse radish peroxidase (POD)-labeled huLYS binding to immobilized sAPPα, but not to immobilized sAPPα(304-612). 10 μg of both sAPPα and sAPPα (304-612) were spotted on a nitrocellulose membrane and probed with POD-HuLYS diluted 1/1000.
Figure 34A:
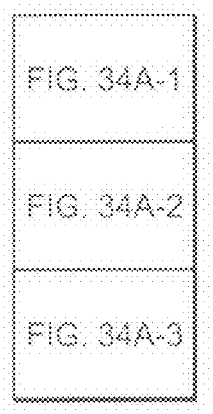

To test whether the β-APP protein binds huLYS, we performed lysozyme binding assays using purified, recombinant forms of β-APP. Both sAPPα (product number: S9564) and sAPPα (302-612) (product number: S8065) were purchased from Sigma-Aldrich (Tres cantos, Madrid, Spain). 10 μg of each protein was spotted onto a Nytran membrane (Scleicher & Schuiell, Dassel, Germany). Non-specific adsorption sites were blocked by incubation for one hour in TBST-milk. After three washes with TBST, the membrane was incubated for one hour with horse radish peroxidase (POD)-labeled human lysozyme diluted 1/1000 in TBST-milk. Next, the membrane was washed three times, for 5 minutes each wash, with TBST. Staining was performed by adding 5 ml of POD chromogenic substrate (TMB, product number: T0565, Sigma). As shown in FIG. 33, huLYS bound to sAPPα, but not to sAPPα (302-612). This observation suggested that the β-APP protein binds to huLYS, and that the binding site is located in the N-terminal region, between residues 92 and 116 of β-APP. These data define a novel pharmacological target for the treatment of Alzheimer disease. Moreover, the β-APP/huLYS protein complex likely serves as a diagnostic marker of Alzheimer's disease.

Diagnostic compositions and methods related to Alzheimer's disease feature fragments of a substantially pure APP-like polypeptide comprising an amino acid sequence of Cys $Xaa_1$ $Xaa_2$ $Xaa_3$ $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$ Cys (SEQ ID NO:177), where $Xaa_1$, $Xaa_2$, $Xaa_3$, $Xaa_4$ and $Xaa_5$ are any amino acid or are absent, $Xaa_6$ is amino acid K, R or H, $Xaa_7$ is A or G, $Xaa_8$ is K, R, or H, $Xaa_9$ and $Xaa_{10}$ are any amino acid or are absent, $Xaa_{11}$ is amino acid K or R, $Xaa_{12}$ is any amino acid or is absent, and $Xaa_{13}$ is amino acid E, D, Q or N. The compositions and methods also feature as nucleic acid molecules encoding this polypeptide fragments, vectors for the expression of such fragments, and host cells containing these vectors. Such fragments may be expressed as recombinant polypeptides and used for the generation of antibodies that recognize the fragment or that recognize the fragment when complexed to a lysozyme polypeptide.

Antibodies that specifically bind to an APP-like polypeptide/lysozyme complex are useful in methods for diagnosing Alzheimer's disease in a subject, where the antibody is used to probe a biological sample from the subject, such as a serum sample, a cerebrospinal fluid sample, or a tissue sample. At present, a definitive diagnosis of Alzheimer's disease generally requires a post-mortem examination of brain tissue from a subject. Thus, the present compositions and methods, which facilitate the diagnosis of Alzheimer's disease in bodily fluids obtained from a living subject, provide a significant improvement over existing diagnostic methods.

Specifically, the present invention provides a method of diagnosing Alzheimer's disease by detecting the presence in a sample from the subject of a complex between an APP-like polypeptide and a lysozyme polypeptide, or the presence of an antibody that binds to such a complex. Further, a method is provided for identifying a candidate compound that modulates binding between the APP-like polypeptide and a lysozyme polypeptide through detecting a reduction in binding between the Tp17-like polypeptide and the lysozyme polypeptide in the presence of the candidate compound.

Example 19

Computer Identification of Novel Tp17-Like Proteins

Peptide sequence databases (Swissprot & TrEMBL) were searched for proteins that share the CX(1,5)[KRH][AG][KRH]X(0,2)[KR]X(0,1)[EDQN]C (SEQ ID NO: 178) consensus sequence defined in FIG. 30. The bacterial, viral and eukaryotic proteins identified as having this sequence are shown in 34A-1 to 34A-3 and 34B-1 to 34B-3. These proteins represent novel therapeutic targets and immunogenic compositions that will likely interfere with the formation of Tp17-like/huLYS protein complexes. Moreover, these proteins, complexed with huLYS, may represent attractive markers for the diagnosis of human, animal and plant diseases.

Example 20

Inhibition and Binding Capacity of Tp17 Mutants

Figures 35A, 35B:
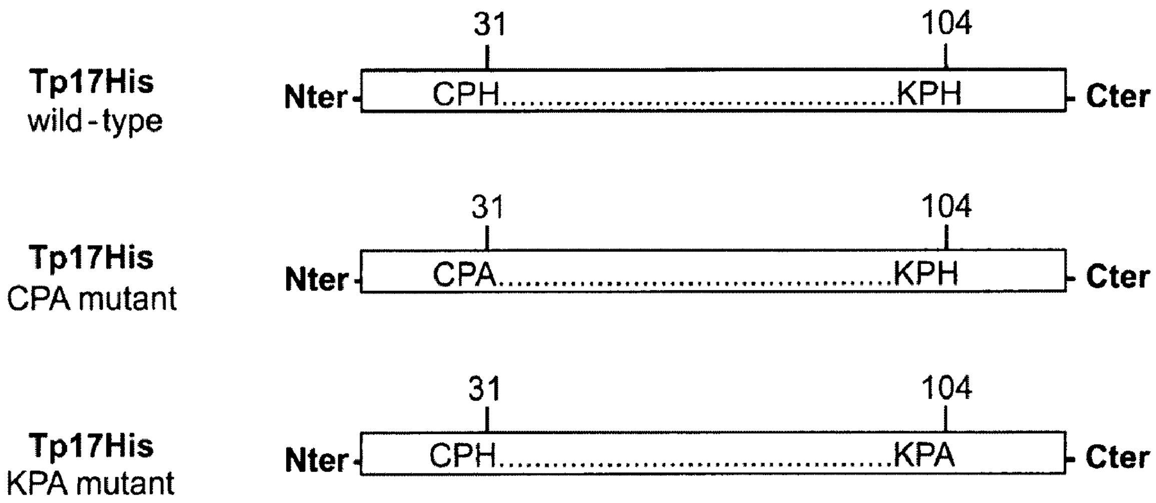
FIG. 35A is a schematic diagram showing a wild-type Tp17 polypeptide and mutant Tp17 CPA and KPA polypeptides. In TP17 CPA the histidine at amino acid position 31 was replaced with alanine, and in Tp17 KPA, the histidine at amino acid position 107 was replaced with alanine.
FIG. 35B is a table showing the inhibitory capacity of the mutant Tp17 CPA and KPA polypeptides relative to the wild-type Tp17 polypeptide.

To determine wether H31 and His 104 of Tp17 contributed to huLYS inhibition, we performed site-directed mutagenesis of the gene encoding GST-Tp17 (FIG. 35A). The $H_{31}A$ and $His_{104}A$ GST-Tp17 mutant polypeptides were generated by introducing two nucleotide changes in the pGEX2T-Tp17 plasmid vector using the QuickChange® Site-directed mutagenesis kit (Stratagene, La Jolla, Calif., USA). For that purpose, mutagenic oligonucleotides Fw_CPAAG (5'-CCG TGT GTC CGG CCG CCG GGA AGG C-3') (SEQ. ID.

NO:298) and Bw_CPAAG (5'-GCC TTC CCG GCG GCC GGA CAC ACG G-3) (SEQ. ID. NO: 299) and oligonucleotides Fw_KPAE (5'-AAT CGA AGG CAC CGG CCG AGA AAG AGC TGT ACG-3) (SEQ. ID NO:300) and Bw_KPAE (5'-CGT ACA GCT CTT TCT CGG CCG GTG CCT TCG ATT-3') (SEQ. ID NO: 301) were separately annealed to denatured pGEX2T-Tp17, and extended using Pfu Turbo DNA polymerase under conditions recommended by the supplier. Non-methylated DNA template was eliminated by Dpn1 digestion and the resulting digestion mixture was used to transform XL-1 Blue® supercompetent cells. Mutant plasmids were selected by restriction mapping the resulting PCR amplicons. The presence of the $H_{31}A$ mutation was confirmed by sequencing the full-length mutated Tp17 gene. Mutant GST-Tp17 carrying the $H_{31}A$ or the $His_{104}A$ mutation was then produced and purified as described in Example 1. Lysozyme inhibition assays were performed as described below.

Each 100 μl reaction mixture contained 25 μl of lysozyme solution (2 units for human lysozyme, dissolved in reaction buffer), 25 μl of a test protein solution, and 50 μl of a suspension of fluorescein-labeled *Micrococcus lysodeikticus* (50 μg/ml). The reaction mixture was then incubated for 45 minutes at 37° C. Fluorescence present in the reaction mixture was measured ($\lambda_{exc.}$=485 nm; $\lambda_{emi.}$=520 nm) using a fluorescence multi-well plate reader model FLx800 (Bio TEK instruments, Winoosky, Vt.) equipped with KC junior data acquisition software (Bio TEK Instruments, Winoosky, Vt.). The resulting fluorescent data, shown in FIG. 35B, represents the mean and standard deviation corresponding to the reading of three independent wells. A negative control well contained 50 μl of deoinized water and 50 μl of Fluorescein-labeled *Micrococcus lysodeikticus* suspension.

Figure 36:
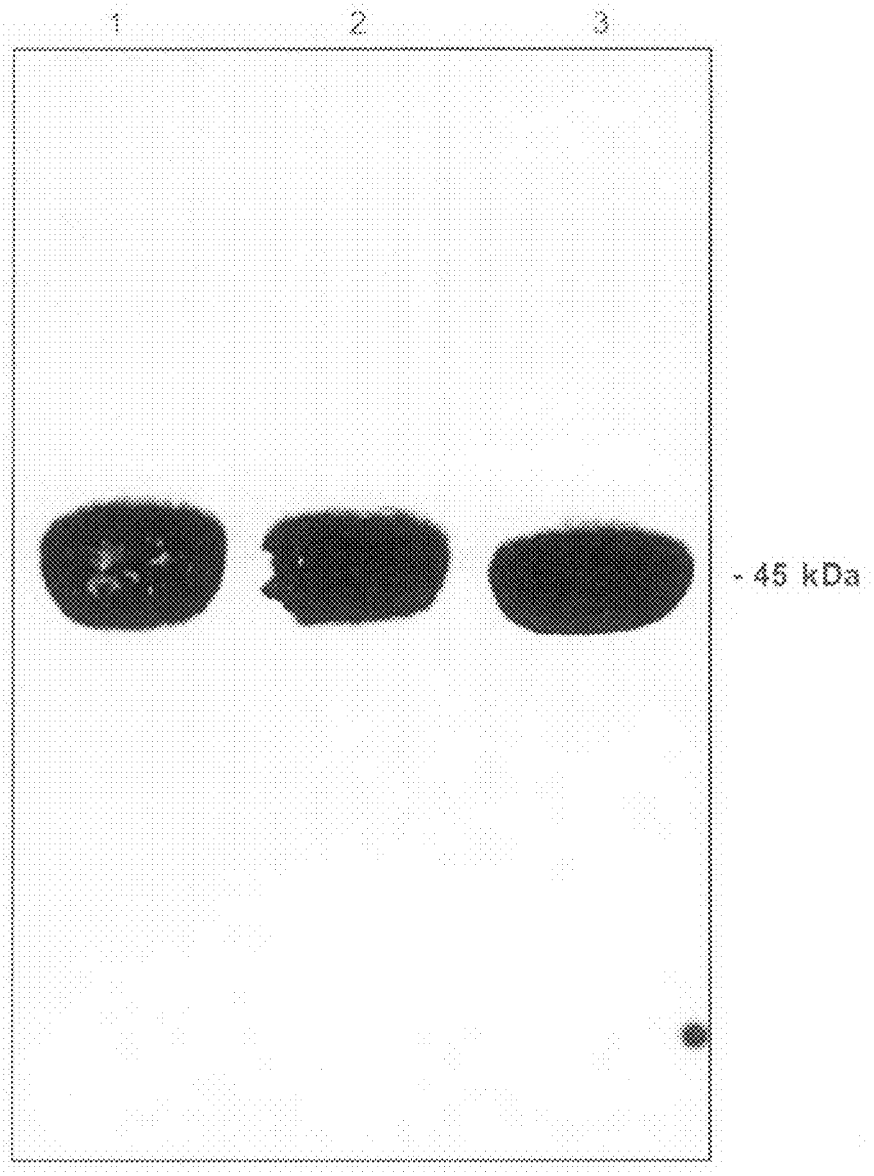
FIG. 36 is a Western blot showing proteins having molecular weights of 45 kDA in each of lanes 1, 2, and 3 where lane 1 is the wild type Tp17, lane 2 CPA mutant, and lane 3 KPA mutant.

As shown in FIGS. 35A and 35B, $H_{31}A$ and $His_{104}A$ mutant polypeptides showed a decrease in lysozyme inhibition, but retained their ability to bind lysozyme (FIG. 36). These data demonstrated that amino acid positions 31 and 104 contribute to lysozyme binding and/or inhibition. Therefore, embodiments of a mutant Tp17 according to the present invention includes one or more mutations at and/or around $H_{31}$ and $His_{104}$ of Tp-17 and corresponding sites in other Tp-17 like pathogens. Such a mutant can interfere with normal inhibition of a Tp-17 like protein in vivo and therefore having therapeutic effects described above.

Example 21

Tp17 May Bind to SLLP1 Lysozyme-Like Protein

A unique, non-bacteriolytic, chicken or conventional-type (C-type) lysozyme-like protein, SLLP1, is present in the acrosome of human sperm (Mandal et al. Biol Reprod. 68:1525-37, 2003). Normally, C-type lysozymes are bacteriolytic and can bind to N-acetylglucosamines linked by beta-1,4 glycosidic bonds. Most of the invariant residues (17 out of 20), including all the cysteines, are conserved in SLLP1, but the two catalytic residues E35 and D52 conserved in C-lysozymes have been replaced in SLLP1 with T and N, respectively, to become T122 and N139. Mandal et al. hypothesized that, after acrosome reaction, SLLP1 could be a potential receptor for the egg oligosaccharide residue N-acetylglucosamine, which is present in the extracellular matrix over the egg plasma membrane, within the perivitelline space, pores of zona pellucida, and cumulus layers.

Figure 38:
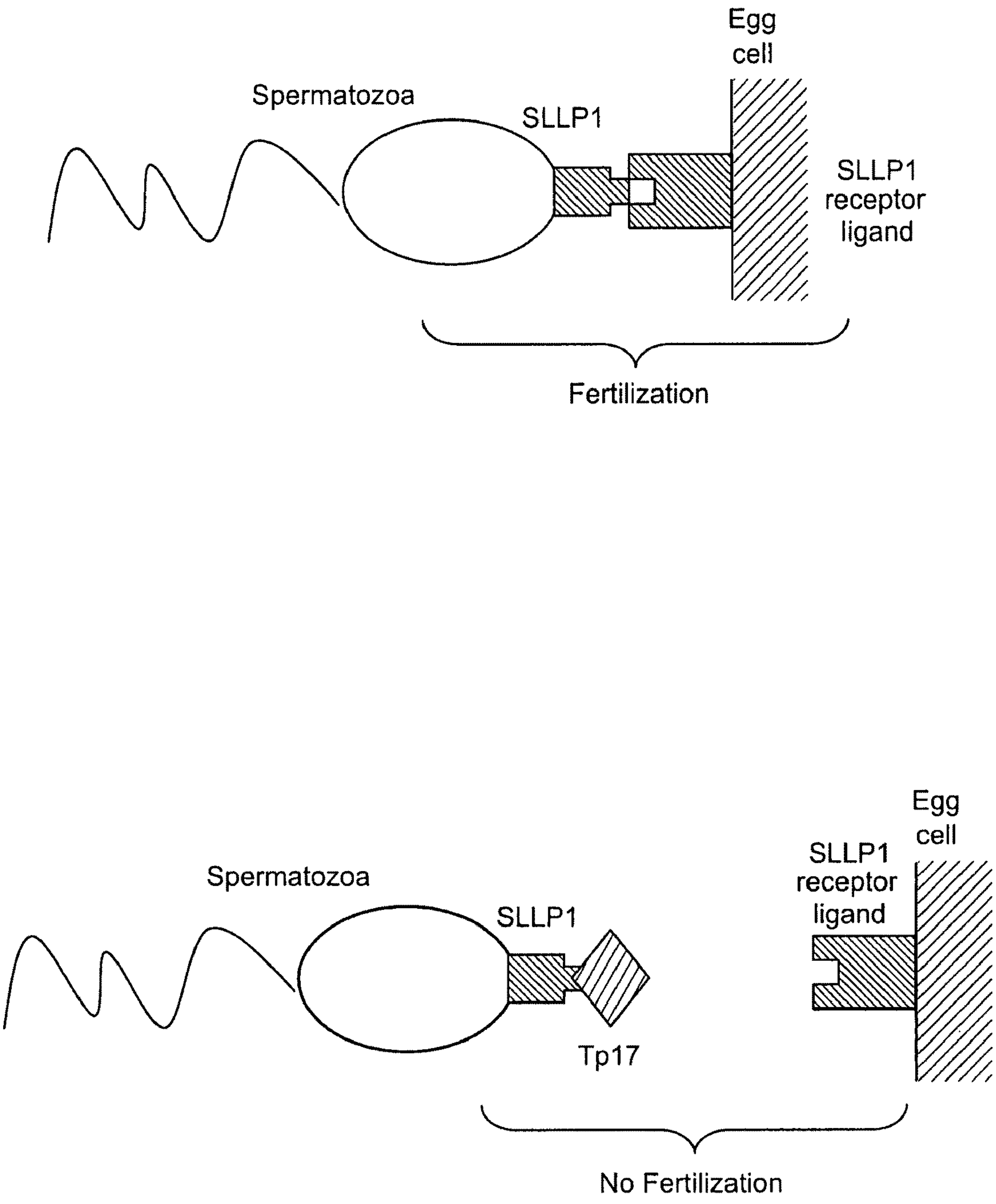
FIG. 38 is a schematic diagram showing that Tp17 may bind SLLP1 at the sperm surface and subsequently interfere with the fertilization process.

We have found that huLYS, chkLYS and SLLP1 share more than 55% sequence identity. As shown in FIG. 37, while human lysozyme and chicken lysozyme share 63% amino acid sequence identity, SLLP1 and human lysozyme share 58% sequence identity. Since Tp17 is able to bind to both huLYS and chkLYS, and based on the high level of sequence identity present between these proteins, it is likely that Tp17-like polypeptides including Tp17 are also capable of binding to SLLP1. This interaction may facilitate pathogen transmission during sexual contact. As shown in FIG. 38, an SLLP1/Tp17-like polypeptide complex represents a promising therapeutic target for the control of human and animal fertility. For example, as illustrated in FIG. 38, administering an effective amount of a Tp-17 like polypeptide may serve as a method of contraception as it interferes with normal docking of a spermatozoa to a cognate receptor at an egg cell surface.

Further, candidate compounds that decrease the binding of a Tp17-like polypeptide to SLLP1 are useful inhibitors of sexually transmitted disease. Methods for screening for such compounds are described above.

In addition, while wild-type SLLP1 is not likely to be bacteriolytic, mutant SLLP1, containing amino acid alterations of T122 to E and/or of N 139 to D, especially the double mutant containing both mutations back to the conserved sequence of C-type lysozyme, are likely to acquire bacteriolytic activity. Mutant SLLP1 containing these mutations would likely fail to bind Tp17-like polypeptides and would likely have increased lysozyme enzymatic activity relative to chicken lysozyme, for example. As such, mutant SLLP1 may be used for its enhanced antimicrobial, e.g., bacteriolytic, capability as a pharmaceutical composition or disinfectant. Other lysozyme variant such as bacteriophage T4's lysozyme, can also be used in a similar way. One embodiment of such a composition may include between about 2 to 100 mg of the lysozyme variant (preferably about 5 mg), about 2 mg of papain and/or about 3 mg of bacitracin. A preferred embodiment is dissolvable for oral intake.

Other Embodiments

The invention may be embodied in other specific forms without departing from the spirit or essential characteristics thereof. Any aspects and features of the above described invention can be combined. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are embraced therein.

INCORPORATION BY REFERENCE

All publications and patent documents cited in this application are incorporated by reference in their entirety for all purposes to the same extent as if the contents of each individual publication or patent document was incorporated herein.

We claim:

1. A composition for detecting anti-pathogen antibodies in a patient sample, the composition comprising:

a first polypeptide having at least 95% identity to a polypeptide comprising amino acids 22-156 of SEQ ID NO:31; and a substantially pure human lysozyme polypeptide from a source other than said patient sample.

2. The composition of claim 1, wherein the first polypeptide is derived from *Treponema pallidum*.

3. The composition of claim 1, wherein the first polypeptide comprises amino acids 22-156 of SEQ ID NO:31.

4. The composition of claim 1, wherein the first polypeptide comprises the sequence C P H A G K A K A E K V B C (SEQ ID NO:41).

5. The composition of claim 1, wherein the first polypeptide is affixed to a solid support.

6. The composition of claim 1, wherein the first polypeptide is a recombinant polypeptide.

7. The composition of claim 1, wherein the first polypeptide is fused to an affinity tag.

8. The composition of claim 1, wherein the human lysozyme polypeptide comprises SEQ ID NO:134.

9. The composition of claim 1, wherein the human lysozyme polypeptide is a recombinant polypeptide.

10. The composition of claim 1, wherein the human lysozyme polypeptide is isolated from a biological sample.

11. The composition of claim 1, further comprising carrier particles.

12. The composition of claim 11, wherein the carrier particles are selected from the group consisting of red blood cells, polypeptide aggregate particles, polymeric particles, inorganic particles, paramagnetic particles, and yeast cells.

13. The composition of claim 1, further comprising a patient sample.

14. A kit providing an assay for detecting anti-pathogen antibodies in a patient sample, the kit comprising:

a first polypeptide having at least 95% identity to a polypeptide comprising amino acids 22-156 of SEQ ID NO. 31; and a substantially pure human lysozyme polypeptide from a source other than said patient sample.

15. The kit of claim 14, further comprising instructions for adding the human lysozyme to the assay.

16. The kit of claim 14, wherein the first polypeptide is derived from Treponema pallidum.

17. The kit of claim 14, wherein the first polypeptide comprises amino acids 22-156 of SEQ ID NO:31.

18. The kit of claim 14, wherein the first polypeptide comprises the sequence C P H A G K A K A E K V E C (SEQ ID NO:41).

19. The kit of claim 14, wherein the first polypeptide is affixed to a solid support.

20. The kit of claim 19, wherein the solid support is selected from the group consisting of a resin, a gel, a bead, a well, a column, a chip, a membrane, a matrix, a plate, and a filter device.

21. The kit of claim 14, wherein the first polypeptide is a recombinant polypeptide.

22. The kit of claim 14, wherein the first polypeptide is fused to an affinity tag.

23. The kit of claim 14, wherein the human lysozyme polypeptide comprises SEQ ID NO:134.

24. The kit of claim 14, wherein the human lysozyme polypeptide is a recombinant polypeptide.

25. The kit of claim 14, wherein the human lysozyme polypeptide is isolated from a biological sample.

26. The kit of claim 14, further comprising carrier particles.

27. The kit of claim 26, wherein the carrier particles are selected from the group consisting of red blood cells, polypeptide aggregate particles, polymeric particles, inorganic particles, paramagnetic particles, and yeast cells.

28. The composition of claim 1, wherein when a patient sample is added to said composition, said substantially pure human lysozyme polypeptide is present in the mixture of sample and composition at an amount greater than an amount of lysozyme polypeptide found in said patient sample alone.

29. The kit of claim 14, wherein when a patient sample is added to said composition, said substantially pure human lysozyme polypeptide is present in the mixture of sample and composition at an amount greater than an amount of lysozyme polypeptide found in said patient sample alone.

* * * * *

UNITED STATES PATENT AND TRADEMARK OFFICE

CERTIFICATE OF CORRECTION

PATENT NO. : 7,700,727 B2
APPLICATION NO. : 11/116144
DATED : April 20, 2010
INVENTOR(S) : Berthet et al.

It is certified that error appears in the above-identified patent and that said Letters Patent is hereby corrected as shown below:

In column 217, line 37, (claim 4), "C P H A G K A K A E K V B C" should read -- C P H A G K A K A E K V E C --.
In column 218, line 27, (claim 16), "Treponema pallidum" should be italicized.

Signed and Sealed this

Seventeenth Day of August, 2010

David J. Kappos
*Director of the United States Patent and Trademark Office*